US008053457B2

(12) United States Patent
Boettcher et al.

(10) Patent No.: US 8,053,457 B2
(45) Date of Patent: Nov. 8, 2011

(54) 3-IMIDAZOLYL-INDOLES FOR THE TREATMENT OF PROLIFERATIVE DISEASES

(75) Inventors: Andreas Boettcher, Basel (CH); Nicole Buschmann, Basel (CH); Pascal Furet, Basel (CH); Jean-Marc Groell, Basel (CH); Jorg Kallen, Basel (CH); Joanna Hergovich Lisztwan, Basel (CH); Keiichi Masuya, Basel (CH); Lorenz Mayr, Basel (CH); Andrea Vaupel, Basel (CH)

(73) Assignee: Novartis AG, Basel (CH)

( * ) Notice: Subject to any disclaimer, the term of this patent is extended or adjusted under 35 U.S.C. 154(b) by 106 days.

(21) Appl. No.: 12/593,721

(22) PCT Filed: Mar. 27, 2008

(86) PCT No.: PCT/EP2008/053667
§ 371 (c)(1),
(2), (4) Date: Sep. 29, 2009

(87) PCT Pub. No.: WO2008/119741
PCT Pub. Date: Oct. 9, 2008

(65) Prior Publication Data
US 2010/0125064 A1 May 20, 2010

(30) Foreign Application Priority Data
Mar. 29, 2007 (EP) .................................... 07105269

(51) Int. Cl.
*A61K 31/397* (2006.01)
*A61K 31/5377* (2006.01)
*A61K 31/496* (2006.01)
*A61K 31/506* (2006.01)
*C07D 401/14* (2006.01)
*C07D 403/14* (2006.01)

(52) U.S. Cl. ........ 514/397; 514/336; 514/326; 514/256; 514/254.05; 514/235.8; 514/210.2; 544/370; 544/333; 544/364; 544/139; 546/272.7; 548/312.1

(58) Field of Classification Search ................. 514/397, 514/336, 326, 256, 254.05, 235.8, 210.2; 544/370, 333, 364, 139; 546/272.7; 548/312.1
See application file for complete search history.

(56) References Cited

U.S. PATENT DOCUMENTS
6,699,883 B1    3/2004   Doemling et al.

FOREIGN PATENT DOCUMENTS
WO    WO 2006/091646 A2    8/2006
WO    WO 2006/136606 A2    12/2006

OTHER PUBLICATIONS
Toledo et al. Int. J. Biochem. Cell Biol. 2007, 39(7-8), 1476-1482.*
Schafer et al. Drug Discovery Today 2008, 13 (21/22), 913-916.*
Horig et al. Journal of Translational Medicine 2004, 2(44).*
Sisko et al., "An Investigation of Imidazole and Oxazole Syntheses Using Aryl-Substituted TosMIC Reagents", Journal of Organic Chemistry, 2000 vol. 65 No. 5 pp. 1516-1524.

* cited by examiner

*Primary Examiner* — Jason M Nolan

(57) ABSTRACT

The invention relates to 3-heterocyclyl indolyl compounds of formula I capable of inhibiting the interaction between p53, or variants thereof, and MDM2 and/or MDM4, or variants thereof, respectively:

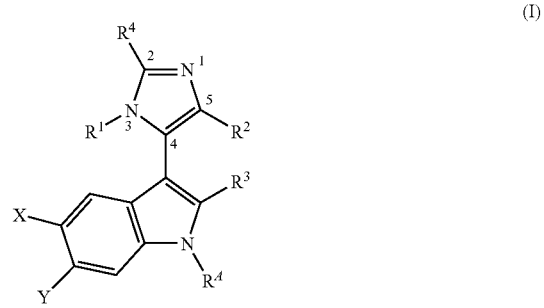

wherein
$R^1$, $R^2$, $R^3$, $R^4$, $R^A$, X and Y are as defined in the specification. Due to their activity, the compounds are useful in the treatment of various disorders and diseases mediated by the activity of MDM2 and/or MDM4, or variants thereof, such as inflammatory or proliferative diseases or in the protection of cells.

11 Claims, No Drawings

3-IMIDAZOLYL-INDOLES FOR THE TREATMENT OF PROLIFERATIVE DISEASES

This application is a U.S. National Phase filing of International Application Ser. No. PCT1EP2008/053667 filed 27 Mar. 2008 and claims priority to E.P. Application Ser. No. 07105269.0 filed 29 Mar. 2007, the contents of which are incorporated herein by reference in their entirety.

The present invention relates to 3-heterocyclyl indolyl compounds capable of inhibiting the interaction between p53, or variants thereof, and MDM2 and/or MDM4, or variants thereof, respectively, especially binding to MDM2 and/or MDM4, or variants thereof, a process for the preparation of such compounds, pharmaceutical preparations comprising such compounds, uses and methods of use for such compounds in the treatment (including therapy and/or prophylaxis), and/or related subject matter as specified below. MDM2 refers to all genes and/or proteins encoded thereof with the names MDM2, Mdm2, HDM2, Hdm2. MDM4 refers to all genes and/or proteins encoded thereof with the names MDM4, Mdm4, HDM4, Hdm4, MDMX, MdmX, HDMX, HdmX.

Protein p53 is known as a tumor suppressor protein which helps to control cellular integrity and prevents the proliferation of permanently damaged cells by initiating growth arrest or apoptosis (controlled cell death). p53 mediates its effects in that it is a transcription factor capable of regulating a number of genes that regulate cell cycle and apoptosis. Thus, p53 is an important cell cycle inhibitor. These activities are tightly controlled by MDM2, an important negative regulator of the p53 tumor suppressor. "MDM2" (originally from the oncogene "murine double minute") refers both to the name of the gene as well as the protein encoded by that gene. MDM2 protein functions both as a E3 ubiquitin ligase that recognizes the N-terminal trans-activation domain (TAD) of the p53 tumor supressor and thus mediates the ubiquitin-dependent degradation of p53, and as an inhibitor of p53 transcriptional activation.

The original mouse oncogene, which codes for the MDM2 protein, was originally cloned from a transformed mouse cell line. The human homologue of this protein was later identified and is sometimes also called HDM2 (for "human double minute 2"). Further supporting the role of MDM2 as an oncogene, several human tumor and proliferative disease types have been shown to have increased levels of MDM2, including inter alia soft tissue sarcomas, bone cancer, e.g. osteosarcomas, breast tumors, bladder cancer, Li-Fraumeni syndrome, brain tumor, rhabdomyosarcoma and adrenocortical carcinoma and the like. Another protein belonging to the MDM2 family is MDM4, also known as MDMX.

Dysregulation of the MDM2/p53 ratio, e.g. due to mutations or molecular defects in the affected cells, can thus be found in many proliferative diseases. MDM2, in view of its mentioned effects, is capable to inhibit the activity of the tumor suppressor protein p53, thus leading to loss of p53's tumor suppressor activity and inhibiting regulatory mechanisms that impede cells from uncontrolled proliferation. As a consequence, uncontrolled proliferation can take place, leading to tumors, leukemias or other proliferative diseases.

Thus there is a need for new drugs that are capable to interfere with the interaction between p53 and mdm2 or especially oncogenic variants thereof and that thus allow p53 to exert its beneficial effect against uncontrolled tumor growth, allowing it e.g. to accumulate, to arrest the cell cycle and/or to cause apoptosis of affected cells.

SUMMARY OF THE INVENTION

It has now been found that a novel class of 3-heterocyclyl indoles shows potent inhibition of the MDM2/p53 interaction (this term including MDM2/p53 interaction and/or MDM4/p53 interaction herein) and the corresponding compounds thus represent a novel type of compounds that are useful in the treatment of a number of disorders, such as proliferative diseases. The invention relates therefore to these compounds as well as to the other inventive embodiments indicated above and below.

DETAILED DESCRIPTION OF THE INVENTION

In a first and preferred embodiment, the invention relates to a compound of the formula I,

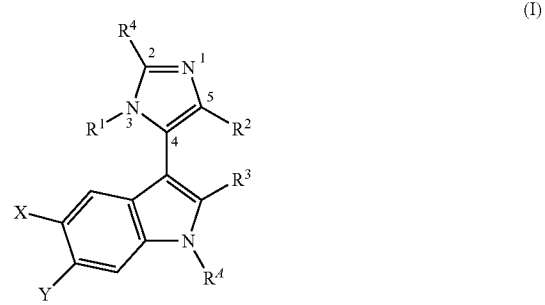

(I)

wherein
$R^1$ is unsubstituted or substituted alkyl, unsubstituted or substituted alkenyl or unsubstituted or substituted alkinyl, unsubstituted or substituted aryl or unsubstituted or substituted heterocyclyl;
$R^2$ is unsubstituted or substituted alkyl, unsubstituted or substituted alkenyl, unsubstituted or substituted alkinyl, unsubstituted or substituted aryl or unsubstituted or substituted heterocyclyl;
$R^3$ is hydrogen, halogen, unsubstituted or substituted alkyl, unsubstituted or substituted alkenyl, unsubstituted or substituted alkinyl, unsubstituted or substituted aryl, carboxy, cyano, esterified carboxy, unsubstituted or substituted heterocyclyl-carbonyl (heterocyclyl-C(=O)—), unsubstituted or substituted carbamoyl or unsubstituted or substituted heterocyclyl;
$R^4$ is hydrogen, halogen, unsubstituted or substituted alkyl, unsubstituted or substituted alkenyl, unsubstituted or substituted alkinyl, unsubstituted or substituted aryl, carboxy, cyano, esterified carboxy, unsubstituted or substituted heterocyclyl-carbonyl (heterocyclyl-C(=O)—), unsubstituted or substituted carbamoyl or unsubstituted or substituted heterocyclyl;
$R^A$ is hydrogen or unsubstituted or substituted alkyl or acyl;
X is hydrogen, $C_1$-$C_7$-alkyl, $C_1$-$C_7$-alkoxy, halo or cyano; and
Y is $C_1$-$C_7$-alkyl, halo-$C_1$-$C_7$-alkyl, $C_1$-$C_7$-alkoxy, halo or cyano;
and/or a tautomer, an N-oxide and/or a (preferably pharmaceutically acceptable) salt thereof.

The general terms used hereinbefore and hereinafter preferably have within the context of this disclosure the following meanings, unless otherwise indicated, where more general terms whereever used may, independently of each other, be replaced by more specific definitions or remain, thus defining more preferred embodiments of the invention:

The prefix "lower" or "$C_1$-$C_7$-" denotes a radical having up to and including a maximum of 7, especially up to and including a maximum of 4 carbon atoms, the radicals in question being either linear or branched with single or multiple branching.

For example, lower alkyl (or $C_1$-$C_7$-alkyl) is preferably alkyl with from and including 1 up to and including 7, preferably from and including 1 to and including 4, and is linear or branched; preferably, lower alkyl is butyl, such as n-butyl, sec-butyl, isobutyl, tert-butyl, propyl, such as n-propyl or isopropyl, ethyl or preferably methyl.

The numbering of the positions of substituents at the central imidazole given in the present disclosure (e.g. in the Examples) is usually (though in exceptional cases this may differ) provided in formula I above by the small numbers 1, 2, 3, 4 and 5.

Halogen, halogeno (or halo) is especially fluoro, chloro, bromo, or iodo, especially fluoro, chloro or bromo.

"Lower alkylsulfonyl" stands for alkyl-$S(=O)_2$— (sometimes also referred to as lower alkanesulfonyl).

Compounds of the formula I may have different isomeric forms. For example, any asymmetric carbon atom may be present in the (R)-, (S)- or (R,S)-configuration, preferably in the (R)- or (S)-configuration. Substituents at a double bond or especially a ring may be present in cis-(=Z—) or trans (=E-) form. The compounds may thus be present as mixtures of isomers or preferably as pure isomers, preferably as pure diastereomers or pure enantiomers.

Where the plural form (e.g. compounds, salts) is used, this includes the singular (e.g. a single compound, a single salt). "A compound" does not exclude that (e.g. in a pharmaceutical formulation) more than one compound of the formula I (or a salt thereof) is present, the "a" merely representing the indefinite article. "A" can thus preferably be read as "one or more", less preferably alternatively as "one".

In unsubstituted or substituted alkyl, alkyl (also in alkoxy or the like) preferably has up to 20, more preferably up to 12 carbon atoms, is linear or branched, and is more preferably $C_1$-$C_7$-alkyl, especially $C_1$-$C_4$-alkyl. Substituted alkyl is preferably $C_1$- to $C_{20}$-alkyl, more preferably $C_1$-$C_7$-alkyl, especially $C_1$-$C_4$-alkyl, that can be linear or branched one or more times (provided the number of carbon atoms allows this), e.g. methyl, ethyl, propyl, n-butyl, sec-butyl, isobutyl, tert-butyl, 2,2-dimethylpropyl, 1,2,2-trimethylpropyl, 1-ethyl-propyl, and that is substituted by one or more, preferably up to three, substituents independently selected from the group consisting of $C_1$-$C_7$-alkyl, hydroxyl-$C_1$-$C_7$-alkyl, $C_1$-$C_7$-alkoxy-$C_1$-$C_7$-alkyl, N-mono- or N,N-di-[$C_1$-$C_7$-alkyl, phenyl, $C_1$-$C_7$-alkanoyl and/or phenyl-$C_1$-$C_7$-alkyl]-amino-$C_1$-$C_7$-alkyl (such as methyl), halo-$C_1$-$C_7$-alkyl, such as trifluoromethyl, hydroxy, $C_1$-$C_7$-alkoxy, $C_1$-$C_7$-alkoxy-$C_1$-$C_7$-alkoxy, ($C_1$-$C_7$-alkoxy)-$C_1$-$C_7$-alkoxy-$C_1$-$C_7$-alkoxy, halo-$C_1$-$C_7$-alkoxy, halo, especially fluoro, chloro of bromo or iodo, phenoxy, naphthyloxy, phenyl- or naphthyl-$C_1$-$C_7$-alkoxy; amino-$C_1$-$C_7$-alkoxy, $C_1$-$C_7$-alkanoyloxy, benzoyloxy, naphthoyloxy, oxo (preferably not at the binding carbon), amino, amino-$C_1$-$C_7$-alkyl, especially aminomethyl, N-mono- or N,N-di-[$C_1$-$C_7$-alkyl, phenyl, $C_1$-$C_7$-alkanoyl and/or phenyl-$C_1$-$C_7$-alkyl]-amino, N-(heterocyclyl-$C_1$-$C_7$-alkyl)- or N-(heterocyclyl-$C_1$-$C_7$-alkyl-)-N—($C_1$-$C_7$-alkyl)-amino wherein heterocyclyl preferably has 3 to 14 ring atoms, respectively, of which 1 to 4 are a heteroatom independently selected from N,S,$S(=O)$, $S(=O)_2$ and O and is saturated, especially (pyrrolidinyl, pyrazolidinyl, imidazolidinyl, piperidinyl, azepanyl, piperazinyl, morpholinyl, thiomorpholinyl, S-oxothiomorpholinyl or S,S-dioxothiomorpholinyl)-$C_1$-$C_7$-alkylamino, formyl (CHO), carboxy, $C_1$-$C_7$-alkoxycarbonyl, phenyl- or naphthyl-$C_1$-$C_7$-alkoxycarbonyl, such as benzyloxycarbonyl; $C_2$-$C_7$-alkanoyl, such as acetyl, benzoyl, naphthoyl, carbamoyl, N-mono- or N,N-di-substituted carbamoyl wherein the substituents are selected from lower alkyl and hydroxy-lower alkyl; amidino, guanidino, ureido, mercapto, $C_1$-$C_7$-alkylthio, phenyl- or naphthylthio, phenyl- or naphthyl-$C_1$-$C_7$-alkylthio, $C_1$-$C_7$-alkyl-phenylthio, $C_1$-$C_7$-alkyl-naphthylthio, halogen-$C_1$-$C_7$-alkylmercapto, sulfonamido, benzolsulfonamido, azido, azido-$C_1$-$C_7$-alkyl, especially azidomethyl, nitro, cyano; unsubstituted or substituted heterocyclyl as described below, especially mono- to tricyclic heterocyclyl that is unsaturated or saturated, has 3 to 14 ring atoms of which 1 to 4 are a heteroatom independently selected from N,S, $S(=O)$, $S(=O)_2$ and O, preferably N, such as pyrrolidinyl, pyrazidinyl, imidazolidinyl, piperidinyl, azepanyl, piperazinyl, morpholinyl, thiomorpholinyl, S-oxothiomorpholinyl, S,S-dioxo-thiomorpholinyl, indolyl, isoindolyl, indazolyl, quinolinyl, isoquinolinyl, phthalazinyl, quinoxalinyl, quinazolinyl, cinnolinyl, benzofuranyl, isobenzofuranyl, chromenyl, isochromenyl, benzothiophenyl, thiochromenyl or isothiochromenyl, and is unsubstituted or substituted as described below for substituted heterocyclyl, especially with one or more, preferably up to three, moieties independently selected from the group consisting of $C_1$-$C_7$-alkyl, hydroxy-$C_1$-$C_7$-alkyl, hydroxy, oxo, amino or N-mono- or N,N-di-($C_1$-$C_7$-alkyl, {amino or mono- or di-($C_1$-$C_7$-alkyl)-amino}-$C_1$-$C_7$-alkyl, $C_1$-$C_7$-alkanoyl and/or $C_1$-$C_7$-alkoxycarbonyl)-amino, $C_1$-$C_7$-alkanoyl, $C_1$-$C_7$-alkylsulfonyl and saturated heterocyclyl with 3 to 14 ring atoms and 1 to 4 heteroatoms independently selected from N,S,$S(=O)$, $S(=O)_2$ and O, preferably N, e.g. pyrrolidinyl, pyrazolidinyl, imidazolidinyl, tetrahydrofuranyl, piperidinyl, azepanyl, piperazinyl, morpholinyl, thiomorpholinyl, S-oxothiomorpholinyl or S,S-dioxothiomorpholinyl, wherein said saturated heterocyclyl is unsubstituted or substituted by one or more, especially up to three, moieties independently selected from $C_1$-$C_7$-alkyl, hydroxy-$C_1$-$C_7$-alkyl, $C_1$-$C_7$-alkoxy-$C_1$-$C_7$-alkyl, oxo, amino, mono- or di-($C_1$-$C_7$-alkyl)-amino), $C_1$-$C_7$-alkanoyl and $C_1$-$C_7$-alkoxycarbonyl; unsubstituted or substituted aryl as defined below, especially naphthyl or phenyl each of which is unsubstituted or substituted by one or more, especially up to three, moieties independently selected from $C_1$-$C_7$-alkyl, halo-$C_1$-$C_7$-alkyl, hydroxyl, $C_1$-$C_7$-alkoxy, hydroxy-$C_1$-$C_7$-alkoxy, $C_1$-$C_7$-alkoxy-$C_1$-$C_7$-alkoxy, ($C_1$-$C_7$-alkoxy-$C_1$-$C_7$-alkoxy)-$C_1$-$C_7$-alkoxy, [amino, mono- or di-($C_1$-$C_7$-alkyl)amino]-$C_1$-$C_7$-alkoxy, amino, mono- or di-[($C_1$-$C_7$-alkyl, $C_1$-$C_7$alkanoyl, $C_1$-$C_7$-alkoxycarbonyl, hydroxy-$C_1$-$C_7$-alkyl, $C_1$-$C_7$-alkoxy-$C_1$-$C_7$alkyl and/or (amino, mono- or di-($C_1$-$C_7$-alkyl)-amino)-$C_1$-$C_7$-alkyl]-amino, halo and saturated heterocyclyl, saturated heterocyclyl-$C_1$-$C_7$-alkyl or saturated heterocyclyl-$C_1$-$C_7$-alkoxy wherein saturated heterocyclyl, respectively, preferably has 3 to 14 ring atoms of which 1 to 4 are a heteroatom independently selected from N,S,$S(=O)$, $S(=O)_2$ and O and is unsubstituted or substituted with one or more, especially up to three, moieties independently selected from $C_1$-$C_7$-alkyl, hydroxyl-$C_1$-$C_7$-alkyl, $C_1$-$C_7$-alkoxy-$C_1$-$C_7$-alkyl, hydroxyl, oxo, amino, mono- or di-($C_1$-$C_7$-alkyl)-amino), $C_1$-$C_7$-alkanoyl and $C_1$-$C_7$-alkoxycarbonyl, especially pyrrolidinyl, pyrazolidinyl, imidazolidinyl, piperidinyl, azepanyl, piperazinyl, [N—($C_1$-$C_7$-alkyl)-piperazinyl or pyrrolidinyl-, pyrazolidinyl-, imidazolidinyl-, piperidinyl-, azepanyl-, piperazinyl- or N—($C_1$-$C_7$-alkyl)piperazinyl]-$C_1$-$C_7$-alkyl or [N—($C_1$-$C_7$-alkyl)-piperazinyl or pyrrolidinyl-, pyrazolidinyl-, imidazolidinyl-, piperidinyl-, azepanyl-, piperazinyl- or N—($C_1$-$C_7$-alkyl)-piperazinyl]-$C_1$-$C_7$-alkoxy, nitro or cyano; and unsubstituted or substituted cycloalkyl, especially $C_3$-$C_8$-cycloalkyl, that is unsubstituted or substituted by one or more, especially up to three, substituents independently selected from the substituents for substituted aryl below;

where each phenyl or naphthyl (also in phenoxy or naphthoxy) mentioned above as substituent or part of a substituent of substituted alkyl (or also of substituted aryl, heterocyclyl etc. mentioned herein) is itself unsubstituted or substituted by one or more, e.g. up to three, preferably 1 or 2, substituents independently selected from $C_1$-$C_7$-alkyl, halo-$C_1$-$C_7$-alkyl, hydroxyl, $C_1$-$C_7$-alkoxy, $C_1$-$C_7$-alkoxy-$C_1$-$C_7$-alkoxy, halo, especially fluoro, chloro, bromo or iodo, halo-$C_1$-$C_7$-alkyl, such as trifluoromethyl, azido, amino, N-mono- or N,N-di-($C_1$-$C_7$-alkyl, phenyl, naphthyl, $C_1$-$C_7$-alkanoyl, phenyl-$C_1$-$C_7$-alkyl and/or naphthyl-$C_1$-$C_7$-alkyl)-amino, carboxy, $C_1$-$C_7$-alkoxycarbonyl carbamoyl, sulfamoyl, nitro and cyano.

Unsubstituted or substituted alkenyl is preferably $C_2$-$C_{20}$-alkenyl, more preferably $C_2$-$C_{12}$-alkenyl, yet more preferably $C_2$-$C_7$-alkenyl, which is linear or branched and includes one or more double bonds. The substituents are preferably one or more, especially up to three, substituents independently selected from those mentioned for substituted alkyl, preferably with the proviso that substituents with active hydrogen (such as amino or hydroxyl) can also be present in tautomeric form (as keto or imino compounds) or are excluded from the substituents where the stability is too low.

Unsubstituted or substituted alkynyl is preferably $C_2$-$C_{20}$-alkynyl, more preferably $C_3$-$C_{12}$-alkynyl, yet more preferably $C_3$-$C_7$-alkynyl, which is linear or branched and includes one or more triple bonds. The substituents are preferably one or more, especially up to three, substituents independently selected from those mentioned for substituted alkyl, preferably with the proviso that substituents with active hydrogen (such as amino or hydroxyl) can also be present in tautomeric form (as keto or imino compounds) or are excluded from the substituents where the stability is too low.

In unsubstituted or substituted aryl, aryl preferably has 6 to 18, more preferably 8 to 14 carbon atoms and is a mono-, di- or polycyclic (preferably up to tricyclic, more preferably up to bicyclic) unsaturated carbocyclic moiety with conjugated double bonds in the ring, especially phenyl, naphthyl, biphenylenyl, indacenyl, acenaphthylenyl, fluorenyl, phenalenyl, phenanthrenyl or anthracenyl. Naphthyl and preferably phenyl are especially preferred. Aryl is unsubstituted or (in the case of substituted aryl) substituted by one or more, e.g. one to three, substituents preferably independently selected from the group consisting of $C_1$-$C_7$-alkyl, such as methyl, ethyl, n-propyl, isopropyl, n-butyl, isobutyl, sec-butyl or tert-butyl; $C_2$-$C_7$-alkenyl; $C_2$-$C_7$-alkinyl; $C_6$-$C_{18}$-aryl-$C_1$-$C_7$-alkyl in which aryl is preferably phenyl, naphthyl, biphenylenyl, indacenyl, acenaphthylenyl, fluorenyl, phenalenyl, phenanthrenyl or anthracenyl and unsubstituted or substituted by $C_1$-$C_7$-alkyl, such as methyl or ethyl, by pyrrolidinyl, especially pyrrolidino, by pyrazolidinyl, especially pyrazolidino, by imidazolidinyl, especially imidazolidino, by piperidinyl, especially piperidin-1-yl, by azepanyl, especially azepan-1-yl, piperazinyl, especially piperazino, by amino, by N-mono- and/or N,N-di-$C_1$-$C_7$-alkylamino, by halo, by hydroxyl, by $C_1$-$C_7$-alkoxy, such as methoxy, and/or by halo-$C_1$-$C_7$-alkyl, such as trifluoromethyl; (pyrrolidinyl (especially pyrrolidino), pyridazinyl, especially pyridazolidino, imidazolidinyl (especially imidazolidino), piperidinyl (especially piperidino), azepanyl (especially azepan-1-yl), piperazinyl (especially piperazino), morpholino, thiomorpholino, pyridinyl, pyrimidinyl, pyrazinyl, pyridazinyl, oxazolyl or thiazolyl)-$C_1$-$C_7$-alkyl wherein pyrrolidinyl, pyrazolidinyl, imidazolidinyl, piperidinyl, azepanyl, piperazinyl, pyridinyl, pyrimidinyl, pyrazinyl, pyridazinyl, oxazolyl or thiazolyl are unsubstituted or substituted by $C_1$-$C_7$-alkyl, such as methyl or ethyl, by pyrrolidinyl, especially pyrrolidino, by pyrazolidinyl, especially pyrazolidino, by imidazolidinyl, especially imidazolidino, by azepanyl, especially azepan-1-yl, by piperazinyl, especially piperazino, by amino, by N-mono- and/or N,N-di-$C_1$-$C_7$-alkylamino, by halo, by $C_1$-$C_7$-alkoxy, such as methoxy, and/or by halo-$C_1$-$C_7$-alkyl, such as trifluoromethyl, for example pyrrolidino-$C_1$-$C_7$-alkyl, pyrazolidino-$C_1$-$C_7$-alkyl, imidazolidino-$C_1$-$C_7$-alkyl, piperidino-$C_1$-$C_7$-alkyl, azepan-1-yl-$C_1$-$C_7$-alkyl, piperazino-$C_1$-$C_7$-alkyl, morpholino-$C_1$-$C_7$-alkyl, thiomorpholino-$C_1$-$C_7$-alkyl, N—$C_1$-$C_7$-alkyl-piperazino-$C_1$-$C_7$-alkyl, or N-mono- or N,N-di-($C_1$-$C_7$-alkyl)-amino-substituted or unsubstituted pyrrolidino-$C_1$-$C_7$-alkyl; (pyrrolidinyl (especially pyrrolidino), pyrazolidinyl, (especially pyrazolidino), imidazolidinyl (especially imidazolidino) piperidinyl (especially piperidino), azepanyl (especially azepan-1-yl), piperazinyl (especially piperazino), pyridinyl, pyrimidinyl, pyrazinyl, pyridazinyl, oxazolyl or thiazolyl)-oxy-$C_1$-$C_7$-alkyl wherein pyrrolidinyl, pyrazolidinyl, imidazolidinyl, piperidinyl, azepanyl, piperazinyl, pyridinyl, pyrimidinyl, pyrazinyl, pyridazinyl, oxazolyl and thiazolyl are unsubstituted or substituted by $C_1$-$C_7$-alkyl, such as methyl or ethyl, by pyrrolidinyl, especially pyrrolidino, by pyrazolidinyl, especially pyrazolidino, by imidazolidinyl, especially imidazolidino, by piperidinyl, especially piperidino, by azepanyl, especially azepan-1-yl, by piperazinyl, especially piperazino, by amino, by N-mono- and/or N,N-di-$C_1$-$C_7$-alkylamino, by halo, by $C_1$-$C_7$-alkoxy, such as methoxy, and/or by halo-$C_1$-$C_7$-alkyl, such as trifluoromethyl; (pyrrolidin (especially pyrrolidino), pyrazolidinyl (especially pyrazolidino), imidazolidinyl (especially imidazolidino), piperidin (especially piperidino), azepan (especially azepan-1-l), piperazin (especially piperazino), pyridin, pyrimidin, pyrazin, pyridazin, oxazoly or thiazol)-carbonyl-$C_1$-$C_7$-alkyl wherein pyrrolidin, pyrazolidin, imidazolidin, piperidin, azepan, piperazin, pyridin, pyrimidin, pyridazin, oxazol or pyridazin are unsubstituted or substituted by $C_1$-$C_7$-alkyl, such as methyl or ethyl, by pyrrolidinyl, especially pyrrolidino, by pyrazolidinyl, especially pyrazolidino, by imidazolidinyl, especially imidazolidino, by azepanyl, especially azepan-1-yl, by piperazinyl, especially piperazino, by amino, by N-mono- and/or N,N-di-$C_1$-$C_7$-alkylamino, by halo, by $C_1$-$C_7$-alkoxy, such as methoxy, and/or by halo-$C_1$-$C_7$-alkyl, such as trifluoromethyl; halo-$C_1$-$C_7$-alkyl, such as trifluoromethyl; hydroxy-$C_1$-$C_7$-alkyl, such as hydroxymethyl; $C_1$-$C_7$-alkoxy-$C_1$-$C_7$-alkyl, such as 3-methoxypropyl or 2-methoxyethyl; $C_1$-$C_7$-alkoxy-$C_1$-$C_7$-alkoxy-$C_1$-$C_7$-alkyl; phenyloxy- or naphthyloxy-$C_1$-$C_7$-alkyl; phenyl-$C_1$-$C_7$-alkoxy- or naphthyl-$C_1$-$C_7$-alkoxy-$C_1$-$C_7$-alkyl; amino-$C_1$-$C_7$-alkyl, such as aminomethyl; N-mono- or N,N-di-($C_1$-$C_7$-alkyl, $C_1$-$C_7$-alkoxy-$C_1$-$C_7$-alkyl and/or (mono- or di-($C_1$-$C_7$-alkyl)-amino)-$C_1$-$C_7$-alkyl)-amino-$C_1$-$C_7$-alkyl; $C_1$-$C_7$-alkoxy-$C_1$-$C_7$-alkylamino-$C_1$-$C_7$-alkyl, mono- or di-[$C_6$-$C_{18}$-aryl-$C_1$-$C_7$-alkyl in which aryl is preferably phenyl, naphthyl, biphenylenyl, indacenyl, acenaphthylenyl, fluorenyl, phenalenyl, phenanthrenyl or anthracenyl and unsubstituted or substituted by $C_1$-$C_7$-alkyl, such as methyl or ethyl, by pyrrolidinyl, especially pyrrolidino, by pyrazolidinyl, especially pyrazolidino, by imidazolidinyl, especially imidazolidino, by piperidinyl, especially piperidino, by azepanyl, especially azepan-1-yl, by piperazinyl, especially piperazino, by amino, by N-mono- and/or N,N-di-$C_1$-$C_7$-alkylamino, by halo, by hydroxyl, by $C_1$-$C_7$-alkoxy, such as methoxy, and/or by halo-$C_1$-$C_7$-alkyl, such as trifluoromethyl; naphthyl- or phenyl-$C_1$-$C_7$-alkyl]-amino-$C_1$-$C_7$-alkyl; $C_1$-$C_7$-alkanoylamino-$C_1$-$C_7$-alkyl; carboxy-$C_1$-$C_7$-alkyl; benzoyl- or naphthoylamino-$C_1$-$C_7$-alkyl; $C_1$-$C_7$-alkylsulfonylamino-$C_1$-$C_7$-alkyl; phenyl- or naphthylsulfonylamino-$C_1$-$C_7$-alkyl wherein phenyl or naphthyl is unsubstituted or substituted by one or more, especially one to three, $C_1$-$C_7$-alkyl moieties; phenyl- or naphthyl-$C_1$-$C_7$-alkylsulfonylamino-$C_1$-$C_7$-alkyl; halo, especially fluoro (preferred), chloro (preferred) or bromo; hydroxy; $C_1$-$C_7$-alkoxy; $C_6$-$C_{18}$-aryl-$C_1$-$C_7$-alkoxy in which aryl is preferably phenyl, naphthyl, biphenylenyl, indacenyl, acenaphthylenyl, fluorenyl, phenalenyl, phenanthrenyl or anthraxcenyl and unsubstituted or substituted by $C_1$-$C_7$-alkyl, such as methyl or ethyl, by $C_1$-$C_7$-alkoxy, by pyrrolidinyl, especially pyrrolidino, by pyrazolidinyl, especially parazolidino, by imidazolidinyl, especially imidazolidino, piperidinyl, especially piperidino, by azepanyl, especially azepan-1-yl, by piperazinyl, especially piperazino, by amino, by N-mono- and/or N,N-di-$C_1$-$C_7$-alkylamino, by halo, by hydroxyl, by $C_1$-$C_7$-alkoxy, such as methoxy, and/or by halo-$C_1$-$C_7$-alkyl, such as trifluoromethyl; such as phenyl-$C_1$-$C_7$-alkoxy wherein phenyl is unsubstituted or substituted by $C_1$-$C_7$-alkoxy and/or halo; halo-$C_1$-$C_7$-alkoxy, such as trifluoromethoxy; hydroxy-$C_1$-$C_7$-alkoxy; $C_1$-$C_7$-alkoxy-$C_1$-$C_7$-alkoxy, such as such as 2-(methoxy)-ethoxy; ($C_1$-$C_7$-alkoxy-$C_1$-$C_7$-alkoxy)-$C_1$-$C_7$-alkoxy; [amino, mono- or di-($C_1$-$C_7$-alkyl)amino]-$C_1$-$C_7$-alkoxy, N—$C_1$-$C_7$-alkanoylamino-$C_1$-$C_7$-alkoxy; N-unsubstituted-, N-mono- or N,N-di-($C_1$-$C_7$-alkyl)carbamoyl-$C_1$-$C_7$-alkoxy; phenyl- or naphthyloxy; phenyl- or naphthyl-$C_1$-$C_7$-alkyloxy; (pyrrolidinyl (especially pyrrolidino), pyrazolidinyl (especially pyrazolidino), imidazolidinyl (especially imidazolidino), piperidinyl (especially piperidino), azepanyl (especially azepan-1-yl), piperazinyl (especially piperazino), pyridinyl, pyrimidinyl, pyrazinyl, pyridazinyl, oxazolyl or thiazolyl)-$C_1$-$C_7$-alkoxy wherein pyrrolidinyl, pyrazolidinyl, imidazolidinyl, piperidinyl, azepanyl, piperazinyl, pyridinyl, pyrimidinyl, pyrazinyl, pyridazinyl, oxazolyl and thiazolyl are unsubstituted or substituted by $C_1$-$C_7$-alkyl, such as methyl or ethyl, by pyrrolidinyl, especially pyrrolidino, by pyrazolidinyl, especially pyrazolidino, by imidazolidinyl, especially imidazolidino, by piperidinyl, especially piperidino, by azepanyl, especially azepan-1-yl, by piperazinyl, especially piperazino, by amino, by N-mono- and/or N,N-di-$C_1$-$C_7$-alkylamino, by halo, by $C_1$-$C_7$-alkoxy, such as methoxy, and/or by halo-$C_1$-$C_7$-alkyl, such as trifluoromethyl; (pyrrolidinyl (especially pyrrolidino), pyrazolidinyl (especially pyrazolidino), imidazolidinyl (especially imidazolidino), piperidinyl (especially piperidino), azepanyl (especially azepan-1-yl), piperazinyl (especially piperazino), pyridinyl, pyrimidinyl, pyrazinyl, pyridazinyl, oxazolyl or thiazolyl)-oxy-$C_1$-$C_7$-alkoxy wherein pyrrolidinyl, pyrazolidinyl, imidazolidinyl, piperidinyl, azepanyl, piperazinyl, pyridinyl, pyrimidinyl, pyrazinyl, pyridazinyl, oxazolyl and thiazolyl are unsubstituted or substituted by $C_1$-$C_7$-alkyl, such as methyl or ethyl, by pyrrolidinyl, especially pyrrolidino, by pyrazolidinyl, especially pyrazolidino, by imidazolidinyl, especially imidazolidino, by piperidinyl, especially piperidino, by azepanyl, especially azepan-1-yl, by piperazinyl, especially piperazino, by amino, by N-mono- and/or N,N-di-$C_1$-$C_7$-alkylamino, by halo, by $C_1$-$C_7$alkoxy, such as methoxy, and/or by halo-$C_1$-$C_7$-alkyl, such as trifluoromethyl; $C_1$-$C_7$-alkanoyloxy; benzoyl- or naphthoyloxy; $C_1$-$C_7$-alkylthio; halo-$C_1$-$C_7$-alkylthio, such as trifluoromethylthio; $C_1$-$C_7$-alkoxy-$C_1$-$C_7$-alkylthio; phenyl- or naphthylthio; phenyl- or naphthyl-$C_1$-$C_7$-alkylthio; $C_1$-$C_7$-alkanoylthio; benzoyl- or naphthaylthio; nitro; amino; mono- or di-[($C_1$-$C_7$-alkyl, $C_1$-$C_7$-alkanoyl, $C_1$-$C_7$-alkoxy-carbonyl, hydroxy-$C_1$-$C_7$-alkyl, $C_1$-$C_7$-alkoxy-$C_1$-$C_7$alkyl and/or (amino, mono- or di-($C_1$-$C_7$-alkyl)-amino)-$C_1$-$C_7$-alkyl]-amino; mono- or di-(naphthyl- or phenyl-$C_1$-$C_7$-alkyl)-amino; $C_1$-$C_7$-alkanoylamino; unsubstituted or amino-, N-mono- or N,N-di-(($C_1$-$C_7$-alkyl and/or phenyl- or naphthyl-$C_1$-$C_7$alkyl)amino-substituted benzoyl- or naphthoylamino; $C_1$-$C_7$-alkoxycarbonylamino; (phenyl or naphthyl)-$C_1$-$C_7$-alkoxycarbonylamino; $C_1$-$C_7$-alkylsulfonylamino (=$C_1$-$C_7$-alkyl-S(=O)$_2$—NH—); phenyl- or naphthylsulfonylamino wherein phenyl or naphthyl is unsubstituted or substituted by one or more, especially one to three, $C_1$-$C_7$-alkyl moieties; phenyl- or naphthyl-$C_1$-$C_7$-alkylsulfonylamino; $C_1$-$C_7$-alkanoyl; $C_1$-$C_7$-alkoxy-$C_1$-$C_7$-alkanoyl; carboxyl (—COOH); $C_1$-$C_7$-alkoxy-carbonyl; phenoxy- or naphthoxycarbonyl; phenyl- or naphthyl-$C_1$-$C_7$-alkoxycarbonyl; $C_1$-$C_{10}$— especially $C_1$-$C_4$-alkylendioxy, such as methylendioxy or 1,2-ethylendioxy; carbamoyl; N-mono- or N,N-di-[$C_1$-$C_7$-alkyl, naphthyl-$C_1$-$C_7$-alkyl, phenyl-$C_1$-$C_7$-alkyl, N'-mono- or N',N'-di-($C_1$-$C_7$alkyl) amino-$C_1$-$C_7$-alkyl, pyrrolidinyl (especially pyrrolidino)-$C_1$-$C_7$-alkyl, pyrazolidinyl (especially pyrazolidino)-$C_1$-$C_7$-alkyl, imidazolidinyl (especially imidazolidino)-$C_1$-$C_7$-alkyl, piperidinyl (especially piperidino)-$C_1$-$C_7$-alkyl, azepanyl (especially azepan-1-yl)-$C_1$-$C_7$-alkyl, piperazinyl- or N—($C_1$-$C_7$-alkyl)piperazinyl(especially piperazino or 4-$C_1$-$C_7$-alkylpiperazino)-$C_1$-$C_7$-alkyl, mono-$C_1$-$C_7$-alkoxy-$C_1$-$C_7$alkyl, (N'-mono- or N',N'-di-($C_1$-$C_7$-alkyl)-amino); phenyl, pyridinyl, oxazolyl or thiazolyl each of which is unsubstituted or substituted by $C_1$-$C_7$-alkoxy, by halo, especially fluoro, by pyrrolidino, by pyrazolidino, by imidazolidino, by piperidino, by azepan-1-yl, by piperazino, by hydroxyl-$C_1$-$C_7$-alkylamino, by hydroxyl-$C_1$-$C_7$-alkyl, by amino or by N-mono- or N,N-di-($C_1$-$C_7$-alkyl)amino; pyrrolidinyl, pyrazolidinyl, imidazolidinyl, piperidinyl, azepanyl, piperazinyl, pyrimidinyl, pyrazinyl and/or pyridazinyl]-amino-carbonyl, such as N-mono- or N,N-di-($C_1$-$C_7$-alkyl)-aminocarbonyl; N—$C_1$-$C_7$-alkoxy-$C_1$-$C_7$-alkylcarbamoyl; pyrrolidin-1-carbonyl; amino-N-pyrrolidin-1-carbonyl; N-mono- or N,N-di($C_1$-$C_7$-alkyl)amino-pyrrolidin-1-carbonyl; imidazolidin-1-carbonyl; piperidin-1-carbonylmorpholine-4-carbonyl; thiomorpholin-4-carbonyl; S-oxo-thiomorpholin-4-carbonyl; S,S-dioxothiomorpholin-4-carbonyl; piperazin-1-carbonyl; N—$C_1$-$C_7$-alkyl-piperazin-1-carbonyl; N—$C_1$-$C_7$-alkoxycarbonyl-piperazin-1-carbonyl; N-mono- or N,N-di-($C_1$-$C_7$-alkyl)-amino-substituted or unsubstituted pyrrolidinyl-$C_1$-$C_7$-alkyl; cyano; $C_1$-$C_7$-alkenylene or alkinylene; $C_1$-$C_7$-alkylsulfonyl; phenyl- or naphthylsulfonyl wherein phenyl or naphthyl is unsubstituted or substituted by one or more, especially one to three, $C_1$-$C_7$-alkyl moieties; phenyl- or naphthyl-$C_1$-$C_7$-alkylsulfonyl; sulfamoyl; N-mono or N,N-di-($C_1$-$C_7$-alkyl, phenyl-, naphthyl-, phenyl-$C_1$-$C_7$-alkyl-, pyrrolidinyl(especially pyrrolidino)-$C_1$-$C_7$-alkyl, pyrazolidinyl(especially pyrazolidino)-$C_1$-$C_7$-alkyl, imidazolyl(especially imidazol-1-yl) piperidinyl(especially piperidino)-$C_1$-$C_7$-alkyl, azepanyl(especially azepan-1-yl))-$C_1$-$C_7$-alkyl, piperazinyl(especially piperazino)-$C_1$-$C_7$-alkyl, N—$C_1$-$C_7$-alkylpiperazinyl(especially 4-$C_1$-$C_7$-alkylpiperazino)-$C_1$-$C_7$-alkyl, naphthyl-$C_1$-$C_7$-alkyl, phenyl which is unsubstituted or substituted by $C_1$-$C_7$-alkoxy, by halo, especially fluoro, by pyrrolidino, by pyrazolidino, by imidazolidino, by azepan-1-yl, by piperidino, by piperazino, by hydroxyl-$C_1$-$C_7$-alkyl or by N-mono- or N,N-di-($C_1$-$C_7$-alkyl)-$C_1$-$C_7$-alkyl; pyrrolidinyl (especially pyrrolidino), pyrazolidinyl (especially pyrazolidino), imidazolidinyl (especially imidazolidino), piperidinyl (especially piperidino), azepanyl (especially azepan-1-yl), piperazinyl (especially piperazino), pyridinyl, pyrimidinyl, pyrazinyl, pyridazinyl, oxazolyl and/or thiazolyl)-aminosulfonyl, pyrazolyl, pyrazolidinyl, pyrrolyl, pyrrolidinyl, pyridyl that is unsubstituted or substituted by $C_1$-$C_7$-alkoxy, such as methoxy, and/or by halo-$C_1$-$C_7$-alkyl, such as trifluoromethyl, pyrrolidinyl, pyrazolidinyl, imidazolidinyl, piperidinyl, azepanyl, piperazinyl, morpholinyl, thiomorpholinyl, S-oxo-thiomorpholinyl, S,S-dioxothiomorpholinyl, piperazinyl, N—$C_1$-$C_7$-alkyl-piperazinyl, 4-(phenyl-$C_1$-$C_7$-alkyl)-piperazinyl, 4-(naphthyl-$C_1$-$C_7$-alkyl)-piperazinyl, 4-($C_1$-$C_7$-alkoxycarbonyl)-piperazinyl, 4-(phenyl-$C_1$-$C_7$-alkoxycarbonyl)-piperazinyl, 4-(naphthyl-$C_1$-$C_7$-alkoxycarbonyl)-piperazinyl, oxazolyl and thiazolyl.

Especially preferably aryl is phenyl or naphthyl, each of which is unsubstituted or substituted as just described, more preferably by one or more, e.g. up to three, substituents independently selected from the group consisting of $C_1$-$C_7$-alkyl, hydroxy-$C_1$-$C_7$-alkyl, such as hydroxymethyl, $C_1$-$C_7$-alkoxy-$C_1$-$C_7$-alkyl, such as methoxymethyl, halo-alkyl, such as trifluoromethyl, amino- or mono- or di-($C_1$-$C_7$-alkyl)-amino-$C_1$-$C_7$-alkyl, halo, hydroxyl, $C_1$-$C_7$-alkoxy, amino, mono- or di-($C_1$-$C_7$-alkyl and/or hydroxyl-$C_1$-$C_7$-alkyl)-amino, $C_1$-$C_7$ benzoylamino, aminobenzoylamino, $C_1$-$C_7$-alkoxycarbonylamino, (phenyl or naphthyl)-$C_1$-$C_7$-alkoxycarbonylamino, carbamoyl, N-mono- or N,N-di-($C_1$-$C_7$-alkyl and/or phenyl-$C_1$-$C_7$-alkyl)amino-carbonyl, phenylaminocarbonyl, halophenyl-aminocarbonyl, N-[N'-mono- or N',N'-di-($C_1$-$C_7$alkyl)-amino-$C_1$-$C_7$-alkyl]-aminocarbonyl, sulfamoyl (=aminosulfonyl) or N-mono- or N,N-di-($C_1$-$C_7$-alkyl and/or phenyl-$C_1$-$C_7$-alkyl)aminosulfonyl.

Unsubstituted or substituted heterocyclyl is preferably a heterocyclic radical that is unsaturated (=carrying the highest possible number of conjugated double bonds in the ring(s), then also called heteroaryl), saturated (then also called saturated heterocyclyl herein) or partially saturated and is mono- or polycyclic, preferably a monocyclic or bicyclic or tricyclic ring; and has 3 to 24, more preferably 4 to 16, most preferably 4 to 10 ring atoms; wherein one or more, preferably one to four, especially one to three carbon ring atoms are replaced by a heteroatom independently selected from the group consisting of nitrogen, oxygen and sulfur (including S(=O) or S(=O)$_2$), the bonding ring preferably having 4 to 12, especially 5 to 7 ring atoms; which heterocyclic radical (heterocyclyl) is unsubstituted or substituted by one or more, especially 1 to 3, substituents independently selected from the group consisting of the substituents defined above for substituted alkyl or for substituted aryl; and where heterocyclyl is especially a heterocyclyl radical selected from the group consisting of oxiranyl, azirinyl, aziridinyl, 1,2-oxathiolanyl, thienyl (=thiophenyl), furanyl, tetrahydrofuryl, pyranyl, thiopyranyl, thianthrenyl, isobenzofuranyl, benzofuranyl, chromenyl, 2H-pyrrolyl, pyrrolyl, pyrrolinyl, pyrrolidinyl, imidazolyl, imidazolidinyl, benzimidazolyl, pyrazolyl, pyrazinyl, pyrazolidinyl, thiazolyl, isothiazolyl, dithiazolyl, oxazolyl, isoxazolyl, pyridyl, pyrazinyl, pyrimidinyl, piperidinyl, piperazinyl, pyridazinyl, morpholinyl, thiomorpholinyl, (S-oxo or S,S-dioxo)thiomorpholinyl, indolizinyl, azepanyl, diazepanyl, especially 1,4-diazepanyl, isoindolyl, 3H-indolyl, indolyl, isoindolyl, indazolyl, benzimidazolyl, cumaryl, triazolyl, tetrazolyl, purinyl, 4H-quinolizinyl, isoquinolyl, isoquinolyl, tetrahydroquinolyl, tetrahydroisoquinolyl, decahydroquinolyl, octahydroisoquinolyl, benzofuranyl, isobenzofuranyl, dibenzofuranyl, benzothiophenyl, dibenzothiophenyl, phthalazinyl, naphthyridinyl, quinoxalyl (=quinoxalinyl), quinazolinyl, quinazolinyl, cinnolinyl, pteridinyl, carbazolyl, beta-carbolinyl, phenanthridinyl, acridinyl, perimidinyl, phenanthrolinyl, furazanyl, phenazinyl, phenothiazinyl, phenoxazinyl, chromenyl, isochromenyl, chromanyl, benzo[1,3]dioxol-5-yl, 2,3-dihydro-benzo[1,4]dioxin-6-yl, thiochromenyl and isothiochromenyl, each of these radicals being unsubstituted or substituted by one or more, preferably up to three, substituents selected from those mentioned above for substituted alkyl and for aryl and from oxo, especially substituents independently selected from the group consisting of $C_1$-$C_7$-alkyl, hydroxy-$C_1$-$C_7$-alkyl, hydroxy, $C_1$-$C_7$-alkoxy, hydroxy-$C_1$-$C_7$-alkoxy, $C_1$-$C_7$-alkoxy-$C_1$-$C_7$-alkoxy, ($C_1$-$C_7$-alkoxy-$C_1$-$C_7$-alkoxy)-$C_1$-$C_7$-alkoxy, (amino-mono- or di-($C_1$-$C_7$-alkyl)-amino)-$C_1$-$C_7$-alkoxy, oxo, amino, N-mono- or N,N-di($C_1$-$C_7$-alkyl, {amino or mono- or di-($C_1$-$C_7$-alkyl)-amino}-$C_1$-$C_7$-alkyl, $C_1$-$C_7$-alkanoyl and/or $C_1$-$C_7$-alkoxycarbonyl)-amino, $C_1$-$C_7$-alkanoyl, $C_1$-$C_7$-alkylsulfonyl and saturated heterocyclyl with 3 to 14 ring atoms and 1 to 4 heteroatoms independently selected from N,S,S(=O), S(=O)$_2$ and O, preferably N, e.g. pyrrolidinyl, imidazolidinyl, piperidinyl, piperazinyl, morpholinyl, thiomorpholinyl, S-oxo-thiomorpholinyl or S,S-dioxothiomorpholinyl, wherein said saturated heterocyclyl is unsubstituted or substituted by one or more, especially up to three, moieties independently selected from $C_1$-$C_7$-alkyl, hydroxy-$C_1$-$C_7$-alkyl $C_1$-$C_7$-alkoxy-$C_1$-$C_7$-alkyl, oxo, amino and mono- or di-($C_1$-$C_7$-alkyl)-amino).

Unsubstituted or substituted cycloalkyl is preferably $C_3$-$C_8$-cycloalkyl, and is unsubstituted or substituted by one or more, especially up to three, substitutents independently selected from the substituents for substituted aryl above.

Carboxy is —COOH.

Esterified carboxy is preferably unsubstituted or substituted alkyloxy-carbonyl (=alkyl-O—C(=O)—), unsubstituted or substituted aryloxy-carbonyl (=aryloxy-C(=O)—), unsubstituted or substituted cycloalkyloxy-carbonyl (=cycloalkyl-O—C(=O)—) or unsubstituted or substituted heterocyclyloxy-carbonyl (=heterocyclyl-O—C(=O)—), wherein alkyl, aryl, cycloalkyl and heterocyclyl and their substituted forms are as defined above. More preferably, esterified carboxy is $C_1$-$C_7$-alkoxycarbonyl or $C_8$-$C_{14}$-aryl-$C_1$-$C_7$-alkoxy-carbonyl.

In unsubstituted or substituted heterocyclyl-carbonyl (heterocyclyl-C(=O)—)—), heterocyclyl is preferably a moiety chosen from heterocyclyl as defined above and is unsubstituted or substituted by one or more, especially up to three, substituents independently selected from those for substituted alkyl and substituted aryl and from oxo, especially from the group consisting of $C_1$-$C_7$-alkyl, hydroxy-$C_1$-$C_7$-alkyl, hydroxy, $C_1$-$C_7$-alkoxy, hydroxy-$C_1$-$C_7$-alkoxy, $C_1$-$C_7$-alkoxy-$C_1$-$C_7$-alkoxy, ($C_1$-$C_7$-alkoxy-$C_1$-$C_7$-alkoxy)-$C_1$-$C_7$-alkoxy, (amino-mono- or di-($C_1$-$C_7$alkyl)-amino)-$C_1$-$C_7$-alkoxy, oxo, amino, N-mono- or N,N-di-($C_1$-$C_7$-alkyl, {amino or mono- or di-($C_1$-$C_7$-alkyl)-amino}-$C_1$-$C_7$-alkyl, $C_1$-$C_7$-alkanoyl and/or $C_1$-$C_7$-alkoxycarbonyl)-amino, $C_1$-$C_7$-alkanoyl, $C_1$-$C_7$-alkylsulfonyl and saturated heterocyclyl with 3 to 14 ring atoms and 1 to 4 heteroatoms independently selected from N,S,S(=O), S(=O)$_2$ and O, preferably N, e.g. pyrrolidinyl, imidazolidinyl, piperidinyl, piperazinyl, morpholinyl, thiomorpholinyl, S-oxothiomorpholinyl or S,S-dioxothiomorpholinyl, wherein said saturated heterocyclyl is unsubstituted or substituted by one or more, especially up to three, moieties independently selected from $C_1$-$C_7$-alkyl, hydroxy-$C_1$-$C_7$-alkyl $C_1$-$C_7$-alkoxy-$C_1$-$C_7$-alkyl, oxo, amino and mono- or di-($C_1$-$C_7$-alkyl)-amino). Preferably heterocyclyl in heterocyclyl-carbonyl is unsaturated or preferably saturated, has 3 to 14 ring atoms of which 1 to 4 are a heteroatom independently selected from N,S,S(=O), S(=O)$_2$ and O, preferably N, and is more preferably selected from the group consisting of pyrrolidinyl, piperidinyl, piperazinyl, morpholinyl, thiomorpholinyl, S-oxo-thiomorpholinyl or S,S-dioxothiomorpholinyl, and is unsubstituted or substituted as described above for substituted aryl, substituted alkyl and from oxo, most especially from the substituents mentioned as preferred after "especially" in the preceding sentence.

In unsubstituted or substituted carbamoyl (=unsubstituted or N-substituted carbamoyl), the (N—) substituents (at the nitrogen of the carbamoyl group —C(=O)—NH$_2$) are preferably selected from one or two (meaning that one or two of the hydrogen atoms at the nitrogen are replaced) substituents independently selected from unsubstituted or substituted $C_1$-$C_7$-alkyl (as defined above), unsubstituted or substituted aryl (as defined above), unsubstituted or substituted cycloalkyl (as defined above) and from unsubstituted or substituted heterocyclyl (as defined above), where preferably either only one carbamoyl N-substituent is present or one N-substituent is $C_1$-$C_7$-alkyl, the other is selected from the group of substituents just mentioned. More preferably, substituted carbamoyl is N-mono- or N,N-di[$C_1$-$C_7$-alkyl, hydroxy-$C_1$-$C_7$-alkyl, $C_1$-$C_7$-alkoxy-$C_1$-$C_7$-alkyl, amino-$C_1$-$C_7$-alkyl, mono- or di-($C_1$-$C_7$-alkyl)-amino-$C_1$-$C_7$-alkyl, $C_6$-$C_{14}$-aryl wherein aryl is unsubstituted or substituted by one or more, especially up to three, moieties independently selected from the group consisting of $C_1$-$C_7$-alkyl, $C_1$-$C_7$-alkoxy, saturated heterocyclyl with 3 to 14 ring atoms and 1 to 4 heteroatoms independently selected from N,S,S(=O), S(=O)$_2$ and O, preferably N, e.g. pyrrolidinyl, imidazolidinyl, piperidinyl, piperazinyl, azepanyl, morpholinyl, thiomorpholinyl, S-oxo-thiomorpholinyl or S,S-dioxothiomorpholinyl, wherein said saturated heterocyclyl is unsubstituted or substituted with one or more, especially up to three, moieties independently selected from $C_1$-$C_7$-alkyl, hydroxy-$C_1$-$C_7$-alkyl, hydroxy, oxo and $C_1$-$C_7$-alkoxycarbonyl, $C_6$-$C_{14}$-aryl-$C_1$-$C_7$-alkyl, and saturated heterocyclyl or (saturated heterocyclyl)-$C_1$-$C_7$-alkyl wherein saturated heterocyclyl in both cases has 3 to 14 ring atoms and 1 to 4 heteroatoms independently selected from N,S,S(=O), S(=O)$_2$ and O, preferably N, e.g. pyrrolidinyl, imidazolidinyl, piperidinyl, piperazinyl, azepanyl, morpholinyl, thiomorpholinyl, S-oxo-thiomorpholinyl, S,S-dioxothiomorpholinyl, indolyl or isoindolyl or (pyrrolidinyl, imidazolidinyl, piperidinyl, piperazinyl, azepanyl, morpholinyl, thiomorpholinyl, S-oxo-thiomorpholinyl, S,S-dioxothiomorpholinyl, indolyl or isoindolyl)-$C_1$-$C_7$-alkyl, wherein said saturated heterocyclyl is unsubstituted or substituted with one or more, especially up to three, moieties independently selected from $C_1$-$C_7$-alkyl, hydroxy-$C_1$-$C_7$-alkyl, $C_1$-$C_7$-alkoxy-$C_1$-$C_7$-alkyl, oxo, $C_1$-$C_7$-alkanoyl and $C_1$-$C_7$-alkoxycarbonyl]-carbamoyl.

In the case of $R^4$ unsubstituted or substituted alkyl, halo and unsubstituted or substituted heterocyclyl are preferably as defined above; more preferably, $R_4$ is $C_1$-$C_7$-alkyl, halo, especially chloro or bromo, pyrrolyl, imidazolyl, pyridyl or pyrazinyl.

In the case of $R^4$, unsubstituted or substituted alkyl is preferably as defined above, more preferably it is $C_1$-$C_7$-alkyl, In the case of Y, $C_1$-$C_7$-alkyl, halo or cyano is preferred, more preferably methyl, fluoro, chloro, bromo or cyano; especially chloro or bromo.

Acyl is preferably unsubstituted or substituted aryl-carbonyl (=aryl-CO—; =aroyl) or sulfonyl (=aryl-S(O)$_2$—), unsubstituted or substituted heterocyclylcarbonyl or -sulfonyl, unsubstituted or substituted cycloalkylcarbonyl or -sulfonyl, formyl or unsubstituted or substituted alkylcarbonyl or -sulfonyl, unsubstituted or substituted alkyloxycarbonyl or -oxysulfonyl, unsubstituted or substituted aryl-oxycarbonyl or -oxysulfonyl, unsubstituted or substituted heterocyclyloxycarbonyl or -oxysulfonyl, unsubstituted or substituted cycloalkyloxycarbonyl or -oxysulfonyl or N-mono- or N,N-di-(unsubstituted or substituted aryl, unsubstituted or substituted heterocyclyl, unsubstituted or substituted cycloalkyl or unsubstituted or substituted alkyl)-aminocarbonyl; wherein unsubstituted or substituted aryl, unsubstituted or substituted heterocyclyl, unsubstituted or substituted cycloalkyl and unsubstituted or substituted alkyl are preferably as described above. Preferred is $C_1$-$C_7$alkanoyl, such as acetyl, unsubstituted or mono-, di- or tri-(halo and/or $C_1$-$C_7$-alkyl)-substituted benzoyl or naphthoyl, $C_3$-$C_8$-cycloalkylcarbonyl, pyrrolidincarbonyl, especially pyrrolidinocarbonyl, pyrazolidincarbonyl, imidazolidincarbonyl, piperidincarbonyl, piperazincarbonyl, 4-$C_1$-$C_7$-alkyl-piperazin-1-yl, $C_1$-$C_7$-alkylsulfonyl, such as methylsulfonyl (=methanesulfonyl), (phenyl- or naphthyl)-$C_1$-$C_7$alkylsulfonyl, such as phenylmethansulfonyl, or (unsubstituted, or [$C_1$-$C_7$-alkyl-, phenyl-, halo-lower alkyl-, halo, oxo-$C_1$-$C_7$-alkyl-$C_1$-$C_7$alkyloxy-, phenyl-$C_1$-$C_7$-alkoxy-, halo-$C_1$-$C_7$-alkyloxy-, phenoxy-, $C_1$-$C_7$-alkanoylamino-, cyano-, $C_1$-$C_7$-alkanoyl- and/or $C_1$-$C_7$-alkylsulfonyl-]substituted) (phenyl or naphthyl)-sulfonyl, such as phenylsulfonyl (=benzenesulfonyl), naphthalene-1-sulfonyl, naphthalene-2-sulfonyl or toluene-4-sulfonyl, carbamoyl, N-mono- or N,N-di-($C_1$-$C_7$-alkyl, (unsubstituted or halo-substituted) phenyl or naphthyl, phenyl-$C_1$-$C_7$-alkyl, naphthyl-$C_1$-$C_7$-alkyl or $C_3$-$C_8$-cycloalkyl)-aminocarbonyl, such as N-ethyl-carbamoyl, or ($C_1$-$C_7$-alkyl, phenyl, naphthyl, phenyl-$C_1$-$C_7$-alkyl and/or napthyl-$C_1$-$C_7$-alkyl)-oxycarbonyl, e.g. $C_1$-$C_7$-alkoxy-carbonyl, such as methoxycarbonyl. Preferred is $C_1$-$C_7$-alkanoyl, $C_1$-$C_7$alkoxycarbonyl or ($C_6$-$C_{14}$-aryl, such as phenyl or naphthyl)-$C_1$-$C_7$-alkoxycarbonyl.

Wherever a compound or compounds of the formula I are mentioned, this is further also intended to include N-oxides of such compounds and/or tautomers thereof.

The term "and/or an N-oxide thereof, a tautomer thereof and/or a (preferably pharmaceutically acceptable) salt thereof" especially means that a compound of the formula I may be present as such or in mixture with its N-oxide, as tautomer (e.g. due to keto-enol, lactamlactim, amide-imidic acid or enamine-imine tautomerism) or in (e.g. equivalency reaction caused) mixture with its tautomer, or as a salt of the compound of the formula I and/or any of these forms or mixtures of two or more of such forms.

Compounds of the formula I can also be modified by appending appropriate functionalities to enhance selective biological properties. Modifications of this kind are known in the art and include those that increase penetration into a given biological system (e.g. blood, lymphatic system, central nervous system, testis), increase bioavailability, increase solubility to allow parenteral administration (e.g. injection, infusion), alter metabolism and/or alter the rate of secretion. Examples of this type of modifications include but are not limited to esterification, e.g. with polyethylene glycols, derivatisation with pivaloyloxy or fatty acid substituents, conversion to carbamates, hydroxylation of aromatic rings and heteroatom substitution in aromatic rings. Whereever compounds of the formula I, and/or N-oxides, tautomers and/or (preferably pharmaceutically acceptable) salts thereof are mentioned, this comprises such modified formulae, while preferably the molecules of the formula I, their N-oxides, their tautomers and/or their salts are meant.

In view of the close relationship between the novel compounds of the formula I in free form and those in the form of their salts, including those salts that can be used as intermediates, for example in the purification or identification of the novel compounds, any reference to the compounds or a compound of the formula I hereinbefore and hereinafter is to be understood as referring to the compound in free form and/or also to one or more salts thereof, as appropriate and expedient, as well as to one or more solvates, e.g. hydrates.

Salts are formed, for example, as acid addition salts, preferably with organic or inorganic acids, from compounds of formula I with a basic nitrogen atom, especially the pharmaceutically acceptable salts. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, octanoic acid, decanoic acid, dodecanoic acid, glycolic acid, lactic acid, fumaric acid, succinic acid, malonic acid, adipic acid, pimelic acid, suberic acid, azelaic acid, malic acid, tartaric acid, citric acid, amino acids, such as glutamic acid or aspartic acid, maleic acid, hydroxymaleic acid, methylmaleic acid, cyclohexanecarboxylic acid, adamantanecarboxylic acid, benzoic acid, salicylic acid, 4-aminosalicylic acid, phthalic acid, phenylacetic acid, mandelic acid, cinnamic acid, methane- or ethane-sulfonic acid, 2-hydroxyethanesulfonic acid, ethane-1,2-disulfonic acid, benzenesulfonic acid, 4-toluenesulfonic acid, 2-naphthalenesulfonic acid, 1,5-naphthalene-disulfonic acid, 2- or 3-methylbenzenesulfonic acid, methylsulfuric acid, ethylsulfuric acid, dodecylsulfuric acid, N-cyclohexylsulfamic acid, N-methyl-, N-ethyl- or N-propyl-sulfamic acid, or other organic protonic acids, such as ascorbic acid.

For isolation or purification purposes it is also possible to use pharmaceutically unacceptable salts, for example picrates or perchlorates. For therapeutic use, only pharmaceutically acceptable salts or free compounds are employed (where applicable in the form of pharmaceutical preparations), and these are therefore preferred.

p53 refers to the human protein itself as described by Matlashewski et al. in EMBO J. 3, 3257-62 (1984) (named also p53 wild type herein) or to any variant (e.g. a mutant, fragment or isoform due to deletion, insertion and/or exchange of one or more, e.g. one to 200, of the amino acids) thereof that is still capable to retain preferably at least 1%, more preferably at least 5%, yet more preferably at least 10%, 20%, 30%, 40%, 50% or more than 50% of the p53 activity in growth suppression, e.g. in the growth suppression assay described in Pietenpol et al., Proc. Nat. Acad. Sci. USA 91, 1998-2002 (1994) and, if compared with the corresponding sequence of p53 wild type, shows at least 20%, more preferably at least 25% identity with the full sequence, e.g. at least 90% identity with a partial sequence thereof.

As already indicated above, MDM2 (especially when mentioned as MDM2 or variants thereof) generally refers to all genes and/or proteins encoded thereof with the names MDM2, Mdm2, HDM2, Hdm2, or a variant thereof. MDM4 (especially when mentioned as MDM4 or variants thereof) refers to all genes and/or proteins encoded thereof with the names MDM4, Mdm4, HDM4, Hdm4, MDMX, MdmX, HDMX, HdmX, or a variant thereof.

MDM2 specifically relates to MDM2 as described in EMBO J. 10, 1565-9, Fakharzadeh et al., 1991, a variant thereof refers to a variant thereof which still binds to p53 in the assay system described below (e.g. an isoform, fragment, mutant or oncogene due to deletion, insertion and/or exchange of one or more, e.g. one to 430, of the amino acids), corresponding to the full length proteins as originally described, preferably at least with 0.5%, more preferably at least with 5%, 10%, 20%, 30%, 40% or especially 50% or more of the affinity of MDM2 to p53, and have at least 20%, more preferably at least 25%, sequence identity to MDM2 or to HDM2 as originally described or as mentioned below specifically. Where not mentioned otherwise, MDM2 generally relates to MDM2, Mdm2, HDM2 or Hdm2, or variants thereof, respectively, as just defined.

MDM4 specifically relates to MDM4 as described in Genomics 43, 34-42, Shvarts et al., 1997, a variant thereof refers to a variant thereof which still binds to p53 in the assay system described below (e.g. an isoform, fragment, mutant or oncogene due to deletion, insertion and/or exchange of one or more, e.g. one to 430, of the amino acids), corresponding to the full length proteins as originally described, preferably at least with 0.5%, more preferably at least with 5%, 10%, 20%, 30%, 40% or especially 50% or more of the affinity of MDM4 to p53, and have at least 20%, more preferably at least 25%, sequence identity to MDM4, to MDMX, to HDM4 or to HDM2 as originally described or as mentioned below specifically. Where not mentioned otherwise, MDM4 generally relates to MDM4, Mdm4, HDM4, Hdm4, MDMX, MdmX, HDMX or HdmX, or variants thereof, respectively, as just defined.

The percentage of sequence identity, often also termed homology, between a protein and a variant thereof is preferably determined by a computer program commonly employed for this purpose, such as the Gap program (Wisconsin Sequence Analysis Package, Version 8 for Unix, Genetics Computer Group, University Reseach Park, Madison Wis., USA, which uses the algorithm of Smith and Waterman (Adv. Appl. Math. 2: 482-489 (1981), especially using an affine gap search with a gap open penalty of 12 and a gap extension penalty of 1.

"Variants thereof" where mentioned means one or more variant(s).

A proto-oncogene is a normal gene that can become an oncogene, either after mutation or increased expression. Proto-oncogenes code for proteins that help to regulate cell growth and differentiation. Proto-oncogenes are often involved in signal transduction and execution of mitogenic signals, usually through their protein products. Upon activation, a protooncogene (or its product) becomes a tumor inducing agent, an oncogene.

Quite unexpectedly, it has now been found that the compounds of formula I have advantageous pharmacological properties and disturb the binding interaction (also referred to herein as p53/MDM2 and p53/MDM4 interaction or as p53/MDM2 interaction solely) between p53 on the one side and MDM2 and/or MDM4 or (especially oncogenic) variants thereof which still are capable of binding to p53, on the other side.

The efficacy of the compounds of formula I and salts thereof as modulators affecting the interaction between can be demonstrated as shown in WO 98/01467 (which especially regarding the assays is included herein by reference) or preferably follows:

Fluorescence Polarisation Assay

The inhibition of p53-Hdm2 interaction is measured by fluorescence polarization. Fluorescence polarization measures the rotational movement of molecules in a homogeneous suspension. For this assay, Hdm2 protein (amino acids 2-185) is combined with a Cy5-labelled p53-derived peptide optimised for Hdm2 binding (*J. Med. Chem.* 2000, 43, 3205-3208). Upon excitation of the Cy5 fluorescent ligand with linearly polarized light, the peptide rotates faster and emits light which is perpendicularly polarized. If the peptide is bound by Hdm2, rotation will slow down and the perpendicular component will decrease. Disruption of the formation of the peptide-Hdm2 complex due to an inhibitor molecule binding to the p53 binding site of Hdm2 results in faster rotation of the peptide. The ratiometric polarization assay readout is calculated from the parallel and perpendicular components of the fluorescence light with respect to the polarization of the excitation light.

The test is performed by combining 7 µl compounds diluted in dimethyl sulfoxide (DMSO) (10% final concentration) with 31.5 µl Hdm2(2-188) (final concentration 3 nM) in reaction buffer (PBS, 0.1% CHAPS, 1 mM DTT (dithiothreitol)). The solution is allowed to preincubate for 5 minutes at room temperature, followed by addition of 31.5 µl peptide in reaction buffer (final concentration 1 nM), and a further 5 minutes of incubation. A final volume of 20 µl (in triplicate) is distributed into small volume black 384-well plates (Greiner Bio-One GmbH, Frickenhausen, Germany). For measurement of samples, an Analyst AD multimode microplate reader (Molecular Devices Corporation, Sunnyvale, Calif., USA) with the following settings is used: Dichroic mirror 650 nm, Excitation 630 nm, Emission 695 nm. Raw values are expressed as percent of DMSO control, where background (reaction buffer with peptide but no Hdm2) is subtracted first from raw values. IC50 values are calculated by curve fitting using XLfit. If not specified, reagents were purchased from Sigma Chemical Co.

Compounds described in the present invention preferably display inhibition of p53-Hdm2 interaction at IC50s ranging from 0.0003 to 25 µM, preferably from 0.0003 to 10 µM.

Time Resolved Fluorescence Energy Transfer (TR-FRET) Assay

The inhibition of p53-Hdm4 interaction is measured by time resolved fluorescence energy transfer (TR-FRET). Fluorescence energy transfer (or Foerster resonance energy transfer) describes an energy transfer between donor and acceptor fluorescent molecules. For this assay, MDM4 protein (amino acids 2-185), tagged with a C-terminal Biotin moiety, is used in combination with a Europium labeled streptavidin (Perkin Elmer, Inc., Waltham, Mass., USA) serving as the donor fluorophore. The p53 derived, Cy5 labeled peptide Cy5-TFS-DLWKLL (p53 aa18-26) is the energy acceptor. Upon excitation of the donor molecule at 340 nm, binding interaction between MDM4 and the p53 peptide induces energy transfer and enhanced response at the acceptor emission wavelength at 665 nm. Disruption of the formation of the p53-MDM4 complex due to an inhibitor molecule binding to the p53 binding site of MDM4 results in increased donor emission at 615 nm. The ratiometric FRET assay readout is calculated from the raw data of the two distinct fluorescence signals measured in time resolved mode (countrate 665 nm/countrate 615 nm×1000).

The test is performed in white 1536w microtiterplates (Greiner Bio-One GmbH, Frickenhausen, Germany) in a total volume of 3.1 µl by combining 100 nl of compounds diluted in 90% DMSO/10% H$_2$O (3.2% final DMSO concentration) with 2 µl Europium labeled streptavidin (final concentration 2.5 nM) in reaction buffer (PBS, 125 mM NaCl, 0.001% Novexin (consists of carbohydrate polymers (Novexin polymers), designed to increase the solubility and stability of proteins; Novexin Ltd., Cambridgeshire, United Kingdom), Gelatin 0.01%, 0.2% Pluronic (block copolymer fromethylenoxide and propyleneoxide, BASF, Ludwigshafen, Germany), 1 mM DTT), followed by the addition of 0.5 µl MDM4-Bio diluted in assay buffer (final concentration 10 nM). Allow the solution to pre-incubate for 15 minutes at room temperature, followed by addition of 0.5 µl Cy5-p53 peptide in assay buffer (final concentration 20 nM). Incubate at room temperature for 10 minutes prior to reading the plate. For measurement of samples, an Analyst GT multimode microplate reader (Molecular Devices) with the following settings is used: Dichroic mirror 380 nm, Excitation 330 nm, Emission Donor 615 nm and Emission Acceptor 665 nm. IC50 values are calculated by curve fitting using XLfit. If not specified, reagents are purchased from Sigma Chemical Co, St. Louis, Mo., USA.

The present invention also relates to novel aspects of the above described assays.

Compounds described in the present invention preferably display inhibition of p53-Hdm4 interaction at IC50s of 0.005 to 100 µM, e.g. from 10 nM to 50 µM.

Inhibitions of p53-Hdm2 and p53-Hdm4 by representative compounds in the present invention are displayed in Table 5 hereinbelow.

Having regard to their inhibitory effect on p53/MDM2 and/or p53/MDM4 interaction, compounds of formula (I) in free or pharmaceutically acceptable salt form, are useful in the treatment of conditions which are mediated by the activity (including normal activity or especially overactivity) of MDM2 and/or MDM4, or variants thereof, respectively, as described, such as proliferative and/or inflammatory conditions, e.g. by activation of the P53/MDM2 interaction, and/or that are responsive (meaning especially in a therapeutically beneficial way) to inhibition of the p53/MDM2 interaction, most especially a disease or disorder as mentioned hereinbelow.

"Treatment" in accordance with the invention may be therapeutic, e.g. symptomatic, palliative and/or curative, and/or prophylactic. Preferred is the treatment of warm-blooded animals, especially humans.

Preferred is a compound of formula I for use or the use thereof in the treatment of a disease or disorder that responds to treatment with a compound of the formula I, especially selected from disease that is based on dysregulation of cell cycle or especially apoptosis: e.g. diseases involving the immune system, e.g. autoimmune diseases or immune diseases resulting due to transplantation (such as rheumatoid arthritis, graft-versus-host disease, systemic lupus erythematosus, Sjögren's syndrome, multiple sclerosis, Hashimoto's thyreoiditis, polymyositis), chronic inflammatory conditions, such as asthma, osteoarthritis, atherosclerosis, Morbus Crohn or inflammatory or allergic conditions of the skin, for example psoriasis, contact dermatitis, atopic dermatitis, alopecia greata, erythema multiforma, dermatitis herpetiformis, scleroderma, vitiligo, hypersensitivity angiitis, urticaria, bullous pemphigoid, pemphigus, epidermolysis bullosa acquisita, or other inflammatory or allergic conditions of the skin, hyperproliferative disorders, (e.g. Li-Fraumeni syndrome, cancer or tumor diseases, such as benign or malignant tumors, sarcomas, such as rhabdomyosarcoma, bone cancer, e.g. osteosarcomas, carcinoma of the brain, e.g. soft tissue brain tumor, kidney, liver, adrenal gland, bladder, breast, stomach, gastric tumors, ovaries, colon, rectum, prostate, pancreas, lung, vagina or thyroid, glioblastomas, multiple myeloma, gastrointestinal cancer, especially colon carcinoma or colorectal adenoma, a tumor of the neck and head, melanoma, prostate hyperplasia, a neoplasia, a neoplasia of epithelial character, a mammary carcinoma, a leukemia, such as B- or T-cell lymphomas adrenocortical carcinoma, including metastasis in other organs, respectively), viral infections (e.g. herpes, papilloma, HIV, viral hepatitis) or other diseases, for example those in which the p53/MDM2 and/or p53/MDM4 interaction is dysregulated and/or that are responsive to inhibition of the p53/MDM2 interaction and/or p53/MDM4.

The invention especially relates to the use of a compound of the formula I (or a pharmaceutical formulation comprising a compound of the formula I) in the treatment of one or more of the diseases mentioned above and below where the disease (s) respond or responds (in a beneficial way, e.g. by partial or complete removal of one or more of its symptoms up to complete cure or remission) to an inhibition of the p53/MDM2 interaction, especially where the involved MDM2 or MDM4 and/or variant shows (e.g. in the context of other regulatory mechanisms, due to overexpression, to mutation or the like) inadequately high or more higher than normal activity.

Whereever the term "use" or "used" or especially use is mentioned, this is intended to include a compound of the formula I for use in the prophylactic and/or therapeutic treatment of a disease of a warm-blooded animal, especially a human, preferably of one or more diseases mentioned above or below, a method of use or a method of treatment comprising administering a compound of the formula I to a person in need of such treatment in an effective amount for the prophylactic and/or therapeutic treatment of a disease as mentioned above and below, the preparation or a method for the preparation of a pharmaceutical formulation/preparation for use in the prophylactic and therapeutic treatment of a disease or disorder mentioned above and below, especially involving combining a compound of the formula I (as therapeutically active ingredient) with at least one pharmaceutically acceptable carrier material, preferably including making it ready for use in such treatment (e.g. adding an instruction insert (e.g. package leaflet or the like), formulation, appropriate preparation, adaptation for specific uses, customizing and the like), and/or the use of a compound of the formula I for such preparation, and/or all other prophylactic or therapeutic uses mentioned hereinbefore or below. The invention can also relate to the use of a compound of the formula I to induce cell cycle deceleration or preferably arrest and/or apoptosis in cells containing p53 or variants thereof that are still functional, for sensitizing cells to one or more additional pharmaceutically active agents, such as inducers of apoptosis and/or of cell cycle deceleration or arrest, and to chemoprotection of normal cells through the inductoin of cell cycle deceleration or arrest prior to treatment with one or more other chemotherapeutic agents, to the use in rendering normal cells resistant to chemotherapeutic agents and/or treatments, and/or the use in protecting cells from toxic side effects of chemotherapeutic agens or treatments, such as side effects resulting in mucositis, stomatitis, xerostomia, gastrointestinal disorders and/or alopecia.

All these aspects are preferred embodiments of the present invention.

There are also experiments that can demonstrate the anti-tumor activity of compounds of the formula (I) in vivo.

For example, female Harlan (Indianapolis, Ind., USA) athymic nu/nu mice with s.c. transplanted human osteosarcoma SJSA-1 tumors can be used to determine the anti-tumor activity of p53/MDM2 interaction inhibitors. On day 0, with the animals under peroral Forene® (1-chloro-2,2,2-trifluoro-ethyldifluormethylether, Abbot, Wiesbaden, Germany) narcosis, 3×106 cells are injected under the skin on the animals' left flank. When tumors reach a volume of 100 mm$^3$, the mice are divided at random into groups of 6-8 animals and treatment commences. The treatment is carried out for a 2-3 weeks period with peroral, intravenous or intra-peritoneal administration once daily (or less frequently) of a compound of formula (I) in a suitable vehicle at defined doses. The tumors are measured twice a week with a slide gauge and the volume of the tumors is calculated.

As an alternative to cell line SJSA-1, other cell lines may also be used in the same manner, for example,
the HCT116 colon carcinoma cell line (ATCC No. CCL-247);
the LNCaP clone FGC prostate carcinoma cell line (ATCC No. CRL-1740);
the RKO colon carcinoma cell line (ATCC No. CRL-2577);
the HT1080 fibrosarcoma cell line (ATCC No. CCL-121);
the A375 malignant melanoma cell line (ATCC No. CRL-1619),
the NCI-H460 large cell lung carcinoma cell line (ATCC No. HTB-177);

A compound of the formula (I) may also be used to advantage in combination with other anti-proliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibittors; mTOR inhibitors, such as RAD001; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; bisphosphonates; biological response modifiers; antiproliferative antibodies, such as HCD122; heparanase inhibitors; inhibitors of Ras oncogenic isoforms; telomerase inhibitors; proteasome inhibitors; compounds used in the treatment of hematologic malignancies, such as FLUDARABINE; compounds which target, decrease or inhibit the activity of Flt-3, such as PKC412; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics and AUY922; temozolomide (TEMODAL®); kinesin spindle protein inhibitors, such as SB715992 or SB743921 from GlaxoSmithKline, or pentamidine/chlorpromazine from CombinatoRx; PI3K inhibitors, such as BEZ235; RAF inhibitors, such as RAF265; MEK inhibitors such as ARRY142886 from Array PioPharma, AZD6244 from AstraZeneca, PD181461 from Pfizer, leucovorin, EDG binders, antileukemia compounds, ribonucleotide reductase inhibittors, S-adenosylmethionine decarboxylase inhibitors, antiproliferative antibodies or other chemotherapeutic compounds. Further, alternatively or in addition they may be used in combination with other tumor treatment approaches, including surgery, ionizing radiation, photodynamic therapy, implants, e.g. with corticosteroids, hormones, or they may be used as radiosensitizers. Also, in anti-inflammatory and/or antiproliferative treatment, combination with anti-inflammatory drugs is included. Combination is also possible with antihistamine drug substances, bronchodilatatory drugs, NSAID or antagonists of chemokine receptors.

The term "aromatase inhibitor" as used herein relates to a compound which inhibits the estrogen production, i.e. the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole. Exemestane can be administered, e.g., in the form as it is marketed, e.g. under the trademark AROMASIN. Formestane can be administered, e.g., in the form as it is marketed, e.g. under the trademark LENTARON. Fadrozole can be administered, e.g., in the form as it is marketed, e.g. under the trademark AFEMA. Anastrozole can be administered, e.g., in the form as it is marketed, e.g. under the trademark ARIMIDEX. Letrozole can be administered, e.g., in the form as it is marketed, e.g. under the trademark FEMARA or FEMAR. Aminoglutethimide can be administered, e.g., in the form as it is marketed, e.g. under the trademark ORIMETEN. A combination of the invention comprising a chemotherapeutic agent which is an aromatase inhibitor is particularly useful for the treatment of hormone receptor positive tumors, e.g. breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen can be administered, e.g., in the form as it is marketed, e.g. under the trademark NOLVADEX. Raloxifene hydrochloride can be administered, e.g., in the form as it is marketed, e.g. under the trademark EVISTA. Fulvestrant can be formulated as disclosed in U.S. Pat. No. 4,659,516 or it can be administered, e.g., in the form as it is marketed, e.g. under the trademark FASLODEX. A combination of the invention comprising a chemotherapeutic agent which is an antiestrogen is particularly useful for the treatment of estrogen receptor positive tumors, e.g. breast tumors.

The term "anti-androgen" as used herein relates to any substance which is capable of inhibiting the biological effects of androgenic hormones and includes, but is not limited to, bicalutamide (CASODEX), which can be formulated, e.g. as disclosed in U.S. Pat. No. 4,636,505.

The term "gonadorelin agonist" as used herein includes, but is not limited to abarelix, goserelin and goserelin acetate. Goserelin is disclosed in U.S. Pat. No. 4,100,274 and can be administered, e.g., in the form as it is marketed, e.g. under the trademark ZOLADEX. Abarelix can be formulated, e.g. as disclosed in U.S. Pat. No. 5,843,901.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148 (compound A1 in WO99/17804). Irinotecan can be administered, e.g. in the form as it is marketed, e.g. under the trademark CAMPTOSAR. Topotecan can be administered, e.g., in the form as it is marketed, e.g. under the trademark HYCAMTIN.

The term "topoisomerase II inhibitor" as used herein includes, but is not limited to the anthracyclines such as doxorubicin (including liposomal formulation, e.g. CAELYX), daunorubicin, epirubicin, idarubicin and nemorubicin, the anthraquinones mitoxantrone and losoxantrone, and the podophillotoxines etoposide and teniposide. Etoposide can be administered, e.g. in the form as it is marketed, e.g. under the trademark ETOPOPHOS. Teniposide can be administered, e.g. in the form as it is marketed, e.g. under the trademark VM 26-BRISTOL. Doxorubicin can be administered, e.g. in the form as it is marketed, e.g. under the trademark ADRIBLASTIN or ADRIAMYCIN. Epirubicin can be administered, e.g. in the form as it is marketed, e.g. under the trademark FARMORUBICIN. Idarubicin can be administered, e.g. in the form as it is marketed, e.g. under the trademark ZAVEDOS. Mitoxantrone can be administered, e.g. in the form as it is marketed, e.g. under the trademark NOVANTRON.

The term "microtubule active compound" relates to microtubule stabilizing, microtubule destabilizing compounds and microtublin polymerization inhibitors including, but not limited to taxanes, e.g. paclitaxel and docetaxel, vinca alkaloids, e.g., vinblastine, especially vinblastine sulfate, vincristine especially vincristine sulfate, and vinorelbine, discodermolides, cochicine and epothilones and derivatives thereof, e.g. epothilone B or D or derivatives thereof. Paclitaxel may be administered e.g. in the form as it is marketed, e.g. TAXOL. Docetaxel can be administered, e.g., in the form as it is marketed, e.g. under the trademark TAXOTERE. Vinblastine sulfate can be administered, e.g., in the form as it is marketed, e.g. under the trademark VINBLASTIN R.P. Vincristine sulfate can be administered, e.g., in the form as it is marketed, e.g. under the trademark FARMISTIN. Discodermolide can be obtained, e.g., as disclosed in U.S. Pat. No. 5,010,099. Also included are Epothilone derivatives which are disclosed in WO 98/10121, U.S. Pat. No. 6,194,181, WO 98/25929, WO 98/08849, WO 99/43653, WO 98/22461 and WO 00/31247. Especially preferred are Epothilone A and/or B.

The term "alkylating compound" as used herein includes, but is not limited to, cyclophosphamide, ifosfamide, melphalan or nitrosourea (BCNU or Gliadel). Cyclophosphamide can be administered, e.g., in the form as it is marketed, e.g. under the trademark CYCLOSTIN. Ifosfamide can be administered, e.g., in the form as it is marketed, e.g. under the trademark HOLOXAN.

The term "histone deacetylase inhibitors" or "HDAC inhibitors" relates to compounds which inhibit the histone deacetylase and which possess antiproliferative activity. This includes compounds such as LDH589 disclosed in WO 02/22577, especially N-hydroxy-3-[4-[[(2-hydroxyethyl)[2-(1H-indol-3-yl)ethyl]-amino]methyl]phenyl]-2E-2-propenamide, N-hydroxy-3-[4-[[[2-(2-methyl-1H-indol-3-yl)-ethyl]-amino]methyl]phenyl]-2E-2-propenamide and pharmaceutically acceptable salts thereof. It further especially includes Suberoylanilide hydroxamic acid (SAHA).

The term "antineoplastic antimetabolite" includes, but is not limited to, 5-Fluorouracil or 5-FU, capecitabine, gemcitabine, DNA demethylating compounds, such as 5-azacytidine and decitabine, methotrexate and edatrexate, and folic acid antagonists such as pemetrexed. Capecitabine can be administered, e.g., in the form as it is marketed, e.g. under the trademark XELODA. Gemcitabine can be administered, e.g., in the form as it is marketed, e.g. under the trademark GEMZAR.

The term "platin compound" as used herein includes, but is not limited to, carboplatin, cisplatin, cisplatinum and oxaliplatin. Carboplatin can be administered, e.g., in the form as it is marketed, e.g. under the trademark CARBOPLAT. Oxaliplatin can be administered, e.g., in the form as it is marketed, e.g. under the trademark ELOXATIN.

The term "compounds targeting/decreasing a protein or lipid kinase activity"; or a "protein or lipid phosphatase activity"; or "further anti-angiogenic compounds" as used herein includes, but is not limited to, protein tyrosine kinase and/or serine and/or threonine kinase inhibitors or lipid kinase inhibitors, e.g., a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, e.g. a N-phenyl-2-pyrimidine-amine derivative, e.g. imatinib, SU101, SU6668 and GFB-111;

b) compounds targeting, decreasing or inhibiting the activity of the fibroblast growth factor-receptors (FGFR);

c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, such as those compounds disclosed in WO 02/092599, or antibodies that target the extracellular domain of IGF-1 receptor or its growth factors;
d) compounds targeting, decreasing or inhibiting the activity of the Trk receptor tyrosine kinase family, or ephrin B4 inhibitors;
e) compounds targeting, decreasing or inhibiting the activity of the Axl receptor tyrosine kinase family;
f) compounds targeting, decreasing or inhibiting the activity of the Ret receptor tyrosine kinase;
g) compounds targeting, decreasing or inhibiting the activity of the Kit/SCFR receptor tyrosine kinase, i.e C-kit receptor tyrosine kinases—(part of the PDGFR family), such as compounds which target, decrease or inhibit the activity of the c-Kit receptor tyrosine kinase family, especially compounds which inhibit the c-Kit receptor, e.g. imatinib;
h) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, e.g. a N-phenyl-2-pyrimidine-amine derivative, e.g. imatinib or nilotinib (AMN107); PD180970; AG957; NSC 680410; PD173955 from ParkeDavis; or dasatinib (BMS-354825)
i) compounds targeting, decreasing or inhibiting the activity of members of the protein kinase C (PKC) and Raf family of serine/threonine kinases, members of the MEK, SRC, JAK, FAK, PDK1, PKB/Akt, and Ras/MAPK family members, and/or members of the cyclin-dependent kinase family (CDK) and are especially those staurosporine derivatives disclosed in U.S. Pat. No. 5,093,330, e.g. midostaurin; examples of further compounds include e.g. UCN-01, safingol, BAY 43-9006, Bryostatin 1, Perifosine; Ilmofosine; RO 318220 and RO 320432; GO 6976; Isis 3521; LY333531/LY379196; isochinoline compounds such as those disclosed in WO 00/09495; FTIs; BEZ235 (a P13K inhibitor) or AT7519 (CDK inhibitor);
j) compounds targeting, decreasing or inhibiting the activity of protein-tyrosine kinase inhibitors, such as compounds which target, decrease or inhibit the activity of protein-tyrosine kinase inhibitors include imatinib mesylate (GLEEVEC) or tyrphostin. A tyrphostin is preferably a low molecular weight (Mr<1500) compound, or a pharmaceutically acceptable salt thereof, especially a compound selected from the benzylidenemalonitrile class or the S-arylbenzenemalonirile or bisubstrate quinoline class of compounds, more especially any compound selected from the group consisting of Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin);
k) compounds targeting, decreasing or inhibiting the activity of the epidermal growth factor family of receptor tyrosine kinases (EGFR, ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, e.g. EGF receptor, ErbB2, ErbB3 and ErbB4 or bind to EGF or EGF related ligands, and are in particular those compounds, proteins or monoclonal antibodies generically and specifically disclosed in WO 97/02266, e.g. the compound of ex. 39, or in EP 0 564 409, WO 99/03854, EP 0520722, EP 0 566 226, EP 0 787 722, EP 0 837 063, U.S. Pat. No. 5,747,498, WO 98/10767, WO 97/30034, WO 97/49688, WO 97/38983 and, especially, WO 96/30347 (e.g. compound known as CP 358774), WO 96/33980 (e.g. compound ZD 1839) and WO 95/03283 (e.g. compound ZM105180); e.g. trastuzumab (Herceptin™) cetuximab (Erbitux™), Iressa, Tarceva, OSI-774, CI-1033, EKB-569, GW-2016, E1.1, E2.4, E2.5, E6.2, E6.4, E2.11, E6.3 or E7.6.3, and 7H-pyrrolo-[2,3-d]pyrimidine derivatives which are disclosed in WO 03/013541; and
l) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF.

Further anti-angiogenic compounds include compounds having another mechanism for their activity, e.g. unrelated to protein or lipid kinase inhibition e.g. thalidomide (THALOMID) and TNP-470.

Compounds which target, decrease or inhibit the activity of a protein or lipid phosphatase are e.g. inhibitors of phosphatase 1, phosphatase 2A, or CDC25, e.g. okadaic acid or a derivative thereof.

Compounds which induce cell differentiation processes are e.g. retinoic acid, α- γ- or δ-tocopherol or α- γ- or γ-tocotrienol.

The term cyclooxygenase inhibitor as used herein includes, but is not limited to, e.g. Cox-2 inhibitors, 5-alkyl substituted 2-arylaminophenylacetic acid and derivatives, such as celecoxib (CELEBREX), rofecoxib (VIOXX), etoricoxib, valdecoxib or a 5-alkyl-2-arylaminophenylacetic acid, e.g. 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. "Etridonic acid" can be administered, e.g., in the form as it is marketed, e.g. under the trademark DIDRONEL. "Clodronic acid" can be administered, e.g., in the form as it is marketed, e.g. under the trademark BONEFOS. "Tiludronic acid" can be administered, e.g., in the form as it is marketed, e.g. under the trademark SKELID. "Pamidronic acid" can be administered, e.g. in the form as it is marketed, e.g. under the trademark AREDIA™ "Alendronic acid" can be administered, e.g., in the form as it is marketed, e.g. under the trademark FOSAMAX. "Ibandronic acid" can be administered, e.g., in the form as it is marketed, e.g. under the trademark BONDRANAT. "Risedronic acid" can be administered, e.g., in the form as it is marketed, e.g. under the trademark ACTONEL. "Zoledronic acid" can be administered, e.g. in the form as it is marketed, e.g. under the trademark ZOMETA.

The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88.

The term "biological response modifier" as used herein refers to a lymphokine or interferons, e.g. interferon γ.

The term "inhibitor of Ras oncogenic isoforms", e.g. H-Ras, K-Ras, or N-Ras, as used herein refers to compounds which target, decrease or inhibit the oncogenic activity of Ras e.g. a "farnesyl transferase inhibitor" e.g. L-744832, DK8G557 or R115777 (Zarnestra).

The term "telomerase inhibitor" as used herein refers to compounds which target, decrease or inhibit the activity of telomerase. Compounds which target, decrease or inhibit the activity of telomerase are especially compounds which inhibit the telomerase receptor, e.g. telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase are e.g. bengamide or a derivative thereof.

The term "proteasome inhibitor" as used herein refers to compounds which target, decrease or inhibit the activity of the proteasome. Compounds which target, decrease or inhibit the activity of the proteasome include e.g. Bortezomid (Velcade™) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors e.g. compounds targeting, decreasing or inhibiting the activity of FMS-like tyrosine kinase receptors (Flt-3R); interferon, 1-b-D-arabinofuransylcytosine (ara-c) and bisulfan; and ALK inhibitors e.g. compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, e.g. PKC412, TK1258, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90 e.g., 17-allylamino, 17-demethoxygeldanamycin (17AAG), a geldanamycin derivative; other geldanamycin related compounds; radicicol and HDAC inhibitors. An example HSP90 inhibitor is AUY922.

The term "antiproliferative antibodies" as used herein includes, but is not limited to, trastuzumab (Herceptin™), Trastuzumab-DM1, erbitux, bevacizumab (Avastin™), rituximab) (Rituxan®, PRO64553 (anti-CD40), 2C4 Antibody and HCD122 antibody (anti-CD40). By antibodies is meant e.g. intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of formula (I) can be used in combination with standard leukemia therapies, especially in combination with therapies used for the treatment of AML. In particular, compounds of formula (I) can be administered in combination with, e.g., farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

The term "antileukemic compounds" includes, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate. Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065, in particular, N-hydroxy-3-[4-[[[2-(2-methyl-1H-indol-3-yl)-ethyl]-amino]-methyl]phenyl]-2E-2-propenamide, or a pharmaceutically acceptable salt thereof and N-hydroxy-3-[4-[(2-hydroxyethyl){2-(1H-indol-3-yl)ethyl)amino]methyl]phenyl}-2E-2-propenamide, or a pharmaceutically acceptable salt thereof, especially the lactate salt. Somatostatin receptor antagonists as used herein refers to compounds which target, treat or inhibit the somatostatin receptor such as octreotide, and SOM230 (pasireotide).

Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in *Principles and Practice of Oncology*, Devita et al., Eds., 4$^{th}$ Edition, Vol. 1, pp. 248-275 (1993).

The term "EDG binders" as used herein refers a class of immunosuppressants that modulates lymphocyte recirculation, such as FTY720.

The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives, such as PL-1, PL-2, PL-3, PL-4, PL-5, PL-6, PL-7 or PL-8 mentioned in Nandy et al., *Acta Oncologica*, Vol. 33, No. 8, pp. 953-961 (1994).

The term "S-adenosylmethionine decarboxylase inhibitors" as used herein includes, but is not limited to the compounds disclosed in U.S. Pat. No. 5,461,076.

Also included are in particular those compounds, proteins or monoclonal antibodies of VEGF disclosed in WO 98/35958, e.g. 1-(4-chloroanilino)-4-(4-pyridylmethyl)phthalazine or a pharmaceutically acceptable salt thereof, e.g. the succinate, or in WO 00/09495, WO 00/27820, WO 00/59509, WO 98/11223, WO 00/27819 and EP 0 769 947; those as described by Prewett et al, *Cancer Res*, Vol. 59, pp. 5209-5218 (1999); Yuan et al., *Proc Natl Acad Sci USA*, Vol. 93, pp. 14765-14770 (1996); Zhu et al., *Cancer Res*, Vol. 58, pp. 3209-3214 (1998); and Mordenti et al., *Toxicol Pathol*, Vol. 27, No. 1, pp. 14-21 (1999); in WO 00/37502 and WO 94/10202; ANGIOSTATIN, described by O'Reilly et al., *Cell*, Vol. 79, pp. 315-328 (1994); ENDOSTATIN, described by O'Reilly et al., *Cell*, Vol. 88, pp. 277-285 (1997); anthranilic acid amides; ZD4190; ZD6474; SU5416; SU6668; bevacizumab; or anti-VEGF antibodies or anti-VEGF receptor antibodies, e.g. rhuMAb and RHUFab, VEGF aptamer e.g. Macugon; FLT-4 inhibitors, FLT-3 inhibitors, VEGFR-2 IgG1 antibody, Angiozyme (RPI 4610) and Bevacizumab (Avastin™).

Photodynamic therapy as used herein refers to therapy which uses certain chemicals known as photosensitizing compounds to treat or prevent cancers. Examples of photodynamic therapy includes treatment with compounds, such as e.g. VISUDYNE and porfimer sodium.

Angiostatic steroids as used herein refers to compounds which block or inhibit angiogenesis, such as, e.g., anecortave, triamcinolone, hydrocortisone, 11-α-epihydrocotisol, cortexolone, 17α-hydroxyprogesterone, corticosterone, desoxycorticosterone, testosterone, estrone and dexamethasone.

Implants containing corticosteroids refers to compounds, such as e.g. fluocinolone, dexamethasone.

"Other chemotherapeutic compounds" include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The structure of the active compounds identified by code nos., generic or trade names may be taken from the actual edition of the standard compendium "The Merck Index" or from databases, e.g. Patents International (e.g. IMS World Publications).

None of the quotations of references made within the present disclosure is to be understood as an admission that the references cited are prior art that would negatively affect the patentability of the present invention.

PREFERRED EMBODIMENTS OF THE INVENTION

In the following preferred embodiments of the invention, more general terms may, individually or some or all, be replaced with more specific terms mentioned above or below to define more preferred embodiments of the invention.

A preferred embodiment of the invention relates to a compound of the formula I wherein $R^1$ is unsubstituted or substituted alkyl, unsubstituted or substituted alkenyl or unsubstituted or substituted alkinyl;

$R^2$ is unsubstituted or substituted aryl;

$R^3$ is hydrogen, unsubstituted or substituted alkyl, carboxy, cyano, esterified carboxy, unsubstituted or substituted heterocyclyl-carbonyl (heterocyclyl-C(=O)—), unsubstituted or substituted carbamoyl, unsubstituted or substituted heterocyclyl or cyano, $R^4$ is hydrogen, unsubstituted or substituted alkyl, halo or unsubstituted or substituted heterocyclyl, $R^4$ is hydrogen or unsubstituted or substituted alkyl or acyl;

X is hydrogen, $C_1$-$C_7$-alkyl, halo-$C_1$-$C_7$-alkyl, $C_1$-$C_7$-alkoxy, halo or cyano; and Y is $C_1$-$C_7$-alkyl, halo-$C_1$-$C_7$-alkyl, $C_1$-$C_7$-alkoxy, halo or cyano;

and/or a tautomer, an N-oxide and/or a salt thereof.

Preferred is especially a compound of the formula I wherein $R^1$ is $C_1$-$C_7$-alkyl that is linear or branched and is unsubstituted or substituted by one or more, especially up to three, moieties independently selected from the group consisting of $C_1$-$C_7$-alkyl, especially methyl, of hydroxyl, of hydroxyl-$C_1$-$C_7$-alkyl, especially hydroxymethyl, of $C_1$-$C_7$-alkoxy-$C_7$-$C_7$-alkyl, especially 2-methoxy-ethoxy or methoxyethoxy or ethoxymethoxy, of $C_6$-$C_{14}$-aryl, especially phenyl, wherein aryl is unsubstituted or substituted by one or more, especially up to three, moieties independently selected from the group consisting of $C_1$-$C_7$-alkyl, especially methyl, halo-$C_1$-$C_7$-alkyl, especially trifluoromethyl, hydroxyl, $C_1$-$C_7$-alkoxy, $C_1$-$C_7$-alkoxy-$C_1$-$C_7$-alkoxy, especially 2-methoxyethoxy or 3-methoxy-propoxy, [amino, mono- or di-($C_1$-$C_7$-alkyl)-amino]-$C_1$-$C_7$-alkoxy, amino, mono- or di-[$C_1$-$C_7$-alkyl, hydroxy-$C_1$-$C_7$-alkyl, $C_1$-$C_7$-alkoxy-$C_1$-$C_7$-alkyl, amino-$C_1$-$C_7$-alkyl, amino and/or mono- or di($C_1$-$C_7$-alkyl)-amino-$C_1$-$C_7$-alkyl]-amino, halo, especially fluoro, chloro or bromo, and saturated heterocyclyl-$C_1$-$C_7$-alkoxy wherein saturated heterocyclyl has 3 to 14 ring atoms of which 1 to 4 are a heteroatom independently selected from N,S,S(=O), S(=O)$_2$ and O and is unsubstituted or substituted with $C_1$-$C_7$-alkyl, especially pyrrolidinyl-, piperidinyl-, piperazinyl- or N—($C_1$-$C_7$-alkyl)-piperazinyl-$C_1$-$C_7$-alkoxy, and of mono- or bicyclic $C_3$-$C_{14}$-heterocyclyl with 3 to 14 ring atoms of which 1 to 4 are a heteroatom independently selected from N,S,S(=O), S(=O)$_2$ and O and is unsubstituted or substituted with $C_1$-$C_7$-alkyl, especially corresponding heteroaryl, more especially indolyl, isoindolyl, indazolyl, quinolinyl, isoquinolinyl, phthalazinyl, quinoxalinyl, quinazolinyl, cinnolinyl, benzofuranyl, isobenzofuranyl, chromenyl, isochromenyl, benzothiophenyl, thiochromenyl or isothiochromenyl, $R^2$ is $C_6$-$C_{14}$-aryl (especially phenyl) that is unsubstituted or substituted by one or more, especially up to three, moieties independently selected from the group consisting of $C_1$-$C_7$-alkyl-phenyl, especially methyl, hydroxyl, and halo, especially fluoro or chloro, $R^3$ is hydrogen or preferably $C_1$-$C_7$-alkyl that is unsubstituted by one or more, especially up to three, moieties independently selected from the group consisting of hydroxyl, amino and heterocyclyl-$C_1$-$C_7$-alkylamino wherein heterocyclyl has 3 to 14 ring atoms of which 1 to 4 are a heteroatom independently selected from N,S,S(=O), S(=O)$_2$ and O and is saturated, especially (morpholinyl, thiomorpholiny, S-oxothiomorpholinyl or S,S-dioxothiomorpholinyl)-$C_1$-$C_7$-alkylamino, cyano, carboxy, $C_1$-$C_7$-alkoxycarbonyl or $C_6$-$C_{14}$-aryl-$C_1$-$C_7$-alkoxycarbonyl;

heterocyclyl-carbonyl (heterocyclyl-C(=O)) wherein heterocyclyl is unsaturated or preferably saturated, has 3 to 14 ring atoms of which 1 to 4 are a heteroatom independently selected from N,S,S(=O), S(=O)$_2$ and O, preferably N, such as pyrrolidinyl, piperidinyl, piperazinyl, morpholinyl, thiomorpholinyl, S-oxothiomorpholinyl or S,S-dioxothiomorpholinyl, and is un-substituted or substituted with one or more, especially one to three, moieties independently selected from the group consisting of $C_1$-$C_7$-alkyl, hydroxy-$C_1$-$C_7$-alkyl, hydroxy, oxo, amino or N-mono- or N,N-di-($C_1$-$C_7$-alkyl, {amino or mono- or di-$C_1$-$C_7$-alkylamino}-$C_1$-$C_7$-alkyl, $C_1$-$C_7$-alkanoyl and/or $C_1$-$C_7$-alkoxycarbonyl)-amino, $C_1$-$C_7$-alkanoyl, $C_1$-$C_7$-alkylsulfonyl and saturated heterocyclyl with 3 to 14 ring atoms and 1 to 4 heteroatoms independently selected from N,S, S(=O), S(=O)$_2$ and O, preferably N, e.g. pyrrolidinyl, imidazolidinyl, piperidinyl, piperazinyl, morpholinyl, thiomorpholinyl, S-oxo-thiomorpholinyl or S,S-dioxothiomorpholinyl, wherein said saturated heterocyclyl is unsubstituted or substituted by one or more, especially up to three, moieties independently selected from $C_1$-$C_7$-alkyl, hydroxy-$C_1$-$C_7$-alkyl $C_1$-$C_7$-alkoxy-$C_1$-$C_7$-alkyl, oxo, amino and mono- or di-($C_1$-$C_7$-alkyl)-amino), carbamoyl, N-mono- or N,N-di-[$C_1$-$C_7$-alkyl, hydroxy-$C_1$-$C_7$-alkyl, $C_1$-$C_7$-alkoxy-$C_1$-$C_7$-alkyl, amino-$C_1$-$C_7$-alkyl, mono- or di-($C_1$-$C_7$-alkyl)-amino-$C_1$-$C_7$-alkyl, $C_6$-$C_{14}$-aryl wherein aryl is unsubstituted or substituted by one or more, especially up to three, moieties independently selected from the group consisting of $C_1$-$C_7$-alkyl, $C_1$-$C_7$-alkoxy, saturated heterocyclyl with 3 to 14 ring atoms and 1 to 4 heteroatoms independently selected from N,S, S(=O), S(=O)$_2$ and O, preferably N, e.g. pyrrolidinyl, imidazolidinyl, piperidinyl, piperazinyl, azepanyl, morpholinyl, thiomorpholinyl, S-oxo-thiomorpholinyl or S,S-dioxothiomorpholinyl, wherein said saturated heterocyclyl is unsubstituted or substituted with one or more, especially up to three, moieties independently selected from $C_1$-$C_7$-alkyl, hydroxy-$C_1$-$C_7$-alkyl, hydroxy, oxo and $C_1$-$C_7$-alkoxycarbonyl, $C_6$-$C_{14}$-aryl-$C_1$-$C_7$-alkyl, and saturated heterocyclyl or (saturated heterocyclyl)-$C_1$-$C_7$-alkyl wherein saturated heterocyclyl in both cases has 3 to 14 ring atoms and 1 to 4 heteroatoms independently selected from N,S,S(=O), S(=O)$_2$ and O, preferably N, e.g. pyrrolidinyl, imidazolidinyl, piperidinyl, piperazinyl, azepanyl, morpholinyl, thiomorpholinyl, S-oxo-thiomorpholinyl, S,S-dioxothiomorpholinyl, indolyl or isoindolyl or (pyrrolidinyl, imidazolidinyl, piperidinyl, piperazinyl, azepanyl, morpholinyl, thiomorpholinyl, S-oxo-thiomorpholinyl, S,S-dioxothiomorpholinyl, indolyl or isoindolyl)-$C_1$-$C_7$-alkyl, wherein said saturated heterocyclyl is unsubstituted or substituted with one or more, especially up to three, moieties independently selected from $C_1$-$C_7$-alkyl, hydroxy-$C_1$-$C_7$-alkyl, $C_1$-$C_7$-alkoxy-$C_1$-$C_7$-alkyl, oxo, $C_1$-$C_7$-alkanoyl and $C_1$-$C_7$alkoxycarbonyl]-carbamoyl, heteroaryl with 3 to 14 ring atoms and 1 to 5 ring heteroatoms independently selected from the group consisting of N,S, S(=O), S(=O)$_2$ and O, especially N, S and O, such as triazolyl or especially tetrazolyl, or cyano, $R^4$ is hydrogen, $C_1$-$C_7$-alkyl, halo or heteroaryl with 3 to 14 ring atoms and 1 to 5 heteroatoms independently selected from the group consisting of N,S,S(=O), S(=O)$_2$ and O, especially N, such as pyridyl, $R^4$ is hydrogen or $C_1$-$C_7$-alkyl, preferably hydrogen;

X is hydrogen, $C_1$-$C_7$-alkyl, halo or cyano, especially hydrogen or fluoro, and Y is $C_1$-$C_7$-alkyl, halo or cyano, especially methyl, fluoro, chloro, bromo or cyano, and/or a tautomer, an N-oxide and/or a pharmaceutically acceptable salt thereof.

Highly preferred is a compound of the formula I wherein $R^1$ is $C_1$-$C_7$-alkyl, especially 3,3-dimethylbutyl, $C_1$-$C_7$-alkylbenzyl, especially methyl-benzyl, more especially 4-methylbenzyl, (halo-$C_1$-$C_7$-alkyl)-benzyl, especially trifluoromethylbenzyl, more especially 4-trifluoromethylbenzyl, hydroxy-halo-benzyl, especially chloro-hydroxybenzyl, more especially 4-chloro-2-hydroxybenzyl, halobenzyl, especially bromobenzyl, more especially 4-bromobenzyl, chlorobenzyl, more especially 4-chlorobenzyl, fluorobenzyl, more especially 4-fluorobenzyl, dichlorobenzyl, more especially 3,4- or 2,4-dichlorobenzyl, chlorofluorobenzyl, more especially 4-chloro-3-fluorobenzyl, 3-chloro-4-fluorobenzyl or 4-chloro-2-fluorobenzyl, (R,S)- or preferably (R)- or (S)-1-(halo-phenyl)-1-($C_1$-$C_7$-alkyl or hydroxy)-$C_1$-$C_7$-alkyl, especially (R,S)- or preferably (R)- or (S)-1-(fluorophenyl, chlorophenyl or bromophenyl)-1-(methyl or hydroxy)-methyl, more especially (R,S)- or preferably (R)- or (S)-1-(4-fluorophenyl, 4-chlorophenyl or 4-bromophenyl)-1-(methyl or hydroxy)-methyl, (R,S)- or preferably (R)- or (S)-1-(halo-phenyl)-1-[(hydroxy or $C_1$-$C_7$-alkoxy)-$C_1$-$C_7$-alkyl]-$C_1$-$C_7$-alkyl, especially (R,S)- or preferably (R)- or (S)-1-(chlorophenyl)-1-(hydroxymethyl or methoxymethyl)-methyl, more especially (R,S)- or preferably (R)- or (S)-1-(4-chlorophenyl)-1-(hydroxymethyl or methoxymethyl)-methyl, $C_1$-$C_7$-alkyl-halo-benzyl, especially methyl-halo-benzyl, more especially 4-chloro-2-methyl-benzyl, hydroxy-halo-benzyl, especially hydroxy-chlorobenzyl, more especially 4-chloro-2-hydroxybenzyl, $C_1$-$C_7$-alkoxy-halo-benzyl, especially methoxy-chloro-benzyl, such as 4-chloro-2-methoxybenzyl, (hydroxy-$C_1$-$C_7$-alkoxy or $C_1$-$C_7$-alkoxy-$C_1$-$C_7$-alkoxy)-halo-benzyl, especially (2-hydroxyethoxy, 3-hydroxypropoxy or 2-methoxy-ethoxy)-chloro-benzyl, more especially 4-chloro-2-(2-hydroxyethoxy, 3-hydroxypropoxy or 2-methoxy-ethoxy)-benzyl, [amino, N-mono- or N,N-di-($C_1$-$C_7$-alkylamino)-$C_1$-$C_7$-alkoxy]-halo-benzyl, especially [2-(N,N-dimethylamino)-ethoxy]-chloro-benzyl, more especially 2-[2-(N,N-dimethylamino)-ethoxy]-4-chloro-benzyl, (hydroxy-$C_1$-$C_7$-alkyl-amino)-halo-benzyl, especially [(2-hydroxymethyl- or 3-hydroxypropyl)-amino]-chloro-benzyl, more especially 2-[(2-hydroxymethyl- or 3-hydroxypropyl)-amino]-4-chloro-benzyl, ($C_1$-$C_7$-alkoxy-$C_1$-$C_7$-alkyl-amino)-halo-benzyl, especially [(2-methoxymethyl- or 3-methoxypropyl)-amino]-chloro-benzyl, more especially 2-[(2-methoxymethyl- or 3-methoxypropyl)-amino]-4-chloro-benzyl, [{amino, N-mono- or N,N-di-($C_1$-$C_7$-alkyl)-amino}-$C_1$-$C_7$-alkylamino]-halo-benzyl, especially [(2-dimethylaminoethyl-amino]-chloro-benzyl, more especially 2-(2-dimethylaminoethyl-amino)-4-chloro-benzyl, (pyrrolidinyl-, piperidinyl-, piperazinyl- or N—($C_1$-$C_7$alkyl)-piperazinyl-$C_1$-$C_7$alkoxy)-halo-benzyl, especially (pyrrolidino-, piperidino-, piperazino- or 4-($C_1$-$C_7$-alkyl)-piperazin-1-yl-$C_1$-$C_7$-alkoxy)-halo-benzyl, more especially 4-chloro-2-[2-(pyrrolidino-, piperidino-, piperazino- or 4-($C_1$-$C_7$-alkyl)-piperazin-1-yl)-ethoxy]-benzyl, indolyl-$C_1$-$C_7$-alkyl, especially indolylmethyl, more especially indol-6-ylmethyl, benzofuranyl-$C_1$-$C_7$-alkyl, especially benzofuranylmethyl, more especially benzofuran-6-ylmethyl, or benzothiophenyl-$C_1$-$C_7$-alkyl, especially benzothiophenylmethyl, more especially benzothiophen-6-ylmethyl;

$R^2$ is phenyl, $C_1$-$C_7$-alkyl-phenyl, especially methylphenyl, more especially 2-methylphenyl, hydroxyphenyl, especially 3-hydroxyphenyl, or halophenyl, especially phenyl or fluoro-, chloro- or fluoro-chloro-phenyl, more especially phenyl, 2-fluoropheny, 3-fluorophenyl or 3-chloro-2-fluoro-phenyl, $R^3$ is hydrogen or preferably hydroxyl-$C_1$-$C_7$-alkyl, especially hydroxymethyl, amino-$C_1$-$C_7$-alkyl, especially 2-aminoethyl, (morpholinyl, thiomorpholiny, S-oxothiomorpholinyl or S,S-dioxothiomorpholinyl)-$C_1$-$C_7$-alkylamino-$C_1$-$C_7$-alkyl, especially N-(2-morpholinoethyl)-aminomethyl, cyano, carboxy, $C_1$-$C_7$alkoxycarbonyl, especially methoxycarbonyl or ethoxycarbonyl, azetidin-carbonyl, especially acetidin-1-ylcarbonyl, pyrrolidin-carbonyl, especially pyrrolidin-1-carbonyl, achiral or (R,S)- or preferably (R)- or (S)-[amino or N'-mono- or N',N'-di-($C_1$-$C_7$-alkyl and/or {amino or mono- or di-$C_1$-$C_7$-alkylamino}-$C_1$-$C_7$-alkyl)-amino]-pyrrolidin-carbonyl, especially (R,S)- or preferably (R)- or (S)-3-(dimethylamino)-pyrrolidin-1-carbonyl, (R,S)- or preferably (R)- or (S)-3-(diethylamino)-pyrrolidin-1-carbonyl, (R,S)- or preferably (R)- or (S)-3-[N-2-(dimethylamino)-ethyl-amino]-pyrrolidin-1-carbonyl, (R,S)- or preferably (R)—or (S)-3-[N-3-(dimethylamino)-propyl-amino]-pyrrolidin-1-carbonyl, (R,S)- or preferably (R)— or (S)-3-[N-2-(dimethylamino)-ethyl-N-methyl-amino]-pyrrolidin-1-carbonyl, or (R,S)- or preferably (R)- or (S)-3-[N-3-(dimethylamino)-propyl-N-methyl-amino]-pyrrolidin-1-carbonyl or (R,S)- , (R,S)- or preferably (R)- or (S)-pyrrolidinyl-pyrrolidin-carbonyl, especially (R,S)- or preferably (R)- or (S)-3-(pyrrolidin-1-yl)-pyrrolidincarbonyl, (R,S)- or preferably (R)- or (S)-[(amino, mono- or di-($C_1$-$C_7$-alkyl)-amino)-piperidinyl]-pyrrolidincarbonyl, especially (R,S)- or preferably (R)- or (S)-3-(4-dimethylamino-piperidin-1-yl)-pyrrolidin-1-carbonyl, (R,S)- or preferably (R)- or (S)-[hydroxy-$C_1$-$C_7$-alkyl, hydroxy, amino or mono- or di-($C_1$-$C_7$-alkyl, $C_1$-$C_7$-alkanoyl, $C_1$-$C_7$-alkoxycarbonyl)-amino]-pyrrolidin-carbonyl, especially (R,S)- or preferably (R)- or (S)-3-hydroxy-pyrrolidin-1-carbonyl, especially (R,S)- or preferably (R)- or (S)-3-hydroxymethyl-pyrrolidin-1-carbonyl, (R,S)- or preferably (R)- or (S)-3-amino-pyrrolidin-1-carbonyl, (R,S)- or preferably (R)- or (S)-3-ethylamino-pyrrolidin-1-carbonyl, (R,S)- or preferably (R)- or (S)-3-tert-butoxycarbonylamino-pyrrolidin-1-carbonyl, (R,S)- or preferably (R)- or (S)-3-(N-methyl-N-acetyl-amino)-pyrrolidin-1-carbonyl, (R,S)- or preferably (R)- or (S)-(piperazinyl, $C_1$-$C_7$-alkylpiperazinyl, (hydroxy-$C_1$-$C_7$-alkyl)-piperazinyl morpholinyl, thiomorpholinyl, S-oxo-thiomorpholinyl or S,S-dioxo-thiomorpholinyl)-pyrrolidin-carbonyl, especially (R,S)- or preferably (R)- or (S)-3-(4-methylpiperazino)-pyrrolidin-1-carbonyl, (R,S)- or preferably (R)- or (S)-3-(4-(2-hydroxyethyl)-piperazino)-pyrrolidin-1-carbonyl, (R,S)- or preferably (R)- or (S)-3-morpholino-pyrrolidin-1-carbonyl or (R,S)- or preferably (R)- or (S)-3-dioxothiomorpholino-pyrrolidin-1-carbonyl, piperidinyl-carbonyl, especially piperidin-1-carbonyl (piperidin-1-yl-C(=O)—), (hydroxy, hydroxy-$C_1$-$C_7$-alkyl, amino or mono- or di-($C_1$-$C_7$-alkyl)amino)-piperidin-carbonyl, especially 4-hydroxymethyl-piperidin-1-carbonyl or 4-dimethylamino-piperidin-1-carbonyl, oxoimidazolidinyl-piperidincarbonyl, especially 4-(2-oxo-imidazolidin-1-yl)-piperidin-1-carbonyl, (phenyl-oxoimidazolidinyl)-piperidin-carbonyl, especially 4-(3-phenyl-2-oxoimidazolidin-1-yl)-piperidin-1-carbonyl, pyrrolidinyl- or oxopyrrolidinyl-piperidincarbonyl, especially 4-(pyrrolidin-1-yl)piperidin-1-carbonyl or 4-(2-oxo-pyrrolidin-1-yl-)-piperidin-1-carbonyl, piperazinyl- or N—($C_1$-$C_7$-alkyl)-piperazinyl-piperidin-carbonyl, especially 4-(4-methyl-piperazin-1-yl)-piperidin-1-carbonyl, (morpholinyl, thiomorpholinyl, S-oxo-thiomorpholinyl or S,S-dioxo-thiomorpholinyl)piperidin-carbonyl, especially 4-morpholino-piperidin-1-carbonyl, (oxo-benzoimidazolidinyl)piperidin-carbonyl, especially (2-oxo-1,3-benzoimidazolidin-1-yl)-piperidin-carbonyl, piperazin-carbonyl, especially piperazin-1-carbonyl, ($C_1$-$C_7$-alkyl or hydroxyl-$C_1$-$C_7$-alkyl)piperazin-carbonyl, especially 4-methyl-, 4-(2-hydroxyethyl)- or 4-(3-hydroxypropyl)-piperazin-1-carbonyl, oxopiperazin-carbonyl, especially 2-oxo-piperazin-4-carbonyl, $C_1$-$C_7$-alkanoyl-piperazin-carbonyl, especially 1-acetyl-piperazin-4-carbonyl, $C_1$-$C_7$-alkylsulfonylpiperazin-carbonyl, especially 4-methanesulfonyl-piperazin-1-carbonyl, morpholin-carbonyl (morpholinyl-C(=O)—), especially morpholin-1-carbonyl, (thiomorpholin, S-oxothiomorpholin or S,S-dioxothiomorpholin)-carbonyl, especially S,S-dioxothiomorpholin-1-carbonyl, carbamoyl (synonymous: amino-carbonyl, —C(=O)—$NH_2$), N-mono- or N,N-di-($C_1$-$C_7$-alkyl)-carbamoyl, especially N-methyl-, N,N-dimethyl-, N-ethyl- or N-tert-butyl-carbamoyl, N-[(hydroxy- or $C_1$-$C_7$-alkoxy)-$C_1$-$C_7$-alkyl]-carbamoyl, especially N-(2-hydroxyethyl)carbamoyl, N-(3-hydroxypropyl)-carbamoyl, N-(2-methoxyethyl)-carbamoyl or N-(3-methoxypropyl)-carbamoyl, N-[(amino, mono- or di-($C_1$-$C_7$-alkyl)-amino)-$C_1$-$C_7$-alkyl]-carbamoyl, especially N-(2-amino-ethyl)-carbamoyl, N-(2-(methylamino)-ethyl-carbamoyl, 2-(N,N-di-(methyl)-amino)-ethyl-carbamoyl, 3-(N,N-di-(methyl)-amino)-propyl-carbamoyl, N-[2-(N,N-di-(methyl)-amino)-ethyl]-N-methyl-carbamoyl, N-[3-(N,N-di-(methyl)-amino)-propyl]-N-methyl-carbamoyl, 2-(N,N-di-(ethyl)-amino)-ethyl-carbamoyl, 3-(N,N-di-(ethyl)-amino)-propyl-carbamoyl, N-[2-(N,N-di-(ethyl)-amino)-ethyl]-N-methyl-carbamoyl, N-[3-(N,N-di-(ethyl)-amino)-propyl]-N-methyl-carbamoyl, N-phenyl-carbamoyl, N—($C_1$-$C_7$-alkoxy-phenyl)-carbamoyl, especially N-(methoxyphenyl)-carbamoyl, [(pyrrolidinyl, piperidinyl, piperazinyl or 1-($C_1$-$C_7$-alkyl)-piperazinyl)-phenyl]-carbamoyl, especially N-[3-(piperazin-4-yl or 1-methyl-piperazin-4-yl)-phenyl]-carbamoyl, N-(phenyl-$C_1$-$C_7$-alkyl)-carbamoyl, especially N-benzyl-carbamoyl, N-(oxoimidazolidinyl-$C_1$-$C_7$-alkyl)-carbamoyl, especially N-[2-oxoimidazol-1-yl)-ethyl]-carbamoyl, N-(pyrrolidinyl-$C_1$-$C_7$-alkyl)-carbamoyl, especially N-(pyrrolidinomethyl)-carbamoyl, N-(2-pyrrolidino-ethyl)-carbamoyl or N-(3-pyrrolidino-propyl)-carbamoyl, N-(oxopyrrolidinyl-$C_1$-$C_7$-alkyl)-carbamoyl, especially N-(2-oxo-pyrrolidinomethyl)-carbamoyl, N-[2-(2-oxopyrrolidino)-ethyl]-carbamoyl or N-[3-(2-oxopyrrolidino)-propyl]-carbamoyl, N-Piperidinyl-carbamoyl, especially N-piperidin-4-yl-carbamoyl, N—[($C_1$-$C_7$-alkyl)-piperidinyl]-carbamoyl, especially N-(1-methyl-piperidin-4-yl)-carbamoyl, N-[(hydroxyl-$C_1$-$C_7$-alkyl)piperidinyl]-carbamoyl, especially N-[1-(2-hydroxyethyl)-piperidin-4-yl]-carbamoyl, N—[N—($C_1$-$C_7$-alkoxycarbonyl)-piperidinyl]-carbamoyl, especially N-[1-(tert-butoxycarbonyl)-piperidin-4-yl]-carbamoyl, N-(piperidinyl-$C_1$-$C_7$-alkyl)-carbamoyl, especially N-(piperidin-1-yl-methyl)-, N-[2-(piperidin-1-yl-)-ethyl]- or N-[3-(piperidin-1-yl)-propyl]-carbamoyl, N-(azepan-$C_1$-$C_7$-alkyl)carbamoyl, especially N-(azepan-1-yl-methyl)-, N-[2-(piperidin-1-yl-)-ethyl]- or N-[3-(piperidin-1-yl)-propyl]-carbamoyl, N-(piperazinyl-$C_1$-$C_7$-alkyl)-carbamoyl, especially N-(piperazin-1-ylmethyl)-, N-[2-(piperazin-1-yl-)-ethyl]- or N-[3-(piperazin-1-yl)-propyl]-carbamoyl, N-(oxopiperazinyl-$C_1$-$C_7$-alkyl)-carbamoyl, especially N-[(2-oxo-piperazin-4-yl-)-methyl]-, N-[2-(2-oxopiperazin-4-yl-)-ethyl]- or N-[3-(2-oxo-piperazin-4-yl)-propyl]-carbamoyl, N—(($C_1$-$C_7$-alkyl)-piperazinyl-$C_1$-$C_7$-alkyl)-carbamoyl, especially N-[(1-methyl-piperazin-4-yl-)-methyl]-, N-[2-(1-methyl-piperazin-4-yl-)-ethyl]- or N-[3-(1-methyl-piperazin-1-yl)-propyl]-carbamoyl, N-(1-(hydroxyl-$C_1$-$C_7$-alkyl)-piperazinyl-$C_1$-$C_7$-alkyl)-carbamoyl, especially N-[(1-(2-hydroxyethyl)-piperazin-4-yl-)-methyl]-, N-[2-(1-(2-hydroxyethyl)-piperazin-4-yl)ethyl]- or N-[3-(1-(2-hydroxy-ethyl)-piperazin-1-yl)-propyl]-carbamoyl, N-(1-($C_1$-$C_7$-alkanoyl)-piperazinyl-$C_1$-$C_7$-alkyl)-carbamoyl, especially N-[(1-acetyl-piperazin-4-yl)methyl]-, N-[2-(1-acetyl-piperazin-4-yl-)-ethyl]- or N-[3-(1-acetyl-piperazin-1-yl)-propyl]-carbamoyl, N-(1-($C_1$-$C_7$-alkoxycarbonyl)-piperazinyl-$C_1$-$C_7$-alkyl)-carbamoyl, especially N-[(1-(tert-butoxycarbonyl)-piperazin-4-yl)-methyl]-, N-[2-(1-(tert-butoxycarbonyl)-piperazin-4-yl)-ethyl]- or N-[3-(1-(tert-butoxycarbonyl)-piperazin-1-yl)-propyl]-carbamoyl, N-[(morpholinyl, thiomorpholinyl, S-oxo-thiomorpholinyl or S,S-dioxo-thiomorpholinyl)-$C_1$-$C_7$-alkyl]-carbamoyl, especially N-morpholinomethyl-, N-(2-morpholinoethyl)-, N-(3-morpholinopropyl)-carbamoyl, N—(S,S-dioxothiomorpholino)-methyl-, N-[2-(S,S-dioxothiomorpholino)-ethyl]- or N-[3-(S,S-dioxothiomorpholino)-propyl]-carbamoyl, N-[dioxo-1H,3H-isoindolyl)-$C_1$-$C_7$-alkyl)-carbamoyl, especially N-(1,7-dioxo-1H, 7H-isoindolin-2-ylmethyl)-, N-[2-(1,7-dioxo-1H,7H-isoindolin-2-yl)-ethyl]- or N-[3-(1,7-dioxo-1H,7H-isoindolin-2-yl)-propyl]-carbamoyl, triazolyl or tetrazolyl, especially tetrazol-5-yl, or cyano, $R^4$ is hydrogen, $C_1$-$C_7$-alkyl, especially methyl, halo, especially bromo or chloro, or pyridyl, especially pyridin-3-, -4- or -2-yl, $R^{4}$ is hydrogen or $C_1$-$C_7$-alkyl, preferably hydrogen;

X is hydrogen, $C_1$-$C_7$-alkyl, halo or cyano, especially hydrogen or fluoro, and Y is $C_1$-$C_7$-alkyl, halo or cyano, especially methyl, fluoro, chloro, bromo or cyano, and/or a tautomer, an N-oxide and/or a pharmaceutically acceptable salt thereof.

Yet more highly preferred is a compound of the formula I wherein $R^1$ is halobenzyl, especially bromobenzyl, more especially 4-bromobenzyl, chlorobenzyl, more especially 4-chlorobenzyl, or fluorobenzyl, more especially 4-fluorobenzyl, $R^2$ is phenyl, $R^3$ is hydroxyl-$C_1$-$C_7$-alkyl, especially hydroxymethyl, carboxy, achiral or (R,S)- or preferably (R)- or (S)-[amino or N'-mono- or N',N'-di-($C_1$-$C_7$-alkyl and/or {amino or mono- or di-$C_1$-$C_7$-alkylamino}-$C_1$-$C_7$-alkyl)-amino]-pyrrolidin-carbonyl, especially (R,S)- or preferably (R)- or (S)-3-[N-2-(dimethylamino)-ethyl-N-methyl-amino]-pyrrolidin-1-carbonyl, amino or mono- or di-($C_1$-$C_7$-alkyl) amino-piperidin-carbonyl, especially 4-dimethylamino-piperidin-1-carbonyl, carbamoyl, N—$C_1$-$C_7$-alkylcarbamoyl, especially N-methyl- or N-ethylcarbamoyl, N—(($C_1$-$C_7$-alkyl)-piperazinyl-$C_1$-$C_7$-alkyl)-carbamoyl, especially N-[(1-methyl-piperazin-4-yl+methyl]-, N-[2-(1-methyl-piperazin-4-yl)-ethyl]- or N-[3-(1-methyl-piperazin-1-yl)-propyl]-carbamoyl, or N-[(morpholinyl or thiomorpholinyl)-$C_1$-$C_7$-alkyl]-carbamoyl, especially N-morpholinomethyl-, N-(2-morpholinoethyl)-, N-(3-morpholinopropyl)-carbamoyl, $R^4$ is hydrogen or $C_1$-$C_7$-alkyl, especially methyl, or halo, especially bromo or chloro, more preferably hydrogen, $R^{4}$ is hydrogen;

X is halo or fluoro, and

Y is halo or cyano, especially chloro or cyano;

and/or a tautomer, an N-oxide and/or a pharmaceutically acceptable salt thereof.

Very preferred are also embodiments of the invention represented in the claims which are therefore incorporated by reference herein.

The invention also preferably relates to a method of manufacture or the USE of any one or more of the compounds of the formula I, and/or tautomers thereof, N-oxides thereof and/or (preferably pharmaceutically acceptable) salts thereof mentioned to be preferred herein, as well as to a pharmaceutical composition comprising it.

The invention relates especially to a compound of the formula I selected from the group of compounds as mentioned below in the examples by their names or formulae, preferably the isomers shown as formulae, respectively, and/or a tautomer thereof, an N-oxide thereof and/or a pharmaceutically acceptable salt thereof, or its use according to the invention, as well as to a pharmaceutical composition comprising it.

Pharmaceutical Formulations, Uses and Methods

The above-mentioned compounds, which can be used in combination with a compound of the formula I, can be prepared and administered as described in the art, such as in the documents cited above.

By "combination", there is meant either a fixed combination in one dosage unit form, or a kit of parts for the combined administration where a compound of the formula I and a combination partner may be administered independently at the same time or separately within time intervals that especially allow that the combination partners show a cooperative, e.g. synergistic effect.

The invention also provides a pharmaceutical preparation, comprising a compound of formula I as defined herein, and/or an N-oxide or a tautomer thereof, and/or a pharmaceutically acceptable salt of such a compound, or a hydrate or solvate thereof (all referred to often as "a compound of the formula I" merely herein), and at least one pharmaceutically acceptable carrier.

A compound of formula I can be administered alone or in combination with one or more other therapeutic compounds, possible combination therapy taking the form of fixed combinations or the administration of a compound of the invention and one or more other therapeutic (including prophylactic) compounds being staggered or given independently of one another, or the combined administration of fixed combinations and one or more other therapeutic compounds. A compound of formula I can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

The dosage of the active ingredient depends upon a variety of factors including type, species, age, weight, sex and medical condition of the patient; the severity of the condition to be treated; the route of administration; the renal and hepatic function of the patient; and the particular compound employed. A physician, clinician or veterinarian of ordinary skill can readily determine and prescribe the effective amount of the drug required to prevent, counter or arrest the progress of the condition. Optimal precision in achieving concentration of drug within the range that yields efficacy requires a regimen based on the kinetics of the drug's availability to target sites. This involves a consideration of the distribution, equilibrium, and elimination of a drug.

The dose of a compound of the formula I or a pharmaceutically acceptable salt thereof to be administered to warm-blooded animals, for example humans of approximately 70 kg body weight, is preferably from approximately 3 mg to approximately 15 g, more preferably from approximately 10 mg to approximately 3 g, yet more preferably from approximately 50 mg to 1.5 g per person per day, undivided in 1 dose or divided preferably into 2 to 4, e.g. 2 or 3, single doses which may, for example, be of the same size. Usually, children receive half of the adult dose.

The compounds of the formula I may be administered by any conventional route, in particular parenterally, for example in the form of injectable solutions or suspensions, enterally, e.g. orally, for example in the form of tablets or capsules, topically, e.g. in the form of lotions, gels, ointments or creams, or in a nasal or a suppository form. Topical administration is e.g. to the skin. A further form of topical administration is to the eye. Pharmaceutical compositions comprising a compound of the invention in association with at least one pharmaceutical acceptable carrier or diluent may be manufactured in conventional manner by mixing with a pharmaceutically acceptable carrier or diluent.

The invention relates also to pharmaceutical compositions comprising an effective amount, especially an amount effective in the treatment of one of the above-mentioned disorders, of a compound of formula I and/or an N-oxide or a tautomer thereof, and/or a pharmaceutically acceptable salt thereof, together with one or more pharmaceutically acceptable carriers that are suitable for topical, enteral, for example oral or rectal, or parenteral administration and that may be inorganic or organic, solid or liquid. There can be used for oral administration especially tablets or gelatin capsules that comprise the active ingredient together with diluents, for example lactose, dextrose, mannitol, and/or glycerol, and/or lubricants and/or polyethylene glycol. Tablets may also comprise binders, for example magnesium aluminum silicate, starches, such as corn, wheat or rice starch, gelatin, methylcellulose, sodium carboxymethylcellulose and/or polyvinylpyrrolidone, and, if desired, disintegrators, for example starches, agar, alginic acid or a salt thereof, such as sodium alginate, and/or effervescent mixtures, or adsorbents, dyes, flavorings and sweeteners. It is also possible to use the pharmacologically active compounds of the present invention in the form of parenterally administrable compositions or in the form of infusion solutions. The pharmaceutical compositions may be sterilized and/or may comprise excipients, for example preservatives, stabilisers, wetting compounds and/or emulsifiers, solubilisers, salts for regulating the osmotic pressure and/or buffers. The present pharmaceutical compositions, which may, if desired, comprise other pharmacologically active substances are prepared in a manner known per se, for example by means of conventional mixing, granulating, confectionning, dissolving or lyophilising processes, and comprise approximately from 1% to 99%, especially from approximately 1% to approximately 20%, active ingredient(s).

Additionally, the present invention provides a compound of formula I, and/or an N-oxide or a tautomer thereof, and/or a pharmaceutically acceptable salt thereof, for use in a method for the treatment of the human or animal body, especially for the treatment of a disease mentioned herein, most especially in a patient requiring such treatment.

The present invention also relates to the use of a compound of formula I and/or an N-oxide or a tautomer thereof, and or a pharmaceutically acceptable salt of such a compound, for the preparation of a medicament for the treatment especially of a proliferative disease.

Furthermore, the invention relates to a method for the treatment of a proliferative disease which responds to an inhibition p53/MDM2 interaction, which comprises administering a compound of formula I, and/or an N-oxide or a tautomer thereof, and/or a pharmaceutically acceptable salt thereof, wherein the radicals and symbols have the meanings as defined above, to a warm-blooded animal requiring such treatment, especially in a quantity effective against said disease and/or capable of inhibiting the p53/MDM2 interaction in said warm-blooded animal.

Furthermore, the invention relates to a pharmaceutical composition for treatment of solid or liquid tumours in warm-blooded animals, including humans, comprising an antiproliferativly effective dose of a compound of the formula I as described above or a pharmaceutically acceptable salt of such a compound together with a pharmaceutical carrier.

Manufacturing Process:

The invention relates also to a process for the manufacture of a compound of the formula I, and/or an N-oxide thereof or a tautomer thereof, and/or a salt thereof.

Compounds of the formula I can be prepared according to or in analogy to methods that, in principle and with other educts, intermediates and final products, are known in the art, especially and according to the invention by a process comprising a) for the manufacture of a compound of the formula I wherein $R^4$ is hydrogen and $R^1$, $R^2$, $R^3$, $R^4$, X and Y are as defined for a compound of the formula I, reacting a formylindole derivative of the formula II

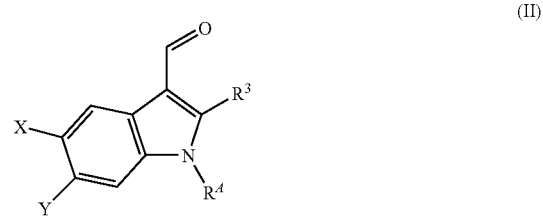

(II)

wherein $R^3$, $R^4$, X and Y are as defined for a compound of the formula I, with an amino compound of the formula III,

$R^1$—$NH_2$ (III)

wherein $R^1$ is as defined for a compound of the formula I in the presence of a tosyl-methyl isocyanide of the formula IV,

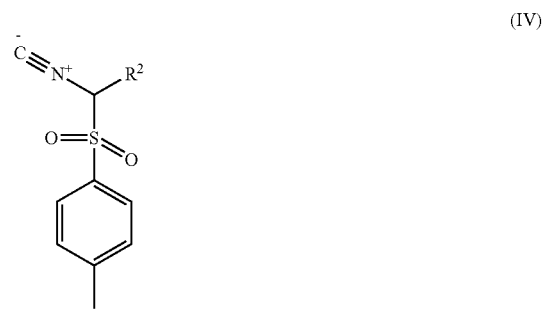

(IV)

wherein $R^2$ is as defined for a compound of the formula I; or b) (for the synthesis of a compound of the formula I) coupling an indole-boronic acid of the formula V,

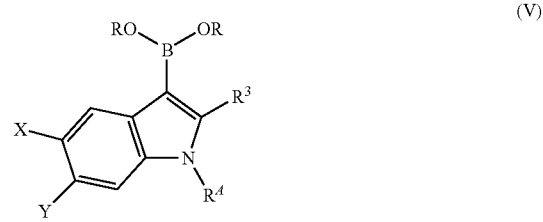

(V)

wherein $R^3$, $R^4$, X and Y are as defined for a compound of the formula I, and each R is aryl, alkenyl or especially alkyl, or wherein the two R form a bridge, especially R is H, lower alkyl or R and R together form 1,1,2,2-tetramethyl-1,2-ethylene, with a halo-imidazole of the formula VI,

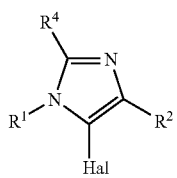

wherein $R^1$, $R^2$ and $R^4$ are as defined for a compound of the formula I and Hal is halo, especially bromo or more especially iodo,
where in the reaction functional groups in the starting materials can be present in protected form and in the obtainable compounds of the formula I carrying one or more protecting groups such protecting groups are removed;
and, if desired, a compound of the formula I obtainable according to the reaction given above is converted into a different compound of the formula I, an obtainable salt of a compound of the formula I is converted into a different salt thereof, an obtainable free compound of the formula I is converted into a salt thereof, and/or an obtainable isomer of a compound of the formula I is separated from one or more different obtainable isomers of the formula I.
Preferred Reaction Conditions:
In the following more detailed description of the process, optional reactions and conversions, synthesis of starting materials and intermediates and the like, $R^1$, $R^2$, $R^3$, $R^4$, $R^A$, X and Y have the meanings given for a compound of the formula I or the compound mentioned specifically, while other moieties if present are as defined for a compound of the formula II, III, IV, V or VI, respectively.
Variant a) is a cyclisation reaction forming the imidazole ring missing in formula II and preferably takes place at elevated temperatures, e.g. at temperatures in the range from 50 to 130° C., e.g. at about 110° C., if required in sealed reaction vessels, in an appropriate solvent, e.g. an ether, preferably a cyclic ether, such as tetrahydrofurane. The heating can, for example, be accomplished by a microwave oven.
Variant b) (which not only allows to synthesize also compound of the formula I wherein $R^4$ is hydrogen but also wherein it has the meanings given for $R^4$ in compounds of the formula I wherein $R^4$ is other than hydrogen)
The reaction preferably takes place under Suzuki-(Miyaura) conditions, that is, by palladium-catalyzed cross-coupling of organoboranes, by reacting the halo- carrying compound of the formula II with the boronic acid of the formula III, or a reactive derivative thereof.
A reactive derivative of a boronic acid of the formula V is preferably one wherein instead of the hydroxyl groups at the boron atom an aryl, alkenyl or especially alkyl moiety is present, or wherein the OH groups are present in bridged form, e.g., together with the boron atom, forming a group of the formula (A)

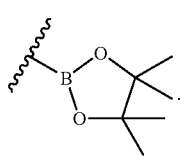

The reaction preferably takes place in a mixture of a polar aprotic solvent, such as dimethyl-formamide (DMF) or tetrahydrofurane, and water in the presence of a catalyst for the crosscoupling, especially a noble metal catalyst, preferably a palladium catalyst, such as palladium(II) complex, for example bis(triphenylphosphine)palladium (II) dichloride, in the presence of a base, such as potassium carbonate, sodium hydroxide or sodium carbonate, at a preferred temperature in the range from 60° C. to 130° C., e.g. at about 80° C.; or according to a another preferred method in an ether solvent, e.g. tetrahydrofurane or 1,2-dimethoxyethane, in the presence of a catalyst for the cross coupling, especially a noble metal catalyst, preferably a palladium (0) complex, for example tris(dibenzylideneacetone)dipalladium(0) or tetrakis (triphenylphosphin)palladium(0), in the presence of a base, such as sodium hydroxide, potassium carbonate of sodium carbonate, if desired in the presence of an appropriate ligand, such as 2-dicyclohexylphosphino-2',6'-dimethoxybiphenyl (SPhos), at a preferred temperature in the range from 60 to 150° C., preferably from 70 to 110° C.; if required conducting the reaction in a sealed vessel (e.g. a seal reactor) if the boiling point of the reaction mixture is exceeded and especially if the heating is effected by microwave excitation. Preferably, oxygen is excluded, e.g. by the presence of an inert gas, such as nitrogen or especially argon.

Advantageously, where $R^A$ in a compound of the formula V is hydrogen, this hydrogen is replaced by an N-protecting group, such as tert-butoxycarbonyl, which can, after the reaction with the compound of the formula VI, be removed according to well-known methods, e.g. as described in the references mentioned below.

Where useful or required, the reactions (as well as those forming starting materials or intermediates) can take place under an inert gas, such as nitrogen or argon.
Protecting Groups
If one or more other functional groups, for example carboxy, hydroxy, amino, or mercapto, are or need to be protected in a starting material, e.g. in any one or more starting materials of the formula II or III or other starting materials, intermediates and educts mentioned below because they should not take part in the reaction or disturb the reaction, these are such groups as are usually used in the synthesis of peptide compounds, and also of cephalosporins and penicillins, as well as nucleic acid derivatives and sugars. Protecting groups are such groups that are no longer present in the final compounds once they are removed, while groups that remain as substitutents are not protecting groups in the sense used here which is groups that are added at a certain intermediate stage and removed to obtain a final compound. For example, tert-butoxy if remaining in a compound of the formula I is a substituent, while if it is removed to obtain the final compound of the formula I it is a protecting group.

The protecting groups may already be present in precursors and should protect the functional groups concerned against unwanted secondary reactions, such as acylations, etherifications, esterifications, oxidations, solvolysis, and similar reactions. It is a characteristic of protecting groups that they lend themselves readily, i.e. without undesired secondary reactions, to removal, typically by acetolysis, protonolysis, solvolysis, reduction, photolysis or also by enzyme activity, for example under conditions analogous to physiological conditions, and that they are not present in the end-products. The specialist knows, or can easily establish, which protecting groups are suitable with the reactions mentioned above and below.

The protection of such functional groups by such protecting groups, the protecting groups themselves, and their removal reactions are described for example in standard reference works, such as J. F. W. McOmie, "Protective Groups in Organic Chemistry", Plenum Press, London and New York 1973, in T. W. Greene, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (*Methods of organic chemistry*), Houben Weyl, 4th edition, Volume 15/I, Georg Thieme Verlag, Stuttgart 1974, in H. D. Jakubke and H. Jescheit, "Aminosäuren, Peptide, Proteine" (*Amino acids, peptides, proteins*), Verlag Chemie, Weinheim, Deerfield Beach, and Basel 1982, and in Jochen Lehmann, "Chemie der Kohlenhydrate: Monosaccharide and Derivate" (*Chemistry of carbohydrates: monosaccharides and derivatives*), Georg Thieme Verlag, Stuttgart 1974.

Optional Reactions and Conversions

A compound of the formula I may be converted into a different compound of the formula I.

For example, a compound of the formula I wherein $R^3$ is esterified carboxy, especially $C_1$-$C_7$-alkoxycarbonyl, may be converted to a compound of the formula I wherein $R^3$ is a different esterified carboxy, carbamoyl, unsubstituted or substituted heterocyclyl-carbonyl (that is, heterocyclyl-C (=O)—) wherein the heterocyclyl is bound via an (in unprotonated form trivalent) nitrogen, or unsubstituted or substituted carbamoyl by, for the synthesis of a corresponding amide, reaction with a compound of the formula VII,

$$R^a\text{—NH—}R^b \qquad \text{(VII)}$$

wherein each of $R^a$ and $R^b$, independently of the other, is unsubstituted or substituted $C_1$-$C_7$-alkyl, unsubstituted or substituted aryl, unsubstituted or substituted cycloalkyl or unsubstituted or substituted heterocyclyl, or $R^a$ and $R^b$ together with the binding nitrogen are heterocyclyl that is preferably a moiety chosen from heterocyclyl as defined above with an NH— in the ring and which is unsubstituted or substituted;

or, for the synthesis of a corresponding ester, an alcohol of the formula VIII,

$$R^c\text{—OH} \qquad \text{(VIII)}$$

wherein $R^c$ is unsubstituted or substituted alkyl, unsubstituted or substituted aryl, unsubstituted or substituted cycloalkyl or unsubstituted or substituted heterocyclyl.

The reaction may either take place by first hydrolysing the esterified carboxy, e.g. $C_1$-$C_7$-alkoxycarbonyl, to carboxy, e.g. in the presence of an acid or preferably a base, such as an alkali metal hydroxide, such as sodium or potassium hydroxide, in an appropriate solvent, such as an alcohol, e.g. methanol or ethanol, preferably at elevated temperatures, e.g. in the range from 50° C. to the reflux temperature of the reaction mixture, followed then by coupling of the free carboxylic acid of the formula I (which is thus also obtainable by conversion) under appropriate coupling conditions, e.g. in the presence of a coupling agent that forms a reactive derivative of the carboxyl group in situ, for example dicyclohexylcarbodiimide/1-hydroxybenzotriazole (DCC/HOBT); bis(2-oxo-3-oxazolidinyl)phosphinic chloride (BOPCl); O-(1,2-dihydro-2-oxo-1-pyridyl)-N,N,N',N'-tetramethyluronium tetrafluoroborate (TPTU); O-benzotriazol-1-yl)-N,N,N',N'-tetramethyluronium tetrafluoroborate (TBTU); (benzotriazol-1-yloxy)-tripyrrolidinophosphonium-hexafluorophosphate (PyBOP), O-(1H-6-chlorobenzotriazole-1-yl)-1,1,3,3-tetramethyluronium hexafluorophosphate, 1-(3-dimethylaminopropyl)-3-ethylcarbodiimide hydrochloride/hydroxybenzotriazole, O-(7-azabenzotriazol-1-yl)-N,N,N', N'-tetramethyluronium-hexafluorophosphat (HATU) or/1-hydroxy-7-azabenzotriazole (EDC/HOBT or EDC/HOAt) or HOAt alone, or with (1-chloro-2-methyl-propenyl)-dimethyl-amine. For review of some other possible coupling agents, see e.g. Klauser; Bodansky, *Synthesis* (1972), 453-463. The reaction mixture, which advantageously can comprise an appropriate solvent, e.g. dimethyl formamide or dioxane, and/or N-methylmorpholine, is preferably kept, e.g. stirred, at a temperature of between approximately −20 and 80° C., especially between 0° C. and 60° C., e.g. at room temperature or at about 50° C.

Alternatively, it is also possible to directly replace the original esterifying group, e.g. $C_1$-$C_7$-alkoxy, by reaction with a compound of the formula VII or VIII, e.g. at elevated temperatures, for example in the range from 30° C. to the reflux temperature, e.g. at about 60° C., in the presence of an appropriate solvent, such as a lower alkanol, e.g. methanol or ethanol.

In a compound of the formula I with carbamoyl $R^3$, this moiety may be converted into cyano, e.g. by reaction of the corresponding compound of the formula I in the presence of trifluoroacetic anhydride in an appropriate solvent, e.g. dichloromethane, e.g. at an elevated temperature in the range from 30° C. to the reflux temperature of the reaction mixture.

In a compound of the formula I with Cyano $R^3$ (obtainable e.g. according to the preceding paragraph), the cyano may be converted into tetrazolyl $R^3$ e.g. by reaction with sodium azide in an appropriate solvent, such as 2-methoxy-ethanol, preferably at elevated temperatures, e.g. at about 130° C.

In a compound of the formula I wherein $R^3$ is carbamoyl or heterocyclyl-carbonyl wherein heterocyclyl is bound via an (in unprotonated form trivalent) nitrogen atom, the binding—C(=O) may be reduced to a methylene bridge (—$CH_2$—), for example by reaction with an appropriate reducing agent, such as a hydride, e.g. lithium aluminium hydride, e.g. in the presence of a Lewis acid, such as aluminiumtrichloride, in an appropriate solvent, e.g. an ether, such as tetrahydrofurane, at preferably elevated temperature, e.g. in the range from 50° C. to the reflux temperature of the reaction mixture, thus yielding unsubstituted or substituted alkyl $R^3$.

In a compound of the formula I wherein $R^3$ is carboxy, this carboxy can also be reduced to the corresponding hydroxymethyl group $R^3$ e.g. by reaction with lithium aluminium hydride in an appropriate solvent, such as tehrahydrofurane, at temperatures in the range from 20° C. to the reflux temperature of the reaction mixture.

A $C_1$-$C_7$-alkoxy substituent of aryl, e.g. as substitutent of aryl $R^2$, can be converted into a corresponding hydroxyl substituent, e.g. by reaction with $BBR_3$ in an appropriate solvent, e.g. dichloromethane, for example at temperatures from 0 to 50° C.

A nitrogen ring atom within a compound of the formula I, e.g. in the imidazolinylindole core or a nitrogen-containing heterocyclic (e.g. heteroaryl) substituent, can be converted into an N-oxide in the presence of a suitable oxidizing agent, e.g. a peroxide, such as m-chloroperbenzoic acid or hydrogen peroxide, if useful in an appropriate solvent.

Other examples of conversion can be deduced from the Examples, e.g. where a reaction from a starting material that is at the same time also a compound of the formula I involves the removal of a group that corresponds to a protecting group, e.g. the cleavage of an ester, e.g. to convert $C_1$-$C_7$-alkoxycarbonyl into carboxyl, the removal of a tert-butoxycarbonyl or methansulfonyl or tert-butyl-dimethylsilyl or the cleavage of isoindol-1,3-dion-2-yl, masking an amino or hydroxy group to give the free hydroxy or amino group, or the cleavage of piperazinyl or N-alkyl-piperazin-1-yl to 2-(N-alkyl-amino) ethyl).

Also in the optional process steps, carried out "if desired", functional groups of the starting compounds which should not take part in the reaction may be present in unprotected form or may be protected for example by one or more of the protecting groups mentioned hereinabove under "protecting groups". The protecting groups are then wholly or partly removed according to one of the methods described there.

Salts of a compound of formula I with a salt-forming group may be prepared in a manner known per se. Acid addition salts of compounds of formula I may thus be obtained by treatment with an acid or with a suitable anion exchange reagent, salts with bases by reaction with suitable kation exchange reagents or with corresponding bases, e.g. metal hydroxides or the like.

Salts can usually be converted to free compounds, e.g. acid addition salts by treating with suitable basic compounds, for example with alkali metal carbonates, alkali metal hydrogencarbonates, or alkali metal hydroxides, typically potassium carbonate or sodium hydroxide, salts with bases by reaction with appropriate acids, such as inorganic acids, e.g. hydrochloric acid or sulfuric acid, or sufficiently strong organic acids, e.g. sulfonic acids.

Stereoisomeric mixtures, e.g. mixtures of diastereomers, can be separated into their corresponding isomers in a manner known per se by means of suitable separation methods. Diastereomeric mixtures for example may be separated into their individual diastereomers by means of fractionated crystallization, chromatography, solvent distribution, and similar procedures. This separation may take place either at the level of a starting compound or in a compound of formula I itself. Enantiomers may be separated through the formation of diastereomeric salts, for example by salt formation with an enantiomer-pure chiral acid, or by means of chromatography, for example by HPLC, using chromatographic substrates with chiral ligands, or by any other method known in the art, e.g. using emulsion crystallization.

It should be emphasized that reactions analogous to the conversions mentioned in this chapter may also take place at the level of appropriate intermediates (and are thus useful in the preparation of corresponding starting materials).

Starting Materials:

The starting materials of the formulae II, III, IV, V, VI, VII and VIII, as well as other starting materials, intermediates or educts mentioned herein, e.g. below, can be prepared according to or in analogy to methods that are known in the art, the materials are known in the art and/or are commercially available, or by or in analogy to methods mentioned in the Examples. Novel starting materials, as well as processes for the preparation thereof, are likewise an embodiment of the present invention. In the preferred embodiments, such starting materials are used and the reaction chosen are selected so as to enable the preferred compounds to be obtained.

For example, a formylindole derivative of the formula II may preferably be obtained by formylation of an indole derivative of the formula IX,

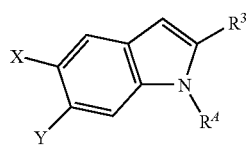

(IX)

wherein $R^3$, $R^4$, X and Y are as defined for a compound of the formula I, by reacting it with a dialkyl formamide, such as dimethylformamide, or with N-methyl-N-phenyl-formamide or under Vilsmeier conditions, e.g. in the presence of phosphorous oxychloride in the presence or preferably absence of a further solvent and at temperatures e.g. in the range from about 0 to about 80° C., or alternatively with hydrogen cyanide (HCN) under Gattermann conditions in the presence of a Lewis catalyst, such as aluminium trichloride, and of hydrogen chloride (HCl), or with Zinc cyanide in the presence of hydrogen chloride (HCl), or under Gattermann-Koch conditions with carbon monoxide, hydrogen chloride and a Lewis acid, by Rieche formylation or the like.

Compounds of the formula IX are known in the art, may be prepared according to methods known in the art, are commercially available and/or can be prepared according or in analogy to methods described in the Examples.

A compound of the formula IX wherein $R^3$ is esterified carboxy may, for example, be obtained from an aniline compound of the formula X,

(X)

wherein X and Y are as defined for a compound of the formula I by iodination, e.g. with N-iodo succinimide in the presence of an acid, such as acetic acid, e.g. at temperatures in the range of from 0 to 50° C., then introduction of a protecting group for the amino function, e.g. by reaction with mesityl chloride in the presence of a base, such as pyridine, in an appropriate solvent, such as dichloromethane, e.g. at temperatures in the range of from 0 to 50° C., followed by removal of one of the two methansulfonyl groups thus introduced at the amino function with potassium carbonate in an appropriate solvent, such as methanol/tetrahydrofurane, e.g. at temperatures in the range of from 0 to 50° C., to give a protected iodo aniline derivative of the formula XI,

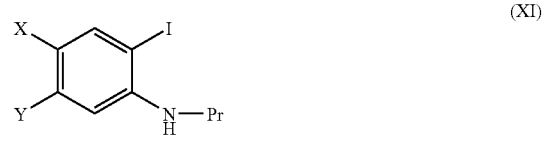

(XI)

wherein Pr is a protecting group, especially methansulfonyl, which compound is then reacted with a propiolate compound of the formula XII,

(XII)

wherein $R^{3*}$ is esterified carboxy, especially methoxycarbonyl, under cyclization in the presence of a base, such as N-ethyl-diisoproplamine, and a catalyst, e.g. tetrakistriphenylphosphine palladium, in an appropriate solvent, such as dioxane, at elevated temperatures, e.g. at the reflux temperature of the solvent, to a corresponding compound of the formula XIII,

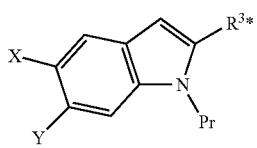 (XIII)

wherein X and Y are as defined for a compound of the formula I and $R^{3*}$ is esterified carboxy, e.g. methoxycarbonyl, which can then be deprotected under removal of the protecting group Pr, e.g. with tetrabutyl ammoniumfluoride in an appropriate solvent, such as tetrahydrofurane, at temperatures e.g. in the range from 0 to 50° C., to the corresponding compound of the formula IX.

Compounds of the formula X and of the formula XII are known in the art, may be prepared according to methods known in the art, are commercially available and/or can be prepared according or in analogy to methods described in the Examples.

Amino compounds of the formula III are known in the art, can be prepared according to methods that are known in the art, are commercially available and/or can be prepared according or in analogy to methods described in the Examples.

For example, a compound of the formula III wherein $R^1$ is 1-(unsubstituted or substituted aryl)-1-hydroxymethyl-methyl can be obtained from the corresponding glycine derivative of the formula XIV,

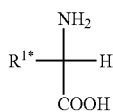 (XIV)

wherein $R^{1*}$ is unsubstituted or substituted aryl, which can be present in (R,S)- or preferably (R)- or (S)-form, by reduction with an appropriate reductant, e.g. lithium aluminium hydride, in an appropriate solvent, e.g. tetrahydrofurane, at preferably elevated temperatures, e.g. at reflux temperature of the reaction mixture, to the corresponding compound wherein a hydroxymethyl is present instead of the carboxy in formula XIV.

Compounds of the formula XIV are known in the art, can be prepared according to methods that are known in the art, are commercially available and/or can be prepared by or in analogy to methods described in the Examples. For example, they can be prepared from aryl boronic acids as described in Tetrahedron, Volume 53, Number 48, 1997, pp. 16463-16470 (8).

Compounds of the formula III wherein $R^1$ is substituted methyl can, for example, be prepared from a cyanide of the formula XV,

 (XV)

wherein $R^{1**}$ is a substitutent as mentioned for substituted alkyl, especially $C_1$-$C_7$-alkyl, unsubstituted or substituted heterocyclyl as described above, or unsubstituted or substituted aryl as defined above, by reduction in the presence of an appropriate hydrogenating agent, such as lithium aluminium-hydride, in an appropriate solvent, e.g. tetrahydrofurane, e.g. at temperatures in the range from −10 to +50° C., e.g. from about 0° C. to about room temperature, to the corresponding compound of the formula III.

The cyanides of the formula XV are known in the art, can be prepared according to methods that are known in the art, are commercially available and/or they can be prepared by or in analogy to methods described in the examples.

Tosyl-methyl isocyanides of the formula IV are known in the art, can be prepared in accordance with methods known in the art, are commercially available and/or can be prepared by or in analogy to methods described in the Examples.

For example, they can be obtained from a tosamide of the formula XVI,

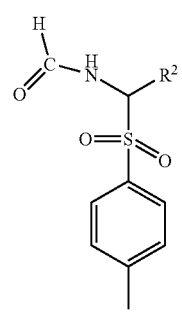 (XVI)

wherein $R^2$ is as defined for a compound of the formula I by reaction with an inorganic acid halide, especially thionyl chloride or phosphourous oxychloride, in an appropriate solvent, e.g. dimethyl ether, dimethyl formamide or preferably tetrahydrofurane, preferably in the presence of a tertiary amine, such as triethylamine, at temperatures e.g. in the range from −20 to 30° C., e.g. at about 0° C.

Tosamides of the formula XVI may, for example, be obtained from aldehydes of the formula XVII, $R^2$—CHO (XVII)

wherein $R^2$ is as defined for a compound of the formula I, by reacting it (in one step or in two steps) with formamide and with p-toluenesulfonic or preferably p-toluenesulfinic acid in an appropriate solvent, e.g. toluene/acetonitrile (with or without dimethylformamide) in the presence of a silyl halogenide, such as trimethylsilyl halogenide, preferably at elevated temperatures, e.g. in the range from 30 to 75° C. For example, they may be prepared as described in *Chem. Lett.* 1988, 9, 1531-1534.

Aldehyde compounds of the formula XVII are known in the art, can be prepared according to methods that are known in the art, are commercially available and/or they can be prepared by or in analogy to methods described in the examples.

Indole-boronic acids of the formula V can be obtained from a compound of the formula XVIII,

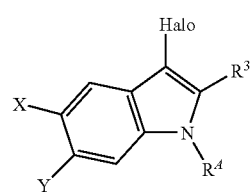 (XVIII)

wherein X, Y, $R^3$ and $R^4$ are as defined for a compound of the formula I and Halo is especially bromo or iodo, or is trifluoromethanesulfonyl, by reacting it to a Grignard or preferably (e.g. with alkyl lithium, e.g. butyl lithium) to a lithium compound (Li instead of Halo in formula XVIII) which is then reacted with an trialkoxyborane or a bis(dialkoxyborane) to the corresponding compound of the formula V, e.g. according to the Miyaura Borylation Reaction, according to the method described in *Org. Lett.*, 2006, 8, 305-307, according to the method described in *Org. Lett.*, 2006, 8, 261-263, or the like.

Halo-imidazoles of the formula VI are known in the art, can be prepared according to methods that are known in the art, are commercially available and/or can be obtained by or in analogy to a method described in the Examples. This is also true for compounds of the formula VII and for alcohols of the formula VIII.

Other starting materials are known in the art, can be prepared according to methods that are known in the art, are commercially available and/or can be prepared according to or in analogy to the methods described in the Examples.

EXAMPLES

The following examples serve to illustrate the invention without limiting the scope thereof. Note that in some cases compounds mentioned as intermediates are also compounds of the formula I according to the invention (it is then mentioned that the compounds fall under formula I).

Abbreviations
Ac acetyl
AcOH acetic acid
$AlCl_3$ aluminum trichloride
aq. aqueous
Boc tert-butoxycarbonyl
Brine saturated (at rt) sodium chloride solution
$^tBu$ tert-butyl
CDI carbonyl diimidazole
Celite trademark of Celite Corp. (World Minerals Inc.), Santa Barbara, Calif., USA, for filtering aid based on kieselguhr
$CH_3CN$ acetonitrile
conc. concentrated
DCM dichloromethane
DMAP 4-dimethylaminopyridine
DMF N,N-dimethylformamide
DMSO dimethylsulfoxide
ES-MS electrospray mass spectrometry
Et ethyl
$Et_3N$ triethylamine
$Et_2O$ diethyl ether
EtOAc ethyl acetate
EtOH ethanol
h hour(s)
HATU O-(7-azabenzotriazol-1-yl)-N,N,N',N'-tetramethyluronium-hexafluorophosphat
HBr hydrogen bromide
HCl hydrogen chloride
HOAt 1-hydroxy-7-azabenzotriazole
HPLC high-pressure liquid chromatography
HyFlo diatomaceous earth based filtering aid, trademark of Johns Manville Corp., Denver, Colo., USA
HV High vacuum
IPr isopropyl
$K_2CO_3$ potassium carbonate
KHMDS potassium hexamethyldisilazide
$KO^tBu$ potassium-tert-butoxylate
KOH potassium hydroxide
$K_3PO_4$ potassium phosphate
LAH lithium aluminium hydride
LDA lithium diisopropylamide
Me methyl
MeI methyl iodide
MeOH methanol
$MgSO_4$ magnesium sulfate
min minute(s)
mL milliliter(s)
MS Mass Spectrometry
MsCl methanesulfonyl chloride
NaH sodium hydride
$NaHCO_3$ sodium bicarbonate
$Na_2CO_3$ sodium carbonate
NaOH sodium hydroxide
NaOMe sodium methoxylate
NaOEt sodium ethoxylate
$NaO^tBu$ sodium tert-butoxylate
$Na_2SO_4$ sodium sulfate
NBS N-bromosuccinimide
NCS N-chlorosuccinimide
$NH_4Cl$ ammonium chloride
NIS N-iodosuccinimide
NMM 4-methylmorpholine
NMR nuclear magnetic resonance
Ph phenyl
PG protecting group
$POCl_3$ phosphorus (III) oxychloride
rt (or RT) room temperature
TBAF tetrabutylammonium fluoride
TBAHS tetrabutylammonium hydrosulfate
TBTU O-(benzotriazol-1-yl)-N,N,N',N'-tetramethylammonium tetrafluoroborate
TFA trifluoroacetic acid
TFAA trifluoroacetic anhydride
THF tetrahydrofurane
TMS trimethylsilyl
TMSCl trimethylsilyl chloride
$t_{Ret}$ retention time
TsCl p-toluenesulfonyl chloride
TsOH p-toluenesulfonic acid
UV ultraviolet Where no specific source is indicated, starting materials are obtainable from customary suppliers, such as Sigma-Aldrich, St. Louis, USA, from Fluka, Switzerland, Buchs, from Merck, Darmstadt, FRG, or from providers indicated specifically.

Synthesis

Flash chromatography is performed by using silica gel (Merck; 40-63 μm). For thin layer chromatography, pre-coated silica gel (Merck 60 F254; Merck KgaA, Darmstadt, Germany)) plates are used. $^1$NMR measurements are performed on a Varian Gemini 400 spectrometer using tetramethylsilane as internal standard. Chemical shifts (δ) are expressed in ppm downfield from tetramethylsilane. Electrospray mass spectra are obtained with a Fisons Instruments VG Platform II. Commercially available solvents and chemicals are used for syntheses.

HPLC Condition A:
Column: Nucleosil 100-3 C18, 70×4.0 mm.
Flow rate: 1.0 mL/min
Mobile phase: A) TFA/water (0.1/100, v/v), B) $TFA/CH_3CN$ (0.1/100, v/v)
Gradient: linear gradient from 20% B to 100% B in 7 min
Detection: UV at 215 nm HPLC Condition B:
Column: Speed ROD RP18e, 50×4.6 mm.
Flow rate: 1.3 ml/min
Mobile phase: A) TFA/water (0.1/100, v/v), B) TFA/CH$_3$CN (0.1/100, v/v)
Gradient: linear gradient from 2% B to 100% B in 1 min then 100% B 2 min
Detection: UV at 215 nm
HPLC Condition C:
Column: Nucleosil 100-3 C18 HD, 125×4.0 mm.
Flow rate: 1.0 mL/min
Mobile phase: A) TFA/water (0.1/100, v/v), B) TFA/CH$_3$CN (0.1/100, v/v)
Gradient: linear gradient from 2% B to 100% B in 7 min then 100% B 2 min
Detection: UV at 215 nm
HPLC Condition D:
Column: Nucleosil 100-3 C18 HD, 125×4.0 mm.
Flow rate: 2.0 mL/min
Mobile phase: A) TFA/water (0.1/100, v/v), B) TFA/CH$_3$CN (0.1/100, v/v)
Gradient: gradient from 1% to 20% B in 1 min, 20% to 100% B in 2 min, then 100% B in 1 min
Detection: UV at 215 nm
HPLC Condition E:
Column: Speed ROD RP18e, 50×4.6 mm.
Flow rate: 1.3 mL/min
Mobile phase: A) TFA/water (0.1/100, v/v), B) TFA/acetonitrile (0.1/100, v/v)
Gradient: linear gradient from 0% B to 100% B in 6 min then 2 min 100% B
Detection: UV at 215 nm The HPLC conditions A, B, C, D and E can be identified by the subscript prefixes of the T$_{Ret}$ values given in the examples. For instance, B in $_B$t$_{Ret}$= . . . min means condition-B in the case of HPLC.

General Scheme 1

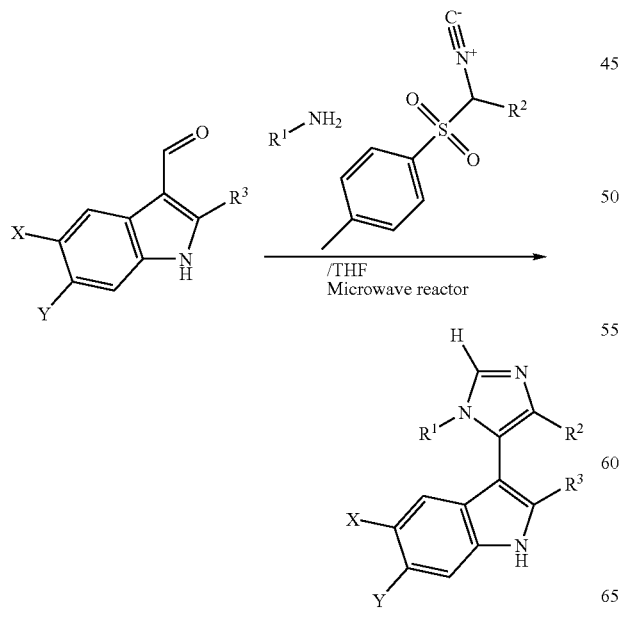

General Scheme 2

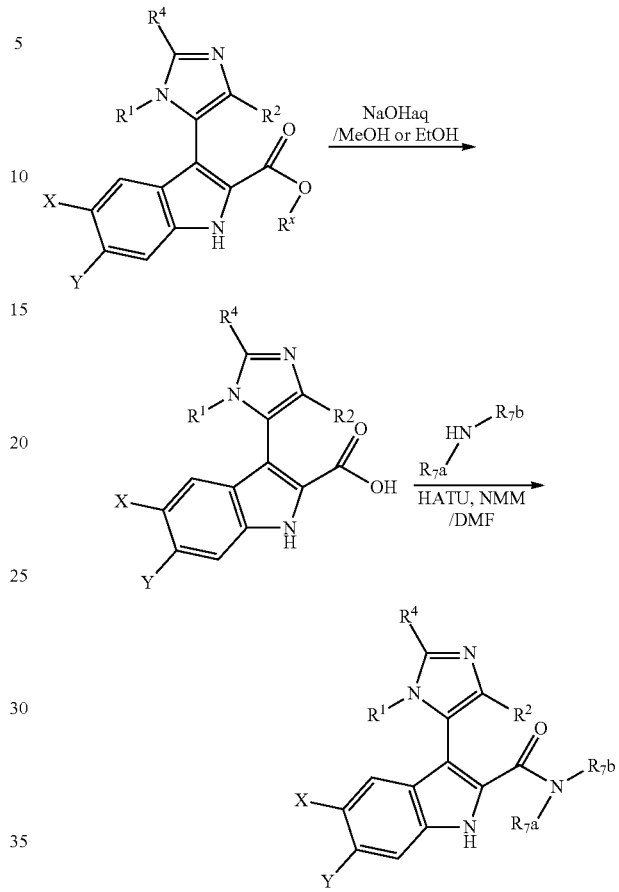

Rx=alkyl, e.g. methyl, ethyl; R$^{7a}$, R$^{7b}$=H, C$_1$-C$_7$-alkyl, phenyl, phenylmethyl or the like, especially as shown in the Examples General Scheme-3

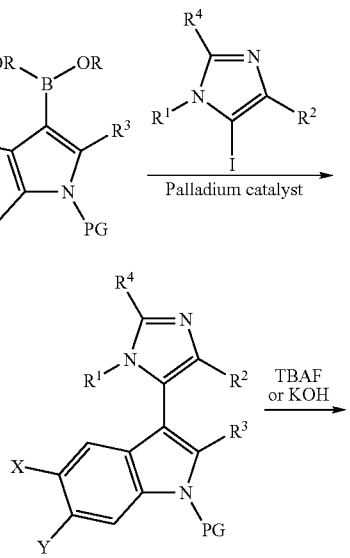

-continued

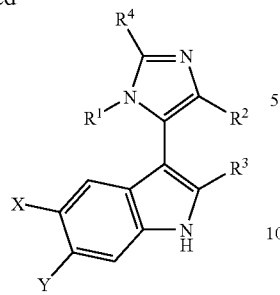

R=H, lower alkyl or R+R form 1,1,2,2-tetramethyl-1,2-ethylene

Example 1

6-Chloro-3-[3-(4-chloro-benzyl)-5-phenyl-3H-imidazol-4-yl]-1H-indole

A mixture of Intermediate 1.1 (100 mg, 0.55 mmol), 4-chlorobenzyl-amine (0.1 mL, 0.83 mmol) and 1-(isocyano-phenyl-methanesulfonyl)-4-methyl-benzene (commercially available from SynChem, Inc., Des Plaines, Ill., USA) (227 mg, 0.83 mmol) in THF (2 mL) is sealed and heated by the microwave reactor at 110° C. for 1 h. After completion, the reaction mixture is quenched by aqueous NaHCO$_3$, EtOAc is added and the organic layer is washed with brine, dried over MgSO$_4$ and evaporated in vacuo. Silica gel flash chromatography of the residue affords the title compound as a colorless powder; ES-MS: M+=418.0; HPLC: $_A t_{Ret}$=4.53 min.

Intermediate 1.1

6-Chloro-1H-indole-3-carbaldehyde

A mixture of 6-chloro-1H-indole (2.0 g, 13.2 mmol) and POCl$_3$ (1.34 mL, 14.5 mmol) in DMF (5 mL) is heated at 45° C. for 1 h. After completion, the reaction mixture is quenched with aqueous NaHCO$_3$, Et$_2$O is added and the organic layer is washed with brine, dried over MgSO$_4$ and evaporated in vacuo. Silica gel flash chromatography of the residue affords the title compound as a colorless powder; ES-MS: M+=179.9; HPLC: $_A t_{Ret}$=3.74 min.

Example 2

6-Chloro-3-[3-(4-chloro-benzyl)-5-phenyl-3H-imidazol-4-yl]-1H-indole-2-carboxylic acid (2-morpholin-4-yl-ethyl)-amide A mixture of Intermediate 2.1 (200 mg, 0.43 mmol), N-(4-aminoethyl)-morpholine (68 mg, 0.52 mmol), NMM (109 mg, 1.08 mmol) and HATU (245 mg, 0.65 mmol) in DMF (2.2 mL) is heated for 1 h at 50° C. EtOAc is added and the organic layer is washed with brine, dried over MgSO$_4$ and evaporated in vacuo. Silica gel flash chromatography of the residue affords the title compound as a colorless crystal; ES-MS: M+H=576.2; HPLC: $_A t_{Ret}$=3.80 min.

Intermediate 2.1

6-Chloro-3-[3-(4-chloro-benzyl)-5-phenyl-3H-imidazol-4-yl]-1H-indole-2-carboxylic acid (Which is Also a Compound of the Formula I)

A mixture of Intermediate 2.2 (900 mg, 1.84 mmol) and 2M aqueous NaOH (35 mL) in EtOH (35 mL) is refluxed for 2.5 h. The resulting mixture is poured into a mixture of ice and water, and after neutralized by 4 M aqueous HCl, EtOAc is added and the organic layer is washed with brine, dried over MgSO$_4$. Concentration in vacuo affords the title compound as a colorless crystal; ES-MS: M+=461.9; HPLC: $_A t_{Ret}$=4.22 min.

Intermediate 2.2

6-Chloro-3-[3-(4-chloro-benzyl)-5-phenyl-3H-imidazol-4-yl]-1H-indole-2-carboxylic acid ethyl ester (Also an Active Compound of the Formula I)

Method A: A mixture of Intermediate 2.3 (1.0 g, 3.97 mmol), 4-chlorobenzyl-amine (731 mg, 5.17 mmol) and 1-(isocyano-phenyl-methanesulfonyl)-4-methyl-benzene (1.62 g, 5.96 mmol) in THF (15 mL) is sealed and heated by means of a microwave reactor at 110° C. for 1 h. After completion, the reaction mixture is quenched by aqueous NaHCO$_3$, EtOAc is added and the organic layer is washed with brine, dried over MgSO$_4$ and evaporated in vacuo. Silica gel flash chromatography of the residue affords the title compound as a colorless powder; ES-MS: M+=490.1; HPLC: $_A t_{Ret}$=4.62 min.

Method B: A mixture of Intermediate 2.3 (6.09 g, 24.2 mmol), 4-chlorobenzyl-amine (3.55 mL, 29.0 mmol), Et$_3$N (10.1 mL, 72.6 mmol) and 1-(isocyano-phenyl-methanesulfonyl)-4-methyl-benzene (7.87 g, 29.0 mmol) in EtOH (120 mL) is heated at 60° C. for 3 h. After completion, the reaction mixture is concentrated in vacuo and quenched by aqueous NaHCO$_3$, EtOAc is added and the organic layer is washed with brine, dried over MgSO$_4$ and evaporated in vacuo. Silica gel flash chromatography of the residue affords the title compound as a colorless powder.

Intermediate 2.3

6-Chloro-3-formyl-1H-indole-2-carboxylic acid ethyl ester

The title compound is prepared according to a published literature procedure (see J. Med. Chem. 2005, 48, 995-1018.) A solution of 6-chloro-1H-indole-2-carboxylic acid ethyl ester (5.0 g, 22.4 mmol) (commercially available from 3D Medical Systems Inc.) and POCl$_3$ (2.46 mL, 26.8 mmol) in DMF (15 mL) is heated at 50° C. for 28 h. After completion, the reaction mixture is quenched by aqueous NaHCO$_3$, Et$_2$O is added and the organic layer is washed with brine, dried over MgSO$_4$ and evaporated in vacuo. Silica gel flash chromatography of the residue affords the title compound as a colorless powder; ES-MS: M-=250.1; HPLC: $_A t_{Ret}$=4.67 min.

Table 1 of further Examples:

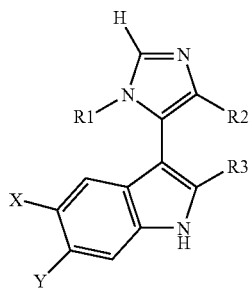

| Example | X and Y | R¹ | R² | R³ | Analysis MS/HPLC/NMR |
|---|---|---|---|---|---|
| 3 | X = H, Y = Cl | neopentyl (CH₂CH₂C(CH₃)₃) | phenyl | H | M+ = 378.0; $_A t_{Ret}$ = 4.61 min |
| 4 | X = H, Y = Cl | 4-fluorobenzyl | phenyl | H | M+ = 402.0; $_A t_{Ret}$ = 4.37 min |
| 5 | X = H, Y = Cl | 3-chloro-4-fluorobenzyl | phenyl | H | M+ = 435.9; $_A t_{Ret}$ = 4.49 min |
| 6 | X = H, Y = Cl | 2,4-dichlorobenzyl | phenyl | H | M + H = 453.7; $_A t_{Ret}$ = 4.65 min |
| 7 | X = H, Y = Cl | 3,4-dichlorobenzyl | phenyl | H | M + H = 455.8; $_A t_{Ret}$ = 4.65 min |
| 8 | X = H, Y = Cl | 4-chloro-2-fluorobenzyl | phenyl | H | M+ = 436.0; $_A t_{Ret}$ = 4.50 min |
| 9 | X = H, Y = Cl | 4-chloro-3-fluorobenzyl | phenyl | H | M− = 436.1; $_A t_{Ret}$ = 4.54 min |
| 10 | X = F, Y = Cl | 4-chlorobenzyl | phenyl | H | M+ = 436.0; $_A t_{Ret}$ = 4.53 min |

-continued

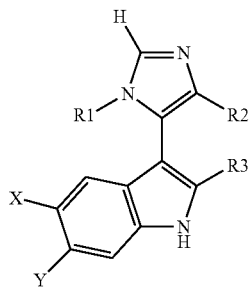

| Example | X and Y | R¹ | R² | R³ | Analysis MS/HPLC/NMR |
|---|---|---|---|---|---|
| 11 | X = H, Y = Cl | 4-Cl, 2-Me-benzyl | phenyl | H | M− = 432.1, $^A t_{Ret}$ = 4.68 min |
| 12 | X = H, Y = Br | 4-Cl-benzyl | phenyl | H | M+ = 436.9, $^A t_{Ret}$ = 4.61 min |
| 13 | X = H, Y = Me | 4-Cl-benzyl | phenyl | H | M+ = 398.1, $^A t_{Ret}$ = 4.51 min |
| 14 | X = H, Y = Cl | 4-Cl-benzyl | 2-F-phenyl | H | M− = 436.0, $^A t_{Ret}$ = 4.47 min |
| 15 | X = H, Y = Cl | 4-Cl-benzyl | 3-F-phenyl | H | M+ = 436.0, $^A t_{Ret}$ = 4.61 min |
| 16 | X = H, Y = Cl | 4-Cl-benzyl | 2-F, 3-Cl-phenyl | H | M + H = 471.9, $^A t_{Ret}$ = 4.69 min |
| 17 | X = H, Y = CN | 4-Cl-benzyl | phenyl | H | M + H = 409.0, $^C t_{Ret}$ = 5.82 min |
| 18 | X = F, Y = F | 4-Cl-benzyl | phenyl | H | M + H = 420.0, $^C t_{Ret}$ = 6.20 min |

-continued

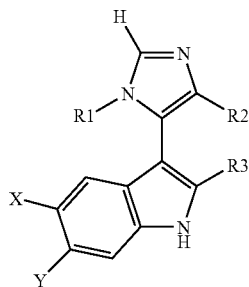

| Example | X and Y | R¹ | R² | R³ | Analysis MS/HPLC/NMR |
|---|---|---|---|---|---|
| 19 | X = H<br>Y = Cl | 4-(trifluoromethyl)benzyl | phenyl | H | M + H = 452.1<br>$_A t_{Ret}$ = 4.60 min |
| 20 | X = H<br>Y = Cl | (S)-1-(4-chlorophenyl)ethyl | phenyl | H | M+ = 432.1<br>$_A t_{Ret}$ = 4.65 min |
| 21 | X = H<br>Y = Cl | (R)-1-(4-chlorophenyl)ethyl | phenyl | H | M+ = 432.1<br>$_A t_{Ret}$ = 4.65 min |
| 22 | X = H<br>Y = Cl | 4-bromobenzyl | phenyl | H | M + H = 463.9<br>$_A t_{Ret}$ = 4.59 min |
| 23 | X = F<br>Y = Cl | 1-(4-chlorophenyl)ethyl | phenyl | H | M + H = 450.0<br>$_C t_{Ret}$ = 6.48 min |
| 24 | X = F<br>Y = F | 1-(4-chlorophenyl)ethyl | phenyl | H | M + H = 434.0<br>$_C t_{Ret}$ = 6.25 min |

-continued

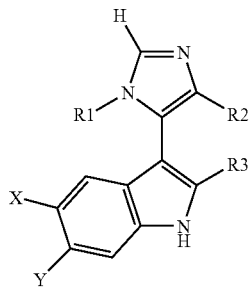

| Example | X and Y | R¹ | R² | R³ | Analysis MS/HPLC/NMR |
|---|---|---|---|---|---|
| 25 | X = H<br>Y = Cl | 4-chlorophenyl-CH(CH₂OH)- | phenyl | H | M+ = 448.0<br>$^A t_{Ret}$ = 4.35 min |
| 26 | X = H<br>Y = CN | 4-chlorophenyl-CH(CH₃)- | phenyl | H | M+ = 423.1<br>$^A t_{Ret}$ = 4.14 min |
| 27 | X = F<br>Y = Cl | 4-chlorophenyl-CH(CH₂OH)- | phenyl | H | M+ = 466.0<br>$^A t_{Ret}$ = 4.32 min |
| 28 | X = H<br>Y = CN | 4-chlorophenyl-CH(CH₂OH)- | phenyl | H | M+ = 439.1<br>$^A t_{Ret}$ = 3.87 min |
| 29 | X = F<br>Y = Cl | 4-chlorophenyl-CH(CH₃)- | phenyl | H | M+ = 450.1<br>$^A t_{Ret}$ = 4.59 min |
| 30 | X = H<br>Y = CN | 4-chlorophenyl-CH(CH₃)- | phenyl | H | M+ = 423.1<br>$^A t_{Ret}$ = 4.14 min |

-continued

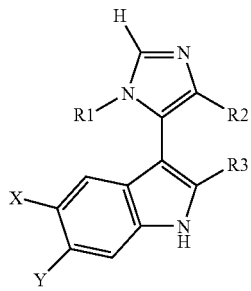

| Example | X and Y | R¹ | R² | R³ | Analysis MS/HPLC/NMR |
|---|---|---|---|---|---|
| 31 | X = F<br>Y = F | 4-chlorophenyl-CH(CH₃)- | phenyl | H | M+ = 434.1<br>$_A t_{Ret}$ = 4.42 min |
| 32 | X = F<br>Y = Cl | 4-chlorophenyl-CH(CH₂OH)- | phenyl | H | M+ = 466.0<br>$_A t_{Ret}$ = 4.33 min |
| 33 | X = H<br>Y = Cl | 4-chlorobenzyl | phenyl | -C(O)NH-(CH₂)₃-morpholinyl | M+ = 587.8<br>$_A t_{Ret}$ = 3.96 min |
| 34 | X = H<br>Y = Cl | 4-chlorobenzyl | pyridyl | -C(O)NH-(CH₂)₃-(2-oxopyrrolidin-1-yl) | M+ = 586.2<br>$_A t_{Ret}$ = 4.35 min |
| 35 | X = H<br>Y = Cl | 4-chlorobenzyl | phenyl | -C(O)NH-CH₂CH₂-OCH₃ | M+ = 520.9<br>$_A t_{Ret}$ = 4.34 min |

-continued

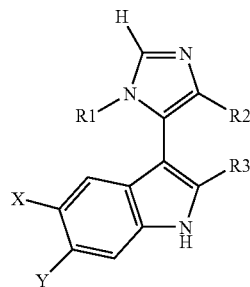

| Example | X and Y | R¹ | R² | R³ | Analysis MS/HPLC/NMR |
|---|---|---|---|---|---|
| 36 | X = H, Y = Cl | 4-Cl-benzyl | phenyl | C(O)NH-CH₂CH₂CH₂-OCH₃ | M+ = 534.9, $^A t_{Ret}$ = 4.41 min |
| 37 | X = H, Y = Cl | 4-Cl-benzyl | phenyl | C(O)NH-CH₂CH₂-pyrrolidinyl | M+ = 559.9, $^A t_{Ret}$ = 3.91 min |
| 38 | X = H, Y = Cl | 4-Cl-benzyl | phenyl | C(O)NH-CH₂CH₂CH₂-pyrrolidinyl | M+ = 573.9, $^A t_{Ret}$ = 3.87 min |
| 39 | X = H, Y = Cl | 4-Cl-benzyl | phenyl | C(O)NH-CH₂CH₂-NHCH₃ | M+ = 519.9, $^A t_{Ret}$ = 3.76 min |
| 40 | X = H, Y = Cl | 4-Cl-benzyl | phenyl | C(O)NH-CH₂CH₂CH₂-(4-methylpiperazin-1-yl) | M+ = 603.3, $^A t_{Ret}$ = 3.51 min |

-continued

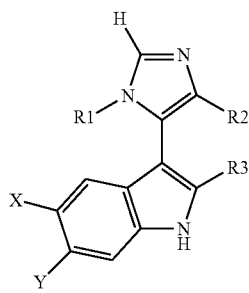

| Example | X and Y | R¹ | R² | R³ | Analysis MS/HPLC/NMR |
|---|---|---|---|---|---|
| 41 | X = H, Y = Cl | 4-Cl-benzyl | phenyl | -NH-CH₂CH₂-(2-oxopyrrolidin-1-yl) amide | M+ = 573.9, $^A t_{Ret}$ = 4.22 min |
| 42 | X = H, Y = Cl | 4-Cl-benzyl | phenyl | -NH-CH₂CH₂-(4-methylpiperazin-1-yl) amide | M+ = 589.3, $^A t_{Ret}$ = 3.61 min |
| 43 | X = H, Y = Cl | 4-Cl-benzyl | phenyl | -NH-CH₂CH₂-NH₂ amide | M+ = 504.0, $^A t_{Ret}$ = 3.67 min |
| 44 | X = H, Y = Cl | 4-Cl-benzyl | phenyl | -NH-CH₂CH₂-(piperazin-1-yl) amide | M+ = 574.4, $^A t_{Ret}$ = 3.52 min |
| 45 | X = H, Y = Cl | 4-Cl-benzyl | phenyl | -NH-CH₂CH₂CH₂-(piperazin-1-yl) amide | M+ = 588.4, $^A t_{Ret}$ = 3.49 min |
| 46 | X = H, Y = Cl | 4-Cl-benzyl | phenyl | -NH-CH₂CH₂-(1,1-dioxothiomorpholin-4-yl) amide | M+ = 621.9, $^A t_{Ret}$ = 3.97 min |

-continued

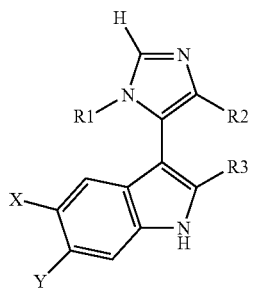

| Example | X and Y | R¹ | R² | R³ | Analysis MS/HPLC/NMR |
|---|---|---|---|---|---|
| 47 | X = H<br>Y = Cl | 4-Cl-benzyl | phenyl | N-(1-methylpiperidin-4-yl)carboxamide | M+ = 558.0<br>$A^{t}{}_{Ret}$ = 3.78 min |
| 48 | X = H<br>Y = Cl | 4-Cl-benzyl | phenyl | 3-(dimethylamino)pyrrolidin-1-yl carbonyl | M+ = 558.0<br>$A^{t}{}_{Ret}$ = 3.73 min |
| 49 | X = H<br>Y = Cl | 4-Cl-benzyl | phenyl | N-(piperidin-4-yl)carboxamide | M+ = 544.0<br>$A^{t}{}_{Ret}$ = 3.71 min |
| 50 | X = H<br>Y = Cl | 4-Cl-benzyl | phenyl | N-[1-(2-hydroxyethyl)piperidin-4-yl]carboxamide | M+ = 588.0<br>$A^{t}{}_{Ret}$ = 3.73 min |
| 51 | X = H<br>Y = Cl | 4-Cl-benzyl | phenyl | 4-(methylsulfonyl)piperazin-1-yl carbonyl | M+ = 607.9<br>$A^{t}{}_{Ret}$ = 4.36 min |

-continued

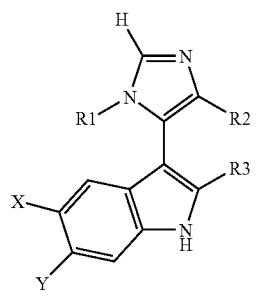

| Example | X and Y | R¹ | R² | R³ | Analysis MS/HPLC/NMR |
|---|---|---|---|---|---|
| 52 | X = H<br>Y = Cl | 4-Cl-benzyl | phenyl | 1-(4-dimethylamino-piperidin-1-yl)carbonyl | M+ = 572.0<br>$^A t_{Ret}$ = 3.78 min |
| 53 | X = H<br>Y = Cl | 4-Cl-benzyl | phenyl | (1-methylpiperidin-4-yl)methyl-NH-C(O)- | M+ = 572.0<br>$^A t_{Ret}$ = 3.81 min |
| 54 | X = H<br>Y = Cl | 4-Cl-benzyl | phenyl | methyl-NH-C(O)- | M+ = 475.0<br>$^C t_{Ret}$ = 6.09 min |
| 55 | X = H<br>Y = Cl | 4-Cl-benzyl | phenyl | ethyl-NH-C(O)- | M+ = 489.0<br>$^C t_{Ret}$ = 6.24 min |
| 56 | X = H<br>Y = Cl | 4-Cl-benzyl | phenyl | HOCH₂CH₂-NH-C(O)- | M+ = 505.0<br>$^C t_{Ret}$ = 5.91 min |
| 57 | X = H<br>Y = Cl | 4-Cl-benzyl | phenyl | HO(CH₂)₃-NH-C(O)- | M+ = 519.0<br>$^C t_{Ret}$ = 5.97 min |

-continued
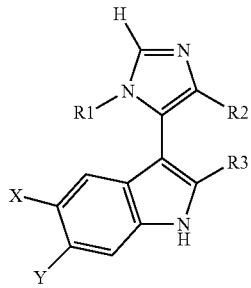
| Example | X and Y | R¹ | R² | R³ | Analysis MS/HPLC/NMR |
|---|---|---|---|---|---|
| 58 | X = H<br>Y = Cl | 4-chlorobenzyl | phenyl | 1-acyl-4-(3-phenyl-2-oxo-imidazolidin-1-yl)piperidine | M − H = 689.0; ¹HNMR (CDCl₃) δ 9.98 (s, 1H), 7.81 (s, 1H), 7.82 (d, 2H), 7.54 (d, 2H), 7.43 (s, 1H), 7.39-7.35 (m, 2H), 7.21-7.15 (m, 3H), 7.03-6.89 (m, 5H), 6.79 (d, 2H), 4.99 (d, 1H), 4.81 (d, 1H), 3.89-3.78 (m, 5H), 3.35-3.17 (m, 2H), 2.78-2.57 (m, 2H), 1.78-1.69 (m, 2H), 1.38-1.07 (m, 2H). |
| 59 | X = H<br>Y = Cl | 4-chlorobenzyl | phenyl | 1-acyl-4-(2-oxopyrrolidin-1-yl)piperidine | M + H = 615.4; ¹HNMR (CDCl₃) δ 9.21 (s, 1H), 7.81 (s, 1H), 7.60 (d, 2H), 7.42 (s, 1H), 7.19-7.03 (m, 4H), 6.79 (d, 2H), 4.96 (d, 1H), 4.79 (d, 1H), 3.99-3.91 (m, 1H), 3.21-3.04 (m, 2H), 2.78-2.43 (m, 2H), 2.37 (t, 2H), 2.02-1.92 (m, 2H), 1.75-1.55 (m, 4H), 1.43-1.16 (m, 2H). |

-continued

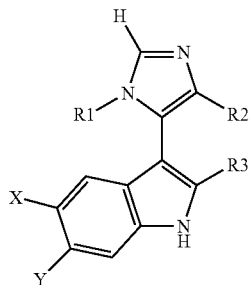

| Example | X and Y | R¹ | R² | R³ | Analysis MS/HPLC/NMR |
|---|---|---|---|---|---|
| 60 | X = H, Y = Cl | 4-Cl-benzyl | phenyl | 1-acyl-4-(2-oxo-imidazolidin-1-yl)piperidine | M + H = 616.4; $^1$HNMR (CDCl$_3$) δ 9.38 (s, 1H), 7.81 (s, 1H), 7.60 (d, 2H), 7.44 (s, 1H), 7.21-7.11 (m, 3H), 7.05-6.89 (m, 4H), 6.78 (d, 2H), 4.95 (d, 1H), 4.79 (d, 1H), 3.78-3.67 (m, 1H), 3.42-3.36 (m, 2H), 3.23-3.18 (m, 2H), 2.79-2.56 (m, 2H), 1.78-1.58 (m, 4H), 1.22-1.04 (m, 2H). |
| 61 | X = H, Y = Cl | 4-Cl-benzyl | phenyl | 1-acyl-4-(2-oxo-benzimidazol-1-yl)piperidine | M + H = 690.1; $^1$HNMR (CDCl$_3$) 9.89 (s, 1H), 7.80 (s, 1H), 7.59 (d, 2H), 7.52 (d, 2H), 7.50 (s, 1H), 7.47 (d, 2H), 7.17 (m, 3H), 7.08-6.90 (m, 4H), 6.79 (d, 2H), 4.99 (d, 1H), 4.80 (d, 1H), 4.85-4.65 (m4h), 3.38-3-19 (m, 2H), 2.80-2.65 (m, 3H), 1.71 (m, 2H), 1.41-1.05 (m, 2H). |
| 62 | X = H, Y = Cl | 4-Cl-benzyl | phenyl | (3R)-1-acyl-3-(dimethylamino)pyrrolidine | M+ = 558.0 $t_{Ret}$ = 5.22 min |
| 63 | X = H, Y = Cl | 4-Cl-benzyl | phenyl | N-[2-(2-oxo-imidazolidin-1-yl)ethyl]acetamide | M+ = 573.0 $t_{Ret}$ = 5.92 min |

-continued

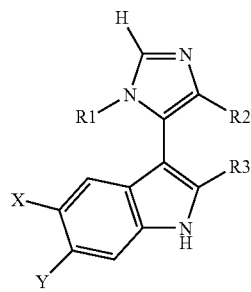

| Example | X and Y | R¹ | R² | R³ | Analysis MS/HPLC/NMR |
|---|---|---|---|---|---|
| 64 | X = H<br>Y = Cl | 4-chlorobenzyl | phenyl | 4-(4-methylpiperazin-1-yl)piperidine-1-carbonyl | M + H = 628.3<br>$_B t_{ret}$ = 1.98 min |
| 65 | X = H<br>Y = Cl | 4-chlorobenzyl | phenyl | N-(2-(piperidin-1-yl)ethyl)acetamide | M+ = 571.9<br>$_B t_{ret}$ = 2.04 min |
| 66 | X = H<br>Y = Cl | 4-chlorobenzyl | phenyl | morpholine-4-carbonyl | M + H = 532.7<br>$_B t_{ret}$ = 2.13 min |
| 67 | X = H<br>Y = Cl | 4-chlorobenzyl | phenyl | 4-methylpiperazine-1-carbonyl | M+ = 543.9<br>$_B t_{ret}$ = 2.01 min |
| 68 | X = H<br>Y = Cl | 4-chlorobenzyl | naphthyl | 4-morpholinopiperidine-1-carbonyl | M+ = 614.0<br>¹HNMR (CDCl₃) 9.39 (s, 1H), 7.80 (s, 1H), 7.59 (d, 2H), 7.41 (s, 1H), 7.21-7.11 (m, 3H), 6.99-6.91 (m, 4H), 6.78 (d, 2H), 4.92 (d, 1h), 4.79 (d, 1H), 3.71-3.62 (m, 4H), 3.71-3.48 (m, 2H), 2.23-2.19 (m, 1H), 2.79-2.58 (m, 4H), 1.19-1.03 (m, 4H). |

-continued

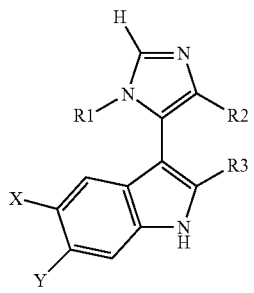

| Example | X and Y | R¹ | R² | R³ | Analysis MS/HPLC/NMR |
|---|---|---|---|---|---|
| 69 | X = H<br>Y = Cl | 4-chlorobenzyl | phenyl | -C(O)NH-CH₂CH₂-N(Et)₂ | M+ = 560.0<br>¹HNMR (CDCl₃) 9.80 (s, 1H), 7.86 (1H), 7.54-7.49 (m, 3H), 7.14-7.10 (m, 7H), 6.74 (d, 2H), 6.70 (s, 1H), 4.80 (d, 2H), 4.11 (q, 4H), 3.37-3.19 (m, 2H), 2.40-2.36 (m, 2H), 0.83 (t, 6H). |
| 70 | X = H<br>Y = Cl | 4-chlorobenzyl | phenyl | -C(O)NH-CH₂CH₂-azepane | M+ = 588.7<br>¹HNMR (CDCl₃) d 9.98 (s, 1H), 7.98 (s, 1H), 7.57-7.43 (m, 3H), 7.19-7.01 (m, 7H), 6.79 (d, 2H), 6.71 (s, 1H), 4.82 (s, 2H), 3.39-3.21 (m, 2H), 2.99-2.64 (m, 6H), 1.81-1.75 (m, 6H). |
| 71 | X = H<br>Y = Cl | 4-chlorobenzyl | phenyl | -C(O)-(4-pyrrolidinyl)piperidine | M+ = 598.0<br>¹HNMR (CDCl₃) 9.29 (s, 1H), 7.81 (s, 1H), 7.60 (d, 2H), 7.40 (s, 1H), 7.16-7.12 (m, 3H), 6.99-6.88 (m, 4H), 6.71 (d, 2H), 4.92 (bs, 1H), 4.73 (d, 1H), 2.62-2.50 (m, 6H), 2.20-2.11 (m, 1H), 1.84-1.67 (m, 10 H). |
| 72 | X = H<br>Y = Cl | 4-chlorobenzyl | phenyl | -C(O)-N-acetylpiperazine | M + H = 573.8<br>Bt_ret = 2.05 min |

-continued

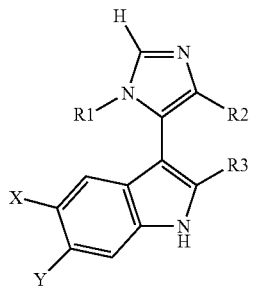

| Example | X and Y | R¹ | R² | R³ | Analysis MS/HPLC/NMR |
|---|---|---|---|---|---|
| 73 | X = H<br>Y = Cl | 4-Cl-benzyl | phenyl | 3-oxopiperazin-1-yl carbonyl | M + H = 545.7<br>$_B t_{ret}$ = 2.06 min |
| 74 | X = H<br>Y = Cl | 4-Cl-benzyl | phenyl | 4-(2-hydroxyethyl)piperazin-1-yl carbonyl | M+ = 573.90<br>$_B t_{ret}$ = 2.03 min |
| 75 | X = H<br>Y = Cl | 4-Cl-benzyl | phenyl | 3-(hydroxymethyl)pyrrolidin-1-yl carbonyl | M + H = 546.8<br>$_B t_{ret}$ = 2.09 min |
| 76 | X = H<br>Y = Cl | 4-Cl-benzyl | phenyl | 3-(dimethylamino)pyrrolidin-1-yl carbonyl | M+ = 557.9<br>$_B t_{ret}$ = 1.99 min |
| 77 | X = H<br>Y = Cl | 4-Cl-benzyl | phenyl | N-[2-(3-oxopiperazin-1-yl)ethyl]carboxamide | M+ = 586.9<br>$_B t_{ret}$ = 1.99 min |
| 78 | X = H<br>Y = Cl | 4-Cl-benzyl | phenyl | (3S)-3-hydroxypyrrolidin-1-yl carbonyl | M + H = 532.7<br>$_B t_{ret}$ = 2.09 min |
| 79 | X = H<br>Y = Cl | 4-Cl-benzyl | phenyl | (3R)-3-hydroxypyrrolidin-1-yl carbonyl | M + H = 532.7<br>$_B t_{ret}$ = 2.11 min |

-continued

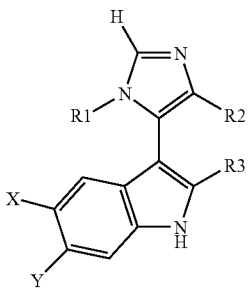

| Example | X and Y | R¹ | R² | R³ | Analysis MS/HPLC/NMR |
|---|---|---|---|---|---|
| 80 | X = H, Y = Cl | 4-Cl-benzyl | phenyl | (3R)-3-aminopyrrolidin-1-yl carbonyl | M+ = 529.9; $_B t_{ret}$ = 1.99 min |
| 81 | X = H, Y = Cl | 4-Cl-benzyl | phenyl | 3-(ethylamino)pyrrolidin-1-yl carbonyl | M+ = 558.0; $_C t_{Ret}$ = 5.56 min |
| 82 | X = H, Y = Cl | 4-Cl-benzyl | phenyl | 3-(N-methyl-acetamido)pyrrolidin-1-yl carbonyl | M+ = 586.0; $_C t_{Ret}$ = 6.07 min |
| 83 | X = H, Y = Cl | 4-Cl-benzyl | phenyl | N-[2-(4-acetylpiperazin-1-yl)ethyl]carboxamide | M+ = 615.0; $_A t_{Ret}$ = 3.71 min |
| 84 | X = F, Y = Cl | 4-Cl-benzyl | phenyl | N-[2-(4-methylpiperazin-1-yl)ethyl]carboxamide | M+ = 607.2; $_A t_{Ret}$ = 3.65 min |
| 85 | X = F, Y = Cl | 4-Cl-benzyl | phenyl | (3S)-3-(dimethylamino)pyrrolidin-1-yl carbonyl | M+ = 578.3; $_A t_{Ret}$ = 3.72 min |

-continued

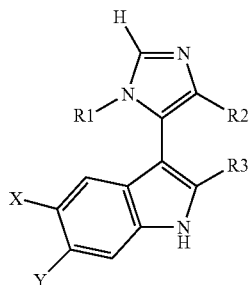

| Example | X and Y | R¹ | R² | R³ | Analysis MS/HPLC/NMR |
|---|---|---|---|---|---|
| 86 | X = F<br>Y = Cl | 4-Cl-benzyl | phenyl | 4-(pyrrolidin-1-yl)piperidine-1-carbonyl | M+ = 618.2<br>$_A t_{Ret}$ = 3.85 min |
| 87 | X = F<br>Y = Cl | 4-Cl-benzyl | phenyl | N-[2-(1,1-dioxo-thiomorpholin-4-yl)ethyl]carbamoyl | M+ = 642.1<br>$_A t_{Ret}$ = 3.95 min |
| 88 | X = H<br>Y = Cl | 4-Cl-benzyl | phenyl | (3S)-3-aminopyrrolidine-1-carbonyl | M+ = 529.9<br>$_B t_{ret}$ = 2.05 min |
| 89 | X = H<br>Y = Cl | 4-Cl-benzyl | phenyl | (3S)-3-morpholinopyrrolidine-1-carbonyl | M+ = 599.9<br>$_B t_{ret}$ = 1.99 min |
| 90 | X = H<br>Y = Cl | 4-Br-benzyl | phenyl | N-[2-(4-methylpiperazin-1-yl)ethyl]carbamoyl | M+ = 634.2<br>$_A t_{Ret}$ = 3.64 min |
| 91 | X = H<br>Y = Cl | 4-Cl-benzyl | phenyl | (3S)-3-(pyrrolidin-1-yl)pyrrolidine-1-carbonyl | M+ = 584.6<br>$_B t_{ret}$ = 2.04 min |

-continued

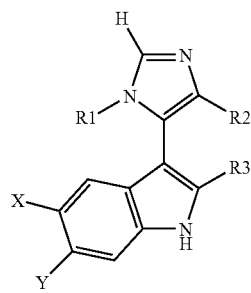

| Example | X and Y | R¹ | R² | R³ | Analysis MS/HPLC/NMR |
|---|---|---|---|---|---|
| 92 | X = F, Y = Cl | 4-Cl-C₆H₄-CH₂- | phenyl | 1-acyl-piperidin-4-yl-imidazolidin-2-one | M− = 631.3, $^A t_{Ret}$ = 4.18 min |
| 93 | X = F, Y = Cl | 4-Cl-C₆H₄-CH₂- | phenyl | 1-acyl-4-(4-methylpiperazin-1-yl)piperidine | M− = 643.0, $^A t_{Ret}$ = 3.69 min |
| 94 | X = H, Y = Cl | 4-Cl-C₆H₄-CH₂- | phenyl | N-(2-(4-(2-hydroxyethyl)piperazin-1-yl)ethyl)amide | M − H = 651.2, $_B t_{ret}$ = 2.00 min |
| 95 | X = H, Y = Cl | 4-Cl-C₆H₄-CH₂- | phenyl | 1-acyl-3-(4-(dimethylamino)piperidin-1-yl)pyrrolidine | M+ = 641.0, $_B t_{ret}$ = 1.96 min |
| 96 | X = H, Y = Cl | 4-Cl-C₆H₄-CH₂- | phenyl | 1-acyl-pyrrolidine | M+ = 515.1, $_B t_{ret}$ = 2.13 min |

-continued

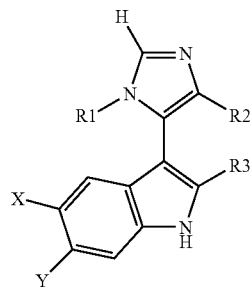

| Example | X and Y | R¹ | R² | R³ | Analysis MS/HPLC/NMR |
|---|---|---|---|---|---|
| 97 | X = H<br>Y = Cl | 4-chlorobenzyl | phenyl | 4-(1,1-dioxo-thiomorpholinyl)carbonyl | M+ = 578.8<br>$_B t_{ret}$ = 2.13 min |
| 98 | X = F<br>Y = Cl | 5-chloro-2-(2-pyrrolidin-1-ylethoxy)benzyl | phenyl | H | M+ = 549.0<br>$_A t_{Ret}$ = 3.87 min |
| 99 | X = F<br>Y = Cl | 5-chloro-2-methoxybenzyl | phenyl | H | M+ = 466.0<br>$_A t_{Ret}$ = 4.63 min |
| 100 | X = H<br>Y = Cl | 4-chlorobenzyl | pyridyl | 4-(dimethylamino)butylaminocarbonyl | M+ = 560.0<br>$_C t_{Ret}$ = 5.57 min |
| 101 | X = H<br>Y = Cl | 4-chlorobenzyl | phenyl | 3-[methyl(3-dimethylaminopropyl)amino]pyrrolidin-1-ylcarbonyl | M − H = 637.1<br>$_C t_{ret}$ = 5.46 min |

-continued

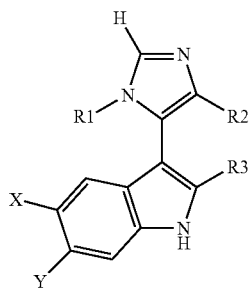

| Example | X and Y | R¹ | R² | R³ | Analysis MS/HPLC/NMR |
|---|---|---|---|---|---|
| 102 | X = F<br>Y = Cl | 4-chlorobenzyl | phenyl | -C(O)NH-(CH₂)₃-pyrrolidin-1-yl | M+ = 591.5<br>$^A t_{Ret}$ = 3.89 min |
| 103 | X = F<br>Y = Cl | 4-chlorobenzyl | phenyl | -C(O)NH-(CH₂)₃-morpholin-4-yl | M+ = 606.0<br>$^A t_{Ret}$ = 3.78 min |
| 104 | X = F<br>Y = Cl | 4-chloro-2-(2-methoxyethoxy)benzyl | phenyl | H | M+ = 510.0<br>$^A t_{Ret}$ = 4.65 min |
| 105 | X = F<br>Y = Cl | 4-chloro-2-(3-methoxypropoxy)benzyl | phenyl | H | M+ = 524.0<br>$^A t_{Ret}$ = 4.75 min |
| 106 | X = F<br>Y = Cl | 1-(4-fluorophenyl)ethyl | phenyl | H | M+ = 434.1<br>$^A t_{Ret}$ = 4.45 min |

-continued

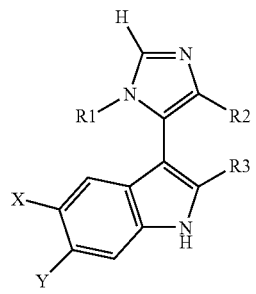

| Example | X and Y | R¹ | R² | R³ | Analysis MS/HPLC/NMR |
|---|---|---|---|---|---|
| 107 | X = F<br>Y = Cl | 5-Cl-2-HO-benzyl | phenyl | H | M+ = 452.0<br>$_A t_{Ret}$ = 4.36 min |
| 108 | X = F<br>Y = Cl | 1-(4-Br-phenyl)ethyl | phenyl | H | M+ = 495.8<br>$_A t_{Ret}$ = 4.65 min |
| 109 | X = H<br>Y = Cl | 4-Cl-benzyl | phenyl | -C(O)-N(CH₃)-CH₂CH₂CH₂-N(CH₃)₂ | M − H = 558.1<br>$_B t_{ret}$ = 2.01 min |
| 110 | X = H<br>Y = Cl | 4-Cl-benzyl | phenyl | -C(O)-NH-CH₂CH₂-N(CH₃)₂ | M − H = 530.2<br>$_B t_{ret}$ = 2.01 min |
| 111 | X = H<br>Y = Cl | 4-Cl-benzyl | phenyl | -C(O)-NH-CH₂CH₂CH₂-N(CH₃)₂ | M − H = 544.2<br>$_B t_{ret}$ = 2.00 min |

-continued

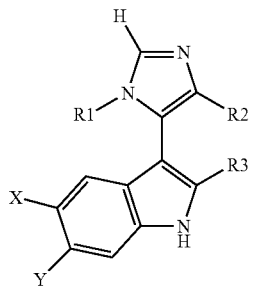

| Example | X and Y | R¹ | R² | R³ | Analysis MS/HPLC/NMR |
|---|---|---|---|---|---|
| 112 | X = H<br>Y = Cl | 4-chlorobenzyl | phenyl | C(O)NH-tBu | M + H = 518.8<br>$_B t_{ret}$ = 2.17 min |
| 113 | X = F<br>Y = Cl | 4-chloro-2-(2-hydroxyethoxy)benzyl | phenyl | H | M+ = 496.0<br>$_A t_{Ret}$ = 4.32 min |
| 114 | X = F<br>Y = Cl | 4-chloro-2-(3-hydroxypropoxy)benzyl | phenyl | H | M+ = 510.0<br>$_A t_{Ret}$ = 4.35 min |
| 115 | X = F<br>Y = Cl | 4-chloro-2-(2-dimethylaminoethoxy)benzyl | phenyl | H | M+ = 523.0<br>$_A t_{Ret}$ = 4.81 min |
| 116 | X = F<br>Y = Cl | 4-chloro-2-(3-methoxypropylamino)benzyl | phenyl | H | M+ = 523.0<br>$_A t_{Ret}$ = 4.81 min |

-continued
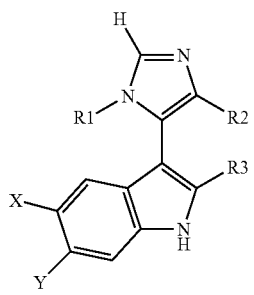
| Example | X and Y | R¹ | R² | R³ | Analysis MS/HPLC/NMR |
|---|---|---|---|---|---|
| 117 | X = F<br>Y = Cl | 5-Cl-2-(NHCH₂CH₂OCH₃)benzyl | phenyl | H | M+ = 509.0<br>$_A t_{Ret}$ = 4.71 min |
| 118 | X = F<br>Y = Cl | 5-Cl-2-(NHCH₂CH₂OH)benzyl | phenyl | H | M+ = 495.0<br>$_A t_{Ret}$ = 4.35 min |
| 119 | X = F<br>Y = Cl | 5-Cl-2-(NHCH₂CH₂CH₂OH)benzyl | phenyl | H | M+ = 509.0<br>$_A t_{Ret}$ = 4.39 min |
| 120 | X = F<br>Y = Cl | 5-Cl-2-(NHCH₂CH₂N(CH₃)₂)benzyl | phenyl | H | M+ = 522.1<br>$_A t_{Ret}$ = 3.88 min |

-continued

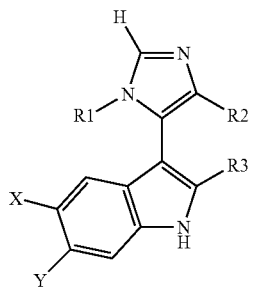

| Example | X and Y | R¹ | R² | R³ | Analysis MS/HPLC/NMR |
|---|---|---|---|---|---|
| 121 | X = H<br>Y = Cl | 4-Cl-benzyl | phenyl | C(O)N(CH₃)₂ | M − H = 488.1<br>¹HNMR (CDCl₃) 9.01 (s, 1H), 7.79 (s, 1H), 7.60 (d, 2H), 7.41 (s, 1H), 7.21-7.17 (m, 3H), 7.03 (d, 2H), 6.97 (s, 2H), 6.79 (d, 2H), 4.89 (d, 1H), 4.79 (d, 1H), 1.59 (s, 1H). |
| 122 | X = H<br>Y = Cl | 4-Cl-benzyl | phenyl | C(O)N(CH₃)CH₂CH₂N(CH₃)₂ | M − H = 544.2<br>¹HNMR (CDCl₃) 7.64 (s, 1H), 7.51 (d, 2H), 7.39 (s, 1H), 7.18-7.03 (m, 6H), 6.98-6.87 (m, 4H), 5.00 (s, 2H), 2.82-2.75 (m2H), 2.59-2.41 (m5H), 1.58 (s, 6H). |
| 123 | X = H<br>Y = Cl | 4-Cl-benzyl | phenyl | C(O)-azetidinyl | M + H = 502.8<br>$_B t_{ret}$ = 2.10 min |
| 124 | X = H<br>Y = Cl | 4-Cl-benzyl | phenyl | C(O)-(3-(4-methylpiperazin-1-yl)pyrrolidin-1-yl) | M − H = 613.0<br>$_C t_{Ret}$ = 5.60 min |
| 125 | X = H<br>Y = Cl | 4-Cl-benzyl | phenyl | C(O)-(3-(4-(2-hydroxyethyl)piperazin-1-yl)pyrrolidin-1-yl) | M − H = 641.3<br>$_B t_{ret}$ = 1.98 min |

-continued

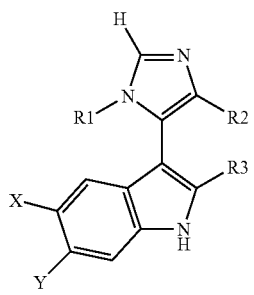

| Example | X and Y | R¹ | R² | R³ | Analysis MS/HPLC/NMR |
|---|---|---|---|---|---|
| 126 | X = H<br>Y = Cl | 4-chlorobenzyl | phenyl | 1-acyl-3-(3-(dimethylamino)propylamino)pyrrolidine | M+ = 615.0<br>$c_{t_{Ret}}$ = 5.46 min |
| 127 | X = H<br>Y = Cl | 4-chlorobenzyl | phenyl | 1-acyl-3-(N-methyl-N-(2-(dimethylamino)ethyl)amino)pyrrolidine | M − H = 613.3<br>$_B t_{ret}$ = 1.98 min |
| 128 | X = H<br>Y = Cl | 4-chlorobenzyl | phenyl | 1-acyl-3-(1,1-dioxothiomorpholin-4-yl)pyrrolidine | M − H = 646.2<br>$_B t_{ret}$ = 1.99 min |
| 129 | X = H<br>Y = Cl | 4-chlorobenzyl | pyridyl | 1-acyl-3-(diethylamino)pyrrolidine | M − H = 584.2<br>$_B t_{ret}$ = 2.01 min |
| 130 | X = H<br>Y = CN | 4-chlorobenzyl | phenyl | N-(2-(4-methylpiperazin-1-yl)ethyl)amide | M+ = 578.1<br>$_A t_{Ret}$ = 3.35 min |

-continued

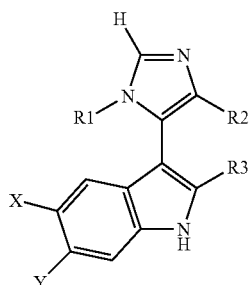

| Example | X and Y | R¹ | R² | R³ | Analysis MS/HPLC/NMR |
|---|---|---|---|---|---|
| 131 | X = H, Y = CN | 4-chlorobenzyl | phenyl | (3R)-1-acyl-3-(dimethylamino)pyrrolidine | M+ = 549.1, $_A t_{Ret}$ = 3.36 min |
| 132 | X = F, Y = Cl | 4-chlorobenzyl | 2-methylphenyl | H | M+ = 451.9, $_A t_{Ret}$ = 4.60 min |
| 133 | X = F, Y = Cl | 1-(4-methylphenyl)ethyl | phenyl | H | M+ = 430.0, $_C t_{Ret}$ = 6.56 min |
| 134 | X = H, Y = Cl | 1-(4-chlorophenyl)ethyl | phenyl | -C(O)NH-CH₂CH₂-(4-methylpiperazin-1-yl) | M+ = 601.0, $_A t_{Ret}$ = 3.79 min |
| 135 | X = F, Y = Cl | (1H-indol-6-yl)methyl | phenyl | H | M+ = 441.0, $_C t_{Ret}$ = 6.26 min |
| 136 | X = F, Y = Cl | (benzothiophen-5-yl)methyl | phenyl | H | M+ = 458.0, $_C t_{Ret}$ = 6.46 min |

(in the table, the tip of the arrow means the end of the bond at which the respective moiety is bound to the rest of the molecule in the formula; for example, if $R^1$ has the formula

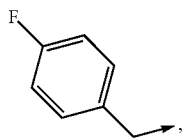

then the corresponding compound has the formula

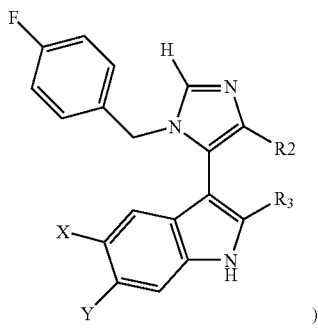

)

Intermediate 10.1

6-Chloro-5-fluoro-1H-indole-3-carbaldehyde

The title compound is synthesized by formylation of 6-chloro-5-fluoro-1H-indole analogously to the preparation of Intermediate 1.1 as a white solid; ES-MS: M+=198.0; HPLC: $_A t_{Ret}$=3.98 min.

Intermediate 16.1

1-Chloro-2-fluoro-3-[isocyano-(toluene-4-sulfonyl)-methyl]-benzene

Intermediate 16.1 is prepared in analogy to a published literature procedure (*Chem. Lett.* 1988, 9, 1531-1534). POCl₃ (0.33 mL, 3.66 mmol) is added to a solution of Intermediate 16.2 (500 mg, 1.46 mmol) in THF (7 mL) at 0° C. After 30 min, Et₃N (1.32 mL, 9.51 mmol) is added to the reaction mixture, then the mixture is stirred for additional 1 h and then quenched by H₂O, EtOAc is added and the organic layer is washed with brine, dried over MgSO₄ and evaporated in vacuo. Silica gel flash chromatography of the residue affords the title compound as a colorless powder; ES-MS: M+H=325.0; HPLC: $_A t_{Ret}$=5.03 min.

Intermediate 16.2

N-[(3-Chloro-2-fluoro-phenyl)-(toluene-4-sulfonyl)-methyl]-formamide

Intermediate 16.2 is prepared in analogy to a published literature procedure (*Chem. Lett.* 1988, 9, 1531-1534). A mixture of 3-chloro-2-fluorobenzaldehyde (2.00 g, 12.6 mmol), p-toluenesulfinic acid (2.96 g, 18.9 mmol), TMSCl (1.75 mL, 13.9 mmol) and formamide (1.25 mL, 31.5 mmol) in toluene (7 mL) and CH₃CN (7 mL) is heated at 50° C. for 5h. After completion, the reaction mixture is quenched by H₂O, EtOAc is added and the organic layer is washed with brine, dried over MgSO₄ and evaporated in vacuo. Silica gel flash chromatography of the residue affords the title compound as a colorless powder; HPLC: $_A t_{Ret}$=4.21 min; ¹HNMR (CDCl₃) 8.18 (s, 1H), 7.72 (d, 2H), 7.50-7.45 (m, 1H), 7.40-7.30 (m, 3H), 7.20-7.10 (m, 1H), 7.00 (d, 1H), 6.60 (d, 1H), 2.45 (s, 3H).

Intermediate 17.1

3-Formyl-1H-indole-6-carbonitrile

The title compound is synthesized by formylation of 1H-indole-6-carbonitrile analogously to the preparation of Intermediate 1.1 as a white solid; ES-MS: M−H=169.0; HPLC: $_C t_{Ret}$=4.96 min.

Intermediate 18.1

5,6-Difluoro-1H-indole-3-carbaldehyde

The title compound is synthesized by formylation of 5,6-difluoro-1'-1-Indole analogously to the preparation of Intermediate 1.1 as a white solid; ES-MS: M−H=180.0; HPLC: $_C t_{Ret}$=5.47 min.

Intermediate 25.1

(S)-2-Amino-2-(4-chloro-phenyl)-ethanol

A mixture of L-4-chloro-phenylglycine (1.74 g, 9.37 mmol) and LAH (712 mg, 18.75 mmol) in THF (40 mL) is refluxed for 1.5 h. After completion, the reaction mixture is quenched by Na₂SO₄.10H₂O and the product is isolated by filtration with Celite, washed with THF and dried under reduced pressure to give the title compound as oil; HPLC: $_A t_{Ret}$=1.46 min; ¹HNMR (DMSO-d₆) 7.35 (d, 2H), 7.30 (d, 2H), 4.80 (bs, 1H), 3.85-3.80 (m, 1H), 3.45-3.20 (m, 2H), 1.85 (bs, 2H).

Intermediate 32.1

(R)-2-Amino-2-(4-chloro-phenyl)-ethanol

The title compound is synthesized by reduction of D-4-chloro-phenylglycine analogously to the preparation of Intermediate 25.1 as a colorless oil; ES-MS: HPLC: $_A t_{Ret}$=1.47 min; ¹HNMR (DMSO-d₆) 7.35 (d, 2H), 7.30 (d, 2H), 4.80 (bs, 1H), 3.85-3.80 (m, 1H), 3.45-3.20 (m, 2H), 1.85 (bs, 2H).

Example 43 is prepared in analogy to a published literature procedure (*J. Med. Chem.* 1989, 32, 1728-1732). A mixture of Intermediate 43.1 (102 mg, 0.16 mmol) and hydrazine hydrate (12 mg, 0.24 mmol) in EtOH (0.8 mL) is refluxed for 2h, After completion, the reaction mixture is quenched by H₂O, EtOAc is added and the organic layer is washed with brine, dried over MgSO₄ and evaporated in vacuo. Silica gel flash chromatography of the residue affords the title compound as a colorless powder.

Intermediate 43.1

6-Chloro-3-[3-(4-chloro-benzyl)-5-phenyl-3H-imidazol-4-yl]-1H-indole-2-carboxylic acid [2-(1,3-dioxo-1,3-dihydro-isoindol-2-yl)-ethyl]-amide (also a compound of the formula I)

The title compound is synthesized by condensation of Intermediate 2.1 and 2-(2-aminoethyl)-isoindole-1,3-dione analogously to the preparation of Example 2 as a colorless solid; ES-MS: M+=636.1; HPLC: $_At_{Ret}$=4.64 min.

Example 44 is prepared in analogy to a published literature procedure (J. Med. Chem. 2003, 46, 3957-3960). A solution of Intermediate 44.1 (97 mg, 0.14 mmol) in dioxane (0.5 mL) is treated with 4M dioxane solution of HCl (4 mL) for 14 h. After completion, the reaction mixture is quenched by saturated aqueous NaHCO$_3$, EtOAc is added and the organic layer is washed with brine, dried over MgSO$_4$ and evaporated in vacuo. Silica gel flash chromatography of the residue affords the title compound as a colorless powder.

Example 45, 49, 80 and 88 are also prepared in analogy to Example 44.

Intermediate 44.1

4-[2-({6-Chloro-3-[3-(4-chloro-benzyl)-5-phenyl-3H-imidazol-4-yl]-1H-indole-2-carbonyl}-amino)-ethyl]-piperazine-1-carboxylic acid tert-butyl ester (also a compound of the formula I)

The title compound is synthesized by condensation of Intermediate 2.1 and 4-(2-aminoethyl)-piperazine-1-carboxylic acid tert-butyl ester analogously to the preparation of Example 2 as a colorless solid; ES-MS: M+=675.3; HPLC: $_At_{Ret}$=4.29 min.

Intermediate 45.1

4-[3-({6-Chloro-3-[3-(4-chloro-benzyl)-5-phenyl-3H-imidazol-4-yl]-1H-indole-2-carbonyl}-amino)-propyl]-piperazine-1-carboxylic acid tert-butyl ester (also a compound of the formula I)

The title compound is synthesized by condensation of Intermediate 2.1 and 4-(3-aminopropyl)-piperazine-1-carboxylic acid tert-butyl ester analogously to the preparation of Example 2 as a colorless solid; ES-MS: M+=689.3; HPLC: $_At_{Ret}$=4.24 min.

Intermediate 49.1

4-({6-Chloro-3-[3-(4-chloro-benzyl)-5-phenyl-3H-imidazol-4-yl]-1H-indole-2-carbonyl}amino)-piperidine-1-carboxylic acid tert-butyl ester (also a compound of the formula I)

The title compound is synthesized by condensation of Intermediate 2.1 and 4-amino-piperidine-1-carboxylic acid tert-butyl ester analogously to the preparation of Example 2 as a colorless solid; ES-MS: M+=643.7; HPLC: $_At_{Ret}$=4.88 min.

Example 56 is prepared in analogy to a published literature procedure (J. Org. Chem. 2006, 71, 1442-1448). A solution of Intermediate 56.1 (142 mg, 0.22 mmol) in DCM (1.5 mL) is treated with 1M THF solution of TBAF (0.45 mL) for 47 h. After completion, the reaction mixture is quenched by saturated aqueous NaHCO$_3$, EtOAc is added and the organic layer is washed with brine, dried over MgSO$_4$ and evaporated in vacuo. Silica gel flash chromatography of the residue affords the title compound as a colorless powder.

Example 57 is also prepared in analogy to Example 56.

Intermediate 56.1

6-Chloro-3-[3-(4-chloro-benzyl)-5-phenyl-3H-imidazol-4-yl]-1H-indole-2-carboxylic acid [2-(tert-butyl-dimethyl-silanyloxy)-ethyl]-amide (also a compound of the formula I)

The title compound is synthesized by condensation of Intermediate 2.1 and 2-(tert-butyldimethyl-silanyloxy)-ethylamine analogously to the preparation of Example 2 as a colorless solid; ES-MS: M+=619.0; HPLC: $_Ct_{Ret}$=7.37 min.

Intermediate 56.2

2-(tert-Butyl-dimethyl-silanyloxy)-ethylamine

A mixture of ethanolamine (0.5 mL, 8.1 mmol), tert-butyldimethylchlorosilane (1.42 g, 8.9 mmol), Et$_3$N (1.25 mL, 8.9 mmol) and DMAP (51 mg, 0.41 mmol) in DCM (25 mL) is stirred at RT for 18 h. The reaction mixture is quenched by H$_2$O, DCM is added and the organic layer is washed with brine, dried over MgSO$_4$ and evaporated in vacuo. Silica gel flash chromatography of the residue affords the title compound as a colorless oil; ES-MS: M+=176.2; $^1$HNMR (CDCl$_3$) 3.95-3.85 (m, 2H), 3.15-3.10 (m, 2H), 0.90 (s, 9H), 0.05 (s, 6H), NH$_2$ is missing.

Intermediate 57.1

6-Chloro-3-[3-(4-chloro-benzyl)-5-phenyl-3H-imidazol-4-yl]-1H-indole-2-carboxylic acid [3-(tert-butyl-dimethyl-silanyloxy)-propyl]-amide (also a compound of the formula I)

The title compound is synthesized by condensation of Intermediate 2.1 and 2-(tert-butyldimethyl-silanyloxy)-propylamine analogously to the preparation of Example 2 as a colorless solid; ES-MS: M+=633.0; HPLC: $_Ct_{Ret}$=7.52 min.

Intermediate 57.2

2-(tert-Butyl-dimethyl-silanyloxy)-propylamine

The title compound is synthesized by condensation of 3-amino-1-propanol and tert-butyldimethylchlorosilane analogously to the preparation of Intermediate 56.2 as a colorless oil; ES-MS: M+=190.2; $^1$HNMR (CDCl$_3$) 3.80-3.70 (m, 2H), 3.10-3.05 (m, 2H), 1.95-1.85 (m, 2H), 0.90 (s, 9H), 0.03 (s, 6H), NH$_2$ is missing.

Intermediate 80.1

((S)-1-{6-Chloro-3-[3-(4-chloro-benzyl)-5-phenyl-3H-imidazol-4-yl]-1H-indole-2-carbonyl}-pyrrolidin-3-yl)-carbamic acid tert-butyl ester (also a compound of the formula I)

The title compound is synthesized by condensation of Intermediate 2.1 and (S)-pyrrolidin-3-yl-carbamic acid tert-butyl ester analogously to the preparation of Example 2 as a colorless solid; ES-MS: M+H=531.8; HPLC: $_Bt_{Ret}$=2.17 min.

Intermediate 84.1

6-Chloro-3-[3-(4-chloro-benzyl)-5-phenyl-3H-imidazol-4-yl]-5-fluoro-1H-indole-2-carboxylic acid (also a compound of the formula I)

The title compound of is synthesized by hydrolysis of Intermediate 84.2 analogously to the preparation of Intermediate 2.1 as a colorless solid; ES-MS: M+=480.0; HPLC: $_At_{Ref}$=4.23 min.

Intermediate 84.2

6-Chloro-3-[3-(4-chloro-benzyl)-5-phenyl-3H-imidazol-4-yl]-5-fluoro-1H-indole-2-carboxylic acid methyl ester (Also a Compound of the Formula I)

The title compound is synthesized by condensation of Intermediate 84.3, 4-chlorobenzyl-amine and 1-(isocyano-phenyl-methanesulfonyl)-4-methyl-benzene analogously to the preparation of Intermediate 2.2 as a colorless solid; ES-MS: HPLC: $_At_{Ref}$=4.51 min; $^1$HNMR (DMSO-d$_6$) 12.5 (s, 1H), 8.05 (s, 1H), 7.58 (d, 1H), 7.35-7.30 (m, 2H), 7.10-7.00 (m, 5H), 6.75-6.65 (m, 3H), 5.00 (d, 1H), 4.85 (d, 1H), 3.65 (s, 3H).

Intermediate 84.3

6-Chloro-5-fluoro-3-formyl-1H-indole-2-carboxylic acid methyl ester

The title compound is synthesized by formylation of Intermediate 84.4 analogously to the preparation of Intermediate 2.3 as a white solid; $_At_{Ref}$4.47 min; $^1$HNMR (DMSO-d$_6$) 13.1 (bs, 1H), 10.5 (s, 1H), 8.05 (d, 1H), 7.70 (d, 1H), 4.00 (s, 3H).

Intermediate 84.4

6-Chloro-5-fluoro-1H-indole-2-carboxylic acid methyl ester

Intermediate 84.4 is prepared in analogy to published literature procedure (*Org. Lett.* 2004, 6, 2953-2956.). A mixture of Intermediate 84.5 (330 mg, 1.08 mmol) and 1M THF solution of TBAF (5.0 mL, 5.0 mmol) is stirred at RT for 1.5 h. The reaction mixture is quenched by saturated aqueous NH$_4$Cl, EtOAc is added and the organic layer is washed with brine, dried over MgSO$_4$ and evaporated in vacuo. Silica gel flash chromatography of the residue affords the title compound as a colorless powder; ES-MS: M-=226.1; HPLC: $_At_{Ref}$=4.71 min.

Intermediate 84.5

6-Chloro-5-fluoro-1-methanesulfonyl-1H-indole-2-carboxylic acid methylester

Intermediate 84.5 is prepared in analogy to published literature procedure (*Org. Lett.* 2004, 6, 2953-2956.). A mixture of Intermediate 84.6 (3.00 g, 8.58 mmol), methyl propiolate (1.4 mL, 17.16 mmol), N-ethyldiisopropylamine (8.8 mL, 51.4 mmol), zinc bromide (5.8 g, 25.7 mmol) and tetrakistriphenylphosphine palladium (300 mg, 0.26 mmol) in dioxane (60 mL) is heated to reflux for 2 h. The reaction mixture is quenched by H$_2$O, EtOAc is added and the organic layer is washed with brine, dried over MgSO$_4$ and evaporated in vacuo. Silica gel flash chromatography of the residue affords the title compound as a colorless powder; ES-MS: M+=306.0; HPLC: $_At_{Ref}$=4.85 min.

Intermediate 84.6

N-(5-Chloro-4-fluoro-2-iodo-phenyl)-methanesulfonamide

A mixture of 3-chloro-4-fluoroaniline (12.9 g, 88.9 mmol) and NIS (22.0 g, 97.8 mmol) in AcOH (90 mL) is stirred at RT for 1.5 h. After completion, the reaction mixture is quenched by H$_2$O, DCM is added and the organic layer is washed with brine, dried over MgSO$_4$ and evaporated in vacuo. Silica gel flash chromatography of the residue affords 5-chloro-4-fluoro-2-iodoaniline as a colorless powder; HPLC: $_At_{Ref}$=4.75 min; $^1$HNMR (CDCl$_3$) 7.40 (d, 1H), 6.75 (d, 1H), 4.00 (bs, 2H).

MsCl (11.8 mL, 152.0 mmol) is added to a mixture of 5-chloro-4-fluoro-2-iodoaniline (15.8 g, 58.4 mmol) and pyridine (16.5 mL, 204.6 mmol) in DCM (200 mL) at RT, and is heated to 50° C. for 18 h. The reaction mixture is quenched by saturated aqueous NaHCO$_3$, DCM is added and the organic layer is washed with brine. The washing is repeatedly extracted with DCM and combined extracts are washed with brine, dried and concentrated to give N-(5-chloro-4-fluoro-2-iodo-phenyl)-bis-methanesulfonamide as a yellow solid, which is submitted to the next step without further purification.

A mixture of N-(5-chloro-4-fluoro-2-iodo-phenyl)-bis-methanesulfonamide and K$_2$CO$_3$ (10.5 g, 76.0 mmol) in MeOH (100 mL) and THF (100 mL) is stirred at RT for 18 h. The reaction mixture is quenched by saturated aqueous NH$_4$Cl, EtOAc is added and the organic layer is washed with brine, dried over MgSO$_4$ and evaporated in vacuo. Silica gel flash chromatography of the residue affords the title compound as a colorless powder; HPLC: $_At_{Ref}$=4.11 min; $^1$HNMR (DMSO-d$_6$) 9.50 (s, 1H), 7.95 (d, 1H), 7.50 (d, 1H), 3.00 (s, 3H).

Intermediate 88.1

((R)-1-{6-Chloro-3-[3-(4-chloro-benzyl)-5-phenyl-3H-imidazol-4-yl]-1H-indole-2-carbonyl}-pyrrolidin-3-yl)-carbamic acid tert-butyl ester (also a compound of the formula I)

The title compound is synthesized by condensation of Intermediate 2.1 and (R)-pyrrolidin-3-yl-carbamic acid tert-butyl ester analogously to the preparation of Example 2 as a colorless solid; ES-MS: M+H=531.8; HPLC: $_Bt_{Ref}$=2.18 min.

Intermediate 89.1

(S)-4-Pyrrolidin-3-yl-morpholine-2HBr salt

Intermediate 89.1 is prepared in analogy to published literature procedure (*J. Org. Chem.* 1998, 63, 8266-8275.). Intermediate 89.2 is dissolved in a 33% HBr/AcOH solution and heated to reflux for 2.5 h. The reaction is then allowed to cool to RT, whereupon the product precipitates. It is isolated by filtration, subsequently washed with AcOH, EtOAc and dried to give the title compound as a yellow powder. ES-MS: M+H=157.4 (free base); $^1$HNMR (MeOH-d4) δ 4.18-4.01 (m, 2H), 3.99-3.90 (m, 4H), 3.86-3.82 (m, 2H), 3.71-3.62 (m, 2H), 3.48-3.37 (m, 2H), 2.63.2.56 (m2H), 2.42-2.35 (m, 2H).

Intermediate 89.2

4-[(S)-1-(Toluene-4-sulfonyl)-pyrrolidin-3-yl]morpholine

Intermediate 89.3 (1.0 g, 2.5 mmol) is dissolved in morpholine (5 mL) and heated to 85° C. in an oil bath for 12 h. After completion the reaction mixture is allowed to cool to RT, diluted with EtOAc and washed with 4M aqueous NaOH solution. The washing is repeatedly extracted with EtOAc and combined extracts are washed with brine, dried and concentrated to give the title compound as a yellow oil, which is submitted to the next step without further purification. $^1$HNMR (CDCl$_3$) δ 7.78 (d, 2H), 7.58 (d, 2H), 3.69-3.61 (m, 4H), 3.55 (dd, 1H), 3.38 (dd, 1H), 3.29-3.21 (m, 1H), 2.98 (dd, 1H), 2.76 (m, 1H), 2.44 (s, 3H), 2.43-2.21 (m, 4H), 2.02-1.98 (m, 1H), 1.71-1.64 (m, 1H); HPLC: $_B t_{Ret}$=1.87 min.

Intermediate 89.3

R-Prolinol (7.0 g, 80.3 mmol, 1 equiv) is dissolved in DCM (40 mL). Pyridine (33 mL) and DMAP (980 mg, 8.0 mmol, 0.1 equiv) are added at RT and the reaction is cooled in an ice bath followed by addition of TsCl (38.3 g, 200.8 mmol, 2.5 equiv). The reaction is then allowed to reach RT and stirred for 2 days. It is concentrated and suspended with hexanes/diethylether (1:1, 150 mL). The solid product is isolated by filtration and dried. It is subsequently dissolved in diethylether/THF (3:1, 600 mL), washed with brine, dried and concentrated to give the title compound as a light yellow powder. ES-MS: M+H=397.3; HPLC: $_B t_{Ret}$=2.33 min.

Intermediate 90.1

3-[3-(4-Bromo-benzyl)-5-phenyl-3H-imidazol-4-yl]-6-chloro-1H-indole-2-carboxylic acid (Also a Compound of the Formula I)

The title compound is synthesized by hydrolysis of Intermediate 90.2 analogously to the preparation of Intermediate 2.1 as a colorless solid; HPLC: $_A t_{Ret}$=4.28 min.; $^1$HNMR (DMSO-d$_6$) 12.4 (s, 1H), 7.45-7.05 (m, 10H), 6.90 (s, 1H), 6.75 (d, 2H), 5.10 (d, 1H), 4.90 (d, 1H).

Intermediate 90.2

3-[3-(4-Bromo-benzyl)-5-phenyl-3H-imidazol-4-yl]-6-chloro-1H-indole-2-carboxylic acid ethyl ester (Also a Compound of the Formula I)

The title compound is synthesized by condensation of Intermediate 2.3, 4-bromobenzylamine and 1-(isocyano-phenyl-methanesulfonyl)-4-methyl-benzene analogously to the preparation of Intermediate 2.2 as a colorless solid; HPLC: $_A t_{Ret}$=4.71 min.; $^1$HNMR (DMSO-d$_6$) 12.3 (s, 1H), 8.05 (s, 1H), 7.50-7.00 (m, 9H), 6.95 (s, 1H), 6.65 (d, 2H), 5.05 (d, 1H), 4.90 (d, 1H), 4.00 (q, 2H), 1.00 (t, 3H).

Intermediate 91.1

(S)-[1,3']Bipyrrolidinyl-2HBr salt

The title compound is synthesized by condensation of Intermediate 89.3 and pyrrolidine analogously to the preparation of Intermediate 89.1 as a yellow powder; ES-MS: M+H=141.5 (free base); $^1$HNMR (DMSO-d$_6$) δ 9.19 (s, 1H), 4.17-3.99 (m, 1H), 3.69-3-49 (m, 2H), 3.43-3.35 (m, 2H), 3.24-3.19 (m, 1H), 3.18-2.99 (m, 2H), 2.60-2.49 (m, 1H), 2.21-2.10 (m, 1H), 2.05-1.95 (m, 2H), 1.94-1.78 (m, 3H).

Intermediate 94.1

2-[4-(2-Amino-ethyl)-piperazin-1-yl]ethanol

2-{2-[4-(2-Hydroxy-ethyl)-piperazin-1-yl]-ethyl}-isoindole-1,3-dione (370 mg, 1.2 mmol) is dissolved in EtOH (8 mL) and hydrazine hydrate (88 mL, 1.8 mmol) is added at RT. The reaction mixture is then refluxed for 3 h and allowed to cool to RT again. The precipitated product is isolated by filtration, washed subsequently with cold EtOH and dried in HV to give the title compound as a white powder. ES-MS: M+H=174.2. $^1$HNMR (MeOH-d4) δ 4.24 (bs, 2H), 3.41 (t, 2H), 2.62 (t, 2H), 2.54-2.50 (m, 2H), 2-39-2.201 (m, 10H).

Intermediate 94.2

2-{2-[4-(2-Hydroxy-ethyl)-piperazin-1-yl]-ethyl}-isoindole-1,3-dione 2-piperazin 1-yl-ethanol (510 mg, 3.9 mmol) is dissolved in CH$_3$CN (5 mL). N-(2-Bromoethyl)-phthalimid (995 mg, 3.9 mmol) and anhydrous K$_2$CO$_3$ (1.1 g, 7.8 mmol) are added at RT and then the reaction mixture is refluxed for 5 h. The reaction mixture is allowed to cool to RT again and the precipitated crude product is isolated by filtration. It is then purified by flash chromatography (SiO$_2$; DCM/MeOH, gradient 1-5% MeOH) to give the title compound as a white powder.: M+H=304.1; HPLC: $_C t_{Ret}$=1.73 min.

Intermediate 95.1

Dimethyl-((S)-1-pyrrolidin-3-yl-piperidin-4-yl)-amine 2HBr salt

The title compound is synthesized by condensation of Intermediate 89.3 and dimethyl-piperidin-4-yl-amine analogously to the preparation of Intermediate 89.1 as a yellow powder; ES-MS: M+H=198.4 (free base); $^1$HNMR (DMSO-d$_6$) δ 9.87 (s, 1H), 3.99 (m 1H), 3.45-3.34 (m, 5H), 3.23-2.95 (m, 4H), 2.48-2.03 (m, 4H), 1.99-1.78 (m, 2H).

Intermediate 98.1

4-Chloro-2-(2-pyrrolidin-1-yl-ethoxy)-benzylamine

A mixture of 4-chloro-2-fluoro-benzonitrile (869 mg, 5.58 mmol) and 2-pyrrolidin-1-yl-ethanol (0.80 mL, 6.70 mmol) in THF (30 mL) is treated with a 0.5 M toluene solution of KHMDS (13.4 mL, 6.7 mmol) at 0° C. After completion of the reaction at RT, the reaction mixture is quenched by H$_2$O. EtOAc is added and the organic layer is washed with brine, dried over MgSO$_4$. Concentration in vacuo affords the corresponding 4-chloro-2-(2-pyrrolidin-1-ylethoxy)-benzonitrile. A THF (7 mL) solution of 4-chloro-2-(2-pyrrolidin-1-yl-ethoxy)-benzonitrile is added to a suspension of LAH (293 mg, 7.71 mmol) in THF (50 mL) at 0° C. The reaction is allowed to stir for 2 h at ambient temperature and then quenched by Na$_2$SO$_4$.10H$_2$O, and the product is isolated by filtration with Celite and washed with THF and dried under reduced pressure to give the title compound as oil; ES-MS: M+=255.2; HPLC: $_At_{Ret}$=1.22 min.

Intermediate 99.1

4-Chloro-2-methoxy-benzylamine

The title compound is synthesized by coupling followed by reduction of 4-chloro-2-fluoro-benzonitrile and methanol analogously to the preparation of Intermediate 98.1 as a colorless oil; HPLC: $_At_{Ret}$=2.24 min; $^1$HNMR (CDCl$_3$) δ 7.20-7.10 (m, 1H), 7.00-6.80 (m 2H), 3.90-3.80 (m, 5H), 1.80 (bs, 2H).

Intermediate 101.1

N,N,N'-Trimethyl-N'-(S)-pyrrolidin-3-yl-propane-1,3-diamine 3HBr salt

The title compound is synthesized by condensation of Intermediate 89.3 and N,N,N'-trimethyl-propane-1,3-diamine analogously to the preparation of Intermediate 89.1 as a yellow powder; ES-MS: M+H=186.2 (free base); $^1$HNMR (DMSO-d$_6$) δ 9.19 (s, 1H), 4.09-4.03 (m, 1H), 3.65-3.59 (m, 1H), 3.31-3.02 (m, 5H), 3.83 (s, 3H), 3.79 (s, 6H), 2.42-2.36 (m, 2H), 2.22-2.03 (m, 4H).

Intermediate 104.1

4-Chloro-2-(2-methoxy-ethoxy)-benzylamine

The title compound is synthesized by coupling followed by reduction of 4-chloro-2-fluoro-benzonitrile and 2-methoxy-ethanol analogously to the preparation of Intermediate 98.1 as a colorless solid; ES-MS: M+=216.1; HPLC: $_At_{Ret}$=2.51 min.

Intermediate 106.1

4-Chloro-2-(3-methoxy-propoxy)-benzylamine

The title compound is synthesized by coupling followed by reduction of 4-chloro-2-fluoro-benzonitrile and 3-methoxy-propanol analogously to the preparation of Intermediate 98.1 as a colorless solid; ES-MS: M+=230.1; HPLC: $_At_{Ret}$=2.81 min.

Intermediate 107.1

3-[3-(2-tert-Butoxy-4-chloro-benzyl)-5-phenyl-3H-imidazol-4-yl]-6-chloro-5-fluoro-1H-indole (Also a Compound of the Formula I)

The title compound is synthesized by condensation of Intermediate 10.1, Intermediate 107.2 and 1-(isocyano-phenyl-methanesulfonyl)-4-methyl-benzene analogously to the preparation of Example 1 as a colorless solid; ES-MS: M+=508.0; HPLC: $_At_{Ret}$=4.98 min.

Intermediate 107.2

2-tert-Butoxy-4-chloro-benzylamine

The title compound of Intermediate 113.1 is synthesized by coupling followed by reduction of 4-chloro-2-fluoro-benzonitrile and $^t$butanol analogously to the preparation of Intermediate 98.1 as a colorless oil; ES-MS: M+H-$^t$Bu=158.0; HPLC: $_At_{Ret}$=3.19 min.

Intermediate 113.1

2-(2-Aminomethyl-5-chloro-phenoxy)-ethanol

A mixture of 4-chloro-2-fluoro-benzonitrile (1.00 g, 6.43 mmol), ethylene glycol (3.59 mL, 64.3 mmol) and K$_2$CO$_3$ (1.33 g, 9.64 mmol) in DMF (30 mL) is stirred at RT for 12 h. The reaction mixture is quenched by H$_2$O. EtOAc is added and the organic layer is washed with brine, dried over MgSO$_4$. Concentration in vacuo affords the corresponding 4-chloro-2-(2-hydroxy-ethoxy)-benzonitrile. A THF (6 mL) solution of 4-chloro-2-(2-hydroxy-ethoxy)benzonitrile (875 mg, 4.43 mmol) is added to a suspension of LAH (504 mg, 13.2 mmol) in THF (45 mL) at 0° C. The reaction is allowed to stir for 2 h at ambient temperature and then quenched by Na$_2$SO$_4$.10H$_2$O, and the product is isolated by filtration with Celite and washed with THF and dried under reduced pressure to give the title compound as colorless solid; ES-MS: M+=202.1; HPLC: $_At_{Ret}$=1.90 min Intermediate 114.1

3-(2-Aminomethyl-5-chloro-phenoxy)-propan-1-ol

The title compound is synthesized by coupling followed by reduction of 4-chloro-2-fluoro-benzonitrile and 1,3-propane-diol analogously to the preparation of Intermediate 113.1 as a colorless solid; ES-MS: M+=216.1; HPLC: $_At_{Ret}$=2.23 min.

Intermediate 115.1

[2-(2-Aminomethyl-5-chloro-phenoxy)-ethyl]-dimethyl-amine

The title compound is synthesized by coupling followed by reduction of 4-chloro-2-fluoro-benzonitrile and 2-dimethylamino-ethanol analogously to the preparation of Intermediate 113.1. colorless oil; ES-MS: M+=229.2; HPLC: $_At_{Ret}$=1.18 min.

Intermediate 116.1

(2-Aminomethyl-5-chloro-phenyl)-(3-methoxy-propyl)-amine

The title compound is synthesized by coupling followed by reduction of 4-chloro-2-fluoro-benzonitrile and 3-methoxy-propylamine analogously to the preparation of Intermediate 113.1. colorless oil; ES-MS: M−=227.1; HPLC: $_At_{Ret}$=2.97 min.

Intermediate 117.1

(2-Aminomethyl-5-chloro-phenyl)-(2-methoxy-ethyl)-amine

The title compound is synthesized by coupling followed by reduction of 4-chloro-2-fluoro-benzonitrile and 3-methoxy-ethylamine analogously to the preparation of Intermediate 113.1 as a colorless oil; ES-MS: M−=213.2; HPLC: $_At_{Ret}$=2.73 min.

Intermediate 118.1

2-(2-Aminomethyl-5-chloro-phenylamino)-ethanol

The title compound is synthesized by coupling followed by reduction of 4-chloro-2-fluoro-benzonitrile and 2-aminoethanol analogously to the preparation of Intermediate 113.1. colorless powder; ES-MS: M−=199.1; HPLC: $_At_{Ret}$=1.90 min.

Intermediate 119.1

3-(2-Aminomethyl-5-chloro-phenylamino)-propan-1-ol

The title compound is synthesized by coupling followed by reduction of 4-chloro-2-fluoro-benzonitrile and 3-amino-propanol analogously to the preparation of Intermediate 113.1. colorless oil; ES-MS: M−=213.1; HPLC: $_At_{Ret}$=2.27 min.

Intermediate 120.1

N-(2-Aminomethyl-5-chloro-phenyl)-N',N'-dimethyl-ethane-1,2-diamine

The title compound is synthesized by coupling followed by reduction of 4-chloro-2-fluoro-benzonitrile and 2-dimethylamino-ethylamine analogously to the preparation of Intermediate 113.1 as a colorless oil; $^1$HNMR (CDCl$_3$) δ 9.20 (bs, 1H), 7.18-7.10 (m, 2H), 6.95 (d, 1H), 4.60 (s, 2H), 3.80 (s, 2H), 3.25-3.05 (m, 4H), 2.25 (s, 6H); HPLC: $_At_{Ret}$=1.26 min.

Intermediate 124.1

1-Methyl-4-(S)-pyrrolidin-3-yl-piperazine 2HBr salt

The title compound is synthesized by condensation of Intermediate 89.3 and 1-methylpiperazine analogously to the preparation of Intermediate 89.1 as a yellow powder; ES-MS: M+H=170.2 (free base); $^1$HNMR (DMSO-d$_6$) δ 9.48 (s, 1H), 4.76-4.59 (m, 1H), 3.42 (d, 2H), 3.39-3-22 (m, 2H), 3.18-2.82 (m, 6H), 2.79 (s, 3H), 2.43-2.14 (m2H), 2.09-2.03 (m, 1H), 1.79-1.72 (m, 1H).

Intermediate 125.1

2-((S)-4-Pyrrolidin-3-yl-piperazin-1-yl)-ethanol 2HBr salt

The title compound is synthesized by condensation of Intermediate 89.3 and 2-piperazin-1-yl-ethanol analogously to the preparation of Intermediate 89.1 as a yellow powder; ES-MS: M+2H=402.0; $^1$HNMR (MeOH-d$_4$) δ 4.42-4.40 (m, 2H), 3.98-3.94 (m, 1H), 3.79-3.76 (m, 1H), 3.65-3.61 (m, 1H), 3.59-3.39 (m, 6H), 3.21-2.99 (m, 4H), 2.39-2.23 (m, 2H), 2.19-2.14 (m, 2H).

Intermediate 126.1

N,N-Dimethyl-N'-(S)-pyrrolidin-3-yl-propane-1,3-diamine-3HBr salt

The title compound is synthesized by condensation of Intermediate 89.3 and 3-dimethylamino-propylamine analogously to the preparation of Intermediate 89.1 as a yellow powder; ES-MS: ES-MS: M+H=158.1; $^1$HNMR (MeOH-d$_4$) δ 4.29.4.19 (m, 1H), 3.84 (dd, 1H), 3.69-3.60 (m, 3H), 3.49-3.41 (m, 1H), 3.39-3.25 (m, 4H), 2.97 (s, 6H), 2.62-2.57 (m, 1H), 2.42-2.37 (m, 1H), 2.35-2.21 (m, 2H).

Intermediate 127.1

N,N,N'-Trimethyl-N'-(S)-pyrrolidin-3-yl-ethane-1,2-diamine.3HBr salt

The title compound is synthesized by condensation of Intermediate 89.3 and 2-dimethylamino-ethylamine analogously to the preparation of Intermediate 89.1 as a yellow powder; ES-MS: M+H=172.1; $^1$HNMR (MeOH-d$_4$) δ 4.47-4.39 (m, 1H), 3.95-3.94 (m, 1H), 3.81-3.73 (m, 5H), 3.68-3.62 (m, 1H), 3.45-3.38 (m, 1H), 3.08-2.97 (m, 9H), 2.70-2.62 (m, 1H), 2.50-2.43 (m, 1H).

Intermediate 128.1

(S)-4-Pyrrolidin-3-yl-thiomorpholine 1,1-dioxide.2HBr salt

The title compound is synthesized by condensation of Intermediate 89.3 and thiomorpholine 1,1-dioxide analogously to the preparation of Intermediate 89.1 as a yellow powder; ES-MS: M+H=201.5.

Intermediate 129.1

Diethyl-(S)-pyrrolidin-3-yl-amine.2HBr salt

The title compound is synthesized by condensation of Intermediate 89.3 and diethylamine analogously to the preparation of Intermediate 89.1 as a yellow powder; ES-MS: M+H=143.1; $^1$HNMR (MeOH-d$_4$) δ 4.37 (quin, 1H), 3.91-3.83 (m, 1H), 3.69-3.61 (m, 2H), 3.44-3.23 (m, 5H), 2.62-2.58 (m, 1H), 2.39-2.28 (m, 2H), 1.39 (t, 6H).

Intermediate 130.1

3-[3-(4-Chloro-benzyl)-5-phenyl-3H-imidazol-4-yl]-6-cyano-1H-indole-2-carboxylic acid (Which is Also a Compound of the Formula I According to the Invention)

The title compound is synthesized by hydrolysis of Intermediate 130.2 analogously to the preparation of Intermediate 2.1 as a colorless solid; ES-MS: M+=453.1; HPLC: $_At_{Ret}$=3.81 min.

Intermediate 130.2

3-[3-(4-Chloro-benzyl)-5-phenyl-3H-imidazol-4-yl]-6-cyano-1H-indole-2-carboxylic acid methyl ester (Which is Also a Compound of the Formula I According to the Invention)

The title compound is synthesized by condensation of Intermediate 130.3, 4-chlorobenzyl-amine and 1-(isocyano-phenyl-methanesulfonyl)-4-methyl-benzene analogously to the preparation of Intermediate 2.2 as a brown solid; ES-MS: M+=467.1; HPLC: $_At_{Ret}$=4.08 min.

Intermediate 130.3

6-Cyano-3-formyl-1H-indole-2-carboxylic acid methyl ester

The title compound is synthesized by formylation of 6-cyano-1H-indole-2-carboxylic acid methyl ester analogously to the preparation of Intermediate 2.3 as a white solid; ES-MS: M−=227.1; HPLC: $_At_{Ret}$=3.79 min.

Intermediate 132.1

1-[isocyano-(toluene-4-sulfonyl)-methyl]-2-methyl benzene

The title compound is synthesized by condensation of 2-methylbenzaldehyde analogously to the preparation of Intermediate 16.1 as a white solid; ES-MS: M−=284.1; HPLC: $_At_{Ret}$=4.94 min.

Intermediate 134.1

6-Chloro-3-{3-[(S)-1-(4-chloro-phenyl)-ethyl]-5-phenyl-3H-imidazol-4-yl}-1H-indole-2-carboxylic acid (Which is Also a Compound of the Formula I According to the Invention)

The title compound is synthesized by hydrolysis of Intermediate 134.2 analogously to the preparation of Intermediate 2.1 as a colorless solid; ES-MS: M+=476.0; HPLC: $_At_{Ret}$=4.33 min.

Intermediate 134.2

6-Chloro-3-{3-[(S)-1-(4-chloro-phenyl)-ethyl]-5-phenyl-3H-imidazol-4-yl}-1H-indole-2-carboxylic acid ethyl ester (Which is Also a Compound of the Formula I According to the Invention)

The title compound is synthesized by condensation of Intermediate 2.3, (S)-1-(4-chlorophenyl)-ethylamine and 1-(isocyano-phenyl-methanesulfonyl)-4-methyl-benzene analogously to the preparation of Intermediate 2.2 as a brown solid; ES-MS: M+=504.0; HPLC: $_At_{Ret}$=4.77 min.

Example 137

6-Chloro-3-[3-(3,3-dimethyl-butyl)-5-phenyl-3H-imidazol-4-yl]-1H-indole-2-carboxylic acid amide A mixture of Intermediate 137.1 (50 mg, 0.11 mmol) and 7M MeOH solution of ammonia (2 mL, 14 mmol) is heated to 60° C. After completion the reaction mixture is allowed to cool to RT, diluted with EtOAc and washed with brine, dried over MgSO$_4$ and evaporated in vacuo. Silica gel flash chromatography of the residue affords the title compound as a colorless powder; ES-MS: M+=421.1; HPLC: $_At_{Ret}$=4.18 min.

Intermediate 137.1

6-Chloro-3-[3-(3,3-dimethyl-butyl)-5-phenyl-3H-imidazol-4-yl]-1H-indole-2-carboxylic acid ethyl ester (Which is also a Compound of the Formula I According to the Invention)

The title compound is synthesized by condensation of Intermediate 2.3, 3,3-dimethyl-butylamine and 1-(isocyano-phenyl-methanesulfonyl)-4-methyl-benzene analogously to the preparation of Intermediate 2.2 as a colorless solid; ES-MS: M+=450.0; HPLC: $_At_{Ret}$=4.77 min.

Example 138

6-Chloro-3-[3-(3,3-dimethyl-butyl)-5-phenyl-3H-imidazol-4-yl]-1H-indole-2-carboxylic acid amide The title compound is synthesized by condensation of Intermediate 2.2 analogously to the preparation of Example 137 as a colorless solid; ES-MS: M+=462.9; HPLC: $_At_{Ret}$=4.17 min.

Example 139

6-Chloro-3-[3-(4-chloro-benzyl)-5-phenyl-3H-imidazol-4-yl]-2-(1H-tetrazol-5-yl)-1H-indole A mixture of Example 139.1 (37 mg, 0.08 mmol) and sodium azide (16 mg, 0.25 mol) in 2-methoxy-ethanol (0.5 mL) is heated to 130° C. After completion the reaction mixture is allowed to cool to RT, diluted with EtOAc and washed with brine, dried over MgSO$_4$ and evaporated in vacuo. Silica gel flash chromatography of the residue affords the title compound as a colorless powder; ES-MS: M+H=487.9; HPLC: $_At_{Ret}$=4.32 min.

Intermediate 139.1

6-Chloro-3-[3-(4-chloro-benzyl)-5-phenyl-3H-imidazol-4-yl]-1H-indole-2-carbonitrile (At the Same Time a Compound of the Formula I According to the Invention)

A mixture of Example 138 (150 mg, 0.33 mmol) and TFAA (1.5 mL) in DCM (1.5 mL) is heated to reflux. After completion the reaction mixture is quenched by saturated aqueous NaHCO$_3$. DCM is added and the organic layer is washed with brine, dried over MgSO$_4$ and evaporated in vacuo. Silica gel flash chromatography of the residue affords the title compound as a colorless powder; ES-MS: M+H=444.9: $_At_{Ret}$=4.44.

Example 140

{6-Chloro-3-[3-(4-chloro-benzyl)-5-phenyl-3H-imidazol-4-yl]-1H-indol-2-yl}-methanol A mixture of Intermediate 2.2 (470 mg, 0.92 mmol) and LAH (70 mg, 1.84 mmol) in THF (4.8 mL) is stirred at RT for 1 h and then refluxed for 2 h. EtOAc is added and the organic layer is washed with brine, dried over MgSO$_4$ and evaporated in vacuo. Silica gel flash chromatography of the residue affords the title compound as a colorless powder; ES-MS: M+H=449.9; HPLC: $_At_{Ret}$=4.29 min.

Example 141

{6-Chloro-3-[3-(4-chloro-benzyl)-5-phenyl-3H-imidazol-4-yl]-1H-indol-2-ylmethyl}-(2-morpholin-4-yl-ethyl)-amine A mixture of Example 2 (101 mg, 0.18 mmol), AlCl$_3$ (117 mg, 0.88 mmol) and LAH (33 mg, 0.88 mmol) in THF (2 mL) is refluxed. After completion the reaction mixture is quenched by sodium-potassium tartarate and neutralized by saturated aqueous NaHCO$_3$. EtOA is added and the organic layer is washed with brine, dried over MgSO$_4$ and evaporated in vacuo. Silica gel flash chromatography of the residue affords the title compound as a colorless powder; ES-MS: M+H=561.8: $_At_{Ret}$=3.74 min.

Example 142

3-[1-(4-Chloro-benzyl)-5-(6-chloro-5-fluoro-1H-indol-3-yl)-1H-imidazol-4-yl]-phenol A solution of Intermediate 142.1 (40 mg, 0.08 mmol) in DCM (2 mL) is treated by 1M solution of BBr$_3$ (0.34 mL, 0.34 mmol) in DCM at RT and is heated to 40° C. After completion the reaction mixture is quenched by MeOH, and neutralized by saturated aqueous NaHCO$_3$. DCM is added and the organic layer is washed with brine, dried over MgSO$_4$ and evaporated in vacuo. Silica gel flash chromatography of the residue affords the title compound as a colorless powder; ES-MS: M+=452.0: $_At_{Ret}$=4.20

Intermediate 142.1

6-Chloro-3-[3-(4-chloro-benzyl)-5-(3-methoxy-phenyl)-3H-imidazol-4-yl]-5-fluoro-1H-indole (at the Same Time a Compound of the Formula I According to the Invention)

The title compound is synthesized by condensation of Intermediate 10.1, 4-chlorobenzyl-amine and Intermediate 142.2 analogously to the preparation of Intermediate 2.2 as a colorless solid; ES-MS: M+=466.0; HPLC: $_At_{Ret}$=4.55 min.

Intermediate 142.2

1-[isocyano-(toluene-4-sulfonyl)-methyl]-3-methoxy benzene

The title compound is synthesized by condensation of 3-methoxybenzaldehyde analogously to the preparation of Intermediate 16.1 as a colorless solid; $^1$HNMR (DMSO-d$_6$) δ 7.65 (d, 2H), 7.50 (d, 2H), 7.40 (t, 1H), 7.10-7.05 (m, 1H), 6.90-6.80 (m, 3H), 3.70 (s, 3H), 2.40 (s, 3H); HPLC: $_At_{Ret}$=4.75 min.

Example 143

{6-Chloro-3-[3-(4-chloro-benzyl)-5-(3-hydroxy-phenyl)-3H-imidazol-4-yl]-1H-indol-2-yl}-((S)-3-dimethylamino-pyrrolidin-1-yl)-methanone The title compound is synthesized by dealkylation of Intermediate 143.1 analogously to the preparation of Example 142 as a colorless solid; ES-MS: M+=574.0; HPLC: $_At_{Ret}$=3.56 min.

Intermediate 143.1

{6-Chloro-3-[3-(4-chloro-benzyl)-5-(3-methoxy-phenyl)-3H-imidazol-4-yl]-1H-indol-2-yl}-((S)-3-dimethylamino-pyrrolidin-1-yl)-methanone (At the Same Time a Compound of the Formula I According to the Invention)

The title compound is synthesized by condensation of Intermediate 143.2, 4-chlorobenzyl-amine and Intermediate 142.2 analogously to the preparation of Intermediate 2.2 as a colorless solid; ES-MS: M+=588.0; HPLC: $_At_{Ret}$=3.80 min.

Intermediate 143.2

6-Chloro-2-((S)-3-dimethylamino-pyrrolidine-1-carbonyl)-1H-indole-3-carbaldehyde The title compound is synthesized by formylation of Intermediate 143.3 analogously to the preparation of Intermediate 2.3 as a brown solid; ES-MS: M+=320.2; HPLC: $_At_{Ret}$=2.91 min.

Intermediate 143.3

(6-Chloro-1H-indol-2-yl)-((S)-3-dimethylamino-pyrrolidin-1-yl)methanone

The title compound is synthesized by condensation of 6-chloro-1H-indole-2-carboxylic acid and dimethyl-(S)-pyrrolidin-3-yl-amine analogously to the preparation of Example 2 as a colorless solid; ES-MS: M+=292.2; HPLC: $_At_{Ret}$=3.15 min.

Example 144

6-Chloro-3-[3-(4-chloro-benzyl)-2-methyl-5-phenyl-3H-imidazol-4-yl]-1H-indole

Intermediate 144.1 (100 mg, 0.24 mmol) and Intermediate 144.3 (127 mg, 0.29 mmol) are dissolved in 1,2 dimethoxethane (1 mL). Pd(PPh$_3$)$_4$ (14.6 mg, 0.012 mmol), K$_3$PO$_4$ (210 mg, 0.96 mmol) and H$_2$O (0.5 mL) are added, the reaction vessel is sealed and heated to 100° C. for 3 h. The mixture is then allowed to cool to RT and diluted with EtOAc. The organic layer is repeatedly washed with brine and combined aqueous washings are extracted with EtOAc Combined extracts are dried and concentrated to give the crude product which is purified by tituration with hexanes/EtOAc to give the title compound as off-white powder. ES-MS: M+H=590.0, $^1$HNMR (DMSO-d6) δ 8.02 (s, 1H), 7.92 (s, 1H), 7.85 (d, 2H), 7.37 (d, 2H), 7.29-7.26 (m, 2H), 7.12-7.09 (m, 3H), 7.04-7.02 (m, 3H), 6.83 (d, 1H), 6.65 (d, 2H), 4.92 (s, 2H), 2.35 (s, 3H), 2.32 (s, 3H).

Intermediate 144.1

6-Chloro-3-(4,4,5,5-tetramethyl-[1,3,2]dioxaborolan-2-yl)-1-(toluene-4-sulfonyl)-1H-indole Intermediate 144.2 (1.0 g, 2.3 mmol) is dissolved in DMSO (20 mL). Bis(pinacolato)diboron (0.89 g, 3.5 mmol), Pd(dppf)Cl$_2$ (0.21 g, 0.23 mmol) and KOAc (0.68 g, 6.9 mmol) are added. The reaction vessel is sealed and heated with stirring to 100° C. for 2 h. It is allowed to cool to RT again, diluted with EtOAc and the organic layer is repeatedly washed with sat. aqueous NaHCO$_3$ solution. After drying and evaporation of the solvents the crude product is purified by flash chromatography (SiO$_2$; hexanes/EtOAc, gradient 0-30% EtOAc) to give the title compound as a white powder. $^1$HNMR (CDCl$_3$) δ 7.95 (s, 2H), 7.84-7.79 (m, 3H), 7.27-7.20 (m, 3H), 1.35 (s, 12H).

Intermediate 144.2

6-Chloro-3-iodo-1-(toluene-4-sulfonyl)-1H-indole

A mixture of 6-chloro-1H-indole (2.0 g, 13.2 mmol) and NIS (4.45 g, 19.8 mmol) in THF (60 mL) is stirred at 0° C.

After completion the reaction mixture is quenched by H₂O. EtOAc is added and the organic layer is washed with brine, dried over MgSO₄ and evaporated in vacuo. Silica gel flash chromatography of the residue affords 6-chloro-3-iodo-1H-indole as a colorless powder. A mixture of 6-chloro-3-iodo-1H-indole (4.14 g, 13.2 mmol), TsCl (3.77 g, 19.8 mmol), TBAHS (672 mg, 1.98 mmol) and NaOH (16.0 g, 400 mmol) in THF (60 mL) and H₂O (25 mL) is stirred at RT. After completion the reaction mixture is quenched by H₂O. EtOAc is added and the organic layer is washed with brine, dried over MgSO₄ and evaporated in vacuo. Re-crystallization from EtOAc of the residue affords the title compound as a colorless powder; ES-MS: M−H=430.0: $_At_{Ret}$=8.66 min.

Intermediate 144.3

1-(4-Chloro-benzyl)-5-iodo-2-methyl-4-phenyl-1H-imidazole

A mixture of Intermediate 144.4 (1.0 g, 3.53 mmol) and NIS (872 mg, 3.88 mmol) in CH₃CN (18 mL) is stirred at 50° C. After completion the reaction mixture is quenched by H₂O. EtOAc is added and the organic layer is washed with brine, dried over MgSO₄ and evaporated in vacuo. Silica gel flash chromatography of the residue affords the title compound as a colorless powder; ES-MS: M+=409.0: $_At_{Ret}$=4.06 min.

Intermediate 144.4

1-(4-Chloro-benzyl)-2-methyl-4-phenyl-1H-imidazole

A mixture of 2-methyl-4-phenyl-1H-imidazole HCl salt (1.51 g, 7.75 mmol), 4-chlorobenzyl bromide (1.75 g, 8.53 mmol) and NaH (745 mg, 18.6 mmol) in DMF (20 mL) is stirred at RT. After completion the reaction mixture is quenched by H₂O. EtOAc is added and the organic layer is washed with brine, dried over MgSO₄ and evaporated in vacuo. Silica gel flash chromatography of the residue affords the title compound as a colorless powder; ES-MS: M+=283.1: $_At_{Ret}$=3.93 min.

Example 145

6-Bromo-3-[2-chloro-3-(4-chloro-benzyl)-5-phenyl-3H-imidazol-4-yl]-1H-indole-2-carboxylic acid ethyl ester A mixture of Intermediate 2.2 (98 mg, 0.20 mmol) and NBS (39 mg, 0.22 mmol) in THF (1.0 mL) is stirred at RT for 3 h. After completion the reaction mixture is quenched by aqueous saturated NaHCO₃. EtOAc is added and the organic layer is washed with brine, dried over MgSO₄ and evaporated in vacuo. Silica gel flash chromatography of the residue affords the title compound as a colorless powder; ES-MS: M+=569.7: $_At_{Ret}$=5.76 min.

Example 146

6-Chloro-3-[2-chloro-3-(4-chloro-benzyl)-5-phenyl-3H-imidazol-4-yl]-1H-indole-2-carboxylic acid ethyl ester A mixture of Intermediate 2.2 (151 mg, 0.31 mmol) and NCS (90 mg, 0.67 mmol) in THF (1.5 mL) is stirred at 60° C. for 1 h. After completion the reaction mixture is quenched by aqueous saturated NaHCO₃. EtOAc is added and the organic layer is washed with brine, dried over MgSO₄ and evaporated in vacuo. Silica gel flash chromatography of the residue affords the title compound as a colorless powder; ES-MS: M+H=525.8: $_At_{Ret}$=5.83 min.

Table 2 of further Examples:

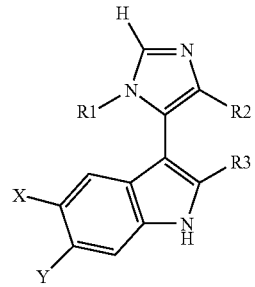

| Example | X and Y | R¹ | R² | R³ | Analysis MS/HPLC/NMR |
|---|---|---|---|---|---|
| 147 | X = H<br>Y = Cl | 4-Cl-benzyl | phenyl | S(=O)₂N(CH₃)— | M+ = 525.0<br>$_At_{Ret}$ = 4.51 min |
| 148 | X = F<br>Y = Cl | 4-Cl-2-(hydroxymethyl)-benzyl | phenyl | H | M + H = 466.0<br>$_Ct_{Ret}$ = 6.07 min |

-continued

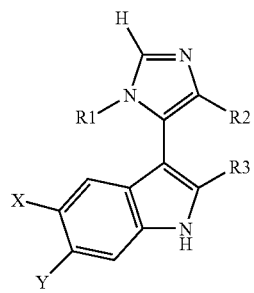

| Example | X and Y | R¹ | R² | R³ | Analysis MS/HPLC/NMR |
|---|---|---|---|---|---|
| 149 | X = H, Y = Cl | 4-chlorophenyl (with stereocenter, methyl) | phenyl | -C(O)NH-CH₂CH₂-piperazine-CH₂CH₂-imidazole | M + H = 681.0, $^C t_{Ret}$ = 5.45 min |
| 150 | X = H, Y = Cl | 4-chlorobenzyl | phenyl | -C(O)NH-CH₂CH₂-(4-ethylpiperazine) | M+ = 601.0, $^A t_{Ret}$ = 3.69 min |
| 151 | X = H, Y = Cl | 4-chlorobenzyl | phenyl | -C(O)NH-CH₂CH₂-(4-isopropylpiperazine) | M+ = 615.0, $^A t_{Ret}$ = 3.67 min |
| 152 | X = H, Y = Cl | 4-chloro-2-(hydroxymethyl)benzyl | phenyl | -C(O)NH-CH₂CH₂-(4-methylpiperazine) | M + H = 617.0, $^C t_{Ret}$ = 5.26 min |
| 153 | X = H, Y = Cl | 4-chloro-2-(hydroxymethyl)benzyl | phenyl | -C(O)-pyrrolidine-NH-CH₂CH₂CH₂-N(CH₃)₂ | M + H = 659.0, $^C t_{Ret}$ = 5.12 min |
| 154 | X = F, Y = Cl | 4-methoxybenzyl | phenyl | H | M + H = 432.1, $^C t_{Ret}$ = 6.18 min |

US 8,053,457 B2

-continued

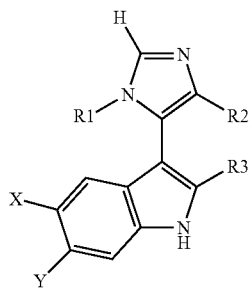

| Example | X and Y | R¹ | R² | R³ | Analysis MS/HPLC/NMR |
|---|---|---|---|---|---|
| 155 | X = H<br>Y = Cl | 4-chlorobenzyl | phenyl | -C(O)NH-CH₂CH₂-piperazinyl-CH₂-(3-pyridyl) | M+ = 664.0<br>$^A t_{Ret}$ = 3.59 min |
| 156 | X = H<br>Y = Cl | 4-chlorobenzyl | phenyl | -C(O)NH-CH₂CH₂-piperazinyl-CH₂CH₂-N(CH₃)₂ | M+ = 643.9<br>$^A t_{Ret}$ = 3.67 min |
| 157 | X = H<br>Y = Cl | 4-chlorobenzyl | phenyl | -C(O)NH-CH₂CH₂-piperazinyl-CH₂CH₂-pyrrolidinyl | M+ = 670.0<br>$^A t_{Ret}$ = 3.66 min |
| 158 | X = H<br>Y = Cl | 4-chlorobenzyl | phenyl | -C(O)NH-CH₂CH₂-piperazinyl-CH₂CH₂CH₂-OCH₃ | M+ = 645.1<br>$^A t_{Ret}$ = 3.77 min |
| 159 | X = H<br>Y = Cl | 4-chlorobenzyl | phenyl | -C(O)NH-CH₂CH₂-piperazinyl-(4-fluorophenyl) | M+ = 666.9<br>$^A t_{Ret}$ = 4.34 min |
| 160 | X = H<br>Y = Cl | 5-chloro-2-(hydroxymethyl)benzyl | phenyl | -C(O)-(3R)-(dimethylamino)pyrrolidinyl | M + H = 588.0<br>$^C t_{Ret}$ = 5.31 min |

-continued

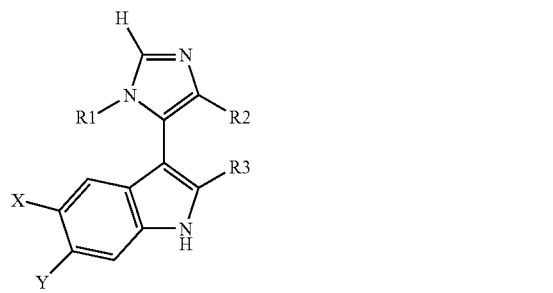

| Example | X and Y | R¹ | R² | R³ | Analysis MS/HPLC/NMR |
|---|---|---|---|---|---|
| 161 | X = H<br>Y = Cl | 4-chlorobenzyl | phenyl | -C(O)NH-CH₂CH₂-N(piperazine)-4-pyridyl | M+ = 650.0<br>$^A t_{Ret}$ = 3.66 min |
| 162 | X = H<br>Y = Cl | 4-chlorobenzyl | phenyl | -C(O)NH-CH₂CH₂-N(piperazine)-CH₂CH₂OCH₃ | M+ = 631.0<br>$^A t_{Ret}$ = 3.69 min |
| 163 | X = H<br>Y = Cl | 4-chlorobenzyl | phenyl | -C(O)NH-CH₂CH₂-N(piperazine)-phenyl | M+ = 648.9<br>$^A t_{Ret}$ = 4.23 min |
| 164 | X = H<br>Y = Cl | 4-chlorobenzyl | phenyl | -C(O)NH-CH₂CH₂-N(piperazine)-2-pyridyl | M+ = 649.9<br>$^A t_{Ret}$ = 3.65 min |
| 165 | X = H<br>Y = Cl | 4-chlorobenzyl | phenyl | -C(O)NH-CH₂CH₂-N(piperazine)-CH₂-phenyl | M+ = 662.9<br>$^A t_{Ret}$ = 3.99 min |
| 166 | X = H<br>Y = Cl | 5-chloro-2-(hydroxymethyl)benzyl | phenyl | -C(O)NH-CH₂CH₂-N(thiomorpholine 1,1-dioxide) | M + H = 651.9<br>$^C t_{Ret}$ = 5.57 min |

-continued

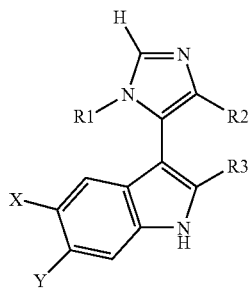

| Example | X and Y | R¹ | R² | R³ | Analysis MS/HPLC/NMR |
|---|---|---|---|---|---|
| 167 | X = H<br>Y = Cl | 4-chlorobenzyl | phenyl | -C(O)NH-CH₂CH₂-N(piperazine)-3-pyridyl | M+ = 649.9<br>$_A t_{Ret}$ = 3.58 min |
| 168 | X = H<br>Y = Cl | 4-chlorobenzyl | phenyl | -C(O)NH-CH₂CH₂-N(piperazine)-(3-methoxyphenyl) | M+ = 678.9<br>$_A t_{Ret}$ = 4.30 min |
| 169 | X = H<br>Y = Cl | 4-chlorobenzyl | phenyl | -C(O)NH-CH₂-(4-pyridyl) | M+ = 551.9<br>$_A t_{Ret}$ = 3.71 min |
| 170 | X = H<br>Y = Cl | 4-chlorobenzyl | phenyl | -C(O)NH-CH₂-(3-pyridyl) | M+ = 551.9<br>$_A t_{Ret}$ = 3.73 min |
| 171 | X = H<br>Y = Cl | 4-chlorobenzyl | phenyl | -C(O)NH-CH₂-(2-pyridyl) | M+ = 551.9<br>$_A t_{Ret}$ = 3.81 min |

-continued

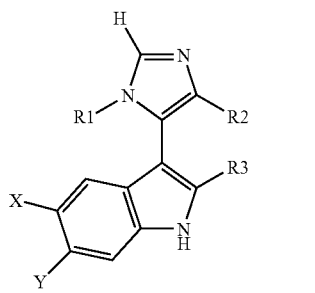

| Example | X and Y | R¹ | R² | R³ | Analysis MS/HPLC/NMR |
|---|---|---|---|---|---|
| 172 | X = H<br>Y = Cl | 4-chlorobenzyl | phenyl | —C(O)NHCH₂CH₂-(4-pyridyl) | M+ = 565.9<br>$^A t_{Ret}$ = 3.74 min |
| 173 | X = H<br>Y = Cl | 4-chlorobenzyl | phenyl | —C(O)NHCH₂CH₂-piperazinyl-CH₂-(2-pyridyl) | M+ = 664.0<br>$^A t_{Ret}$ = 3.72 min |
| 174 | X = H<br>Y = Cl | 4-chlorobenzyl | phenyl | —C(O)NHCH₂CH₂-piperazinyl-cyclopentyl | M+ = 641.0<br>$^A t_{Ret}$ = 3.91 min |
| 175 | X = H<br>Y = Cl | 4-chlorobenzyl | phenyl | —C(O)NHCH₂CH₂-(2-pyridyl) | M+ = 566.0<br>$^A t_{Ret}$ = 3.80 min |
| 176 | X = H<br>Y = Cl | 4-chlorobenzyl | phenyl | —C(O)NHCH₂CH₂-piperazinyl-CH₂-cyclohexyl | M+ = 669.0<br>$^A t_{Ret}$ = 4.11 min |
| 177 | X = H<br>Y = Cl | 4-chlorobenzyl | phenyl | —C(O)NHCH₂CH₂-piperidinyl-morpholinyl | M+ = 656.9<br>$^A t_{Ret}$ = 3.61 min |

-continued

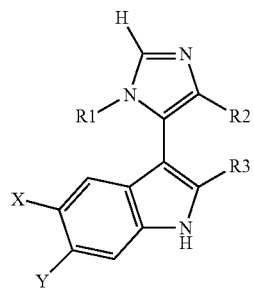

| Example | X and Y | R¹ | R² | R³ | Analysis MS/HPLC/NMR |
|---|---|---|---|---|---|
| 178 | X = H<br>Y = Cl | 4-chlorobenzyl | phenyl | -C(O)NH-CH₂CH₂-(3-pyridyl) | M+ = 565.9<br>$A^{t}{}_{Ret}$ = 3.82 min |
| 179 | X = H<br>Y = Cl | 4-chlorobenzyl | phenyl | -C(O)NH-CH₂CH₂-(4-piperidin-1-yl-piperidin-1-yl) | M+ = 655.0<br>$A^{t}{}_{Ret}$ = 3.67 min |
| 180 | X = H<br>Y = Cl | 4-chlorobenzyl | phenyl | -C(O)NH-CH₂CH₂-(4-pyrrolidin-1-yl-piperidin-1-yl) | M+ = 641.0<br>$A^{t}{}_{Ret}$ = 3.62 min |
| 181 | X = H<br>Y = Cl | 4-chloro-2-(hydroxymethyl)benzyl | phenyl | -C(O)NH-CH₂CH₂-(4-isopropyl-piperazin-1-yl) | M + H = 644.9<br>$C^{t}{}_{Ret}$ = 5.36 min |
| 182 | X = H<br>Y = Cl | 1-(4-chlorophenyl)ethyl | phenyl | -C(O)NH-CH₂CH₂-(4-isopropyl-piperazin-1-yl) | M + H = 629.0<br>$C^{t}{}_{Ret}$ = 5.70 min |
| 183 | X = H<br>Y = Cl | 4-chlorobenzyl | phenyl | -C(O)NH-CH₂CH₂-(4-((tetrahydrofuran-2-yl)methyl)piperazin-1-yl) | M+ = 656.9<br>$A^{t}{}_{Ret}$ = 3.82 min |

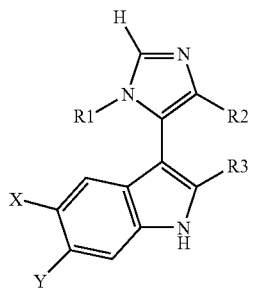

| Example | X and Y | R¹ | R² | R³ | Analysis MS/HPLC/NMR |
|---|---|---|---|---|---|
| 184 | X = H<br>Y = Cl | 4-chlorobenzyl | phenyl | -C(O)NH-CH₂CH₂-N(piperazine)-CH₂-(4-pyridyl) | M+ = 663.9<br>$^A t_{Ret}$ = 3.50 min |
| 185 | X = H<br>Y = Cl | (R)-1-(4-chlorophenyl)ethyl | phenyl | -C(O)NH-CH₂CH₂-N(piperazine)-ethyl | M + H = 614.9<br>$^C t_{Ret}$ = 5.64 min |
| 186 | X = H<br>Y = Cl | (R)-1-(4-chlorophenyl)ethyl | phenyl | -C(O)NH-CH₂CH₂-N(piperazine)-CH₂-(3-pyridyl) | M + H = 677.9<br>$^C t_{Ret}$ = 5.53 min |
| 187 | X = H<br>Y = Cl | 4-chloro-2-(hydroxymethyl)benzyl | phenyl | -C(O)NH-CH₂CH₂-N(piperazine)-CH₂-(4-pyridyl) | M+ = 693.9<br>$^A t_{Ret}$ = 3.33 min |
| 188 | X = H<br>Y = Cl | 4-chloro-2-(hydroxymethyl)benzyl | phenyl | -C(O)NH-CH₂CH₂-N(piperazine)-CH₂-(2-pyridyl) | M+ = 693.9<br>$^A t_{Ret}$ = 3.44 min |

-continued

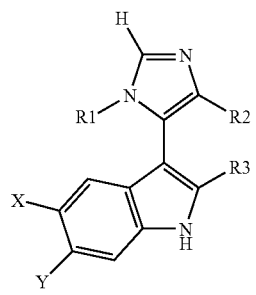

| Example | X and Y | R¹ | R² | R³ | Analysis MS/HPLC/NMR |
|---|---|---|---|---|---|
| 189 | X = H<br>Y = Cl | 5-chloro-2-(hydroxymethyl)benzyl | phenyl | -C(O)NH-CH₂CH₂-piperazinyl-4-pyridyl | M+ = 680.0<br>$^A t_{Ret}$ = 3.32 min |
| 190 | X = H<br>Y = Cl | 5-chloro-2-(hydroxymethyl)benzyl | phenyl | -C(O)NH-CH₂CH₂-piperazinyl-3-pyridyl | M+ = 679.9<br>$^A t_{Ret}$ = 3.31 min |
| 191 | X = H<br>Y = Cl | 5-chloro-2-(hydroxymethyl)benzyl | phenyl | -C(O)NH-CH₂CH₂-piperazinyl-benzyl | M+ = 692.9<br>$^A t_{Ret}$ = 3.86 min |
| 192 | X = H<br>Y = Cl | 5-chloro-2-(hydroxymethyl)benzyl | phenyl | -C(O)NH-CH₂CH₂-piperazinyl-CH₂-3-pyridyl | M+ = 693.9<br>$^A t_{Ret}$ = 3.37 min |
| 193 | X = H<br>Y = Cl | 4-chlorobenzyl | phenyl | -C(O)-pyrrolidinyl-O-CH₂-3-pyridyl | M+ = 621.9<br>$^A t_{Ret}$ = 3.82 min |
| 194 | X = H<br>Y = Cl | 1-(4-chlorophenyl)ethyl | phenyl | -C(O)NH-CH₂CH₂-piperazinyl-CH₂-4-pyridyl | M + H = 678.0<br>$^C t_{Ret}$ = 5.53 min |

-continued

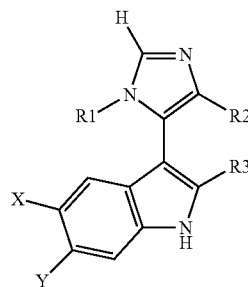

| Example | X and Y | R¹ | R² | R³ | Analysis MS/HPLC/NMR |
|---|---|---|---|---|---|
| 195 | X = H, Y = Cl | 4-Cl-phenyl (α-methyl) | phenyl | —C(O)NH-CH₂CH₂-N(piperazine)-3-pyridyl | M + H = 664.0; $c_{tRet}$ = 5.55 min |
| 196 | X = H, Y = Cl | 4-Cl-phenyl (α-methyl) | phenyl | —C(O)NH-CH₂CH₂-N(piperazine)-CH₂-2-pyridyl | M + H = 678.1; $c_{tRet}$ = 5.59 min |
| 197 | X = H, Y = Cl | 4-Cl-benzyl | phenyl | —C(O)-N(pyrrolidinyl)-O-CH₂-2-pyridyl | M+ = 621.9; $A_{tRet}$ = 3.87 min |
| 198 | X = H, Y = Cl | 4-Cl-benzyl | phenyl | —C(O)-N(pyrrolidinyl)-O-CH₂-4-pyridyl | M+ = 622.0; $A_{tRet}$ = 3.79 min |
| 199 | X = H, Y = Cl | 4-Cl-benzyl | phenyl | —C(O)NH-CH₂CH₂-N(piperidinyl)-N(CH₃)₂ | M+ = 615.0; $A_{tRet}$ = 3.54 min |
| 200 | X = H, Y = Cl | 4-Cl-benzyl | phenyl | —C(O)NH-CH₂CH₂-N(piperazine)-CH(Et)₂ | M+ = 643.0; $A_{tRet}$ = 3.94 min |

-continued

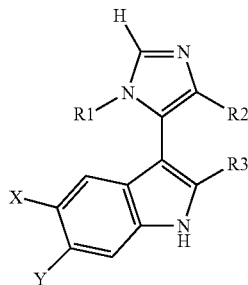

| Example | X and Y | R¹ | R² | R³ | Analysis MS/HPLC/NMR |
|---|---|---|---|---|---|
| 201 | X = H, Y = Cl | 4-Cl-C₆H₄-CH(CH₃)- | phenyl | -C(O)NH-CH₂CH₂-N(piperazinyl)-iPr | M + H = 629.0, $^C t_{Ret}$ = 5.47 min |
| 202 | X = H, Y = Cl | 4-Cl-C₆H₄-CH₂- | phenyl | -C(O)NH-CH₂CH₂-N(piperidinyl)-4-NEt₂ | M+ = 643.0, $^A t_{Ret}$ = 3.75 min |
| 203 | X = H, Y = Cl | 4-Cl-C₆H₄-CH₂- | phenyl | -C(O)NH-CH₂CH₂-N(piperazinyl)-iBu | M+ = 629.0, $^A t_{Ret}$ = 3.91 min |
| 204 | X = H, Y = Cl | 4-Cl-C₆H₄-CH₂- | phenyl | -C(O)NH-CH₂CH₂-N(piperazinyl)-adamantyl | M+ = 707.0, $^A t_{Ret}$ = 4.20 min |
| 205 | X = H, Y = Cl | 4-Cl-C₆H₄-CH₂- | phenyl | -C(O)NH-CH₂CH₂-N(piperidinyl)-4-N(nPr)₂ | M+ = 671.0, $^A t_{Ret}$ = 3.96 min |
| 206 | X = H, Y = Cl | 4-Cl-C₆H₄-CH(CH₃)- | phenyl | -C(O)NH-CH₂CH₂-N(piperazinyl)-4-pyridyl | M + H = 663.9, $^C t_{Ret}$ = 5.66 min |

-continued

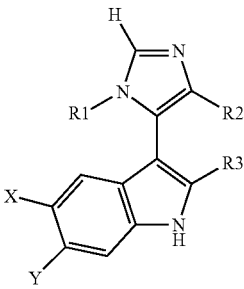

| Example | X and Y | R¹ | R² | R³ | Analysis MS/HPLC/NMR |
|---|---|---|---|---|---|
| 207 | X = H, Y = Cl | 4-Cl-benzyl | phenyl | C(O)NH-CH₂CH₂-piperazine-N-tBu | M+ = 628.9; $^A t_{Ret}$ = 3.72 min |
| 208 | X = H, Y = Cl | 4-Cl-benzyl | phenyl | C(O)NH-CH₂CH₂-piperazine-N-(2-pyrimidinyl) | M+ = 651.0; $^A t_{Ret}$ = 4.01 min |
| 209 | X = H, Y = Cl | 4-Cl-2-F-benzyl | phenyl | C(O)NH-CH₂CH₂-N-methylpiperazine | M + H = 604.8; $^C t_{Ret}$ = 5.69 min |
| 210 | X = H, Y = Cl | 4-Cl-benzyl | phenyl | C(O)-piperazine-N-(2-pyridyl) | M + H = 607.0; $^C t_{Ret}$ = 5.77 min |
| 211 | X = H, Y = Cl | 4-Cl-benzyl | phenyl | C(O)-piperazine-N-(3-pyridyl) | M + H = 607.0; $^C t_{Ret}$ = 5.72 min |

-continued

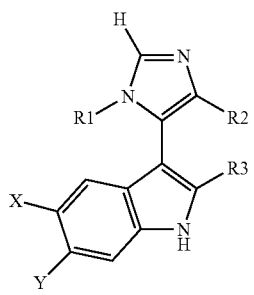

| Example | X and Y | R¹ | R² | R³ | Analysis MS/HPLC/NMR |
|---|---|---|---|---|---|
| 212 | X = H, Y = Cl | 4-chlorobenzyl | phenyl | 4-(pyridin-4-yl)piperazin-1-yl carbonyl | M + H = 607.0; $t_{Ret}$ = 5.72 min |
| 213 | X = H, Y = Cl | 4-chlorobenzyl | phenyl | 4-(pyridin-2-ylmethyl)piperazin-1-yl carbonyl | M + H = 621.0; $t_{Ret}$ = 5.81 min |
| 214 | X = H, Y = Cl | 4-chlorobenzyl | phenyl | N-methyl-N-[2-(4-methylpiperazin-1-yl)ethyl]carbamoyl | M + H = 601.0; $t_{Ret}$ = 5.54 min |
| 215 | X = H, Y = Cl | 4-chlorobenzyl | phenyl | 4-(pyridin-3-ylmethyl)piperazin-1-yl carbonyl | M + H = 621.0; $t_{Ret}$ = 5.56 min |
| 216 | X = H, Y = Cl | 4-chlorobenzyl | phenyl | 4-[2-(pyridin-4-yl)ethyl]piperazin-1-yl carbonyl | M + H = 635.0; $t_{Ret}$ = 5.40 min |
| 217 | X = H, Y = Cl | 4-chlorobenzyl | phenyl | 4-[2-(pyridin-2-yl)ethyl]piperazin-1-yl carbonyl | M + H = 635.0; $t_{Ret}$ = 5.56 min |

-continued

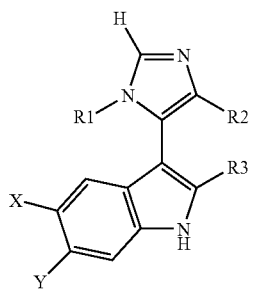

| Example | X and Y | R¹ | R² | R³ | Analysis MS/HPLC/NMR |
|---|---|---|---|---|---|
| 218 | X = H<br>Y = Cl | 4-chlorobenzyl | phenyl | 4-(pyridin-4-ylmethyl)piperazine-1-carbonyl | M + H = 621.0<br>$t_{Ret}$ = 5.61 min |
| 219 | X = H<br>Y = Cl | 4-chlorobenzyl | 4-fluorophenyl | N-(2-(4-methylpiperazin-1-yl)ethyl)carbamoyl | M + H = 605.0<br>$t_{Ret}$ = 5.58 min |
| 220 | X = H<br>Y = Cl | 1-(4-chlorophenyl)ethyl | phenyl | N-(2-(piperazin-1-yl)ethyl)carbamoyl | M + H = 587.1<br>$t_{Ret}$ = 5.52 min |
| 221 | X = H<br>Y = Cl | 4-chlorobenzyl | 2-fluorophenyl | N-(2-(4-methylpiperazin-1-yl)ethyl)carbamoyl | M + H = 605.0<br>$t_{Ret}$ = 5.48 min |
| 222 | X = H<br>Y = Cl | 1-(4-chlorophenyl)ethyl | phenyl | 4-(dimethylamino)piperidine-1-carbonyl | M + H = 586.0<br>$t_{Ret}$ = 5.76 min |
| 223 | X = H<br>Y = Cl | 4-chloro-2-(hydroxymethyl)benzyl | phenyl | 4-(dimethylamino)piperidine-1-carbonyl | M + H = 602.0<br>$t_{Ret}$ = 5.38 min |

-continued

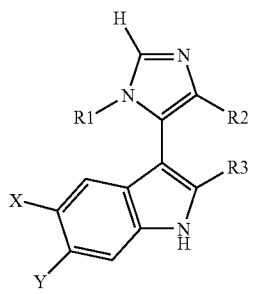

| Example | X and Y | R¹ | R² | R³ | Analysis MS/HPLC/NMR |
|---|---|---|---|---|---|
| 224 | X = H, Y = Cl | 4-chlorobenzyl | phenyl | -C(O)NH-CH₂CH₂-(4-benzylpiperidin-1-yl) | M+ = 662.0, $^A t_{Ret}$ = 4.52 min |
| 225 | X = H, Y = Cl | 4-chlorobenzyl | phenyl | -C(O)NH-CH₂CH₂-(4-(pyridin-2-ylmethyl)piperidin-1-yl) | M+ = 663.0, $^A t_{Ret}$ = 3.60 min |
| 226 | X = H, Y = Cl | 3,3-dimethylbutyl | phenyl | -C(O)-(3-(N-methyl-N-(3-dimethylaminopropyl)amino)pyrrolidin-1-yl) | M + H = 589.2, $^C t_{Ret}$ = 5.35 min |
| 227 | X = H, Y = Cl | 4-chlorobenzyl | phenyl | -C(O)NH-CH₂CH₂-(4-tert-butylpiperidin-1-yl) | M + H = 628.1, $^C t_{Ret}$ = 6.38 min |
| 228 | X = H, Y = Cl | 4-chlorobenzyl | phenyl | -C(O)NH-CH₂CH₂-(4-(3-methoxypropyl)piperidin-1-yl) | M + H = 644.0, $^C t_{Ret}$ = 6.00 min |
| 229 | X = H, Y = Cl | 4-chlorobenzyl | phenyl | -C(O)NH-CH₂CH₂-(4-(2-(pyrrolidin-1-yl)ethyl)piperidin-1-yl) | M + H = 669.0, $^C t_{Ret}$ = 5.52 min |

-continued

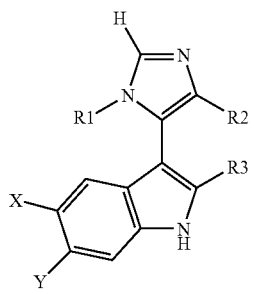

| Example | X and Y | R¹ | R² | R³ | Analysis MS/HPLC/NMR |
|---|---|---|---|---|---|
| 230 | X = H<br>Y = Cl | 4-Cl-benzyl | phenyl | C(=O)NH-CH₂CH₂-NH-(2-pyridyl) | M + H = 581.0<br>$_C t_{Ret}$ = 5.79 min |
| 231 | X = H<br>Y = Cl | 4-Cl-benzyl | phenyl | C(=O)NH-CH₂CH₂-NH-(4-pyridyl) | M + H = 581.0<br>$_C t_{Ret}$ = 5.62 min |
| 232 | X = H<br>Y = Cl | 4-Cl-benzyl | phenyl | C(=O)NH-CH₂CH₂-N(4-hydroxypiperidinyl) | M + H = 588.0<br>$_C t_{Ret}$ = 5.56 min |
| 233 | X = H<br>Y = Cl | 4-Cl-benzyl | phenyl | C(=O)-N-pyrrolidinyl-3-NH-benzyl | M − H = 618.0<br>$_E t_{Ret}$ = 4.16 min |
| 234 | X = H<br>Y = Cl | 4-Cl-benzyl | phenyl | C(=O)-N-pyrrolidinyl-3-NH-CH₂-(3-pyridyl) | M − H = 620.0<br>$_E t_{Ret}$ = 3.77 min |
| 235 | X = H<br>Y = Cl | 4-Cl-benzyl | phenyl | C(=O)-N-pyrrolidinyl-3-NH-CH₂-(2-pyridyl) | M − H = 619.0<br>$_E t_{Ret}$ = 3.97 min |

-continued

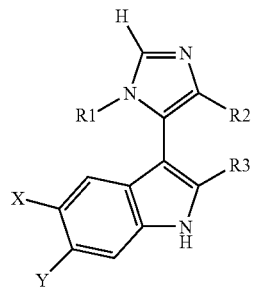

| Example | X and Y | R¹ | R² | R³ | Analysis MS/HPLC/NMR |
|---|---|---|---|---|---|
| 236 | X = H, Y = Cl | 4-chlorobenzyl | phenyl | 1-acyl-3-((pyridin-4-ylmethyl)amino)pyrrolidine | M − H = 619.2; $_E t_{Ret}$ = 3.79 min |
| 237 | X = H, Y = Cl | 4-chlorobenzyl | phenyl | 1-acyl-3-((furan-3-ylmethyl)amino)pyrrolidine | M − H = 608.1; $_E t_{Ret}$ = 4.03 min |
| 238 | X = H, Y = Cl | 4-chlorobenzyl | phenyl | 1-acyl-3-((thiophen-2-ylmethyl)amino)pyrrolidine | M − H = 624.0; $_E t_{Ret}$ = 4.00 min |
| 239 | X = H, Y = Cl | 4-chlorobenzyl | phenyl | 1-acyl-3-(((1-methyl-1H-imidazol-2-yl)methyl)amino)pyrrolidine | M − H = 622.1; $_E t_{Ret}$ = 3.79 min |
| 240 | X = H, Y = Cl | 4-chlorobenzyl | phenyl | 1-acyl-3-((thiazol-2-ylmethyl)amino)pyrrolidine | M − H = 625.0; $_E t_{Ret}$ = 3.98 min |
| 241 | X = H, Y = Cl | 4-chlorobenzyl | phenyl | 1-acyl-3-(((4-methylthiophen-2-yl)methyl)amino)pyrrolidine | M − H = 638.0; $_E t_{Ret}$ = 4.22 min |
| 242 | X = F, Y = Cl | 2-bromo-4-chlorobenzyl | phenyl | H | M + H = 515.8; $_C t_{Ret}$ = 6.55 min |

-continued

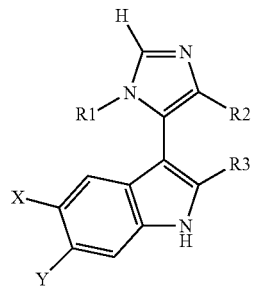

| Example | X and Y | R¹ | R² | R³ | Analysis MS/HPLC/NMR |
|---|---|---|---|---|---|
| 243 | X = H, Y = Cl | 4-Cl-benzyl | phenyl | -C(O)NH-CH2CH2-N(piperidin-1-yl)-4-phenoxy | M + H = 664.0, $c_{tRet}$ = 5.25 min |
| 244 | X = H, Y = Cl | 4-Cl-benzyl | phenyl | -C(O)NH-CH2CH2-N(piperidin-1-yl)-4-(pyridin-4-yl) | M + H = 649.0, $c_{tRet}$ = 5.42 min |
| 245 | X = H, Y = Cl | 4-Cl-benzyl | phenyl | -C(O)NH-CH2CH2-(piperidin-4-yl) | M + H = 572.0, $c_{tRet}$ = 5.58 min |
| 246 | X = H, Y = Cl | 4-Cl-benzyl | phenyl | -C(O)NH-CH2CH2-N(piperidin-1-yl)-4-(O-CH2CH2-OMe) | M+ = 646.0, $A_{tRet}$ = 3.91 min |
| 247 | X = H, Y = Cl | 4-Cl-benzyl | phenyl | -C(O)NH-CH2CH2-N(piperazin-1-yl)-4-(CH2CH2-pyridin-2-yl) | M + H = 678.0, $c_{tRet}$ = 5.44 min |
| 248 | X = H, Y = Cl | 4-Cl-benzyl | phenyl | -C(O)NH-CH2CH2-N(3-methylpiperazin-1-yl)-4-benzyl | M + H = 677.0, $c_{tRet}$ = 5.95 min |

-continued

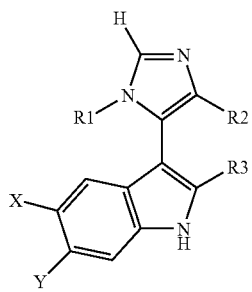

| Example | X and Y | R¹ | R² | R³ | Analysis MS/HPLC/NMR |
|---|---|---|---|---|---|
| 249 | X = H<br>Y = Cl | 4-Cl-phenyl-CH₂- | phenyl | 1-acyl-3-(dimethylamino)piperidine | M+ = 572.0<br>$^A t_{Ret}$ = 3.85 min |
| 250 | X = H<br>Y = Cl | 4-Cl-phenyl-CH₂- | phenyl | 1-acyl-3-hydroxypiperidine | M+ = 545.0<br>$^A t_{Ret}$ = 4.29 min |
| 251 | X = H<br>Y = Cl | 4-Cl-phenyl-CH₂- | phenyl | -C(O)NH-CH₂CH₂-N(spiro[piperidine-4,1'-indane]) | M+ = 674.0<br>$^A t_{Ret}$ = 4.55 min |
| 252 | X = H<br>Y = Cl | 4-Cl-phenyl-CH₂- | phenyl | -C(O)NH-CH₂CH₂-N(4-benzyl-4-hydroxypiperidine) | M + H = 678.0<br>$^C t_{Ret}$ = 6.09 min |
| 253 | X = H<br>Y = Cl | 4-Cl-phenyl-CH₂- | phenyl | -C(O)NH-CH₂CH₂-N(4-hydroxy-4-phenylpiperidine) | M + H = 664.0<br>$^C t_{Ret}$ = 6.06 min |
| 254 | X = H<br>Y = Cl | 4-Cl-phenyl-CH₂- | phenyl | -C(O)NH-CH₂CH₂-N(7-benzyl-4,7-diazaspiro[2.5]octane) | M + H = 689.1<br>$^C t_{Ret}$ = 6.23 min |

-continued

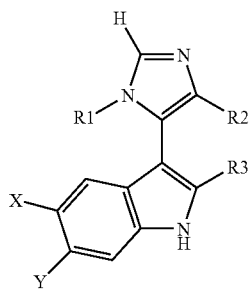

| Example | X and Y | R¹ | R² | R³ | Analysis MS/HPLC/NMR |
|---|---|---|---|---|---|
| 255 | X = F, Y = Cl | 4-Cl-benzyl | 3-pyridyl | H | M + H = 437.0; $t_{Ret}$ = 5.57 min |
| 256 | X = H, Y = Cl | 4-Cl-benzyl | phenyl | -C(O)NH-CH₂CH₂-(2,5-dimethylpiperazinyl)-CH₂-(3-pyridyl) | M + H = 692.0; $t_{Ret}$ = 5.42 min |
| 257 | X = H, Y = Cl | 4-Cl-benzyl | phenyl | -C(O)NH-CH₂CH₂-piperazinyl-indanyl | M + H = 689.0; $t_{Ret}$ = 5.95 min |
| 258 | X = H, Y = Cl | 4-Cl-benzyl | phenyl | -C(O)NH-CH₂CH₂-piperazinyl-CH₂CH₂-imidazolyl | M + H = 667.0; $t_{Ret}$ = 5.39 min |
| 259 | X = H, Y = Cl | 4-Cl-benzyl | phenyl | -C(O)NH-CH₂CH₂-piperazinyl-CH₂CH₂-O-phenyl | M + H = 693.0; $t_{Ret}$ = 5.97 min |
| 260 | X = H, Y = Cl | 4-Cl-benzyl | phenyl | -C(O)NH-CH₂CH₂-benzimidazolyl | M + H = 605.0; $t_{Ret}$ = 5.74 min |

-continued

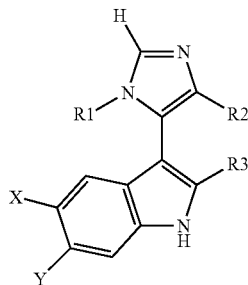

| Example | X and Y | R¹ | R² | R³ | Analysis MS/HPLC/NMR |
|---|---|---|---|---|---|
| 261 | X = H, Y = Cl | 4-Cl-benzyl | phenyl | -C(O)NH-CH2CH2-piperazine-CH2CH2-morpholine | M + H = 686.0; $t_{Ret}$ = 5.40 min |
| 262 | X = H, Y = Cl | 4-Cl-benzyl | phenyl | -C(O)NH-CH2CH2-piperazine-CH2-(N-methylpiperidine) | M + H = 684.0; $t_{Ret}$ = 5.34 min |
| 263 | X = H, Y = Cl | 4-Cl-benzyl | phenyl | -C(O)NH-CH2CH2-piperazine-CH2CH2-OEt | M + H = 645.0; $t_{Ret}$ = 5.61 min |
| 264 | X = H, Y = Cl | 4-Cl-benzyl | phenyl | -C(O)NH-CH2CH2-piperazine-CH2CH2-phenyl | M + H = 677.0; $t_{Ret}$ = 5.92 min |
| 265 | X = H, Y = Cl | (R)-1-(4-Cl-phenyl)ethyl | phenyl | -C(O)NH-CH2CH2-piperazine-CH2CH2CH2-OMe | M + H = 659.0; $t_{Ret}$ = 5.67 min |
| 266 | X = H, Y = Cl | (R)-1-(4-Cl-phenyl)ethyl | phenyl | -C(O)NH-CH2CH2-piperazine-CH2-(N-methylpiperidine) | M + H = 698.0; $t_{Ret}$ = 5.44 min |

-continued

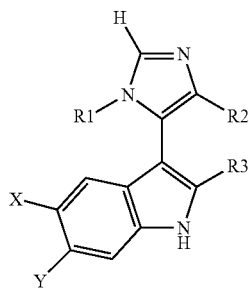

| Example | X and Y | R¹ | R² | R³ | Analysis MS/HPLC/NMR |
|---|---|---|---|---|---|
| 267 | X = H, Y = Cl | 4-Cl-phenyl (stereo) | phenyl | -C(O)NH-CH2CH2-piperazine-CH2CH2-morpholine | M + H = 700.0; cTRet = 5.51 min |
| 268 | X = H, Y = Cl | 4-Cl-phenyl (stereo) | phenyl | -C(O)NH-CH2CH2-piperazine-CH2CH2-O-ethyl | M + H = 659.0; cTRet = 5.74 min |
| 269 | X = H, Y = Cl | 4-Cl-phenyl (stereo) | phenyl | -C(O)NH-CH2CH2-(3-oxopiperazine)-CH2-(3-pyridyl) | M + H = 691.9; cTRet = 5.49 min |
| 270 | X = H, Y = Cl | 4-Cl-benzyl | phenyl | -C(O)NH-CH2CH2-piperazine-CH2-C(O)NH-(2-pyridyl) | M + H = 707.0; cTRet = 5.50 min |
| 271 | X = H, Y = Cl | 4-Cl-benzyl | phenyl | -C(O)NH-CH2CH2-piperazine-CH2-C(O)NH-(3-pyridyl) | M + H = 707.0; cTRet = 5.35 min |
| 272 | X = H, Y = Cl | 4-Cl-benzyl | phenyl | -C(O)NH-CH2CH2-piperazine-CH2-C(O)-pyrrolidine | M + H = 684.0; cTRet = 5.62 min |

-continued

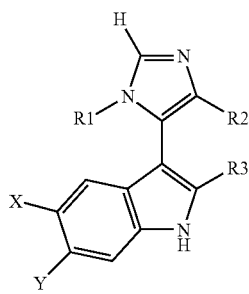

| Example | X and Y | R¹ | R² | R³ | Analysis MS/HPLC/NMR |
|---|---|---|---|---|---|
| 273 | X = H, Y = Cl | 4-Cl-phenylmethyl | phenyl | -C(O)NH-CH₂CH₂-(2-phenylimidazol-1-yl) | M + H = 631.0, $t_{Ret}$ = 5.75 min |
| 274 | X = H, Y = Cl | 4-Cl-phenyl(CH)- | phenyl | -C(O)NH-CH₂CH₂-piperazinyl-CH₂CH₂-(2-pyridyl) | M + H = 692.0, $t_{Ret}$ = 5.54 min |
| 275 | X = H, Y = Cl | 4-Cl-phenyl(CH)- | phenyl | -C(O)NH-CH₂CH₂-piperazinyl-CH(Et)₂ | M + H = 657.1, $t_{Ret}$ = 5.82 min |
| 276 | X = H, Y = Cl | 4-Cl-phenyl(CH)- | phenyl | -C(O)NH-CH₂CH₂-(4-piperidinyl-piperidinyl) | M + H = 669.0, $t_{Ret}$ = 5.57 min |
| 277 | X = H, Y = Cl | 4-Cl-phenyl(CH)- | phenyl | -C(O)NH-CH₂CH₂-piperazinyl-CH₂-cyclohexyl | M + H = 683.0, $t_{Ret}$ = 6.03 min |

-continued

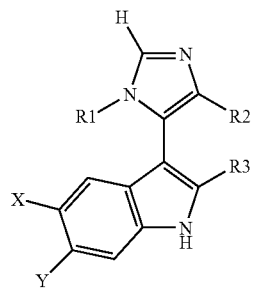

| Example | X and Y | R¹ | R² | R³ | Analysis MS/HPLC/NMR |
|---|---|---|---|---|---|
| 278 | X = H, Y = Cl | 4-chlorobenzyl | phenyl | 1-(piperazin-3-yl)azetidine carbonyl | M+ = 585.0, $^A t_{Ret}$ = 3.60 min |
| 279 | X = H, Y = Cl | (R)-1-(4-chlorophenyl)ethyl | phenyl | N-(2-(4-(2-oxo-2-(pyrrolidin-1-yl)ethyl)piperazin-1-yl)ethyl)carbamoyl | M + H = 698.0, $^C t_{Ret}$ = 5.72 min |
| 280 | X = H, Y = Cl | (R)-1-(4-chlorophenyl)ethyl | phenyl | N-(2-(3-oxo-4-(pyridin-3-ylmethyl)piperazin-1-yl)ethyl)carbamoyl | M + H = 691.8, $^C t_{Ret}$ = 5.63 min |
| 281 | X = H, Y = Cl | (5-chloropyridin-2-yl)methyl | phenyl | N-(2-(4-(pyridin-3-ylmethyl)piperazin-1-yl)ethyl)carbamoyl | M + H = 664.8, $^C t_{Ret}$ = 5.10 min |
| 282 | X = H, Y = Cl | (R)-1-(4-chlorophenyl)ethyl | phenyl | N-(2-oxo-2-(4-(pyridin-3-ylmethyl)piperazin-1-yl)ethyl)carbamoyl | M + H = 692.0, $^C t_{Ret}$ = 5.41 min |

-continued

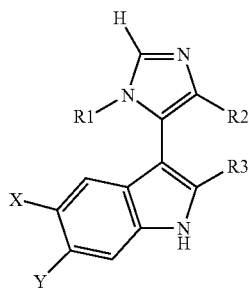

| Example | X and Y | R¹ | R² | R³ | Analysis MS/HPLC/NMR |
|---|---|---|---|---|---|
| 283 | X = H<br>Y = Cl | 4-Cl-C6H4-CH(CH3)- | phenyl | -C(O)NH-CH2CH2-N(piperidine)-4-NH-(2-pyridyl) | M + H = 678.0<br>$_A t_{Ret}$ = 5.41 min |
| 284 | X = H<br>Y = Cl | 4-Cl-C6H4-CH(CH3)- | phenyl | -C(O)NH-CH2CH2-N(piperidine)-4-N(CH3)-(2-pyridyl) | M + H = 691.9<br>$_A t_{Ret}$ = 5.41 min |
| 285 | X = H<br>Y = Cl | 4-Cl-C6H4-CH(CH3)- | phenyl | -C(O)NH-CH2CH2-N(piperidine)-4-O-(2-pyridyl) | M + H = 679.0<br>$_D t_{Ret}$ = 2.88 min |
| 286 | X = F<br>Y = Cl | 4-Cl-C6H4-CH(CH2COOH)- | phenyl | H | M + H = 495.7<br>$_A t_{Ret}$ = 4.28 min |
| 287 | X = F<br>Y = Cl | 4-Cl-C6H4-CH(CH2C(O)NHCH3)- | phenyl | H | M + H = 507.0<br>$_C t_{Ret}$ = 6.17 min |

-continued

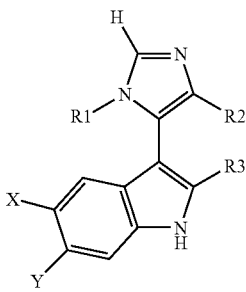

| Example | X and Y | R¹ | R² | R³ | Analysis MS/HPLC/NMR |
|---|---|---|---|---|---|
| 288 | X = F, Y = Cl | 4-chlorophenyl-CH(CH₂C(O)NH-CH₂CH₂-OMe)- | phenyl | H | M + H = 551.0; $c_{tRet}$ = 6.23 min |
| 289 | X = F, Y = Cl | 4-chlorophenyl-CH(CH₂C(O)NH-CH₂CH₂-NMe₂)- | phenyl | H | M + H = 564.0; $c_{tRet}$ = 5.72 min |
| 290 | X = F, Y = Cl | 4-chlorophenyl-CH(CH₂C(O)-(4-methylpiperazin-1-yl))- | phenyl | H | M + H = 576.0; $c_{tRet}$ = 5.73 min |
| 291 | X = H, Y = Cl | 4-chlorobenzyl | phenyl | -C(O)NH-CH₂CH₂-(4-(pyridine-3-carbonyl)piperazin-1-yl) | M+ = 677.8; $A_{tRet}$ = 3.71 min |

-continued

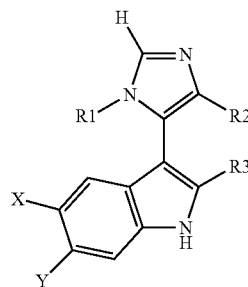

| Example | X and Y | R¹ | R² | R³ | Analysis MS/HPLC/NMR |
|---|---|---|---|---|---|
| 292 | X = H<br>Y = Cl | 4-Cl-C₆H₄-CH₂- | phenyl | -C(O)-NH-CH₂CH₂-N(piperazine)-CH(CH₃)-(2-pyridyl) | M+ = 677.9<br>$^A t_{Ret}$ = 3.65 min |
| 293 | X = H<br>Y = Cl | 4-Cl-C₆H₄-CH₂- | phenyl | -C(O)-NH-CH₂CH₂-N(piperazine)-C(O)-(6-fluoropyridin-3-yl) | M+ = 695.9<br>$^A t_{Ret}$ = 3.92 min |
| 294 | X = H<br>Y = Cl | 4-Cl-C₆H₄-CH₂- | phenyl | -C(O)-NH-CH₂CH₂-N(piperazine)-C(O)-(2-pyridyl) | M+ = 678.0<br>$^A t_{Ret}$ = 3.82 min |
| 295 | X = H<br>Y = Cl | 4-Cl-C₆H₄-CH₂- | pyridyl | -C(O)-NH-CH₂CH₂-N(piperazine)-C(O)-(4-pyridyl) | M+ = 677.9<br>$^A t_{Ret}$ = 3.59 min |
| 296 | X = H<br>Y = Cl | 4-Cl-C₆H₄-CH₂- | phenyl | -C(O)-NH-CH₂CH₂-N(piperazine)-C(O)-cyclohexyl | M+ = 683.0<br>$^A t_{Ret}$ = 4.24 min |

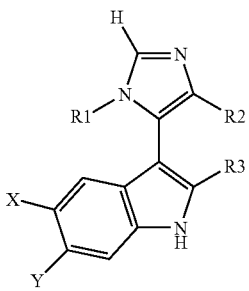

| Example | X and Y | R¹ | R² | R³ | Analysis MS/HPLC/NMR |
|---|---|---|---|---|---|
| 297 | X = H<br>Y = Cl | 4-chlorobenzyl | phenyl | -C(O)NH-CH₂CH₂-piperazine-N-CH(CH₃)-pyrazinyl | M+ = 679.0<br>$^At_{Ret}$ = 3.80 min |
| 298 | X = H<br>Y = Cl | 4-chlorobenzyl | phenyl | -C(O)NH-CH₂CH₂-piperazine-N-C(O)-C(CH₃)₃ | M+ = 657.0<br>$^At_{Ret}$ = 4.05 min |
| 299 | X = H<br>Y = Cl | 4-chlorobenzyl | phenyl | -C(O)NH-CH₂CH₂-piperazine-N-C(O)-CH(Et)₂ | M − H = 670.6<br>$^At_{Ret}$ = 4.15 min |
| 300 | X = H<br>Y = Cl | 4-chlorobenzyl | phenyl | -C(O)NH-CH₂CH₂-piperazine-N-C(O)-(6-methylpyridin-3-yl) | M+ = 691.9<br>$^At_{Ret}$ = 3.58 min |
| 301 | X = H<br>Y = Cl | 4-chlorobenzyl | phenyl | -C(O)NH-CH₂CH₂-piperazine-N-C(O)-pyrazinyl | M+ = 678.9<br>$^At_{Ret}$ = 3.78 min |

-continued

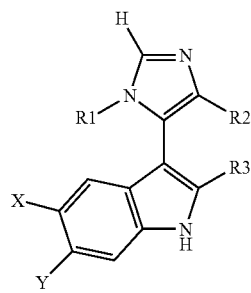

| Example | X and Y | R¹ | R² | R³ | Analysis MS/HPLC/NMR |
|---|---|---|---|---|---|
| 302 | X = H<br>Y = Cl | 4-chlorobenzyl | phenyl | -NHC(O)CH₂-piperazine-C(O)-(6-methylpyridin-2-yl) | M+ = 692.0<br>$^A t_{Ret}$ = 3.82 min |
| 303 | X = H<br>Y = Cl | 4-chlorobenzyl | phenyl | -NHC(O)CH₂-piperazine-C(O)-(6-fluoropyridin-2-yl) | M+ = 695.9<br>$^A t_{Ret}$ = 3.96 min |
| 304 | X = H<br>Y = Cl | 4-chlorobenzyl | phenyl | -NHC(O)CH₂-piperazine-CH(CH₃)-(pyridin-3-yl) | M+ = 678.0<br>$^A t_{Ret}$ = 3.60 min |
| 305 | X = H<br>Y = Cl | (R)-1-(4-chlorophenyl)ethyl | phenyl | -NHC(O)CH₂-piperazine-C(O)-(pyridin-3-yl) | M+ = 692.9<br>$^A t_{Ret}$ = 3.75 min |
| 306 | X = H<br>Y = Cl | (R)-1-(4-chlorophenyl)ethyl | phenyl | -NHC(O)CH₂-piperazine-C(O)-(pyrazin-2-yl) | M+ = 692.9<br>$^A t_{Ret}$ = 3.88 min |

-continued

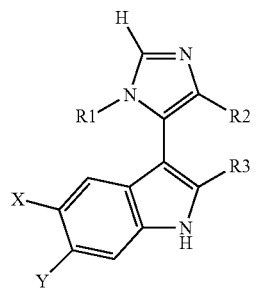

| Example | X and Y | R¹ | R² | R³ | Analysis MS/HPLC/NMR |
|---|---|---|---|---|---|
| 307 | X = H<br>Y = Cl | 4-Cl-benzyl | phenyl | -C(O)NH-CH₂CH₂-piperazine-C(O)-tetrahydropyran | M+ = 685.0<br>$A^{t_{Ret}}$ = 3.78 min |
| 308 | X = H<br>Y = Cl | 1-(4-Cl-phenyl)ethyl | phenyl | -C(O)NH-CH₂CH₂-piperazine-C(O)-(6-methylpyridin-2-yl) | M+ = 706.0<br>$A^{t_{Ret}}$ = 3.97 min |
| 309 | X = H<br>Y = Cl | 4-Cl-benzyl | phenyl | -C(O)NH-CH₂CH₂-piperazine-C(O)NH-(pyridin-3-yl) | M+ = 693.0<br>$A^{t_{Ret}}$ = 3.55 min |
| 310 | X = H<br>Y = Cl | 4-Cl-benzyl | phenyl | -C(O)NH-CH₂CH₂-piperazine-S(O)₂-(pyridin-3-yl) | M+ = 713.9<br>$A^{t_{Ret}}$ = 4.02 min |
| 311 | X = H<br>Y = Cl | 4-Cl-benzyl | phenyl | -C(O)NH-CH₂CH₂-piperidine-CH₂-(pyridin-3-yl) | M + H = 663.0<br>$C^{t_{Ret}}$ = 5.51 min |

-continued

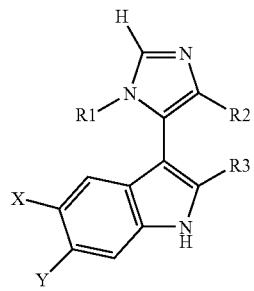

| Example | X and Y | R¹ | R² | R³ | Analysis MS/HPLC/NMR |
|---|---|---|---|---|---|
| 312 | X = H, Y = Cl | 4-Cl-benzyl | phenyl | -NH-C(O)-CH2CH2-piperidine-N-C(O)-(2-pyridyl) | M + H = 677.0; $t_{Ret}^c$ = 6.15 min |
| 313 | X = H, Y = Cl | 1-(4-Cl-phenyl)ethyl | phenyl | -NH-C(O)-CH2CH2-piperazine-N-C(O)-CH2-(3-pyridyl) | M + H = 706.0; $t_{Ret}^c$ = 5.35 min |
| 314 | X = H, Y = Cl | 1-(4-Cl-phenyl)ethyl | phenyl | -NH-C(O)-CH2CH2-piperazine-N-C(O)-(1-methylpiperidin-4-yl) | M + H = 712.0; $t_{Ret}^c$ = 5.34 min |
| 315 | X = H, Y = Cl | 1-(4-Cl-phenyl)ethyl | phenyl | -NH-C(O)-CH2CH2-piperazine-N-C(O)-(1-methylpiperidin-3-yl) | M + H = 712.0; $t_{Ret}^c$ = 5.38 min |
| 316 | X = H, Y = Cl | 1-(4-Cl-phenyl)ethyl | phenyl | -NH-C(O)-CH2CH2-piperazine-N-C(O)-CH2-OMe | M + H = 659.0; $t_{Ret}^c$ = 5.59 min |
| 317 | X = H, Y = Cl | 1-(4-Cl-phenyl)ethyl | phenyl | -NH-C(O)-CH2CH2-piperazine-N-C(O)-CH2-(2-pyridyl) | M + H = 706.0; $t_{Ret}^c$ = 5.38 min |

-continued

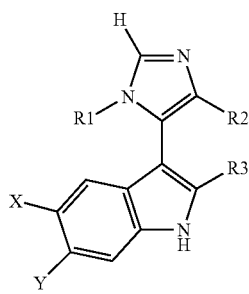

| Example | X and Y | R¹ | R² | R³ | Analysis MS/HPLC/NMR |
|---|---|---|---|---|---|
| 318 | X = H<br>Y = Cl | 4-Cl-benzyl | phenyl | 4,5-dihydrooxazol-2-yl | M + H = 487.0<br>$^C t_{Ret}$ = 6.27 min |
| 319 | X = H<br>Y = Cl | 4-Cl-benzyl | phenyl | 5-(2-oxo-2,3-dihydro-1,3,4-oxadiazol-2-yl) | M+ = 502.0<br>$^A t_{Ret}$ = 4.23 min |
| 320 | X = H<br>Y = Cl | 4-Cl-benzyl | phenyl | 5-(pyridin-3-ylamino)-1,3,4-oxadiazol-2-yl | M+ = 578.0<br>$^A t_{Ret}$ = 3.86 min |
| 321 | X = H<br>Y = Cl | 4-Cl-benzyl | phenyl | 5-((pyridin-3-ylmethyl)amino)-1,3,4-oxadiazol-2-yl | M+ = 592.0<br>$^A t_{Ret}$ = 3.72 min |
| 322 | X = H<br>Y = Cl | 4-Cl-benzyl | phenyl | 5-(pentan-3-ylamino)-1,3,4-oxadiazol-2-yl | M+ = 571.0<br>$^A t_{Ret}$ = 4.70 min |
| 323 | X = H<br>Y = Cl | 4-Cl-benzyl | phenyl | 3-(pyridin-3-ylmethyl)-2-oxo-2,3-dihydro-1,3,4-oxadiazol-5-yl | M+ = 592.9<br>$^A t_{Ret}$ = 3.87 min |

-continued

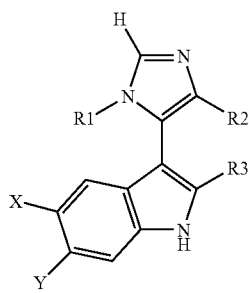

| Example | X and Y | R¹ | R² | R³ | Analysis MS/HPLC/NMR |
|---|---|---|---|---|---|
| 324 | X = F<br>Y = Cl | 5-Cl-2-((4-methylpiperazin-1-yl)methyl)benzyl | phenyl | H | M + H = 548.1<br>$t_{Ret}$ = 5.59 min |
| 325 | X = F<br>Y = Cl | 5-Cl-2-((2-methoxyethylamino)methyl)benzyl | phenyl | H | M + H = 523.0<br>$t_{Ret}$ = 5.50 min |
| 326 | X = F<br>Y = Cl | 5-Cl-2-(morpholinomethyl)benzyl | phenyl | H | M + H = 535.0<br>$t_{Ret}$ = 5.45 min |
| 327 | X = F<br>Y = Cl | 5-Cl-2-((methylamino)methyl)benzyl | pyridyl | H | M + H = 479.0<br>$t_{Ret}$ = 5.38 min |
| 328 | X = H<br>Y = Cl | 4-chlorobenzyl | phenyl | N-(2-(3-(pyridin-2-ylmethyl)-2-oxoimidazolidin-1-yl)ethyl)carboxamide | M + H = 664.0<br>$t_{Ret}$ = 5.63 min |

-continued

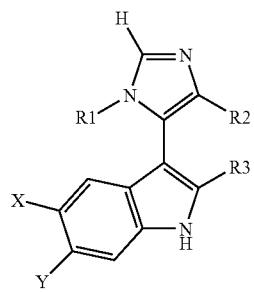

| Example | X and Y | R¹ | R² | R³ | Analysis MS/HPLC/NMR |
|---|---|---|---|---|---|
| 329 | X = H, Y = Cl | 4-Cl-phenyl (R) | phenyl | -C(O)-NH-CH₂CH₂-piperazine-C(O)-tetrahydropyran | M + H = 698.9, $_C t_{Ret}$ = 5.63 min |
| 330 | X = H, Y = Cl | 4-Cl-phenyl (R) | phenyl | -C(O)-NH-CH₂CH₂-piperazine-C(O)-CH₂-pyrrolidine | M + H = 691.9, $_C t_{Ret}$ = 5.23 min |
| 331 | X = H, Y = Cl | 4-Cl-benzyl | phenyl | -C(O)-pyrrolidinyl-NH-CH₂CH₂-O-C(O)CH₃ | M − H = 614.0, $_E t_{Ret}$ = 4.00 min |
| 332 | X = H, Y = Cl | 4-Cl-benzyl | phenyl | -C(O)-pyrrolidinyl-NH-CH₂CH₂-OH | M − H = 601.9, $_E t_{Ret}$ = 3.89 min |
| 333 | X = H, Y = Cl | 4-Cl-benzyl | phenyl | -C(O)-pyrrolidinyl-NH-CH₂CH₂-pyrrolidine | M − H = 625.0, $_E t_{Ret}$ = 3.79 min |
| 334 | X = H, Y = Cl | 4-Cl-benzyl | phenyl | -C(O)-pyrrolidinyl-NH-CH₂CH₂CH₂-pyrrolidine | M − H = 639.1, $_E t_{Ret}$ = 3.77 min |

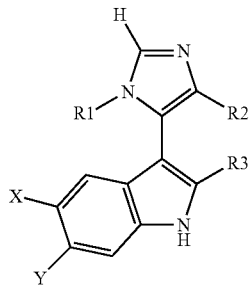

| Example | X and Y | R¹ | R² | R³ | Analysis MS/HPLC/NMR |
|---|---|---|---|---|---|
| 335 | X = H<br>Y = Cl | Cl-C₆H₄-CH₂- | phenyl | pyrrolidine-methoxyethyl-methylamide | M − H = 601.9<br>$_E t_{Ret}$ = 3.89 min |

Example 147 is synthesized by condensation of 4-Chlorobenzyl-amine, Intermediate 147.1 and 1-(isocyano-phenyl-methanesulfonyl)-4-methyl-benzene analogously to the preparation of Intermediate 2.2 as a colorless solid.

Intermediate 147.1

6-Chloro-3-formyl-1H-indole-2-sulfonic acid dimethylamide

The title compound is synthesized by formylation of Intermediate 147.2 analogously to the preparation of Intermediate 1.1 as a white solid; ES-MS: M+=287.1; HPLC: $_A t_{Ret}$=4.33 min.

Intermediate 147.2

6-Chloro-1H-indole-2-sulfonic acid dimethylamide

Step 1; A solution of Intermediate 147.3 (1.0 g, 3.27 mmol) in the mixture of hexane (11 mL) and Et₂O (11 mL) is treated with 2M THF/heptane solution of LDA (1.8 mL, 3.6 mmol) for 1 h at 0° C. The reaction mixture is cooled to −30° C., and is treated with sulfuryl chloride (0.52 mL, 6.5 mmol) for 4 h. The reaction mixture is quenched by H₂O and diluted with EtOAc, then the organic layer is dried over Na₂SO₄ and evaporated in vacuo to provide crude product, which is submitted to the next step without further purification.

Step 2; A solution of 6-Chloro-1-(toluene-4-sulfonyl)-1H-indole-2-sulfonyl chloride in THF (17 mL) is treated with the excess of 2M THF solution of dimethylamine (17.3 mL, 34.6 mmol) at RT. After completion the reaction mixture is quenched with saturated aqueous NaHCO₃ and diluted with EtOAc. The organic layer is dried over Na₂SO₄ and evaporated in vacuo. Silica gel flash chromatography of the residue affords 6-Chloro-1-(toluene-4-sulfonyl)-1H-indole-2-sulfonic acid dimethylamide as a red solid; ES-MS: M+=413.0: $_A t_{Ret}$=5.36.

Step 3; A mixture of 6-Chloro-1-(toluene-4-sulfonyl)-1H-indole-2-sulfonic acid dimethylamide (160 mg, 0.39 mmol) and 1M THF solution of TBAF (1.8 mL) is stirred at RT. After completion, the reaction mixture is quenched by saturated aqueous NH₄Cl, EtOAc is added and the organic layer is washed with brine, dried over MgSO₄ and evaporated in vacuo. Silica gel flash chromatography of the residue affords the title compound as a white powder; ES-MS: M+=259.1: $_A t_{Ret}$=4.43.

Intermediate 147.3

6-Chloro-1-(toluene-4-sulfonyl)-1H-indole

Intermediate 147.3 is prepared in analogy to a published literature procedure (J. Med. Chem. 2006, 49, 3101-3115). 55% of NaH in mineral oil (881 mg, 20.2 mmol) is added to a solution of 6-Chloroindole (3.0 g, 19.8 mmol) in THF (28 mL) at 0° C. After 1 h, TsCl (3.85 g, 20.2 mmol) is added, and the reaction mixture is stirred at RT. After completion, the reaction mixture is quenched by saturated aqueous NaHCO₃ and diluted with Et₂O. The organic layer is dried over Na₂SO₄ and evaporated in vacuo to provide crude solid. The crude product is washed with small amount of Et₂O to give the title compound as orange crystal; ES-MS: M+=306.1: $_A t_{Ret}$=5.60.

Example 148 is synthesized by condensation of Intermediate 148.1, Intermediate 10.1 and 1-(isocyano-phenyl-methanesulfonyl)-4-methyl-benzene analogously to the preparation of Intermediate 2.2 as a colorless solid.

Intermediate 148.1

(2-Aminomethyl-5-chloro-phenyl)-methanol

Intermediate 148.1 is prepared in analogy to a published literature procedure (J. Org. Chem. 2004, 69, 3620-3627).

Step 1; A mixture of methyl 2-bromo-5-chlorobenzoate (3 g, 12.0 mmol) and copper cyanide (1.2 g, 13.2 mmol) in DMF (15 mL) is heated at 90° C. for 4 h and then cooled to 10° C. Toluene (15 mL) is added followed by the slow addition of a 9:1 aqueous solution (15 ml) of 10% (w/v) NH₄Cl/30% NH₄OH to maintain the internal temperature <25° C. The reaction mixture is exposed to air and the resulting biphasic mixture stirred for 14 h. Then blue aqueous layer is removed and this process is repeated until the aqueous layer is no longer blue. The organic layer is dried over Na$_2$SO$_4$ and evaporated in vacuo to provide crude solid. Silica gel flash chromatography of the residue affords 5-Chloro-2-cyano-benzoic acid methyl ester as a yellow solid; $_ct_{Ret}$=6.82.

Step 2; A mixture of ZnCl$_2$ (338 mg, 2.43 mmol) and LiBH$_4$ (117 mg, 5.11 mmol) in THF (5.2 mL) is heated at 60° C. for 90 min followed by the slow addition of toluene (2.6 ml) solution of 5-Chloro-2-cyano-benzoic acid methyl ester (500 mg, 2.56 mmol) and stirred for 12 h. The resulting mixture is cooled to 10° C. and quenched by 3N HCl and this biphasic mixture is then heated to 40° C. for 30 min. This mixture is neutralized by 10N NaOH to pH 12, and toluene layer is concentrated in vacuo. Silica gel flash chromatography of the residue affords the title compound as a yellow solid; ES-MS: M+H=172.0: $_ct_{Ret}$=3.88.

Intermediate 149.1

2-[4-(2-Imidazol-1-yl-ethyl)-piperazin-1-yl]ethylamine

A solution of Intermediate 149.2 (1.1 g, 5.0 mmol) in THF (15 mL) is treated by LAH (393 mg, 10.0 mmol) at 0° C. After completion the reaction mixture is quenched by Na$_2$SO$_4$.10H$_2$O (8.4 g, excess) and stirred for 30 min. The product is isolated by filtration with Celite and washed with THF and dried under reduced pressure to give the title compound as oil; ES-MS: M+H=224.2: $_ct_{Ref}$=1.58.

Intermediate 149.2

[4-(2-Imidazol-1-yl-ethyl)-piperazin-1-yl]acetonitrile

A mixture of 1-(2-Imidazol-1-yl-ethyl)-piperazine (commercially available from CHESS GmbH) (1.0 g, 5.44 mmol), bromoacetonitrile (740 mg, 6.0 mmol) and K$_2$CO$_3$ (1.65 g, 12.0 mmol) in CH$_3$CN (15 mL) is stirred at RT. After completion the product is isolated by filtration with Celite and washed with CH$_3$CN and dried under reduced pressure to give the title compound as oil; ES-MS: M+H=220.2: $_ct_{Ret}$=1.70.

Intermediate 150.1

2-(4-Ethyl-piperazin-1-yl)-ethylamine

The title compound is synthesized by reduction of Intermediate 150.2 analogously to the preparation of Intermediate 149.1 as a orange oil; ES-MS: M+H=158.2: $^1$HNMR (DMSO-d$_6$) 2.60-2.20 (m, 16H), 0.95 (t, 3H).

Intermediate 150.2

(4-Ethyl-piperazin-1-yl)-acetonitrile

The title compound is synthesized by coupling of 1-Ethyl-piperazine and bromoacetonitrile analogously to the preparation of Intermediate 149.2 as a orange oil; ES-MS: M+=154.1: $^1$HNMR(DMSO-d$_6$) 3.70 (s, 2H), 2.40-2.20 (m, 10H), 0.95 (t, 3H).

Intermediate 151.1

2-(4-Isopropyl-piperazin-1-yl)-ethylamine

The title compound is synthesized by reduction of Intermediate 151.2 analogously to the preparation of Intermediate 149.1 as a colorless oil; ES-MS: M+=172.2: $^1$HNMR (DMSO-d$_6$) 2.60-2.20 (m, 15H), 0.95 (d, 6H).

Intermediate 151.2

(4-Isopropyl-piperazin-1-yl)-acetonitrile

The title compound is synthesized by coupling of 1-Isopropyl-piperazine and bromoacetonitrile analogously to the preparation of Intermediate 149.2 as a colorless oil; ES-MS: M+=168.1; $^1$HNMR(DMSO-d$_6$) 3.70 (s, 2H), 2.70-2.40 (m, 9H), 0.95 (d, 6H).

Intermediate 152.1

6-Chloro-3-[3-(4-chloro-2-hydroxymethyl-benzyl)-5-phenyl-3H-imidazol-4-yl]-1H-indole-2-carboxylic acid (Which is Also a Compound of the Formula I According to the Invention)

The title compound is synthesized by hydrolysis of Intermediate 152.2 analogously to the preparation of Intermediate 2.1 as a colorless solid; ES-MS: M+H=492.0: $_ct_{Ret}$=5.85.

Intermediate 152.2

6-Chloro-3-[3-(4-chloro-2-hydroxymethyl-benzyl)-5-phenyl-3H-imidazol-4-yl]-1H-indole-2-carboxylic acid ethyl ester (Which is Also a Compound of the Formula I According to the Invention)

The title compound is synthesized by condensation of Intermediate 2.3, Intermediate 148.1 and 1-(isocyano-phenyl-methanesulfonyl)-4-methyl-benzene analogously to the preparation of Intermediate 2.2 as a colorless solid; ES-MS: M+H=520.0: $_ct_{Ret}$=6.20.

Intermediate 155.1

2-(4-Pyridin-3-ylmethyl-piperazin-1-yl)-ethylamine

The title compound is synthesized by reduction of Intermediate 155.2 analogously to the preparation of Intermediate 149.1 as a colorless oil; ES-MS: M+=221.2: $^1$HNMR (DMSO-d$_6$) 8.45-8.40 (m, 2H), 7.65-7.60 (m, 1H), 7.45-7.30 (m, 1H), 3.45 (s, 2H), 2.55 (t, 2H), 2.40-2.20 (m, 12H).

Intermediate 155.2

(4-Pyridin-3-ylmethyl-piperazin-1-yl)-acetonitrile

The title compound is synthesized by coupling of 1-Pyridin-3-ylmethyl-piperazine
(commercially available from CHESS GmbH) and bromoacetonitrile analogously to the preparation of Intermediate 149.2 as a colorless oil; ES-MS: M+=217.2.

Intermediate 156.1

2-[4-(2-Dimethylamino-ethyl)-piperazin-1-yl]ethylamine

The title compound is synthesized by reduction of Intermediate 156.2 analogously to the preparation of Intermediate 149.1 as a colorless oil; ES-MS: M+H=201.3.

Intermediate 156.2

[4-(2-Dimethylamino-ethyl)-piperazin-1-yl]acetonitrile

The title compound is synthesized by coupling of Dimethyl-(2-piperazin-1-yl-ethyl)-amine (commercially available from CHESS GmbH) and bromoacetonitrile analogously to the preparation of Intermediate 149.2 as a colorless oil; ES-MS: M+=197.2.

Intermediate 157.1

2-[4-(2-Pyrrolidin-1-yl-ethyl)-piperazin-1-yl]-ethylamine

The title compound is synthesized by reduction of Intermediate 157.2 analogously to the preparation of Intermediate 149.1 as a colorless oil; ES-MS: M+H=227.3.

Intermediate 157.2

[4-(2-Pyrrolidin-1-yl-ethyl)-piperazin-1-yl]-acetonitrile

The title compound is synthesized by coupling of 1-(2-Pyrrolidin-1-yl-ethyl)-piperazine (commercially available from ABCR GmbH) and bromoacetonitrile analogously to the preparation of Intermediate 149.2 as a colorless solid; ES-MS: M+H=223.3.

Intermediate 158.1

2-[4-(3-Methoxy-propyl)-piperazin-1-yl]-ethylamine

The title compound is synthesized by reduction of Intermediate 158.2 analogously to the preparation of Intermediate 149.1 as a colorless oil; ES-MS: M+=202.2; $^1$HNMR (DMSO-$d_6$) 3.30 (t, 2H), 3.20 (s, 3H), 2.55 (t, 2H), 2.40-2.20 (m, 14H), 1.65-1.55 (m, 2H).

Intermediate 158.2

[4-(3-Methoxy-propyl)-piperazin-1-yl]acetonitrile

The title compound is synthesized by coupling of 1-(3-Methoxy-propyl)-piperazine (commercially available from CHESS GmbH) and bromoacetonitrile analogously to the preparation of Intermediate 149.2 as a colorless oil; ES-MS: M+=198.2; $^1$HNMR(DMSO-$d_6$) 3.65 (s, 2H), 3.30 (s, 3H), 2.45-2.20 (m, 12H), 1.65-1.55 (m, 2H).

Intermediate 159.1

2-[4-(4-Fluoro-phenyl)-piperazin-1-yl]ethylamine

The title compound is synthesized by reduction of Intermediate 159.2 analogously to the preparation of Intermediate 149.1 as a colorless oil; ES-MS: M+=224.2; $_At_{Ret}$=1.54.

Intermediate 159.2

4-(4-Fluoro-phenyl)-piperazin-1-yl]acetonitrile

The title compound is synthesized by coupling of 1-(4-Fluoro-phenyl)-piperazine and bromoacetonitrile analogously to the preparation of Intermediate 149.2 as a colorless oil; ES-MS: M+=220.2: $_At_{Ret}$=2.48.

Intermediate 161.1

2-(4-Pyridin-4-yl-piperazin-1-yl)-ethylamine

The title compound is synthesized by reduction of Intermediate 161.2 analogously to the preparation of Intermediate 149.1 as a colorless oil; ES-MS: M+=207.2.

Intermediate 161.2

(4-Pyridin-4-yl-piperazin-1-yl)-acetonitrile

The title compound is synthesized by coupling of 1-Pyridin-4-yl-piperazine and bromoacetonitrile analogously to the preparation of Intermediate 149.2 as a colorless oil; ES-MS: M+=202.2: $^1$HNMR(DMSO-$d_6$) 8.15 (d, 2H), 6.80 (d, 2H), 3.80 (s, 1H), 3.35 (t, 4H), 2.50 (t, 4H).

Intermediate 162.1

2-[4-(2-Methoxy-ethyl)-piperazin-1-yl]-ethylamine

The title compound is synthesized by reduction of Intermediate 162.2 analogously to the preparation of Intermediate 149.1 as a colorless oil; ES-MS: M+=188.2.

Intermediate 162.2

[4-(2-Methoxy-ethyl)-piperazin-1-yl]-acetonitrile

The title compound is synthesized by coupling of 1-(2-Methoxy-ethyl)-piperazine and bromoacetonitrile analogously to the preparation of Intermediate 149.2 as a colorless oil; ES-MS: M+=184.2.

Intermediate 163.1

2-[4-Phenyl-piperazin-1-yl]-ethylamine

The title compound is synthesized by reduction of Intermediate 163.2 analogously to the preparation of Intermediate 149.1 as a colorless oil; ES-MS: M+=206.2: $_At_{Ret}$=1.20.

Intermediate 163.2

(4-Phenyl-piperazin-1-yl)-acetonitrile

The title compound is synthesized by coupling of 1-Phenyl-piperazine and bromoacetonitrile analogously to the preparation of Intermediate 149.2 as a white solid; ES-MS: M+=202.2: $_At_{Ret}$=1.95.

Intermediate 164.1

2-(4-Pyridin-2-yl-piperazin-1-yl)-ethylamine

The title compound is synthesized by reduction of Intermediate 164.2 analogously to the preparation of Intermediate 149.1 as a colorless oil; ES-MS: M+=207.2.

Intermediate 164.2

(4-Pyridin-2-yl-piperazin-1-yl)-acetonitrile

The title compound is synthesized by coupling of 1-Pyridin-2-yl-piperazine and bromoacetonitrile analogously to the preparation of Intermediate 149.2 as a colorless oil; ES-MS: M+=203.2: $^1$HNMR(DMSO-d$_6$) 8.05 (dd, 1H), 7.50 (dd, 1H), 6.80 (d, 1H), 6.60 (dd, 1H), 3.80 (s, 1H), 3.50 (t, 4H), 2.50 (t, 4H).

Intermediate 165.1

2-(4-Benzyl-piperazin-1-yl)-ethylamine

The title compound is synthesized by reduction of Intermediate 165.2 analogously to the preparation of Intermediate 149.1 as a colorless oil; ES-MS: M+=220.2: $_At_{Ret}$=1.10.

Intermediate 165.2

(4-Benzyl-piperazin-1-yl)-acetonitrile

The title compound is synthesized by coupling of 1-Benzyl-piperazine and bromoacetonitrile analogously to the preparation of Intermediate 149.2 as a white solid; ES-MS: M+=216.2: $_At_{Ret}$=1.50.

Intermediate 167.1

2-(4-Pyridin-3-yl-piperazin-1-yl)-ethylamine

The title compound is synthesized by reduction of Intermediate 167.2 analogously to the preparation of Intermediate 149.1 as a colorless oil; ES-MS: M+=207.2.

Intermediate 167.2

(4-Pyridin-3-yl-piperazin-1-yl)-acetonitrile

The title compound is synthesized by coupling of 1-Pyridin-3-yl-piperazine and bromoacetonitrile analogously to the preparation of Intermediate 149.2 as a white solid; ES-MS: M+=203.2: $_At_{Ret}$=1.10.

Intermediate 168.1

2-[4-(3-Methoxy-phenyl)-piperazin-1-yl]-ethylamine

The title compound is synthesized by reduction of Intermediate 168.2 analogously to the preparation of Intermediate 149.1 as a colorless oil; ES-MS: M+=236.2: $_At_{Ret}$=1.44.

Intermediate 168.2

[4-(3-Methoxy-phenyl)-piperazin-1-yl]acetonitrile

The title compound is synthesized by coupling of 1-(3-Methoxy-phenyl)-piperazine and bromoacetonitrile analogously to the preparation of Intermediate 149.2 as a white solid; ES-MS: M+=232.2: $_At_{Ret}$=2.62.

Intermediate 173.1

2-(4-Pyridin-2-ylmethyl-piperazin-1-yl)-ethylamine

The title compound is synthesized by reduction of Intermediate 173.2 analogously to the preparation of Intermediate 149.1 as a colorless oil; ES-MS: M+=221.2.

Intermediate 173.2

(4-Pyridin-2-ylmethyl-piperazin-1-yl)-acetonitrile

The title compound is synthesized by coupling of 1-Pyridin-2-ylmethyl-piperazine (commercially available from CHESS GmbH) and bromoacetonitrile analogously to the preparation of Intermediate 149.2 as a brown solid; ES-MS: M+=217.2: $^1$HNMR(DMSO-d$_6$) 8.45 (dd, 1H), 7.75 (td, 1H), 7.40 (d, 1H), 7.25-7.20 (m, 1H), 3.70 (s, 2H), 3.60 (s, 2H), 2.50-2.35 (m, 8H).

Intermediate 174.1

2-(4-Cyclopentyl-piperazin-1-yl)-ethylamine

The title compound is synthesized by reduction of Intermediate 174.2 analogously to the preparation of Intermediate 149.1 as a colorless oil; ES-MS: M+=198.2: $^1$HNMR (DMSO-d$_6$) 2.55 (t, 2H), 2.40-2.30 (m, 10H), 2.25 (t, 2H), 1.80-1.70 (m, 2H), 1.60-1.40 (m, 4H), 1.30-1.20 (m, 3H).

Intermediate 174.2

(4-Cyclopentyl-piperazin-1-yl)-acetonitrile

The title compound is synthesized by coupling of 1-Cyclopentyl-piperazine (commercially available from CHESS GmbH) and bromoacetonitrile analogously to the preparation of Intermediate 149.2 as a colorless oil; ES-MS: M+=194.2: $^1$HNMR(DMSO-d$_6$) 3.65 (s, 2H), 2.45-2.20 (m, 9H), 1.80-1.20 (m, 8H).

Intermediate 176.1

2-(4-Cyclohexylmethyl-piperazin-1-yl)-ethylamine

The title compound is synthesized by reduction of Intermediate 176.2 analogously to the preparation of Intermediate 149.1 as a colorless oil; ES-MS: M+=226.3: $^1$HNMR (DMSO-d$_6$) 2.25 (t, 2H), 2.40-2.20 (m, 12H), 2.00 (d, 2H), 1.70-1.55 (m, 5H), 1.50-1.40 (m, 1H), 1.20-1.05 (m, 3H), 0.85-0.70 (m, 2H).

Intermediate 176.2

(4-Cyclohexylmethyl-piperazin-1-yl)-acetonitrile

The title compound is synthesized by coupling of 1-Cyclohexylmethyl-piperazine piperazine (commercially available from Fluorochem Ltd) and bromoacetonitrile analogously to the preparation of Intermediate 149.2 as a colorless oil; ES-MS: M+=222.2: $^1$HNMR(DMSO-d$_6$) 3.65 (s, 2H), 2.45-2.20 (m, 8H), 2.00 (d, 2H), 1.70-1.55 (m, 5H), 1.50-1.40 (m, 1H), 1.20-1.05 (m, 3H), 0.85-0.70 (m, 2H).

Intermediate 177.1

2-(4-Morpholin-4-yl-piperidin-1-yl)-ethylamine

The title compound is synthesized by reduction of Intermediate 177.2 analogously to the preparation of Intermediate 149.1 as a colorless oil; ES-MS: M+=214.3: $^1$HNMR (DMSO-d$_6$) 3.55 (t, 4H), 3.30 (bs, 2H), 2.55 (t, 2H), 2.40 (t, 4H), 2.20 (t, 2H), 2.10-2.00 (m, 1H), 1.85-1.80 (m, 2H), 1.80-1.70 (m, 2H), 1.40-1.20 (m, 2H).

Intermediate 177.2

(4-Morpholin-4-yl-piperidin-1-yl)-acetonitrile

The title compound is synthesized by coupling of 4-Piperidin-4-yl-morpholine (commercially available from CHESS GmbH) and bromoacetonitrile analogously to the preparation of Intermediate 149.2 as a colorless oil; ES-MS: M+=210.1: $^1$HNMR(DMSO-d$_6$) 3.65 (s, 2H), 3.55 (t, 4H), 2.80-2.75 (m, 2H), 2.40 (t, 4H), 2.15-2.00 (m, 3H), 1.80-1.70 (m, 2H), 1.40-1.30 (m, 2H).

Intermediate 179.1

2-[1,4']Bipiperidinyl-1'-yl-ethylamine

The title compound is synthesized by reduction of Intermediate 179.2 analogously to the preparation of Intermediate 149.1 as a colorless oil; ES-MS: M+=212.3: $^1$HNMR (DMSO-d$_6$) 3.30 (bs, 2H), 2.85-2.80 (m, 2H), 2.55 (t, 2H), 2.40 (t, 4H), 2.20 (t, 2H), 2.10-2.05 (m, 1H), 1.85-1.75 (m, 2H), 1.65-1.55 (m, 2H), 1.45-1.30 (m, 8H).

Intermediate 179.2

[1,4']Bipiperidinyl-1'-yl-acetonitrile

The title compound is synthesized by coupling of [1,4']Bipiperidinyl (commercially available from Fluorochem Ltd) and bromoacetonitrile analogously to the preparation of Intermediate 149.2 as a colorless oil; ES-MS: M+=208.2.

Intermediate 180.1

2-(4-Pyrrolidin-1-yl-piperidin-1-yl)-ethylamine

The title compound is synthesized by reduction of Intermediate 180.2 analogously to the preparation of Intermediate 149.1 as a colorless oil; ES-MS: M+=198.2: $^1$HNMR (DMSO-d$_6$) 3.30 (bs, 2H), 2.80-2.75 (m, 2H), 2.55 (t, 2H), 2.45-2.35 (m, 4H), 2.20 (t, 2H), 1.90-1.55 (m, 9H), 1.40-1.30 (m, 2H).

Intermediate 180.2

(4-Pyrrolidin-1-yl-piperidin-1-yl)-acetonitrile

The title compound is synthesized by coupling of 4-Pyrrolidin-1-yl-piperidine (commercially available from CHESS GmbH) and bromoacetonitrile analogously to the preparation of Intermediate 149.2 as a white solid; ES-MS: M+=194.1: $^1$HNMR(DMSO-d$_6$) 3.65 (s, 2H), 2.75-2.70 (m, 2H), 2.45-2.40 (m, 4H), 2.20-2.10 (m, 2H), 1.90-1.75 (m, 3H), 1.65-1.60 (m, 4H), 1.45-1.30 (m, 2H).

Intermediate 183.1

2-[4-(Tetrahydro-furan-2-ylmethyl)-piperazin-1-yl] ethylamine

The title compound is synthesized by reduction of Intermediate 183.2 analogously to the preparation of Intermediate 149.1 as a colorless oil; ES-MS: M+=214.3.

Intermediate 183.2

[4-(Tetrahydro-furan-2-ylmethyl)-piperazin-1-yl]-acetonitrile

The title compound is synthesized by coupling of 1-(Tetrahydro-furan-2-ylmethyl)-piperazine (commercially available from CHESS GmbH) and bromoacetonitrile analogously to the preparation of Intermediate 149.2 as a white solid; ES-MS: M+=210.2.

Intermediate 184.1

2-(4-Pyridin-4-ylmethyl-piperazin-1-yl)-ethylamine

The title compound is synthesized by reduction of Intermediate 184.2 analogously to the preparation of Intermediate 149.1 as a colorless oil; ES-MS: M+=221.2: $^1$HNMR(CDCl$_3$) 8.50 (d, 2H), 7.20 (d, 2H), 3.50 (s, 2H), 2.80 (t, 2H), 2.60-2.30 (m, 12H).

Intermediate 184.2

(4-Pyridin-4-ylmethyl-piperazin-1-yl)-acetonitrile

The title compound is synthesized by coupling of 1-Pyridin-4-ylmethyl-piperazine (commercially available from ABCR GmbH) and bromoacetonitrile analogously to the preparation of Intermediate 149.2 as a colorless oil; ES-MS: M+=217.2: $^1$HNMR(CDCl$_3$) 8.55 (d, 2H), 7.25 (d, 2H), 3.50 (s, 4H), 2.70-2.40 (m, 8H).

Intermediate 193.1

3-((R)-Pyrrolidin-3-yloxymethyl)-pyridine 2HCl salt

Intermediate 193.2 (609 mg, 2.19 mmol) is treated with 1M EtOH solution of HCl (10 mL) at RT. After 5 h, the reaction mixture is evaporated in vacuo to provide the title compound as a white solid with high purity, which is submitted to the next step without further purification; ES-MS: M+=179.1; $^1$HNMR(DMSO-d$_6$) 9.50 (bs, 2H), 8.95 (s, 1H), 8.80 (d, 1H), 8.50 (d, 1H), 7.95 (dd, 1H), 4.70 (s, 2H), 4.35 (t, 1H), 3.40-3.10 (m, 5H), 2.10-1.95 (m, 2H).

Intermediate 193.2

(R)-3-(Pyridin-3-ylmethoxy)-pyrrolidine-1-carboxylic acid tert-butyl ester

55% of NaH in mineral oil (160 mg, 6.68 mmol) is added to a solution of (R)-3-Hydroxy-pyrrolidine-1-carboxylic acid tert-butyl ester (500 mg, 2.67 mmol) in THF (8 mL) at 0° C. After 15 min, 3-chloromethyl-pyridine HCl salt (526 mg, 3.20 mmol) is added, and the reaction mixture is stirred at 40° C. After completion, the reaction mixture is quenched by H$_2$O, EtOAc is added and the organic layer is washed with brine, dried over MgSO$_4$ and evaporated in vacuo. Silica gel flash chromatography of the residue affords the title compound as a white powder; ES-MS: M+=279.2: $_{At_{Ret}}$=2.80.

Intermediate 197.1

2-((R)-Pyrrolidin-2-yloxymethyl)-pyridine 2HCl salt

The title compound is synthesized by deprotection of Intermediate 197.2 analogously to the preparation of Intermediate 193.1 as a white solid; ES-MS: M+=179.1; $^1$HNMR(DMSO-d$_6$) 9.60 (bs, 1H), 9.40 (bs, 1H), 8.75 (d, 1H), 8.35 (t, 1H), 7.90 (d, 1H), 7.80 (dd, 1H), 4.80 (s, 2H), 4.40 (t, 1H), 3.50-3.10 (m, 5H), 2.10-1.90 (m, 2H).

Intermediate 197.2

(R)-3-(Pyridin-2-ylmethoxy)-pyrrolidine-1-carboxylic acid tert-butyl ester

The title compound is synthesized by coupling of (R)-3-Hydroxy-pyrrolidine-1-carboxylic acid tert-butyl ester and 2-chloromethyl-pyridine HCl salt analogously to the preparation of Intermediate 193.2 as a white solid; ES-MS: M+=279.2: $_A t_{Ret}$=2.81.

Intermediate 198.1

4-((R)-Pyrrolidin-4-yloxymethyl)-pyridine

The title compound is synthesized by deprotection of Intermediate 198.2 analogously to the preparation of Intermediate 193.1 as a white solid; ES-MS: M+=179.1; $^1$HNMR(DMSO-d$_6$) 9.50 (bs, 2H), 8.85 (d, 2H), 7.95 (d, 2H), 4.80 (s, 2H), 4.40 (t, 1H), 3.40-3.15 (m, 5H), 2.20-1.90 (m, 2H).

Intermediate 198.2

(R)-3-(Pyridin-4-ylmethoxy)-pyrrolidine-1-carboxylic acid tert-butyl ester

The title compound is synthesized by coupling of (R)-3-Hydroxy-pyrrolidine-1-carboxylic acid tert-butyl ester and 4-chloromethyl-pyridine HCl salt analogously to the preparation of Intermediate 193.2 as a white solid; ES-MS: M+=279.2: $_A t_{Ret}$=2.84.

Intermediate 199.1

[1-(2-Amino-ethyl)-piperidin-4-yl]-dimethyl-amine

The title compound is synthesized by reduction of Intermediate 199.2 analogously to the preparation of Intermediate 149.1 as a colorless oil; ES-MS: M+=172.1: $^1$HNMR (DMSO-d$_6$) 3.30 (s, 2H), 2.85-2.75 (m, 2H), 2.55 (t, 2H), 2.20 (t, 2H), 2.10 (s, 6H), 2.00-1.95 (m, 1H), 1.90-1.80 (m, 2H), 1.70-1.60 (m, 2H), 1.40-1.20 (m, 2H).

Intermediate 199.2

(4-Dimethylamino-piperidin-1-yl)-acetonitrile

The title compound is synthesized by coupling of Dimethyl-piperidin-4-yl-amine and bromoacetonitrile analogously to the preparation of Intermediate 149.2 as a colorless oil; ES-MS: M+=168.1: $^1$HNMR(DMSO-d$_6$) 3.65 (s, 2H), 2.80-2.75 (m, 2H), 2.15-2.05 (m, 8H, including a singlet at 2.10), 2.00-1.95 (m, 1H), 1.75-1.65 (m, 2H), 1.40-1.30 (m, 2H).

Intermediate 200.1

2-[4-(1-Ethyl-propyl)-piperazin-1-yl]ethylamine

The title compound is synthesized by reduction of Intermediate 200.2 analogously to the preparation of Intermediate 149.1 as a colorless oil; ES-MS: M+=200.3: $^1$HNMR (DMSO-d$_6$) 3.30 (bs, 2H), 2.55 (t, 2H), 2.40-2.25 (m, 8H), 2.20 (t, 2H), 2.10-2.00 (m, 1H), 1.45-1.35 (m, 2H), 1.25-1.05 (m, 2H), 0.90 (t, 6H).

Intermediate 200.2

4-(1-Ethyl-propyl)-piperazin-1-yl]-acetonitrile

The title compound is synthesized by coupling of 1-(1-Ethyl-propyl)-piperazine (commercially available from CHESS GmbH) and bromoacetonitrile analogously to the preparation of Intermediate 149.2 as a colorless oil; ES-MS: M+=196.2: $^1$HNMR(DMSO-d$_6$) 3.65 (s, 2H), 2.50-2.35 (m, 8H), 2.15-2.05 (m, 1H), 1.45-1.35 (m, 2H), 1.25-1.05 (m, 2H), 0.90 (t, 6H).

Intermediate 202.1

[1-(2-Amino-ethyl)-piperidin-4-yl]-diethyl-amine

The title compound is synthesized by reduction of Intermediate 202.2 analogously to the preparation of Intermediate 149.1 as a colorless oil; ES-MS: M+=200.3: $^1$HNMR (DMSO-d$_6$) 3.30 (bs, 2H), 2.85-2.75 (m, 2H), 2.55 (t, 2H), 2.45-2.30 (m, 5H), 2.20 (t, 2H), 1.90-1.80 (m, 2H), 1.60-1.55 (m, 2H), 1.40-1.30 (m, 2H), 0.95 (t, 6H).

Intermediate 202.2

(4-Diethylamino-piperidin-1-yl)-acetonitrile

The title compound is synthesized by coupling of Diethyl-piperidin-4-yl-amine (commercially available from CHESS GmbH) and bromoacetonitrile analogously to the preparation of Intermediate 149.2 as a colorless oil; ES-MS: M+=196.2: $^1$HNMR(DMSO-d$_6$) 3.65 (s, 2H), 2.80-2.75 (m, 2H), 2.45-2.30 (m, 5H), 2.15-2.05 (m, 2H), 1.70-1.60 (m, 2H), 1.45-1.35 (m, 2H), 0.95 (t, 6H).

Intermediate 203.1

2-(4-Isobutyl-piperazin-1-yl)-ethylamine

The title compound is synthesized by reduction of Intermediate 203.2 analogously to the preparation of Intermediate 149.1 as a colorless oil; ES-MS: M+=186.2: $^1$HNMR (DMSO-d$_6$) 3.30 (bs, 2H), 2.50 (t, 2H), 2.40-2.20 (m, 10H), 1.95 (d, 2H), 1.75-1.65 (m, 1H), 0.95 (d, 6H).

Intermediate 203.2

(4-Isobutyl-piperazin-1-yl)-acetonitrile

The title compound is synthesized by coupling of 1-Isobutyl-piperazine amine (commercially available from CHESS GmbH) and bromoacetonitrile analogously to the preparation of Intermediate 149.2 as a colorless oil; ES-MS: M+=182.2: $^1$HNMR(DMSO-d$_6$) 3.65 (s, 2H), 2.45-2.20 (m, 8H), 2.00 (d, 2H), 1.80-1.70 (m, 1H), 0.90 (d, 6H).

Intermediate 204.1

2-(4-Adamantan-1-yl-piperazin-1-yl)-ethylamine

The title compound is synthesized by reduction of Intermediate 204.2 analogously to the preparation of Intermediate 149.1 as a colorless oil; ES-MS: M+=264.4: $^1$HNMR (DMSO-d$_6$) 3.30 (bs, 2H), 2.60-2.50 (m, 6H), 2.40-2.20 (m, 6H), 2.00 (bs, 3H), 1.60-1.50 (m, 12H).

Intermediate 204.2

(4-Adamantan-1-yl-piperazin-1-yl)-acetonitrile

The title compound is synthesized by coupling of 1-Adamantyl-piperazine (commercially available from CHESS GmbH) and bromoacetonitrile analogously to the preparation of Intermediate 149.2 as a colorless oil; ES-MS: M+=260.3: $^1$HNMR(DMSO-d$_6$) 3.65 (s, 2H), 2.60-2.50 (m, 4H), 2.45-2.40 (m, 4H), 2.00 (bs, 3H), 1.60-1.50 (m, 12H).

Intermediate 205.1

[1-(2-Amino-ethyl)-piperidin-4-yl]-dipropyl-amine

The title compound is synthesized by reduction of Intermediate 205.2 analogously to the preparation of Intermediate 149.1 as a colorless oil; ES-MS: M+=228.3: $^1$HNMR (DMSO-d$_6$) 3.30 (bs, 2H), 2.85-2.80 (m, 2H), 2.60 (t, 2H), 2.40-2.25 (m, 5H), 2.20 (t, 2H), 1.85-1.80 (m, 2H), 1.60-1.50 (m, 2H), 1.40-1.25 (m, 6H), 0.90 (t, 6H).

Intermediate 205.2

(4-Dipropylamino-piperidin-1-yl)-acetonitrile

The title compound is synthesized by coupling of Dipropyl-piperidin-4-yl-amine (commercially available from CHESS GmbH) and bromoacetonitrile analogously to the preparation of Intermediate 149.2 as a colorless oil; ES-MS: M+=224.3: $^1$HNMR(DMSO-d$_6$) 3.65 (s, 2H), 2.80-2.75 (m, 2H), 2.40-2.30 (m, 5H), 2.15-2.05 (m, 2H), 1.65-1.60 (m, 2H), 1.50-1.30 (m, 6H), 0.90 (t, 6H).

Intermediate 207.1

2-(4-tert-Butyl-piperazin-1-yl)-ethylamine

The title compound is synthesized by reduction of Intermediate 207.2 analogously to the preparation of Intermediate 149.1 as a colorless oil; ES-MS: M+=186.2; $^1$HNMR (DMSO-d$_6$) 2.60 (t, 2H), 2.50-2.20 (m, 10H), 1.40 (bs, 2H), 0.95 (s, 9H).

Intermediate 207.2

(4-$^t$Butyl-piperazin-1-yl)-acetonitrile

The title compound is synthesized by coupling of 1-$^t$Butyl-piperazine (commercially available from Wako Pure Chemical Industries, Ltd) and bromoacetonitrile analogously to the preparation of Intermediate 149.2 as a colorless oil; ES-MS: M+=182.2: $^1$HNMR(DMSO-d$_6$) 3.65 (s, 2H), 2.50-2.40 (m, 8H), 1.00 (s, 9H).

Intermediate 208.1

2-(4-Pyrimidin-2-yl-piperazin-1-yl)-ethylamine

The title compound is synthesized by reduction of Intermediate 208.2 analogously to the preparation of Intermediate 149.1 as a colorless oil; ES-MS: M+=208.2.

Intermediate 208.2

(4-Pyrimidin-2-yl-piperazin-1-yl)-acetonitrile

The title compound is synthesized by coupling of 2-piperazin-1-yl-pyrimidine and bromoacetonitrile analogously to the preparation of Intermediate 149.2 as a white solid; ES-MS: M+=204.2: $^1$HNMR(DMSO-d$_6$) 8.35 (d, 2H), 6.60 (t, 1H), 3.80-3.70 (m, 6H), 2.45-2.40 (m, 4H).

Intermediate 209.1

6-Chloro-3-[3-(4-chloro-2-fluoro-benzyl)-5-phenyl-3H-imidazol-4-yl]-1H-indole-2-carboxylic acid (At the Same Time a Compound of the Formula I According to the Invention)

The title compound is synthesized by hydrolysis of Intermediate 209.2 analogously to the preparation of Intermediate 2.1 as a colorless solid; ES-MS: M+=480.0: $_A$t$_{Ref}$=4.23.

Intermediate 209.2

6-Chloro-3-[3-(4-chloro-2-fluoro-benzyl)-5-phenyl-3H-imidazol-4-yl]-1H-indole-2-carboxylic acid ethyl ester (Which is Also a Compound of the formula I According to the Invention)

The title compound is synthesized by condensation of Intermediate 2.3, 4-chloro-2-fluoro-benzylamine and 1-(isocyano-phenyl-methanesulfonyl)-4-methyl-benzene analogously to the preparation of Intermediate 2.2 as a colorless solid; ES-MS: M+=508.0: $_A$t$_{Ref}$=4.63.

Intermediate 219.1

6-Chloro-3-[3-(4-chloro-benzyl)-5-(4-fluoro-phenyl)-3H-imidazol-4-yl]-1H-indole-2-carboxylic acid (Which is Also a Compound of the Formula I According to the Invention)

The title compound is synthesized by hydrolysis of Intermediate 219.2 analogously to the preparation of Intermediate 2.1 as a colorless solid; ES-MS: M+H=480.0: HPLC$_C$t$_{Ref}$=6.24.

Intermediate 219.2

6-Chloro-3-[3-(4-chloro-benzyl)-5-(4-fluoro-phenyl)-3H-imidazol-4-yl]-1H-indole-2-carboxylic acid ethyl ester (Which is Also a Compound of the Formula I According to the Invention)

The title compound is synthesized by condensation of Intermediate 2.3, 4-chloro-benzylamine and 1-(isocyano-4-fluoro-phenyl-methanesulfonyl)-4-methyl-benzene (commercially available from SynChem, Inc) analogously to the preparation of Intermediate 2.2 as a colorless solid; ES-MS: M+H=508.0: HPLC: $_C$t$_{Ref}$=6.59.

Example 220 is synthesized by deprotection of Intermediate 220.1 analogously to the preparation of Example 44 as a colorless solid; ES-MS: M+H=587.0; HPLC: $_C$t$_{Ref}$=5.36 min.

Intermediate 220.1

4-{2-[(6-Chloro-3-{3-[(S)-1-(4-chloro-phenyl)-ethyl]-5-phenyl-3H-imidazol-4-yl}-1H-indole-2-carbonyl)-amino]-ethyl}-piperazine-1-carboxylic acid tert-butyl ester (Which is Also a Compound of the Formula I According to the Invention)

The title compound is synthesized by condensation of Intermediate 134.1 and 4-(2-aminoethyl)-piperazine-1-carboxylic acid tert-butyl ester analogously to the preparation of Example 2 as a colorless solid; ES-MS: M+H=687.0; HPLC: $_{C}t_{Ret}$=6.12 min.

Intermediate 221.1

6-Chloro-3-[3-(4-chloro-benzyl)-5-(2-fluoro-phenyl)-3H-imidazol-4-yl]-1H-indole-2-carboxylic acid (Which is Also a Compound of the Formula I According to the Invention)

The title compound is synthesized by hydrolysis of Intermediate 221.2 analogously to the preparation of Intermediate 2.1 as a colorless solid; ES-MS: M+H=480.0: $_{C}t_{Ret}$=6.12.

Intermediate 221.2

6-Chloro-3-[3-(4-chloro-benzyl)-5-(2-fluoro-phenyl)-3H-imidazol-4-yl]-1H-indole-2-carboxylic acid ethyl ester (Which is also a Compound of the Formula I According to the Invention)

The title compound is synthesized by condensation of Intermediate 2.3, 4-chloro-benzylamine and 1-(isocyano-2-fluoro-phenyl-methanesulfonyl)-4-methyl-benzene (commercially available from SpeedChemical Corp. Ltd) analogously to the preparation of Intermediate 2.2 as a colorless solid; ES-MS: M+H=508.0: $_{C}t_{Ret}$=6.50.

Intermediate 224.1

2-(4-Benzyl-piperidin-1-yl)-ethylamine

The title compound is synthesized by reduction of Intermediate 224.2 analogously to the preparation of Intermediate 149.1 as a colorless oil; ES-MS: M+H=219.3: $_{A}t_{Ret}$=2.04.

Intermediate 224.2

(4-Benzyl-piperidin-1-yl)-acetonitrile

The title compound is synthesized by coupling of 4-Benzyl-piperidine and bromoacetonitrile analogously to the preparation of Intermediate 149.2 as a colorless oil; ES-MS: M+=215.2: $_{A}t_{Ret}$=2.90.

Intermediate 225.1

2-(4-Pyridin-2-ylmethyl-piperidin-1-yl)-ethylamine

The title compound is synthesized by reduction of Intermediate 225.2 analogously to the preparation of Intermediate 149.1 as a colorless oil; ES-MS: M+=220.3.

Intermediate 225.2

(4-Pyridin-2-ylmethyl-piperidin-1-yl)-acetonitrile

The title compound is synthesized by coupling of 2-Piperidin-4-ylmethyl-pyridine (commercially available from Array Biopharma) and bromoacetonitrile analogously to the preparation of Intermediate 149.2 as a colorless oil; ES-MS: M+=216.2.

Intermediate 226.1

6-Chloro-3-[3-(3,3-dimethyl-butyl)-5-phenyl-3H-imidazol-4-yl]-1H-indole-2-carboxylic acid (Which is Also a Compound of the Formula I According to the Invention)

The title compound is synthesized by hydrolysis of Intermediate 137.1 analogously to the preparation of Intermediate 2.1 as a colorless solid; ES-MS: M+=422.0: $_{A}t_{Ret}$=4.30.

Intermediate 227.1

2-(4-$^t$Butyl-piperidin-1-yl)-ethylamine

The title compound is synthesized by reduction of Intermediate 227.2 analogously to the preparation of Intermediate 149.1 as a colorless oil; ES-MS: M+H=185.3; $^1$HNMR (DMSO-$d_6$) 3.40 (bs, 2H), 2.90-2.80 (m, 2H), 2.55 (t, 2H), 2.20 (t, 2H), 1.80-1.70 (m, 2H), 1.60-1.50 (m, 2H), 1.25-1.05 (m, 2H), 1.00-0.90 (m, 1H), 0.80 (s, 9H).

Intermediate 227.2

(4-$^t$Butyl-piperidin-1-yl)-acetonitrile

The title compound is synthesized by coupling of 4-$^t$Butyl-piperidine (commercially available from Matrix Scientific) and bromoacetonitrile analogously to the preparation of Intermediate 149.2 as a colorless oil; ES-MS: M+=181.2; $^1$HNMR(DMSO-$d_6$) 3.65 (s, 2H), 2.80-2.75 (m, 2H), 2.05-2.00 (m, 2H), 1.65-1.60 (m, 2H), 1.25-1.05 (m, 2H), 1.00-0.90 (m, 1H), 0.80 (s, 9H).

Intermediate 228.1

2-[4-(3-Methoxy-propyl)-piperidin-1-yl]ethylamine

The title compound is synthesized by reduction of Intermediate 228.2 analogously to the preparation of Intermediate 149.1 as a colorless oil; ES-MS: M+H=201.3.

Intermediate 228.2

[4-(3-Methoxy-propyl)-piperidin-1-yl]-acetonitrile

The title compound is synthesized by coupling of 4-(3-Methoxy-propyl)-piperidine (commercially available from ChemBridge Corporation) and bromoacetonitrile analogously to the preparation of Intermediate 149.2 as a colorless oil; ES-MS: M+=197.2; $^1$HNMR(DMSO-$d_6$) 3.65 (s, 2H), 3.30 (t, 2H), 3.00 (s, 3H), 2.75-2.70 (m, 2H), 2.10-2.00 (m, 2H), 1.65-1.40 (m, 4H), 1.20-1.00 (m, 5H).

Intermediate 229.1

2-[4-(2-Pyrrolidin-1-yl-ethyl)-piperidin-1-yl]ethylamine

The title compound is synthesized by reduction of Intermediate 229.2 analogously to the preparation of Intermediate 149.1 as a colorless oil; ES-MS: M+=226.3; $^1$HNMR (DMSO-d$_6$) 2.75 (d, 2H), 2.55 (t, 2H), 2.40-2.30 (m, 6H), 2.20 (t, 2H), 1.80-1.75 (m, 2H), 1.65-1.50 (m, 6H), 1.30-1.00 (m, 7H).

Intermediate 229.2

4-(2-Pyrrolidin-1-yl-ethyl)-piperidin-1-yl]-acetonitrile

The title compound is synthesized by coupling of 4-(2-Pyrrolidin-1-yl-ethyl)-piperidine (commercially available from ABCR GmbH) and bromoacetonitrile analogously to the preparation of Intermediate 149.2 as a colorless oil; ES-MS: M+=222.3; $^1$HNMR(CDCl$_3$) 3.45 (s, 2H), 2.70 (d, 2H), 2.45-2.20 (m, 8H), 1.80-1.60 (m, 6H), 1.40-1.20 (m, 5H).

Example 233

((S)-3-Benzylamino-pyrrolidin-1-yl)-{6-chlorobenzyl)-5-phenyl-3H imidazol-4-yl]-1H-indol-2-yl}metanone Sodium cyano borohydride (9 mg, 0.12 mmol) is added to a solution of Example 80 (50 mg, 0.09 mmol) in 1,2-dichloroethan (2 mL) at RT. After 1 h of stirring the reaction mixture is quenched by addition of DCM and saturated NaHCO$_3$ solution. The organic layer is separated and washed with H$_2$O and brine, dried and concentrated. Silica gel flash chromatography of the crude product affords the title compound as a white solid. ES-MS: M–H=618.0; HPLC: $_ct_{Ret}$=4.16 min.

Example 234, 235, 236, 237, 238, 239, 240 and 241 are also prepared in analogy to Example 233.

Intermediate 243.1

2-(4-Phenoxy-piperidin-1-yl)-ethylamine

The title compound is synthesized by reduction of Intermediate 243.2 analogously to the preparation of Intermediate 149.1 as a colorless oil; ES-MS: M+H=221.2: $_ct_{Ret}$=3.95.

Intermediate 243.2

(4-Phenoxy-piperidin-1-yl)-acetonitrile

The title compound is synthesized by coupling of 4-Phenoxy-piperidine (commercially available from Alfa Aesar) and bromoacetonitrile analogously to the preparation of Intermediate 149.2 as a colorless oil; ES-MS: M+H= 217.2: $_ct_{Ret}$=4.80.

Intermediate 244.1

2-(3,4,5,6-Tetrahydro-2H-[4,4']bipyridinyl-1-yl)-ethylamine

The title compound is synthesized by reduction of Intermediate 244.2 analogously to the preparation of Intermediate 149.1 as a colorless oil; ES-MS: M+H=206.2: $_ct_{Ret}$=1.60.

Intermediate 244.2

(3,4,5,6-Tetrahydro-2H-[4,4']bipyridinyl-1-yl)-acetonitrile

The title compound is synthesized by coupling of 1,2,3,4,5,6-Hexahydro-[4,4']bipyridinyl (commercially available from CHESS GmbH) and bromoacetonitrile analogously to the preparation of Intermediate 149.2 as a colorless oil; ES-MS: M+H=202.2: $_ct_{Ret}$=2.41.

Example 245 is synthesized by deprotection of Intermediate 245.1 analogously to the preparation of Example 44 as a colorless solid; ES-MS: M+H=572.0; HPLC: $_ct_{Ret}$=5.58 min.

Intermediate 245.1

4-[2-({6-Chloro-3-[3-(4-chloro-benzyl)-5-phenyl-3H-imidazol-4-yl]-1H-indole-2-carbonyl}-amino)-ethyl]-piperidine-1-carboxylic acid tert-butyl ester (Which is Also a Compound of the Formula I According to the Invention)

The title compound is synthesized by condensation of Intermediate 2.1 and 4-(2-Amino-ethyl)-piperidine-1-carboxylic acid tert-butyl ester analogously to the preparation of Example 2 as a colorless solid; ES-MS: M+H=672.0; HPLC: $_ct_{Ret}$=6.93 min.

Intermediate 246.1

2-[4-(2-Methoxy-ethoxy)-piperidin-1-yl]-ethylamine

The title compound is synthesized by reduction of Intermediate 246.2 analogously to the preparation of Intermediate 149.1 as a colorless oil; ES-MS: M+=203.2; $^1$HNMR (DMSO-d$_6$) 3.45 (dd, 2H), 3.40 (dd, 2H), 3.25-3.20 (m, 4H), 2.70-2.50 (m, 4H), 2.20 (t, 2H), 2.05-1.70 (m, 4H), 1.40-1.20 (m, 4H).

Intermediate 246.2

2-[4-(2-Methoxy-ethoxy)-piperidin-1-yl]-acetonitrile

The title compound is synthesized by coupling of 4-(2-Methoxy-ethoxy)-piperidine (commercially available from ChemBridge Corporation) and bromoacetonitrile analogously to the preparation of intermediate 149.2 as a colorless oil; ES-MS: M+=199.2; $^1$HNMR(DMSO-d$_6$) 3.65 (s, 2H), 3.50 (dd, 2H), 3.40 (dd, 2H), 3.30-3.25 (m, 1H), 3.20 (s, 3H), 2.70-2.60 (m, 2H), 2.25-2.20 (m, 2H), 1.85-1.80 (m, 2H), 1.50-1.40 (m, 2H).

Intermediate 247.1

2-[4-(2-Pyridin-2-yl-ethyl)-piperazin-1-yl]-ethylamine

The title compound is synthesized by reduction of Intermediate 247.2 analogously to the preparation of Intermediate 149.1 as a colorless oil; ES-MS: M+H=235.2: $_ct_{Ret}$=1.81.

Intermediate 247.2

[4-(2-Pyridin-2-yl-ethyl)-piperazin-1-yl]acetonitrile

The title compound is synthesized by coupling of 1-(2-Pyridin-2-yl-ethyl)-piperazine (commercially available from ABCR GmbH) and bromoacetonitrile analogously to the preparation of Intermediate 149.2 as a colorless oil; ES-MS: M+H=231.2: $_ct_{Ret}$=2.17.

Intermediate 248.1

2-(4-Benzyl-2-methyl-piperazin-1-yl)-ethylamine

The title compound is synthesized by reduction of Intermediate 248.2 analogously to the preparation of Intermediate 149.1 as a colorless oil; ES-MS: M+=234.3; ¹HNMR (DMSO-d₆) 7.35-7.20 (m, 5H), 3.40 (dd, 2H), 2.70-2.50 (m, 6H), 2.40-2.00 (m, 4H), 1.80 (t, 1H), 1.20 (bs, 2H), 0.90 (d, 3H).

Intermediate 248.2

(4-Benzyl-2-methyl-piperazin-1-yl)-acetonitrile

The title compound is synthesized by coupling of 4-Benzyl-2-methyl-piperazine (commercially available from CHESS GmbH) and bromoacetonitrile analogously to the preparation of Intermediate 149.2 as a colorless oil; ES-MS: M+=230.2: $_At_{Ret}$=1.86.

Intermediate 251.1

The title compound is synthesized by reduction of Intermediate 251.2 analogously to the preparation of Intermediate 149.1 as a colorless oil; ES-MS: M+=231.3: $_At_{Ret}$=2.27.

Intermediate 251.2

The title compound is synthesized by coupling of 2,3-Dihydrospiro[indene-1,4'-piperidine] (commercially available from Parkway Scientific) and bromoacetonitrile analogously to the preparation of Intermediate 149.2 as a colorless oil; ES-MS: M+=227.2: $_At_{Ret}$=3.10.

Intermediate 252.1

1-(2-Amino-ethyl)-4-benzyl-piperidin-4-ol

The title compound is synthesized by reduction of Intermediate 252.2 analogously to the preparation of Intermediate 149.1 as a colorless oil; ES-MS: M+=235.2: $_At_{Ret}$=1.27.

Intermediate 251.2

(4-Benzyl-4-hydroxy-piperidin-1-yl)-acetonitrile

The title compound is synthesized by coupling of 4-Benzyl-4-hydroxy-piperidine (commercially available from ABCR GmbH) and bromoacetonitrile analogously to the preparation of Intermediate 149.2 as a colorless oil; ES-MS: M+=231.2: $_At_{Ret}$=1.81.

Intermediate 253.1

1-(2-Amino-ethyl)-4-phenyl-piperidin-4-ol

The title compound is synthesized by reduction of Intermediate 253.2 analogously to the preparation of Intermediate 149.1 as a colorless oil; ES-MS: M+=221.2; ¹HNMR (DMSO-d₆) 7.50-7.40 (m, 2H), 7.30-7.10 (m, 3H), 3.30 (s, 2H), 2.70-2.60 (m, 4H), 2.40-2.20 (m, 4H), 1.95-1.70 (m, 3H), 1.60-1.50 (m, 2H).

Intermediate 253.2

(4-Hydroxy-4-phenyl-piperidin-1-yl)-acetonitrile

The title compound is synthesized by coupling of 4-Hydroxy-4-phenyl-piperidine and bromoacetonitrile analogously to the preparation of Intermediate 149.2 as a colorless oil; ES-MS: M+=217.2: $_At_{Ret}$=1.51.

Intermediate 254.1

2-(4-Benzyl-4,7-diaza-spiro[2.5]oct-7-yl)-ethylamine

The title compound is synthesized by reduction of Intermediate 254.2 analogously to the preparation of Intermediate 149.1 as a colorless oil; ES-MS: M+H=246.3: $_ct_{Ref}$=3.81.

Intermediate 254.2

(4-Benzyl-4,7-diaza-spiro[2.5]oct-7-yl)-acetonitrile

The title compound is synthesized by coupling of 4-Benzyl-4,7-diaza-spiro[2.5]octane (which prepared in analogy to a published literature procedure (WO030828859)) and bromoacetonitrile analogously to the preparation of Intermediate 149.2 as a colorless oil; ES-MS: M+H=242.2: $_ct_{Ref}$=3.84.

Intermediate 255.1

3-[isocyano-(toluene-4-sulfonyl)-methyl]-pyridine

The title compound is synthesized by condensation of Pyridine-3-carbaldehyde analogously to the preparation of Intermediate 16.1 as a colorless solid; ES-MS: M+H=273.1: $_ct_{Ref}$=5.45.

Intermediate 256.1

2-((2S,5R)-2,5-Dimethyl-4-pyridin-3-ylmethyl-piperazin-1-yl)ethylamine

The title compound is synthesized by reduction of Intermediate 256.2 analogously to the preparation of Intermediate 149.1 as a colorless oil; ES-MS: M+H=249.2; ¹HNMR (DMSO-d₅) 8.50 (s, 1H), 8.40 (d, 1H), 7.65 (d, 1H), 7.35 (dd, 1H), 4.00 (d, 1H), 3.05 (d, 1H), 2.80-1.70 (m, 12H), 1.05 (d, 3H), 0.90 (d, 3H).

Intermediate 256.2

((2S,5R)-2,5-Dimethyl-4-pyridin-3-ylmethyl-piperazin-1-yl)acetonitrile

The title compound is synthesized by coupling of Intermediate 256.3 and bromoacetonitrile analogously to the preparation of Intermediate 149.2 as a colorless oil; ES-MS: M+H=245.2: $_ct_{Ref}$=2.88.

Intermediate 256.3

(2R,5S)-2,5-Dimethyl-1-pyridin-3-ylmethyl-piperazine

The title compound is synthesized by deprotection of Intermediate 256.4 analogously to the preparation of Example 44 as a colorless solid; ES-MS: M+H=206.2; HPLC: $_ct_{Ref}$=2.56 min.

Intermediate 256.4

(2S,5R)-2,5-Dimethyl-4-pyridin-3-yl methyl-piperazine-1-carboxylic acid tert-butyl ester The title compound is synthesized by alkylation of Intermediate 256.5 with 3-Picolyl chloride hydrochloride analo-

Intermediate 256.5

(2S,5R)-2,5-Dimethyl-piperazine-1-carboxylic acid tert-butyl ester

A mixture of trans-2,5-Dimethyl-piperazine (1.0 g, 8.76 mmol) (commercially available from ABCR GmbH), (Boc)$_2$O (1.91 g, 8.76 mmol) and Et$_3$N (2.44 mL, 17.5 mmol) in DCM (50 mL) is stirred for 16 h at RT. After completion, the reaction mixture is quenched by H$_2$O, DCM is added and the organic layer is washed with brine, dried over MgSO$_4$ and evaporated in vacuo. Silica gel flash chromatography of the residue affords the title compound as a colorless oil; ES-MS: M+H=215.2: $^1$HNMR(DMSO-d$_6$) 3.95-3.90 (m, 1H), 3.35 (dd, 1H), 3.20 (bs, 1H), 3.05 (dd, 1H), 3.00-2.90 (m, 2H), 2.30 (dd, 1H), 1.40 (s, 9H), 1.05 (d, 3H), 1.00 (d, 3H).

Intermediate 257.1

2-(4-Indan-1-yl-piperazin-1-yl)-ethylamine

The title compound is synthesized by reduction of Intermediate 257.2 analogously to the preparation of Intermediate 149.1 as a colorless oil; ES-MS: M+H=246.3: $ct_{Ret}$=3.69.

Intermediate 257.2

(4-Indan-1-yl-piperazin-1-yl)-acetonitrile

The title compound is synthesized by coupling of 1-Indan-1-yl-piperazine (commercially available from CHESS GmbH) and bromoacetonitrile analogously to the preparation of Intermediate 149.2 as a colorless oil; ES-MS: M+H=242.2: $ct_{Ret}$=4.25.

Intermediate 259.1

2-[4-(2-Phenoxy-ethyl)-piperazin-1-yl]-ethylamine

The title compound is synthesized by reduction of Intermediate 259.2 analogously to the preparation of Intermediate 149.1 as a colorless oil; ES-MS: M+H=250.2: $ct_{Ref}$=3.78.

Intermediate 259.2

2-[4-(2-Phenoxy-ethyl)-piperazin-1-yl]-acetonitrile

The title compound is synthesized by coupling of 1-(2-Phenoxy-ethyl)-piperazine (commercially available from CHESS GmbH) and bromoacetonitrile analogously to the preparation of Intermediate 149.2 as a colorless oil; ES-MS: M+H=246.2: $ct_{Ret}$=4.31.

Intermediate 260.1

2-Benzoimidazol-1-yl-ethylamine

The title compound is synthesized by reduction of Intermediate 260.2 analogously to the preparation of Intermediate 149.1 as a colorless oil; ES-MS: M+H=162.1: $ct_{Ret}$=3.45.

Intermediate 260.2

Benzoimidazol-1-yl-acetonitrile

The title compound is synthesized by coupling of Benzimidazole and bromoacetonitrile analogously to the preparation of Intermediate 149.2 as a colorless solid; ES-MS: M+H=158.0: $ct_{Ret}$=3.42.

Intermediate 261.1

2-[4-(2-Morpholin-4-yl-ethyl)-piperazin-1-yl]-ethylamine

The title compound is synthesized by reduction of Intermediate 261.2 analogously to the preparation of Intermediate 149.1 as a colorless oil; ES-MS: M+H=243.0; $^1$HNMR (DMSO-d$_6$) 7.95 (bs, 2H), 3.80-3.60 (m, 4H), 3.40-2.70 (m, 20H).

Intermediate 261.2

[4-(2-Morpholin-4-yl-ethyl)-piperazin-1-yl]-acetonitrile

The title compound is synthesized by coupling of 4-(2-piperazin-1-yl-ethyl)-morpholine (commercially available from ABCR GmbH) and bromoacetonitrile analogously to the preparation of Intermediate 149.2 as a colorless oil; ES-MS: M+H=239.3; $^1$HNMR(DMSO-d$_6$) 3.70 (s, 2H), 3.30 (bs, 4H), 2.60-2.30 (m, 16H).

Intermediate 262.1

2-[4-(1-Methyl-piperidin-4-ylmethyl)-piperazin-1-yl]-ethylamine

The title compound is synthesized by reduction of Intermediate 262.2 analogously to the preparation of Intermediate 149.1 as a colorless oil; ES-MS: M+H=241.0; $^1$HNMR (DMSO-d$_6$) 2.70-2.50 (m, 5H), 2.40-2.20 (m, 10H), 2.10 (s, 3H), 2.15-2.00 (m, 2H), 1.75 (t, 2H), 1.60 (d, 2H), 1.40-1.30 (m, 2H), 10.5 (dq, 2H).

Intermediate 262.2

[4-(1-Methyl-piperidin-4-ylmethyl)-piperazin-1-yl]-acetonitrile

The title compound is synthesized by coupling of 1-(1-Methyl-piperidin-4-ylmethyl)-piperazine (commercially available from CHESS GmbH) and bromoacetonitrile analogously to the preparation of Intermediate 149.2 as a colorless oil; ES-MS: M+H=237.3.

Intermediate 263.1

2-[4-(2-Ethoxy-ethyl)-piperazin-1-yl]-ethylamine

The title compound is synthesized by reduction of Intermediate 263.2 analogously to the preparation of Intermediate 149.1 as a colorless oil; ES-MS: M+H=202.2; ¹HNMR (DMSO-d₅) 3.40 (q, 2H), 3.35 (q, 2H), 2.55 (t, 2H), 2.40-2.20 (m, 14H), 1.05 (t, 3H).

Intermediate 263.2

[4-(2-Ethoxy-ethyl)-piperazin-1-yl]-acetonitrile

The title compound is synthesized by coupling of 4-(2-Ethoxy-ethyl)-piperazine (commercially available from ABCR GmbH) and bromoacetonitrile analogously to the preparation of Intermediate 149.2 as a colorless oil; ES-MS: M+H=198.2; ¹HNMR(DMSO-d₆) 3.70 (s, 2H), 3.45 (q, 2H), 3.40 (q, 2H), 2.40-2.30 (m, 10H), 1.05 (t, 3H).

Intermediate 264.1

2-(4-Phenethyl-piperazin-1-yl)-ethylamine

The title compound is synthesized by reduction of Intermediate 264.2 analogously to the preparation of Intermediate 149.1 as a colorless oil; ES-MS: M+H=234.3: $ct_{Ret}$=3.74.

Intermediate 264.2

(4-Phenethyl-piperazin-1-yl)-acetonitrile

The title compound is synthesized by coupling of 4-Phenylethyl-piperazine (commercially available from ABCR GmbH) and bromoacetonitrile analogously to the preparation of Intermediate 149.2 as a colorless oil; ES-MS: M+H= 230.2: $ct_{Ret}$=4.20.

Intermediate 269.1

4-(2-Amino-ethyl)-1-pyridin-3-ylmethyl-piperazin-2-one

The title compound is synthesized by deprotection of Intermediate 269.2 analogously to the preparation of Example 44 as a colorless oil; ES-MS: M+H=235.2: $ct_{Ret}$=1.76.

Intermediate 269.2

[2-(3-Oxo-4-pyridin-3-ylmethyl-piperazin-1-yl)-ethyl]-carbamic acid tert-butyl ester A mixture of Intermediate 269.3 (1.7 g, 6.44 mmol), 2-Boc-aminoethyl-bromide (1.58 g, 7.08 mmol) and K₂CO₃ (5.34 g, 38.6 mmol) in DMF (30 mL) is stirred at RT. After completion, the reaction mixture is quenched by H₂O, EtOAc is added and the organic layer is washed with brine, dried over MgSO₄ and evaporated in vacuo. Silica gel flash chromatography of the residue affords the title compound as a colorless oil; ES-MS: M+H=335.3: $ct_{Ret}$=3.73.

Intermediate 269.3

1-Pyridin-3-ylmethyl-piperazin-2-one 2HCl salt

A solution of Intermediate 269.4 (2.03 g, 6.97 mmol) in Dioxane (25 mL) is treated by 4M Dioxane solution of HCl (25 mL) at RT. After completion, the reaction mixture is concentrated in vacuo to provide crude product, which is submitted to the next step without further purification; ES-MS: M+H=192.1: $ct_{Ret}$=1.40.

Intermediate 269.4

3-Oxo-4-pyridin-3-ylmethyl-piperazine-1-carboxylic acid tert-butyl ester

A mixture of 3-Oxo-piperazine-1-carboxylic acid tert-butyl ester (2.0 g, 9.99 mmol) and 3-Picolyl chloride hydrochloride (1.63 g, 9.99 mmol) in DMF (20 mL) is treated by 60% NaH in mineral oil (0.80 g, 19.98 mmol) at 0° C. After completion, the reaction mixture is quenched by H₂O, EtOAc is added and the organic layer is washed with brine, dried over MgSO₄ and evaporated in vacuo. Silica gel flash chromatography of the residue affords the title compound as a colorless oil; ES-MS: M+H=292.2$_{et}$=4.15.

Intermediate 270.1

2-[4-(2-Amino-ethyl)-piperazin-1-yl]-N-pyridin-2-yl-acetamide

The title compound is synthesized by deprotection of Intermediate 270.2 analogously to the preparation of Example 44 as a colorless oil; ES-MS: M+H=264.2: $ct_{Ret}$=2.70.

Intermediate 270.2

{2-[4-(Pyridin-2-ylcarbamoylmethyl)-piperazin-1-yl]-ethyl}-carbamic acid tert-butyl ester The title compound is synthesized by coupling of 2-piperazin-1-yl-N-pyridin-2-yl-acetamide trihydrochloride dehydrate (commercially available from ABCR GmbH) and (2-Bromo-ethyl)-carbamic acid tert-butyl ester analogously to the preparation of Intermediate 269.2 as a colorless oil; ES-MS: M+H=364.3: $ct_{Ret}$=4.07.

Intermediate 271.1

2-[4-(2-Amino-ethyl)-piperazin-1-yl]N-pyridin-3-yl-acetamide

The title compound is synthesized by deprotection of Intermediate 271.2 analogously to the preparation of Example 44 as a colorless oil; ES-MS: M+H=264.2: $ct_{Ret}$=1.62.

Intermediate 271.2

{2-[4-(Pyridin-3-ylcarbamoylmethyl)-piperazin-1-yl]-ethyl}-carbamic acid tert-butyl ester The title compound is synthesized by coupling of 2-piperazin-1-yl-N-pyridin-2-yl-acetamide trihydrochloride (commercially available from CHESS GmbH) and (2-Bromo-ethyl)-carbamic acid tert-butyl ester analogously to the preparation of Intermediate 269.2 as a colorless oil; ES-MS: M+H=364.2: $ct_{Ret}$=3.88.

Intermediate 272.1

2-[4-(2-Amino-ethyl)-piperazin-1-yl]-1-pyrrolidin-1-yl-ethanone

The title compound is synthesized by deprotection of Intermediate 272.2 analogously to the preparation of Example 44 as a colorless oil; ES-MS: M+H=241.3: $ct_{Ret}$=2.88.

Intermediate 272.2

{2-[4-(2-Oxo-2-pyrrolidin-1-yl-ethyl)-piperazin-1-yl]-ethyl}-carbamic acid tert-butyl ester The title compound is synthesized by coupling of 2-piperazin-1-yl-1-pyrrolidin-1-yl-ethanone (commercially available from CHESS GmbH) and (2-Bromo-ethyl)-carbamic acid tert-butyl ester analogously to the preparation of Intermediate 269.2 as a colorless oil; ES-MS: M+H=341.3: $_C t_{Ret}$=4.08.

Intermediate 273.1

2-(2-Phenyl-imidazol-1-yl)-ethylamine

The title compound is synthesized by reduction of Intermediate 273.2 analogously to the preparation of Intermediate 149.1 as a colorless oil; ES-MS: M+H=188.1: $_C t_{Ret}$=2.37.

Intermediate 273.2

(2-Phenyl-imidazol-1-yl)-acetonitrile

The title compound is synthesized by coupling of 2-Phenyl-1H-imidazole and bromoacetonitrile analogously to the preparation of Intermediate 269.4 as a colorless oil; ES-MS: M+H=184.1: $_C t_{Ref}$=3.48.

Example 278 is synthesized by deprotection of Intermediate 278.1 analogously to the preparation of Example 44 as a colorless solid.

Intermediate 278.1

4-(1-{6-Chloro-3-[3-(4-chloro-benzyl)-5-phenyl-3H-imidazol-4-yl]-1H-indole-2-carbonyl}-azetidin-3-yl)-piperazine-1-carboxylic acid tert-butyl ester (Which is Also a Compound of the Formula I According to the Invention)

The title compound is synthesized by condensation of Intermediate 2.1 and Intermediate 278.2 analogously to the preparation of Example 2 as a colorless solid; ES-MS: M+=685.0; HPLC: $_A t_{Ret}$=4.21 min.

Intermediate 278.2

4-Azetidin-3-yl-piperazine-1-carboxylic acid tert-butyl ester

A mixture of Intermediate 278.3 (1.0 g, 2.45 mmol) and 5% Pd/C (200 mg) in MeOH is shaken under a H$_2$-atmosphere (1 bar). After 22 h, the reaction mixture is filtered through Celite and carefully washed with THF. Concentration in vacuo to provide crude product, which is submitted to the next step without further purification; ES-MS: M+=242.3.

Intermediate 278.3

4-(1-Benzhydryl-azetidin-3-yl)-piperazine-1-carboxylic acid tert-butyl ester

The title compound is synthesized by condensation of piperazine-1-carboxylic acid tert-butyl ester and Methanesulfonic acid 1-benzhydryl-azetidin-3-yl ester (commercially available from Fluorochem Ltd) analogously to the preparation of Intermediate 149.2 as a white solid; ES-MS: M+=408.3; HPLC: $_A t_{Ret}$=3.84 min.

Intermediate 280.1

1-(2-Amino-ethyl)-4-pyridin-3-ylmethyl-piperazin-2-one

The title compound is synthesized by deprotection of Intermediate 280.2 analogously to the preparation of Example 44 as a colorless oil; ES-MS: M+H=235.1: $_C t_{Ret}$=1.86.

Intermediate 280.2

[2-(2-Oxo-4-pyridin-3-ylmethyl-piperazin-1-yl)-ethyl]carbamic acid tert-butyl ester The title compound is synthesized by coupling of Intermediate 280.3 and (2-Bromo-ethyl)carbamic acid tert-butyl ester analogously to the preparation of Intermediate 269.2 as a colorless oil; ES-MS: M+H=335.2: $_C t_{Ret}$=4.06.

Intermediate 280.3

4-Pyridin-3-ylmethyl-piperazin-2-one

The title compound is synthesized by coupling of piperazin-2-one and Picolyl chloride hydrochloride analogously to the preparation of Intermediate 269.2 as a white solid; ES-MS: M+H=192.1: $_C t_{Ret}$=1.74.

Intermediate 281.1

6-Chloro-3-[3-(5-chloro-pyridin-2-ylmethyl)-5-phenyl-3H-imidazol-4-yl]-1H-indole-2-carboxylic acid (Which is Also a Compound of the Formula I According to the Invention)

The title compound is synthesized by hydrolysis of Intermediate 281.2 analogously to the preparation of Intermediate 2.1 as a colorless solid; ES-MS: M+H=462.8: $_C t_{Ret}$=5.77.

Intermediate 281.2

6-Chloro-3-[3-(5-chloro-pyridin-2-ylmethyl)-5-phenyl-3H-imidazol-4-yl]-1H-indole-2-carboxylic acid ethyl ester (Which is Also a Compound of the Formula I According to the Invention)

The title compound is synthesized by condensation of Intermediate 2.3, Intermediate 281.3 and 1-[isocyano-(toluene-4-sulfonyl)-methyl]-2-fluoro-benzene analogously to the preparation of Intermediate 2.2 as a colorless solid; ES-MS: M+H=490.8: $_C t_{Ret}$=6.14.

Intermediate 281.3

C-(5-Chloro-pyridin-2-yl)-methylamine

A mixture of 5-Chloro-2-cyanopyridine (1.5 g, 10.8 mmol) and 10% Pd/C (0.4 g) in EtOH (40 mL) and conc HCl (1.2 mL) is shaken under a H$_2$-atmosphere (1 bar). After 2 h, the reaction mixture is filtered through Celite and carefully washed with THF. Concentration in vacuo and silica gel flash chromatography of the residue affords the title compound as a white solid; ES-MS: M+H=143.0: $_C t_{Ret}$=3.33.

Intermediate 282.1

2-Amino-1-(4-pyridin-3-ylmethyl-piperazin-1-yl)-ethanone

The title compound is synthesized by deprotection of Intermediate 282.2 analogously to the preparation of Example 44 as a colorless oil; ES-MS: M+H=235.2: $_C t_{Ret}$=1.62.

Intermediate 282.1

[2-Oxo-2-(4-pyridin-3-ylmethyl-piperazin-1-yl)-ethyl]-carbamic acid tert-butyl ester The title compound is synthesized by condensation of 1-Pyridin-3-ylmethyl-piperazine and N-Boc-glycine analogously to the preparation of Example 2 as a colorless solid; ES-MS: M+H=335.3; HPLC: $_A t_{Ret}$=3.93 min.

Intermediate 283.1

[1-(2-Amino-ethyl)-piperidin-4-yl]-pyridin-2-yl-amine

The title compound is synthesized by reduction of Intermediate 283.2 analogously to the preparation of Intermediate 149.1 as a colorless oil; ES-MS: M+H=221.0: $_A t_{Ret}$=2.29.

Intermediate 283.2

[4-(Pyridin-2-ylamino)-piperidin-1-yl]acetonitrile

The title compound is synthesized by coupling of Intermediate 283.3 and bromoacetonitrile analogously to the preparation of Intermediate 149.2 as a colorless oil; ES-MS: M+H=217.1: $_A t_{Ret}$=3.11.

Intermediate 283.3

Piperidin-4-yl-pyridin-2-yl-amine 3HCl

The title compound is synthesized by deprotection of Intermediate 283.4 analogously to the preparation of Intermediate 193.1 as a colorless oil; ES-MS: M+H=178.0: $_A t_{Ret}$=2.48.

Intermediate 283.4

4-(Pyridin-2-ylamino)-piperidine-1-carboxylic acid tert-butyl ester

A mixture of 4-Amino-1-Boc-piperidine (2.0 g, 9.7 mmol), 2-Bromo-pyridine (1.93 mL, 19.4 mmol), NaO$^t$Bu (2.7 g, 27.1 mmol), 2-Dicyclohexylphosphino-2'-(N,N-dimethylamino)biphenyl (472 mg, 1.16 mmol) and Tris(dibenzylideneacetone)dipalladium Chloroforme Complex (620 mg, 0.58 mmol) in dioxane (10 mL) is heated to 90° C. After completion, the reaction mixture is quenched by H$_2$O, DCM is added and the organic layer is washed with brine, dried over MgSO$_4$ and evaporated in vacuo. Silica gel flash chromatography of the residue affords the title compound as a white powder; ES-MS: M+H=278.3: $_A t_{Ret}$=4.75.

Intermediate 284.1

[1-(2-Amino-ethyl)piperidin-4-yl]methyl-pyridin-2-yl-amine

The title compound is synthesized by reduction of Intermediate 284.2 analogously to the preparation of Intermediate 149.1 as a colorless oil; ES-MS: M+H=253.3: $_A t_{Ret}$=2.31.

Intermediate 284.2

[4-(Methyl-pyridin-2-yl-amino)-piperidin-1-yl]acetonitrile

The title compound is synthesized by coupling of Intermediate 284.3 and bromoacetonitrile analogously to the preparation of Intermediate 149.2 as a colorless oil; ES-MS: M+H=231.3: $_A t_{Ret}$=3.29.

Intermediate 284.3

Methyl-piperidin-4-yl-pyridin-2-yl-amine

The title compound is synthesized by deprotection of Intermediate 284.4 analogously to the preparation of Intermediate 193.1 as a colorless oil; ES-MS: M+H=192.2: $_A t_{Ret}$=2.62.

Intermediate 284.4

4-(Methyl-pyridin-2-yl-amino)-piperidine-1-carboxylic acid tert-butyl ester A mixture of Intermediate 283.4 (1.14 g, 4.0 mmol) and MeI (0.37 mL, 6.0 mmol) in DMF (10 mL) is treated with 60% NaH in mineral oil (240 mg, 6.0 mmol) at RT. After completion, the reaction mixture is quenched by H$_2$O, EtOAc is added and the organic layer is washed with brine, dried over MgSO$_4$ and evaporated in vacuo. Silica gel flash chromatography of the residue affords the title compound as a white powder; ES-MS: M+H=232.3: $_A t_{Ret}$=4.87.

Intermediate 285.1

2-[4-(Pyridin-2-yloxy)-piperidin-1-yl]-ethylamine

The title compound is synthesized by reduction of Intermediate 285.2 analogously to the preparation of Intermediate 149.1 as a colorless oil; ES-MS: M+H=222.3: $_D t_{Ret}$=1.46.

Intermediate 285.2

[4-(Pyridin-2-yloxy)-piperidin-1-yl]-acetonitrile

The title compound is synthesized by coupling of Intermediate 285.3 and bromoacetonitrile analogously to the preparation of Intermediate 149.2 as a colorless oil; ES-MS: M+H=218.3: $_D t_{Ret}$=1.78.

Intermediate 285.3

2-(Piperidin-4-yloxy)-pyridine

The title compound is synthesized by deprotection of Intermediate 285.4 analogously to the preparation of Intermediate 193.1 as a colorless oil; ES-MS: M+=179.1: $_D t_{Ret}$=1.47.

Intermediate 285.4

4-(Pyridin-2-yloxy)-piperidine-1-carboxylic acid tert-butyl ester

A mixture of tert-Butyl-4-hydroxy-1-piperidine-carboxylate (2.0 g, 9.64 mmol) and 2-Fluoropyridine (0.93 mL, 10.6 mmol) in DMF (10 mL) is treated with 60% NaH in mineral oil (600 mg, 12.5 mmol) at RT. After completion, the reaction mixture is quenched by $H_2O$, EtOAc is added and the organic layer is washed with brine, dried over $MgSO_4$ and evaporated in vacuo. Silica gel flash chromatography of the residue affords the title compound as a white powder; ES-MS: M+H=279.0: $_Dt_{Ret}$=2.82.

Example 286 is synthesized by condensation of (S)-3-Amino-3-(4-chloro-phenyl)-propionic acid, Intermediate 10.1 and 1-(isocyano-phenyl-methanesulfonyl)-4-methyl-benzene analogously to the preparation of Example 1 as a colorless solid; ES-MS: M+H=495.7; HPLC: $_At_{Ret}$=4.28 min.

Example 287

(S)-3-[5-(6-Chloro-5-fluoro-1H-indol-3-yl)-4-phenyl-imidazol-1-yl]-3-(4-chloro-phenyl)-N-methyl-propionamide The title compound is synthesized by condensation of Example 286 and methylamine HCl salt analogy to the preparation of Example 2 as a white solid.

Example 288, 289 and 290 are also prepared in analogy to Example 287.

Example 291

6-Chloro-3-[3-(4-chloro-benzyl)-5-phenyl-3H-imidazol-4-yl]-1H-indole-2-carboxylic acid {2-[4-(pyridine-3-carbonyl)-piperazin-1-yl]-ethyl}-amide A solution of Example 44 (109 mg, 0.19 mmol) in pyridine (1.0 mL) is treated with nicotinyl chloride hydrochloride salt (41 mg, 0.23 mmol) at RT. After completion, the reaction mixture is quenched by $H_2O$, EtOAc is added and the organic layer is washed with brine, dried over $MgSO_4$ and evaporated in vacuo. Silica gel flash chromatography of the residue affords the title compound as a white powder.

Example 294, 295, 296, 298, 299, 305, 309, 310 and 312 are also prepared in analogy to Example 291.

Example 292

6-Chloro-3-[3-(4-chloro-benzyl)-5-phenyl-3H-imidazol-4-yl]-1H-indole-2-carboxylic acid {2-[4-(1-pyridin-2-yl-ethyl)-piperazin-1-yl]-ethyl}-amide A mixture of Example 44 (80 mg, 0.14 mmol), $K_2CO_3$ (39 mg, 0.28 mmol) and Intermediate 292.1 in toluene (0.5 mL) and $CH_3CN$ (0.5 mL) is heated to at 85° C. After completion, the reaction mixture is quenched by $H_2O$, EtOAc is added and the organic layer is washed with brine, dried over $MgSO_4$ and evaporated in vacuo. Silica gel flash chromatography of the residue affords the title compound as a white powder.

Example 297, 304 and 311 are also prepared in analogy to Example 292.

Intermediate 292.1

Methanesulfonic acid 1-pyridin-2-yl-ethyl ester

A mixture of Intermediate 292.2 (1.0 g, 8.12 mmol) and $Et_3N$ (2.3 mL, 16.2 mmol) in DCM (10 mL) is treated by methanesulfonylchloride (0.66 ml, 8.53 mmol) at 0° C. After completion, the reaction mixture is quenched by $H_2O$, DCM is added and the organic layer is washed with brine, dried over $MgSO_4$ and evaporated in vacuo to provide crude product, which is submitted to the next step without further purification; ES-MS: M+=202.1; $_At_{Ret}$=1.37.

Intermediate 292.2

1-Pyridin-2-yl-ethanol

A solution of 2-Acetyl-pyridine (2.0 g, 16.5 mmol) in MeOH (33 mL) is treated by $NaBH_4$ (624 mg, 16.5 mmol) at 0° C. After completion, the reaction mixture is quenched by $H_2O$, EtOAc is added and the organic layer is washed with brine, dried over $MgSO_4$ and evaporated in vacuo to provide crude product, which is submitted to the next step without further purification; ES-MS: M+=124.0; $^1$HNMR(DMSO-$d_6$) 8.45 (d, 1H), 7.75 (td, 1H), 7.50 (d, 1H), 7.20 (dd, 1H), 5.30 (d, 1H), 4.70-4.60 (m, 1H), 1.30 (d, 3H).

Example 293

6-Chloro-3-[3-(4-chloro-benzyl)-5-phenyl-3H-imidazol-4-yl]-1H-indole-2-carboxylic acid {2-[4-(6-fluoro-pyridine-3-carbonyl)-piperazin-1-yl]-ethyl}-amide The title compound is synthesized by condensation of Example 44 (100 mg, 0.17 mmol) and 6-Fluoro-nicotinic acid (37 mg, 0.26 mmol) analogy to the preparation of Example 2 as a white solid.

Example 300, 301, 302, 303, 306, 307, 308, 313, 314, 315, 316, 317, 329 and 330 are also prepared in analogy to Example 293.

Intermediate 297.1

Methanesulfonic acid 1-pyrazin-2-yl-ethyl ester

The title compound is synthesized by methansulfonylation of Intermediate 297.2 analogously to the preparation of Intermediate 292.1 as a colorless oil; ES-MS: M+=203.1: $_At_{Ret}$=1.77.

Intermediate 297.2

1-Pyrazin-2-yl-ethanol

The title compound is synthesized by reduction of Acetylpyrazine analogously to the preparation of Intermediate 292.2 as a colorless oil; ES-MS: M+=125.0; $^1$HNMR (DMSO-$d_6$) 8.75 (s, 1H), 8.55-8.50 (m, 2H), 5.60 (d, 1H), 4.85-4.75 (m, 1H), 1.40 (d, 3H).

Intermediate 304.1

The title compound is synthesized by methansulfonylation of Intermediate 304.2 analogously to the preparation of Intermediate 292.1 as a colorless oil; ES-MS: M+=202.1: $_At_{Ret}$=1.10.

Intermediate 304.2

The title compound is synthesized by reduction of 3-Acetyl-pyridine analogously to the preparation of Intermediate 292.2 as a colorless oil; ES-MS: M+=124.0; $^1$HNMR (DMSO-d$_6$) 8.50 (d, 1H), 8.40 (dd, 1H), 7.70 (td, 1H), 7.30 (dd, 1H), 5.30 (d, 1H), 4.80-4.70 (m, 1H), 1.35 (d, 3H).

Example 318

6-Chloro-3-[3-(4-chloro-benzyl)-5-phenyl-3H-imidazol-4-yl]-2-(4,5-dihydro -oxazol-2-yl)-1H-indole A mixture of Intermediate 2.1 (600 mg, 1.3 mmol), CDI (260 mg, 1.56 mmol), 2-Bromoethylamine hydrobromide (411 mg, 1.95 mmol) and Et$_3$N (0.55 mL, 3.89 mmol) in THF (6 mL) is heated to reflux. After completion, the reaction mixture is quenched by H$_2$O, EtOAc is added and the organic layer is washed with brine, dried over MgSO$_4$ and evaporated in vacuo. Silica gel flash chromatography of the residue affords the title compound as a white powder.

Example 319

5-{6-Chloro-3-[3-(4-chloro-benzyl)-5-phenyl-3H-imidazol-4-yl]-1H-indol-2-yl}-3H-[1,3,4]oxadiazol-2-one A mixture of Intermediate 319.1 (200 mg, 0.42 mmol), CDI (89 mg, 0.54 mmol) and Et$_3$N (0.1 mL, 0.71 mmol) in THF (3.6 mL) and DMF (0.4 mL) is heated to reflux. After completion, the reaction mixture is quenched by H$_2$O, EtOAc is added and the organic layer is washed with brine, dried over MgSO$_4$ and evaporated in vacuo. Silica gel flash chromatography of the residue affords the title compound as a white powder.

Intermediate 319.1

6-Chloro-3-[3-(4-chloro-benzyl)-5-phenyl-3H-imidazol-4-yl]-1H-indole-2-carboxylic acid hydrazide (Which is Also a Compound of the Formula I According to the Invention)

A mixture of Intermediate 2.2 (1.0 g, 2.0 mmol) and hydrazine (0.49 mL, 10.2 mmol) in EtOH (50 mL) is heated to reflux. After completion, the reaction mixture is concentrated in vacuo, DCM is added and the organic layer is washed with brine, dried over MgSO$_4$ and evaporated in vacuo. Silica gel flash chromatography of the residue affords the title compound as a white powder. ES-MS: M+=476.1: $_At_{Ret}$=3.88.

Example 320

(5-{6-Chloro-3-[3-(4-chloro-benzyl)-5-phenyl-3H-imidazol-4-yl]-1H-indol-2-yl}-[1,3,4]oxadiazol-2-yl)-pyridin-3-yl-amine A mixture of Intermediate 319.1 (400 mg, 0.84 mmol), 3-Isothiocyanato-pyridine (94 µL, 0.84 mmol) and pyridine (0.14 mL, 1.76 mmol) in THF (2.8 mL) is heated to at 50° C. After 15 min, TsCl (198 mg, 1.0 mmol) and pyridine (0.14 mLI, 1.76 mmol) are added and stirred for 16 h at 70° C. After completion, the reaction mixture is concentrated in vacuo, EtOAc is added and the organic layer is washed with brine, dried over MgSO$_4$ and evaporated in vacuo. Silica gel flash chromatography of the residue affords the title compound as a white powder.

Example 321 and 322 are also prepared in analogy to Example 320.

Example 323

5-{6-Chloro-3-[3-(4-chloro-benzyl)-5-phenyl-3H-imidazol-4-yl]-1H-indol-2-yl}-3-pyridin-3-ylmethyl-3H-[1,3,4]oxadiazol-2-one The title compound is synthesized by coupling of Example 319 and 3-Chloromethyl-pyridine HCl salt analogy to the preparation of Example 292 as a white solid.

Example 324

6-Chloro-3-{3-[4-chloro-2-(4-methyl-piperazin-1-ylmethyl)-benzyl]-5-phenyl-3H-imidazol-4-yl}-5-fluoro-1H-indole A mixture of Intermediate 324.1 (100 mg, 0.177 mmol), 1-Methylpiperazine (30 µL 0.266 mmol) and K$_2$CO$_3$ (36.8 mg, 0.266 mmol) in DMF (2 mL) is stirred at RT. After completion, the reaction mixture is concentrated in vacuo, EtOAc is added and the organic layer is washed with brine, dried over MgSO$_4$ and evaporated in vacuo. Silica gel flash chromatography of the residue affords the title compound as a white powder.

Example 325, 326 and 327 are also prepared in analogy to Example 324.

Intermediate 324.1

6-Chloro-3-[3-(4-chloro-2-chloromethyl-benzyl)-5-phenyl-3H-imidazol-4-yl]-5-fluoro-1H-indole A mixture of Example 148 (1.1 g, 2.36 mmol) and Et$_3$N (0.49 mL, 3.53 mmol) in DMF (25 mL) is treated by MsCl (0.20 mL, 2.59 mmol) at 0° C. After completion, the reaction mixture is concentrated in vacuo, EtOAc is added and the organic layer is washed with brine, dried over MgSO$_4$ and evaporated in vacuo. Silica gel flash chromatography of the residue affords the title compound as a white powder. ES-MS: M+H=485.9: $_Ct_{Ret}$=6.52.

Example 328

6-Chloro-3-[3-(4-chloro-benzyl)-5-phenyl-3H-imidazol-4-yl]-1H-indole-2-carboxylic acid [2-(2-oxo-3-pyridin-2-ylmethyl-imidazolidin-1-yl)-ethyl]-amide A mixture of Intermediate 328.1 (24 mg, 0.038 mmol) and CDI (6.7 mg, 0.041 mmol) in DCM (0.5 mL) is stirred at RT. After completion, DCM is added to the reaction mixture and the organic layer is washed with brine, dried over MgSO$_4$ and evaporated in vacuo. Silica gel flash chromatography of the residue affords the title compound as a white powder. ES-MS: M+H=664.0: $_Ct_{Ret}$=5.63.

Intermediate 328.1

6-Chloro-3-[3-(4-chloro-benzyl)-5-phenyl-3H-imidazol-4-yl]-1H indole-2-carboxylic acid (2-{2-[(pyridin-2-ylmethyl)-amino]-ethylamino}-ethyl)-amide (Which is Also a Compound of the Formula I According to the Invention)

The title compound is synthesized by reductive amination of Intermediate 328.2 and pyridine-2-carbaldehyde analogously to the preparation of Example 233 as a colorless solid; ES-MS: M+H=638.0; HPLC: $_c$t$_{Ret}$=5.50 min.

Intermediate 328.2

6-Chloro-3-[3-(4-chloro-benzyl)-5-phenyl-3H-imidazol-4-yl]-1H-indole-2-carboxylic acid [2-(2-amino-ethylamino)-ethyl]-amide (which is also a compound of the Formula I According to the Invention)

The title compound is synthesized by deprotection of Intermediate 328.3 analogously to the preparation of Example 44 as a colorless solid; ES-MS: M+H=547.1; HPLC: $_c$t$_{Ret}$=5.29 min.

Intermediate 328.3

{2-[2-({6-Chloro-3-[3-(4-chloro-benzyl)-5-phenyl-3H-imidazol-4-yl]-1H-indole-2-carbonyl}-amino)-ethylamino]-ethyl}-carbamic acid tert-butyl ester (Which is Also a Compound of the Formula I According to the Invention)

The title compound is synthesized by condensation of Intermediate 2.1 and [2-(2-Amino-ethylamino)-ethyl]-carbamic acid tert-butyl ester analogously to the preparation of Example 2 as a colorless solid; ES-MS: M+H=647.0; HPLC: $_c$t$_{Ref}$=6.02 min.

Intermediate 331.1

Acetic acid 2-((S)-pyrrolidin-3-ylamino)-ethyl ester 2HBr salt

The title compound is synthesized according to the procedure described for Intermediate 89.1 as the corresponding HBr salt; ES-MS: M+H=173.1.

Example 332

{6-Chloro-3-[3-(4-chloro-benzyl)-5-phenyl-3H-imidazol-4-yl]-1H-indol-2-yl}-[(S)-3-(2-hydroxy-ethylamino)-pyrrolidin-1-yl]-methanone $K_2CO_3$ (17 mg, 0.12 mmol) is added to a solution of Example 331 (50 mg, 0.08 mmol) in MeOH (1 mL) at RT. $H_2O$ (0.5 mL) is added and the reaction mixture is stirred under reflux for 3 h. It is allowed to cool to rt and carefully neutralized by addition of 0.1M aqueous HCl solution followed by aqueous work up. The crude product is recrystallized from EtOAc/$CH_2Cl_2$ to afford the title compound as a white solid.

Intermediate 333.1

(S)-Pyrrolidin-3-yl-(2-pyrrolidin-1-yl-ethyl)-amine 3HBr salt

The title compound is synthesized according to the procedure described for Intermediate 89.1 as the corresponding HBr salt; ES-MS: M+H=184.2.

Intermediate 334.1

(S)-Pyrrolidin-3-yl-(3-pyrrolidin-1-yl-propyl)-amine 3HBr salt

The title compound is synthesized according to the procedure described for Intermediate 89.1 as the corresponding HBr salt; ES-MS: M+H=198.3.

Intermediate 335.1

(2-Methoxy-ethyl)-methyl-(S)-pyrrolidin-3-yl-amine 2HBr salt

The title compound is synthesized according to the procedure described for Intermediate 89.1 as the corresponding HBr salt; ES-MS: M+H=159.2; $^1$HNMR(CDCl$_3$) 3.43 (t, 2H), 3.38 (s, 3H), 3.17-3.03 (m, 2H), 2.99-2.91 (m, 2H), 2.80 (dd, 1H), 2.67-2.57 (m, 3H), 2.24 (s, 3H).

Table 3 for further examples

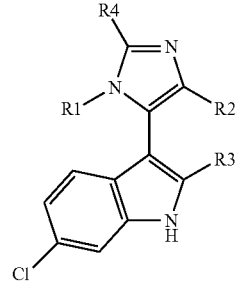

for further examples

| Example | R$^1$ | R$^2$ | R$^3$ | R$^4$ | Analysis MS/HPLC/NMR |
|---|---|---|---|---|---|
| 336 | ![Cl-benzyl] | ![phenyl] | ![pyrrolidinyl-dimethylamino carbonyl] | ![pyridinyl] | M+ = 635.0 $_A$t$_{Ret}$ = 3.83 min |

-continued for further examples

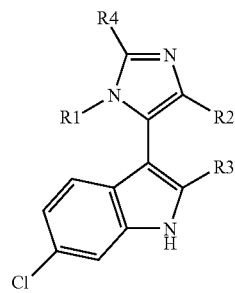

| Example | R¹ | R² | R³ | R⁴ | Analysis MS/HPLC/NMR |
|---|---|---|---|---|---|
| 337 | 4-Cl-benzyl | phenyl | (S)-1-acyl-3-(dimethylamino)pyrrolidine | 2-methoxypyridin-5-yl | M+ = 665.0<br>$_A t_{Ret}$ = 4.07 min |
| 338 | 4-Cl-benzyl | phenyl | (S)-1-acyl-3-(dimethylamino)pyrrolidine | pyrimidin-5-yl | M+ = 635.9<br>$_A t_{Ret}$ = 3.97 min |
| 339 | 4-Cl-benzyl | phenyl | H | diethoxymethyl | M + H = 521.8<br>$_E t_{Ret}$ = 5.16 min |
| 340 | 4-Cl-benzyl | phenyl | H | 2-hydroxyethyl | M + H = 449.9<br>$_E t_{ret}$ = 4.53 min |
| 341 | 4-Cl-benzyl | phenyl | H | pyridin-4-yl | M − H = 493.1<br>$_E t_{ret}$ = 4.65 min |
| 342 | 4-Cl-benzyl | phenyl | H | 2-hydroxypropyl | M + H = 463.9<br>$_E t_{ret}$ = 4.51 min |
| 343 | 4-Cl-benzyl | phenyl | H | 2-(N-methyl-N-ethylamino)-2-(dimethylamino)ethyl | M = H = 545.2<br>$_E t_{ret}$ = 4.03 min |

-continued for further examples

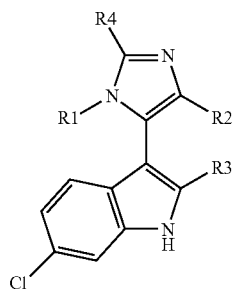

| Example | R¹ | R² | R³ | R⁴ | Analysis MS/HPLC/NMR |
|---|---|---|---|---|---|
| 344 | 4-Cl-benzyl | phenyl | H | 4-ethylpiperazin-1-ylmethyl | M − H = 542.2; $_E t_{ret}$ = 4.09 min |
| 345 | 4-Cl-benzyl | phenyl | H | morpholin-4-ylmethyl | M − H = 519.0; $_E t_{ret}$ = 4.68 min |
| 346 | 4-Cl-benzyl | phenyl | H | dimethylaminomethyl | M − H = 473.1; $_E t_{ret}$ = 4.57 min |
| 347 | 4-Cl-benzyl | phenyl | H | ethoxycarbonylpropyl | M − H = 516.0; $_E t_{ret}$ = 4.89 min |
| 348 | 4-Cl-benzyl | phenyl | H | carboxypropyl | M − H = 488.9; $_E t_{ret}$ = 4.55 min |
| 349 | 4-Cl-benzyl | phenyl | H | 3-hydroxypropyl | M + H = 478.2; $_E t_{ret}$ = 4.51 min |
| 350 | 4-Cl-benzyl | phenyl | H | N,N-dimethylcarbamoylpropyl | M − H = 519.2; $_E t_{ret}$ = 4.61 min |

-continued for further examples

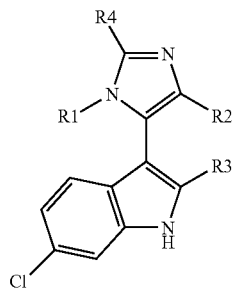

| Example | R¹ | R² | R³ | R⁴ | Analysis MS/HPLC/NMR |
|---|---|---|---|---|---|
| 351 | 4-Cl-benzyl | phenyl | H | N-methyl-N-(2-methoxyethyl)butanamide | M − H = 559.0; $_E t_{ret}$ = 4.67 min |
| 352 | 4-Cl-benzyl | phenyl | H | N-(2-methoxyethyl)butanamide | M − H = 549.2; $_E t_{ret}$ = 4.55 min |
| 353 | 4-Cl-benzyl | phenyl | H | N-methyl-N-(3-dimethylaminopropyl)butanamide | M − H = 590.2; $_E t_{ret}$ = 4.11 min |
| 354 | 4-Cl-benzyl | phenyl | H | N-methyl-N-(2-methoxyethyl)propyl | M − H = 545.1; $_E t_{Ret}$ = 4.13 min |
| 355 | 4-Cl-benzyl | phenyl | H | N-methyl-N-(3-dimethylaminopropyl)propyl | M − H = 572.2; $_E t_{Ret}$ = 3.99 min |
| 356 | 4-Cl-benzyl | phenyl | H | 1H-pyrrol-3-ylmethyl | M − H = 481.1; ¹HNMR(CDCl₃) δ 8.36 (bs 1H), 8.31 (bs, 1H), 7.61 (s, 2H), 7.39 (s, 1H), 7.21-7.12 (m, 7H), 6.99 (d, 1H), 6.89 (s, 1H), 6.86 (d, 2H), 6.80-6.76 (m, 1H), 6.49-6.46 (m, 1H), 5.07 (s, 2H). |

-continued for further examples

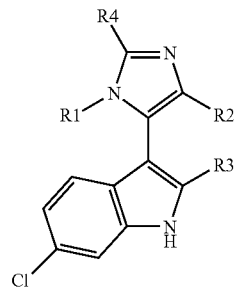

| Example | R¹ | R² | R³ | R⁴ | Analysis MS/HPLC/NMR |
|---|---|---|---|---|---|
| 357 | Cl-C₆H₄-CH₂- | phenyl | -C(O)NH-CH₂CH₂-N(piperazinyl-N-Me) | Me | M − H = 599.0 $_E t_{Ret}$ = 3.88 min |

All compounds without Example 336, 337, 338 obtained by KOH or TBAF mediated deprotection of corresponding N-Tosyl protected precursors Typical Procedure for Tbaf Mediated Deprotection:

The N-protected intermediate (0.1 mmol) is added to a 3 M solution of TBAF in THF at rt and stirred until completion of the reaction. Aqueous workup and silicagel flash chromatography of the crude material affords the final examples.

Typical Procedure for KOH Mediated Deprotction:

The N-protected intermediate (0.1 mmol, 1.0 equiv) is dissolved in MeOH (5 mL) and treated with powdered KOH (0.15 mmol, 1.5 equiv) at rt. The reaction is then warmed to 65° C. and stirred until completion. It is cooled in an ice bath and carefully neutralized by addition of 0.1 M aqueous HCl solution followed by aqueous workup and silica gel flash chromatography of the crude material to afford the final examples.

Example 336

{6-Chloro-3-[3-(4-chloro-benzyl)-5-phenyl-2-pyridin-3-yl-3H-imidazol-4-yl]-1H-indol-2-yl}-((S)-3-dimethylamino-pyrrolidin-1-yl)-methanone A mixture of Intermediate 336.1 (100 mg, 0.15 mmol), Pyridine-3-boronic acid (38 mg, 0.31 mmol), Pd(PPh₃)₄ (18 mg, 0.015 mmol) and K₂CO₃ (85 mg, 0.62 mmol) in dioxane (0.8 mL) and H₂O (0.4 mL) is heated at 90° C. After completion, the reaction mixture is quenched by H₂O, EtOAc is added and the organic layer is washed with brine, dried over MgSO₄ and evaporated in vacuo. Silica gel flash chromatography of the residue affords the title compound as a white powder.

Example 337 and 338 are also prepared in analogy to Example 336.

Intermediate 336.1

{3-[2-Bromo-3-(4-chloro-benzyl)-5-phenyl-3H-imidazol-4-yl]-6-chloro-1H-indol-2-yl}-((S)-3-dimethylamino-pyrrolidin-1-yl)-methanone (Which is Also a Compound of the Formula I According to the Invention)

The title compound is synthesized by condensation of Intermediate 336.2 and Dimethyl-(S)pyrrolidin-3-yl-amine analogously to the preparation of Example 2 as a colorless solid; ES-MS: M+=637.7; HPLC: $_A t_{Ret}$=4.67 min Intermediate 336.2

3-[2-Bromo-3-(4-chloro-benzyl)-5-phenyl-3H-imidazol-4-yl]-6-chloro-1H-indole-2-carboxylic acid (Which is Also a Compound of the Formula I According to the Invention)

The title compound is synthesized by hydrolysis of Example 145 analogously to the preparation of Intermediate 2.1 as a colorless solid; ES-MS: M+=541.7; HPLC: $_A t_{Ret}$=5.10 min.

Intermediate 339.1

6-Chloro-3-[3-(4-chlorobenzyl)-2-diethoxymethyl-5-phenyl-3H-imidazol-4-yl]-1-(toluene-4-sulfonyl)-1H-indole A solution of intermediate 144.1 (1.7 g, 3.4 mmol), intermediate 339.2 (1.8 g, 4.2 mmol), Pd(PPh₃)₄ (410 mg, 0.34 mmol), K₃PO₄ (1.9 g, 8.7 mmol) in dioxane/H₂O (3:1; 40 mL) is heated to 100° C. in a sealed tube under argon atmosphere for 30 min. It then allowed to cool to rt and diluted to EtOAc. The organic layer is washed with H₂O, aqueous citric acid solution (15% wt) and brine, dried and concentrated.

Silica gel flash chromatography of the crude product affords the title compound as a greenish solid. ES-MS: M+H= 677.2: $_Et_{Ret}$=5.91 min.

Intermediate 339.2

1-(4-Chlorobenzyl)-2-diethoxymethyl-5-iodo-4-phenyl-1H-imidazole

NIS (5.5 g, 24 mmol) is added to a solution of intermediate 339.3 (5.9 g, 15.9 mmol) in CH$_3$CN (60 mL) at rt. The reaction mixture is then warmed to 85° C. and stirred for 3 d. After completion it is allowed to cool to it and diluted with EtOAc. The organic layer is washed repeatedly with sat. aqueous NaHCO$_3$ solution, dried and concentrated. Silica gel flash chromatograpy of the crude product affords the title compound as a yellow oil. ES-MS: M+H=498.3: $_Et_{Ret}$=5.40 min.

Intermediate 339.3

1-(4-Chlorobenzyl)-2-diethoxymethyl-4-phenyl-1H-imidazole

60% of NaH in mineral oil (0.83 g, 20.8 mmol) is added to a solution of intermediate 339.4 (3.9 g, 16.0 mmol) in THF (20 mL) at RT. The reaction is allowed to stir for 20 min followed by addition of 4-chloro benzylbromide (3.4 g, 16.0 mmol). Stirring is continued for 1 h at RT and then the reaction is quenched by addition of EtOAc and H$_2$O. The organic layer is separated, washed with brine, dried and concentrated to give the title compound which was submitted without further purification to the next stage. ES-MS: M+H=371.2: $_Et_{Ret}$=4.65 min.

Intermediate 339.4

2-Diethoxymethyl-4-phenyl-1H-imidazole

NaOMe (18% wt solution in MeOH, 2.83 g, 51 mmol) is added to a solution of diethoxyacetonitrile (4.9 mL, 34.3 mmol) in MeOH (60 mL) and stirred for 1 h at rt. Phenylacylamine hydrochloride (3.0 g, 17.1 mmol) is then added to the reaction mixture followed by NaOMe (18% wt solution in MeOH, 2.83 g, 51 mmol). After 2 h of stirring at it the reaction mixture is diluted with EtOAc and the organic layer is washed with H$_2$O and brine. The organic layer is then dried and concentrated. The crude product is the purified by tituration with EtOAc/hexanes. Yellow solid. ES-MS: M+H=247.1: $^1$HNMR (DMSO d6) δ 7.73 (d, 2H), 7.52 (s, 1H), 7.30 (dd, 2H), 7.27 (dd, 1H), 5.51 (s, 1H), 3.60 (q, 2H), 3.54 (q, 2H), 1.14 (t, 6H).

Intermediate 340.1

{1-(4-Chlorobenzyl)-5-[6-chloro-1-(toluene-4-sulfonyl)-1H-indol-3-yl]-4-phenyl-1H-imidazol-2-yl}-methanol A solution of intermediate 340.2 (43 mg, 0.06 mmol) in THF (2 mL) is treated with LAH (2M solution in THF; 30 μL, 0.06 mmol) at 0° C. The reaction mixture is allowed to warm to RT and stirred for 15 min. It is quenched by addition of EtOAc. The organic layer is washed with aqueous citric acid (15% wt) and brine, dried and concentrated to give the title compound as an off white solid. ES-MS: M−H= 600.4: $_Et_{Ret}$=5.31 min.

Intermediate 340.2

1-(4-Chlorobenzyl)-5-[6-chloro-1-(toluene-4-sulfonyl)-1H-indol-3-yl]-4-phenyl-1H-imidazole-2-carbaldehyde A solution of intermediate 339.1 (1.5 g, 2.2 mmol) in THF (30 mL) is treated with HCl (1M solution in H$_2$O; 11 mL) at RT. The reaction mixture is then warmed to reflux and stirred for 1 h. After cooling to rt it is diluted with EtOAc and the organic layer is washed with saturated aqueous NaHCO$_3$ solution and brine, dried and concentrated to give the title compound as a white solid. ES-MS: M−H=599.2: $_Et_{Ret}$=6.67 min.

Example 341 is synthesized by coupling of Intermediate 144.1 and 4-Pyridineboronic acid analogously to the preparation of Example 144 as a white solid.

Intermediate 342.1

{1-(4-Chlorobenzyl)-5-[6-chloro-1-(toluene-4-sulfonyl)-1H-indol-3-yl]-4-phenyl-1H-imidazol-2-yl}-ethanol A solution of intermediate 340.2 (70 mg, 0.12 mmol) in THF (1 mL) is treated with MeMgBr (3M solution in THF; 120 μL) at rt. The reaction mixture is allowed to stir for 1 h and is then quenched by addition of EtOAc. The organic layer is repeatedly washed with aqueous citric acid (15% wt) and brine, dried and concentrated to give the title compound as a yellow solid. ES-MS: M−CH$_3$=600.0: $_Et_{Ret}$=5.33 min.

Intermediate 343.1

N-{1-(4-Chlorobenzyl)-5-[6-chloro-1-(toluene-4-sulfonyl)-1H-indol-3-yl]-4-phenyl-1H-imidazol-2-ylmethyl}-N,Nˆ,Nˆ-trimethylpropane-1,3-diamine AcOH (5 μL, 0.08 mmol) and sodium cyano borohydride (8 mg, 0.12 mmol) are added to a solution of intermediate 340.2 (50 mg, 0.08 mmol) and N,N,N-trimethylpropane diamine (13 μL, 0.09 mmol) in THF (2 mL) at RT. The reaction mixture is stirred for 12 h and then diluted with EtOAc. The organic layer is washed with satureated aqueous NaHCO$_3$ solution, H$_2$O and brine, dried and concentrated. Silica gel flash chromatography of the crude product affords the title compound as a white foam. $_Et_{Ret}$=5.50 min.

Intermediate 344.1

6-Chloro-3-[3-(4-chlorobenzyl)-4-ethyl-piperazin-1-ylmethyl-5-phenyl-3H-imidazole-4-yl]-1-(toluene-4-sulfonyl)-1H-indole The title compound is synthesized by reductive amination analogously to the preparation of Intermediate 343.1 as a colorless solid; ES-MS: M+H=772.0: $_Et_{Ret}$=4.87 min.

Intermediate 345.1

6-Chloro-3-[3-(4-chlorobenzyl)-2-morpholin-4-ylmethyl-5-phenyl-3H-imidazole-4-yl]-1-(toluene-4-sulfonyl)-1H-indole The title compound is synthesized by reductive amination analogously to the preparation of Intermediate 343.1 as a colorless solid; ES-MS: M+H=773.2: $_Et_{Ret}$=5.40 min.

Intermediate 346.1

{1-(4-Chlorobenzyl)-5-[6-chloro-1-(toluene-4-sulfonyl)-1H-indol-3-yl]-4-phenyl-1H-imidazol-2-ylmethyl}-dimethylamine The title compound is synthesized by reductive amination analogously to the preparation of Intermediate 343.1 as a colorless solid; ES-MS: M+H=631.1: $_Et_{Ret}$=5.39 min.

Intermediate 347.1

3-[1-(4-Chloro-benzyl)-5-[6-chloro-1-(toluene-4-sulfonyl)-1H-indol-3-yl]-4-phenyl-1H-imidazol-2-yl]-propionic acid ethyl ester $ZnBr_2$ (280 mg, 1.2 mmol) and Pd—C (5%, Engelhard 4709, 260 mg) are added to a solution of Intermediate 347.2 (910 mg, 1.2 mmol) in EtOAc (20 mL) at RT. The reaction mixture is stirred under an atmosphere of $H_2$ at RT for 1d. It is then diluted with EtOAc and filtered over a plug of celite and concentrated. Silica gel flash chromatography of the crude product affords the title compound as a yellow solid. ES-MS: M+H=674.2: $_Et_{Ret}$=5.57 min.

Intermediate 347.2

(E)-3-{1-(4-Chloro-benzyl)-5-[6-chloro-1-(toluene-4-sulfonyl)-1H-indol-3-yl]-4-phenyl-1H-imidazol-2-yl}-acrylic acid ethyl ester A solution of triethyl phosphono acetate (320 µL, 1.6 mmol) in THF (10 mL) is treated with 60% of NaH in mineral oil (62 mg, 1.6 mmol) at 0° C. The solution is stirred for 5 min and then added via a canula to a solution of intermediate 340.2 (845 mg, 1.4 mmol) in THF (10 mL) at RT. The resulting reaction mixture is stirred for 30 min at it and then diluted with EtOAc. The organic layer is washed with $H_2O$ and brine, dried and concentrated to give the title compound as a yellow solid. ES-MS: M−H=669.9: $_Et_{Ret}$=6.27 min.

Example 348

3-[1-(4-Chlorobenzyl)-5-(6-chloro-1H-indol-3-yl)-4-phenyl-1H-imidazol-2-yl]N-(2-methoxy-ethyl)-carboxylic acid Powdered KOH (140 mg, 2.2 mmol) is added to a solution of intermediate 347.1 (583 mg, 0.87 mmol) in EtOH (10 mL) at RT. The reaction mixture is then heated to 80° C. for 20 h. After cooling to RT it is transferred to an ice bath and acidified by careful addition of aqueous HCl solution (5M). Stirring is continued for 30 min at 0° C. and the resulting precipitate of the title compound is isolated by filtration and dried under reduced pressure to give a yellow solid.

Intermediate 349.1

3-[1-(4-Chloro-benzyl)-5-[6-chloro-1-(toluene-4-sulfonyl)-1H-indol-3-yl]-4-phenyl-1H-imidazol-2-yl]-propan-1-ol A solution of intermediate 347.1 (150 mg, 0.22 mmol) in THF (5 mL) is treated with LAH (2M solution in THF; 224 µL, 0.44 mmol) at 0° C. The reaction mixture is allowed to warm to RT and stirred for 30 min. It is quenched by addition of EtOAc. The organic layer is washed with aqueous citric acid (15% wt) and brine, dried and concentrated to give the title compound as an off white solid. ES-MS: M−H=628.0: $_Et_{Ret}$=5.27 min.

Example 350

3-[1-(4-Chlorobenzyl)-5-(6-chloro-1H-indol-3-yl)-4-phenyl-1H-imidazol-2-yl]-N,N-dimethyl-propionamide N-Methylmorpholine (67 µL, 0.61 mmol) and HATU (93 mg, 0.24 mmol) are added to a solution of Example 348 (100 mg, 0.2 mmol) in THF (5 mL) at RT. The reaction mixture is stirred for 5 min followed by addition of N,N dimethyl amine (2M solution in THF, 310 µL, 0.62 mmol). Stirring is continued at it and after 1 h the reaction mixture is diluted with EtOAc. The organic layer is washed with saturated aqueous $NaHCO_3$ solution and brine, dried and concentrated. The remaining crude product is purified by flash chromatography ($SiO_2$; DCM/MeOH, gradient 0-10% MeOH) to give the title compound as a white solid.

Example 351, 352 and 353 are also prepared in analogy to Example 350.

Example 354

{3-[1-(4-Chlorobenzyl)-5-(6-chloro-1H-indol-3-yl)-4-phenyl-1H-imidazol-2-yl]-propyl}-(2-methoxy-ethyl)-methylamine A solution of Example 351 (40 mg, 0.07 mmol) in THF (3 mL) is treated with LAH (2M solution in THF; 36 µL) at 0° C. The reaction is allowed to warm to it and stirred for 3 h. It is then quenched by addition of EtOAc and $H_2O$. The organic layer is separated and washed with brine, dried and concentrated. Silica gel flash chromatography of the crude product affords the title compound as a yellow solid.

Example 355 is also prepared in analogy to Example 354.

Intermediate 356.1

6-Chloro-3-[3-(4-chlorobenzyl)-5-phenyl-2-(triisopropylsilanyl-1H-pyrrol-3-yl)-3H-imidazol-4-yl]-6-chloro-1-(toluene-4-sulfonyl)-1H-indole The title compound is synthesized by coupling of Intermediate 356.2 and 2-(triisopropylsilanyl-1H-pyrrol-3-yl) boronic acid analogously to the preparation of Example 341 as a colorless solid; ES-MS: M+H=792.7; $^1$HNMR ($CDCl_3$) δ 8.02 (s, 1H), 7.61 (d, 2H), 7.47 (d, 2H), 7.40 (s, 1H), 7.19 (dd, 4H), 7.09-7.04 (m, 4H), 7.00 (d, 1H), 6.91 (s, 1H), 6.59 (s, 1H), 5.01 (s, 2H), 2.39 (s, 3H), 1.37-1.31 (m, 3H), 1.03 (d, 18H).

Intermediate 356.2

3-[2-Bromo-3-(4-chlorobenzyl)-5-phenyl-3H-imidazol-4-yl]-6-chloro-1-(toluene-4-sulfonyl)-1H-indole NBS (728 mg, 4.1 mmol) is added to a solution of Intermediate 356.3 (1.9 g, 3.4 mmol) in THF (100 mL) at 0° C. The reaction mixture is allowed to reach rt and stirred for 4 h. The product is isolated by aqueous workup and purified by silica gel flash chromatography to give the title compound. ES-MS: M−H=649.7: $_Et_{Ret}$=6.71 min.

Intermediate 356.3

6-Chloro-3-[3-(4-chlorobenzyl)-5-phenyl-3H-imidazol-4-yl]-1-(toluene-4-sulfonyl)-1H-indole 50% of NaH in mineral oil (284 mg, 5.9 mmol) is added to a solution of Example 1 (1.65 g, 3.9 mmol) in THF (40 mL) at 0° C. The reaction mixture is allowed to warm to rt and stirred for 15 min. TsCl (902 mg, 4.7 mmol) is added and stirring continued for 1 h. The reaction is quenched by addition of EtOAc and $H_2O$. The organic layer is separated, washed with brine, dried and concentrated. The crude product is purified by tituration with EtOAc/hexanes to give the title compound as a white solid. ES-MS: M+H=573.7: $_Et_{Ret}$=5.33 min.

Intermediate 357.1

6-Chloro-3-3-(4-chloro-benzyl)-2-methyl-5-phenyl-3H-imidazol-4-yl]-1H-indole-2-carboxylic acid (Which is Also a Compound of the Formula I According to the Invention)

A solution of Intermediate 357.2 (36 mg, 0.07 mmol) in EtOH (5 mL) is treated with powdered KOH (7 mg, 0.11 mmol) and heated with stirring to 90° C. for 16 h. After completion of the reaction it is allowed to cool to rt and neutralized by careful addition of 1 N HCl in EtOH. It is concentrated and the remaining crude product taken up in EtOAc. The organic layer is repeatedly washed with $H_2O$, dried and concentrated to give the title as a white solid. ES-MS: M−H=474.0: $_Et_{Ret}$=4.45 min

Intermediate 357.2

6-Chloro-3-3-(4-chloro-benzyl)-2-methyl-5-phenyl-3H-imidazol-4-yl]-1H-indole-2-carboxylic acid ethyl ester (Which is Also a Compound of the Formula I According to the Invention)

A mixture of Example 145 (125 mg, 0.19 mmol), trimethylboroxine (110 µL, 0.78 mmol), Pd(PPh$_3$)$_4$ (23 mg, 0.02 mmol), $K_3PO_4$ (170 mg, 0.78 mmol), $H_2O$ (3 mL) and dioxane (3 mL) is placed in a sealed tube under argon atmosphere and heated to 80° C. for 1 h. After completion the reaction mixture is quenched by addition of $H_2O$. EtOAc is added and the organic layer is washed with brine, dried over $MgSO_4$ and evaporated in vacuo. Silica gel flash chromatography of the residue affords the title compound as a colorless powder; ES-MS: M−H=502.0: $_Et_{Ret}$=4.72 min.

Table 4 for further examples for further examples

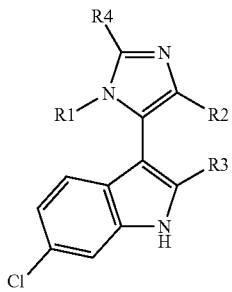

| Example | $R^1$ | $R^2$ | $R^3$ | $R^4$ | Analysis MS/HPLC/NMR |
|---|---|---|---|---|---|
| 358 | 4-Cl-benzyl | phenyl | 1-(piperidin-4-yl)-N-(3-(dimethylamino)propyl)-N-methyl, acyl | H | M + H = 642.9  $_Dt_{Ret}$ = 2.65 min |
| 359 | 4-Cl-benzyl | phenyl | 1-(piperidin-4-yl)-N-(4-(dimethylamino)butyl)-N-methyl, acyl | H | M + H = 657.0  $_Dt_{Ret}$ = 2.65 min |

-continued for further examples

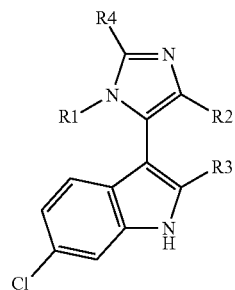

| Example | R¹ | R² | R³ | R⁴ | Analysis MS/HPLC/NMR |
|---|---|---|---|---|---|
| 360 | 4-Cl-phenyl (chiral) | phenyl | –C(O)NH-CH2-C(O)-piperazine-N-CH2-(N-methylpiperidine) | H | M + H = 711.9; $_C t_{Ret}$ = 5.35 min |
| 361 | 4-Cl-phenyl (chiral) | phenyl | –C(O)NH-CH2CH2-piperazine-N-C(O)-(piperidin-4-yl) | H | M + H = 697.8; $_C t_{Ret}$ = 5.32 min |
| 362 | 4-Cl-phenyl (chiral) | phenyl | –C(O)NH-CH2CH2-piperazine-N-CH2-C(CH3)3 | H | M + H = 657.2; $_A t_{Ret}$ = 5.70 min |
| 363 | 4-Cl-phenyl (chiral) | phenyl | –C(O)NH-CH2CH2-piperazine-N-CH2-cyclopentyl | H | M + H = 668.9; $_A t_{Ret}$ = 5.72 min |
| 364 | 4-Cl-benzyl | phenyl | –C(O)NH-CH2CH2-piperazine-N-CH2-(2-fluorophenyl) | H | M + H = 680.9; $_D t_{Ret}$ = 2.84 min |

-continued
for further examples

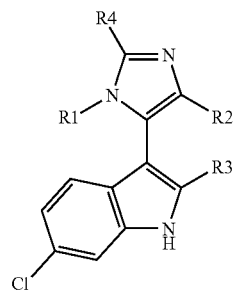

| Example | R¹ | R² | R³ | R⁴ | Analysis MS/HPLC/NMR |
|---|---|---|---|---|---|
| 365 | 4-Cl-benzyl | phenyl | -C(O)NH-CH₂CH₂-N(piperazine)-N-CH₂-(2,6-difluorophenyl) | H | M + H = 698.8; $_Dt_{Ret}$ = 2.87 min |
| 366 | 4-Cl-benzyl | phenyl | -C(O)NH-CH₂CH₂-N(piperazine)-N-CH₂-(3-fluorophenyl) | H | M + H = 680.9; $_Dt_{Ret}$ = 2.85 min |
| 367 | 4-Cl-benzyl (chiral) | phenyl | -C(O)NH-CH₂CH₂-N(piperazine)-N-CH₂-(pyran-4-yl) | H | M + H = 684.8; $_Ct_{Ret}$ = 5.54 min |
| 368 | 4-Cl-benzyl (chiral) | phenyl | -C(O)NH-CH₂CH₂-N(piperazine)-N-CH₂CH₂-(tetrahydropyran-4-yl) | H | M + H = 698.9; $_Ct_{Ret}$ = 5.43 min |

Intermediate 358.1

N,N,N'-Trimethyl-N'-piperidin-4-yl-propane-1,3-diamine

The title compound is synthesized by hydrogenation of Intermediate 358.2 analogously to the preparation of Intermediate 347.1 as a colorless solid; ES-MS: M+H=200.2; TLC: Rf=0.14 (DCM/MeOH/NH₃=70:30:1).

Intermediate 358.2

4-[(3-Dimethylamino-propyl)-methyl-amino]-piperidine-1-carboxylic acid benzyl ester The title compound is synthesized by reductive amination of Intermediate 358.3 and formaldehyde analogously to the preparation of Example 233 as a colorless oil; ES-MS: M+H=334.3; $_Dt_{Ret}$=2.25 min.

Intermediate 358.3

4-(3-Dimethylamino-propylamino)-piperidine-1-carboxylic acid benzyl ester

The title compound is synthesized by reductive amination of 4-Oxo-piperidine-1-carboxylic acid benzyl ester and N,N-dimethyl-propylamine analogously to the preparation of Example 233 as a colorless oil; ES-MS: M+H=320.2; $_Dt_{Ret}$=2.22 min.

Intermediate 359.1

N,N,N'-Trimethyl-N'-piperidin-4-yl-butane-1,4-diamine

The title compound is synthesized by hydrogenation of Intermediate 359.2 analogously to the preparation of Intermediate 347.1 as a colorless solid; ES-MS: M+H=214.1; TLC: Rf=0.05 (DCM/MeOH/NH$_3$=70:30:1).

Intermediate 359.2

4-[(4-Dimethylamino-butyl)-methyl-amino]-piperidine-1-carboxylic acid benzyl ester The title compound is synthesized by reductive amination of Intermediate 359.3 and formaldehyde analogously to the preparation of Example 233 as a colorless oil; ES-MS: M+H=348.3; $_Dt_{Ret}$=2.27 min.

Intermediate 359.3

4-(4-Dimethylamino-butylamino)-piperidine-1-carboxylic acid benzyl ester

The title compound is synthesized by reductive amination of 4-Oxo-piperidine-1-carboxylic acid benzyl ester and N,N-dimethyl-butylamine analogously to the preparation of Example 233 as a colorless oil; ES-MS: M+H=334.2; $_Dt_{Ret}$=2.23 min.

Intermediate 360.1

2-Amino-1-[4-(1-methyl-piperidin-4-ylmethyl)-piperazin-1-yl]-ethanone 3HCl salt The title compound is synthesized by deprotection of Intermediate 360.2 analogously to the preparation of Example 44 as a colorless oil; ES-MS: M+H=255.2.

Intermediate 360.2

{2-[4-(1-Methyl-piperidin-4-ylmethyl)-piperazin-1-yl]-2-oxo-ethyl}-carbamic acid tert-butyl ester The title compound is synthesized by condensation of 1-Pyridin-3-ylmethyl-piperazine and N-Boc-glycine analogously to the preparation of Example 2 as a colorless solid; ES-MS: M+H=355.2.

Intermediate 361.1

4-(4-{2-[(6-Chloro-3-{3-[(S)-1-(4-chloro-phenyl)-ethyl]-5-phenyl-3H-imidazol-4-yl}-1H-indole-2-carbonyl)-amino]-ethyl}-piperazine-1-carbonyl)-piperidine-1-carboxylic acid tert-butyl ester Intermediate 361.1 is also prepared in analogy to Example 293. ES-MS: M+H=797.9; $_Ct_{Ret}$=6.10 min.

Intermediate 362.1

2-[4-(2,2-Dimethyl-propyl)-piperazin-1-yl]ethylamine

The title compound is synthesized by reduction of Intermediate 362.2 analogously to the preparation of Intermediate 149.1 as a colorless oil; ES-MS: M+H=200.2: TLC: Rf=0.30 (DCM/MeOH/NH$_3$=40:10:1).

Intermediate 362.2

[4-(2,2-Dimethyl-propyl)-piperazin-1-yl]acetonitrile

The title compound is synthesized by coupling of Intermediate 362.3 and bromoacetonitrile analogously to the preparation of Intermediate 149.2 as a colorless oil; ES-MS: M+H=196.2: TLC: Rf=0.93 (DCM/MeOH/NH$_3$=40:10:1).

Intermediate 362.3

1-(2,2-Dimethyl-propyl)-piperazine 2HCl salt

The title compound is synthesized by deprotection of Intermediate 362.4 analogously to the preparation of Intermediate 193.1 as a colorless oil; ES-MS: M+H=157.2: TLC: Rf=0.60 (DCM/MeOH/NH$_3$=40:10:1).

Intermediate 362.4

4-(2,2-Dimethyl-propyl)-piperazine-1-carboxylic acid tert-butyl ester

The title compound is synthesized by reductive amination of 1-Boc-piperazine and Pivalaldehyde analogously to the preparation of Example 233 as a colorless oil; ES-MS: M+H=257.3; TLC: Rf=0.82 (DCM/EtOAc=4:1).

Intermediate 363.1

2-(4-Cyclopentylmethyl-piperazin-1-yl)-ethylamine

The title compound is synthesized by reduction of Intermediate 363.2 analogously to the preparation of Intermediate 149.1 as a colorless oil; ES-MS: M+H=212.2: TLC: Rf=0.17 (DCM/MeOH/NH$_3$=40:10:1).

Intermediate 363.2

(4-Cyclopentylmethyl-piperazin-1-yl)-acetonitrile

The title compound is synthesized by coupling of Intermediate 363.3 and bromoacetonitrile analogously to the preparation of Intermediate 149.2 as a colorless oil; ES-MS: M+H=208.2: TLC: Rf=0.70 (DCM/MeOH/NH$_3$=80:10:1).

Intermediate 363.3

1-Cyclopentylmethyl-piperazine 2HCl salt

The title compound is synthesized by deprotection of Intermediate 363.4 analogously to the preparation of Intermediate 193.1 as a colorless oil; ES-MS: M+H=169.2: TLC: Rf=0.16 (DCM/MeOH/NH$_3$=80:10:1).

Intermediate 362.4

4-Cyclopentylmethyl-piperazine-1-carboxylic acid tert-butyl ester

The title compound is synthesized by reductive amination of 1-Boc-piperazine and Cyclopentane-carboaldehyde analogously to the preparation of Example 233 as a colorless oil; ES-MS: M+H=269.2; TLC: Rf=0.45 (DCM/EtOAc=1:1).

Example 364

6-Chloro-3-[3-(4-chloro-benzyl)-5-phenyl-3H-imidazol-4-yl]-1H-indole-2-carboxylic acid {2-[4-(2-fluoro-benzyl)-piperazin-1-yl]ethyl}-amide The title compound is synthesized by reductive amination of Example 44 and 2-Fluorobenzaldehyde analogously to the preparation of Example 233 as a colorless solid.

Example 365 and 366 are also prepared in analogy to Example 364.

TABLE 5

Mdm2 and Mdm4 inhibitory activity of representative compounds of the present invention

| compound | IC$_{50}$ (µM) of p53-Hdm2 inhibition Fluorescence polarisation assay | IC$_{50}$ (µM) of p53-Hdm4 inhibition (TR-FRET) Assay |
| --- | --- | --- |
| 42 | 0.30 | 10.4 |
| 101 | 0.015 | 1.32 |
| 135 | 7.2 | 68.3 |
| 142 | 0.64 | 43.4 |
| 148 | 0.11 | 55.3 |
| 271 | 0.30 | 54.9 |
| 328 | 0.19 | 63.7 |

Example 369

Tablets Comprising Compounds of the Formula I

Tablets, comprising, as active ingredient, 100 mg of any one of the compounds of formula I of Examples 1 to 146 are prepared with the following composition, following standard procedures:

Composition

| | |
| --- | --- |
| Active Ingredient | 100 mg |
| crystalline lactose | 240 mg |
| Avicel | 80 mg |
| PVPPXL | 20 mg |
| Aerosil | 2 mg |
| magnesium stearate | 5 mg |
| | 447 mg |

Manufacture: The active ingredient is mixed with the carrier materials and compressed by means of a tabletting machine (Korsch EKO, Stempeldurchmesser 10 mm).

Avicel® is microcrystalline cellulose (FMC, Philadelphia, USA). PVPPXL is polyvinylpolypyrrolidone, cross-linked (BASF, Germany). Aerosil® is silicium dioxide (Degussa, Germany).

The invention claimed is:

1. A compound of the formula I,

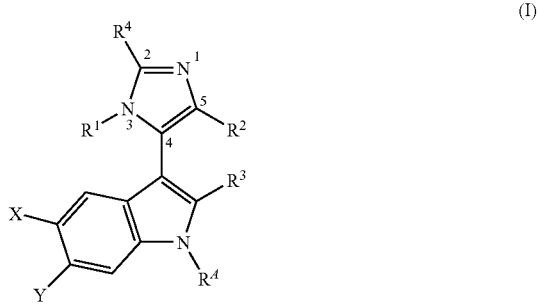

(I)

wherein
R$^1$ is unsubstituted or substituted alkyl, unsubstituted or substituted alkenyl or unsubstituted or substituted alkinyl, unsubstituted or substituted aryl or unsubstituted or substituted heterocyclyl;
R$^2$ is unsubstituted or substituted alkyl, unsubstituted or substituted alkenyl, unsubstituted or substituted alkinyl, unsubstituted or substituted aryl or unsubstituted or substituted heterocyclyl;
R$^3$ is hydrogen, halogen, unsubstituted or substituted alkyl, unsubstituted or substituted alkenyl, unsubstituted or substituted alkinyl, unsubstituted or substituted aryl, carboxy, cyano, esterified carboxy, unsubstituted or substituted heterocyclyl-carbonyl (heterocyclyl-C)=O)—), unsubstituted or substituted carbamoyl or unsubstituted or substituted heterocyclyl;
R$^4$ is hydrogen, halogen, unsubstituted or substituted alkyl, unsubstituted or substituted alkenyl, unsubstituted or substituted alkinyl, unsubstituted or substituted aryl, carboxy, cyano, esterified carboxy, unsubstituted or substituted heterocyclyl-carbonyl (heterocyclyl-C)=O)—), unsubstituted or substituted carbamoyl or unsubstituted or substituted heterocyclyl;
R$^A$ is hydrogen or unsubstituted or substituted alkyl or acyl;
X is hydrogen, C$_1$-C$_7$-alkyl, halo-C$_1$-C$_7$-alkyl, C$_1$-C$_7$-alkoxy, halo or cyano; and
Y is C$_1$-C$_7$-alkyl, halo-C$_1$-C$_7$-alkyl, C$_1$-C$_7$-alkoxy, halo or cyano;
and/or a tautomer, an N-oxide and/or a salt thereof.

2. A compound of the formula I according to claim 1, wherein
R$^1$ is unsubstituted or substituted alkyl, unsubstituted or substituted alkenyl or unsubstituted or substituted alkinyl;
R$^2$ is unsubstituted or substituted aryl;
R$^3$ is hydrogen, unsubstituted or substituted alkyl, carboxy, cyano, esterified carboxy, unsubstituted or substituted heterocyclyl-carbonyl (heterocyclyl-C)=O)—), unsubstituted or substituted carbamoyl, unsubstituted or substituted heterocyclyl or cyano,
R$^4$ is hydrogen, unsubstituted or substituted alkyl, halo or unsubstituted or substituted heterocyclyl,
R$^A$ is hydrogen or unsubstituted or substituted alkyl or acyl;

X is hydrogen, $C_1$-$C_7$-alkyl, halo-$C_1$-$C_7$-alkyl, $C_1$-$C_7$-alkoxy, halo or cyano; and Y is $C_1$-$C_7$-alkyl, halo-$C_1$-$C_7$-alkyl, $C_1$-$C_7$-alkoxy, halo or cyano;

and/or a tautomer, an N-oxide and/or a salt thereof.

3. A compound of the formula I according to claim 1, wherein for the substituents $R^1$, $R^2$, $R^3$, $R^4$, $R^{4'}$, X and Y in unsubstituted or substituted alkyl having up to 12 carbon atoms and is unsubstituted or substituted by one or more substituents independently selected from the group consisting of $C_1$-$C_7$-alkyl, hydroxyl-$C_1$-$C_7$-alkyl, $C_1$-$C_7$-alkoxy-$C_1$-$C_7$-alkyl, N-mono- or N,N-di-[$C_1$-$C_7$-alkyl, phenyl, $C_1$-$C_7$-alkanoyl and/or phenyl-$C_1$-$C_7$-alkyl]-amino-$C_1$-$C_7$-alkyl, halo-$C_1$-$C_7$-alkyl, hydroxy, $C_1$-$C_7$-alkoxy, $C_1$-$C_7$-alkoxy-$C_1$-$C_7$-alkoxy, ($C_1$-$C_7$-alkoxy)-$C_1$-$C_7$-alkoxy-$C_1$-$C_7$-alkoxy, halo-$C_1$-$C_7$-alkoxy, halo, phenoxy, naphthyloxy, phenyl- or naphthyl-$C_1$-$C_7$-alkoxy; amino-$C_1$-$C_7$-alkoxy, $C_1$-$C_7$-alkanoyloxy, benzoyloxy, naphthoyloxy, oxo which is not at the binding carbon atom, amino, amino-$C_1$-$C_7$-alkyl, N-mono- or N,N-di-[$C_1$-$C_7$-alkyl, phenyl, $C_1$-$C_7$-alkanoyl and/or phenyl-$C_1$-$C_7$-alkyl]-amino, N-(heterocyclyl-$C_1$-$C_7$-alkyl)- or N-(heterocyclyl-$C_1$-$C_7$-alkyl-)-N-($C_1$-$C_7$-alkyl)-amino wherein heterocyclyl has 3 to 14 ring atoms of which 1 to 4 are a heteroatom independently selected from N, S, S(=O), S(=O)$_2$ and O and is saturated, formyl (CHO), carboxy, $C_1$-$C_7$-alkoxy-carbonyl, phenyl- or naphthyl-$C_1$-$C_7$-alkoxy-carbonyl, $C_2$-$C_7$-alkanoyl, benzoyl, naphthoyl, carbamoyl, N-mono- or N,N-di-substituted carbamoyl wherein the substituents are selected from lower alkyl and hydroxy-lower alkyl; amidino, guanidino, ureido, mercapto, $C_1$-$C_7$-alkylthio, phenyl- or naphthylthio, phenyl- or naphthyl-$C_1$-$C_7$-alkylthio, $C_1$-$C_7$-alkyl-phenylthio, $C_1$-$C_7$-alkyl-naph-thylthio, halogen-$C_1$-$C_7$-alkylmercapto, sulfonamido, benzosulfonamido, azido, azido-$C_1$-$C_7$-alkyl, nitro, cyano; unsubstituted or substituted heterocyclyl which is mono- to tricyclic heterocyclyl that is unsaturated or saturated, has 3 to 14 ring atoms of which 1 to 4 are a heteroatom independently selected from N, S, S(=O), S(=O)$_2$ and O, and is unsubstituted or substituted with one to three, moieties independently selected from the group consisting of $C_1$-$C_7$-alkyl, hydroxy-$C_1$-$C_7$-alkyl, hydroxy, oxo, amino or N-mono- or N,N-di-($C_1$-$C_7$-alkyl, {amino or mono- or di-($C_1$-$C_7$-alkyl)-amino}-$C_1$-$C_7$-alkyl, $C_1$-$C_7$-alkanoyl and/or $C_1$-$C_7$-alkoxycarbonyl)-amino, $C_1$-$C_7$-alkanoyl, $C_1$-$C_7$-alkylsulfonyl and saturated heterocyclyl with 3 to 14 ring atoms and 1 to 4 heteroatoms independently selected from N, S, S(=O), S(=O)$_2$ and O, wherein said saturated heterocyclyl is unsubstituted or substituted by one to three, moieties independently selected from $C_1$-$C_7$-alkyl, hydroxy-$C_1$-$C_7$-alkyl, $C_1$-$C_7$-alkoxy -$C_1$-$C_7$-alkyl, oxo, amino, mono- or di-($C_1$-$C_7$-alkyl)-amino), $C_1$-$C_7$-alkanoyl and $C_1$-$C_7$-alkoxycarbonyl; naphthyl or phenyl each of which is unsubstituted or substituted by one or more moieties independently selected from $C_1$-$C_7$-alkyl, halo-$C_1$-$C_7$-alkyl, hydroxyl, $C_1$-$C_7$-alkoxy, hydroxy-$C_1$-$C_7$-alkoxy, $C_1$-$C_7$-alkoxy-$C_1$-$C_7$-alkoxy, ($C_1$-$C_7$-alkoxy-$C_1$-$C_7$-alkoxy)-$C_1$-$C_7$-alkoxy, [amino, mono- or di-($C_1$-$C_7$-alkyl)amino]-$C_1$-$C_7$-alkoxy, amino, mono- or di-[($C_1$-$C_7$-alkyl, $C_1$-$C_7$-alkanoyl, $C_1$-$C_7$-alkoxycarbonyl, hydroxy-$C_1$-$C_7$-alkyl, $C_1$-$C_7$-alkoxy-$C_1$-$C_7$alkyl and/or (amino, mono- or di-($C_1$-$C_7$-alkyl)-amino)-$C_1$-$C_7$-alkyl]-amino, halo and saturated heterocyclyl, saturated heterocyclyl-$C_1$-$C_7$-alkyl or saturated heterocyclyl-$C_1$-$C_7$-alkoxy wherein saturated heterocyclyl, respectively, has 3 to 14 ring atoms of which 1 to 4 are a heteroatom independently selected from N, S, S(=O), S(=O)$_2$ and O and is unsubstituted or substituted with one to three, moieties independently selected from $C_1$-$C_7$-alkyl, hydroxyl-$C_1$-$C_7$-alkyl, $C_1$-$C_7$-alkoxy-$C_1$-$C_7$-alkyl, hydroxyl, oxo, amino, mono- or di-($C_1$-$C_7$-alkyl)-amino), $C_1$-$C_7$-alkanoyl and $C_1$-$C_7$-alkoxycarbonyl, nitro or cyano; and C3-C8-cycloalkyl, that is unsubstituted or substituted by one to three, substituents independently selected from the substituents for substituted aryl below;

where each phenyl or naphthyl mentioned above as substituent or part of a substituent of substituted alkyl is itself unsubstituted or substituted by one to three, substituents independently selected from $C_1$-$C_7$-alkyl, halo-$C_1$-$C_7$-alkyl, hydroxyl, $C_1$-$C_7$-alkoxy, $C_1$-$C_7$-alkoxy-$C_1$-$C_7$-alkoxy, halo, halo-$C_1$-$C_7$-alkyl, azido, amino, N-mono- or N,N-di-($C_1$-$C_7$-alkyl, phenyl, naphthyl, $C_1$-$C_7$-alkanoyl, phenyl-$C_1$-$C_7$-alkyl and/or naphthyl-$C_1$-$C_7$-alkyl)-amino, carboxy, $C_1$-$C_7$-alkoxycarbonyl carbamoyl, sulfamoyl, nitro and cyano;

unsubstituted or substituted alkenyl is $C_2$-$C_{20}$-alkenyl which is linear or branched and includes one or more double bonds, where the substituents are one or more substituents independently selected from those mentioned for substituted alkyl;

unsubstituted or substituted alkynyl is $C_2$-$C_{20}$-alkynyl which is linear or branched and includes one or more triple bonds, where the substituents are one or more substituents independently selected from those mentioned for substituted alkyl;

in unsubstituted or substituted aryl, aryl has 6 to 18 carbon atoms and is a mono-, di- or polycyclic unsaturated carbocyclic moiety with conjugated double bonds in the ring, which is unsubstituted or substituted by one or more substituents independently selected from the group consisting of $C_1$-$C_7$-alkyl, $C_2$-$C_7$-alkenyl; $C_2$-$C_7$-alkinyl; $C_6$-$C_{18}$-aryl-$C_1$-$C_7$-alkyl in which aryl is unsubstituted or substituted by $C_1$-$C_7$-alkyl, by pyrrolidinyl, by pyrazolidinyl, by imidazolidinyl, by piperidinyl, by azepanyl, by piperazinyl, by amino, by N-mono- and/or N,N-di-$C_1$-$C_7$-alkylamino, by halo, by hydroxyl, by $C_1$-$C_7$-alkoxy, and/or by halo-$C_1$-$C_7$-alkyl; (pyrrolidinyl, pyridazolidinyl, imidazolidinyl, piperidinyl, azepanyl, piperazinyl, morpholino, thiomorpholino, pyridinyl, pyrimidinyl, pyrazinyl, pyridazinyl, oxazolyl or thiazolyl)-$C_1$-$C_7$-alkyl wherein pyrrolidinyl, pyrazolidinyl, imidazolidinyl, piperidinyl, azepanyl, piperazinyl, pyridinyl, pyrimidinyl, pyrazinyl, pyridazinyl, oxazolyl or thiazolyl are unsubstituted or substituted by $C_1$-$C_7$-alkyl, by pyrrolidinyl, by pyrazolidinyl, by imidazolidinyl, by azepanyl, by piperazinyl, by amino, by N-mono- and/or N,N-di-$C_1$-$C_7$-alkylamino, by halo, by $C_1$-$C_7$-alkoxy, and/or by halo-$C_1$-$C_7$-alkyl; (pyrrolidinyl, pyrazolidinyl, imidazolidinyl, piperidinyl, azepanyl, piperazinyl, pyridinyl, pyrimidinyl, pyrazinyl, pyridazinyl, oxazolyl or thiazolyl)-oxy-$C_1$-$C_7$-alkyl wherein pyrrolidinyl, pyrazolidinyl, imidazolidinyl, piperidinyl, azepanyl, piperazinyl, pyridinyl, pyrimidinyl, pyrazinyl, pyridazinyl, oxazolyl and thiazolyl are unsubstituted or substituted by $C_1$-$C_7$-alkyl, by pyrrolidinyl, by pyrazolidinyl, by imidazolidinyl, by piperidinyl, by azepanyl, by piperazinyl, by amino, by N-mono- and/or N,N-di-$C_1$-$C_7$-alkylamino, by halo, by $C_1$-$C_7$-alkoxy, and/or by halo-$C_1$-$C_7$-alkyl; (pyrrolidin, pyrazolidinyl, imidazolidinyl, piperidin, azepan, piperazin, pyridin, pyrimidin, pyrazin, pyridazin, oxazoly or thiazol)-carbonyl-$C_1$-$C_7$-alkyl wherein pyrrolidin, pyrazolidin, imidazolidin, piperidin, azepan, piperazin, pyridin, pyrimidin, pyridazin, oxazol or pyridazin are unsubstituted or substituted by $C_1$-$C_7$-alkyl, by pyrrolidinyl, by pyrazolidinyl, by imidazolidinyl, by azepanyl, by piperazinyl, by amino, by N-mono- and/or N,N-di-$C_1$-$C_7$-alkylamino, by halo, by $C_1$-$C_7$-alkoxy, and/or by halo-$C_1$-$C_7$-alkyl; halo-$C_1$-$C_7$-alkyl, hydroxy-$C_1C_7$-alkyl; $C_1C_7$-alkoxy-$C_1$-$C_7$-alkyl; $C_1$-$C_7$-alkoxy-$C_1$-$C_7$-alkoxy-$C_1$-$C_7$-alkyl; phenyloxy- or naphthyloxy-$C_1$-$C_7$-alkyl; phenyl-$C_1$-$C_7$-alkoxy- or naphthyl-$C_1$-$C_7$-alkoxy-$C_1$-$C_7$-alkyl; amino-$C_1$-$C_7$-alkyl; N-mono- or N,N-di-($C_1$-$C_7$-alkyl, $C_1$-$C_7$-alkoxy-$C_1$-$C_7$-alkyl and/or (mono- or di-($C_1$-$C_7$-alkyl)-amino)-$C_1$-$C_7$-alkyl)-amino-$C_1$-$C_7$-alkyl; $C_1$-$C_7$-alkoxy-$C_1$-$C_7$-alkylamino-$C_1$-$C_7$-alkyl; mono- or di-[$C_6$-$C_{18}$-aryl-$C_1$-$C_7$-alkyl in which aryl is unsubstituted or substituted by $C_1$-$C_7$-alkyl, by pyrrolidinyl, by pyrazolidinyl, by imidazolidinyl, by piperidinyl, by azepanyl, by piperazinyl, by amino, by N-mono- and/or N,N-di-$C_1$-$C_7$-alkylamino, by halo, by hydroxyl, by $C_1$-$C_7$-alkoxy, and/or by halo-$C_1$-$C_7$-alkyl; naphthyl- or phenyl-$C_1$-$C_7$-alkyl]-amino-$C_1$-$C_7$-alkyl; $C_1C_7$-alkanoylamino-$C_1C_7$-alkyl; carboxy-$C_1$-$C_7$-alkyl; benzoyl- or naphthoylamino-$C_1$-$C_7$-alkyl; $C_1$-$C_7$-alkylsulfonylamino-$C_1$-$C_7$-alkyl; phenyl- or naphthylsulfonylamino-$C_1$-$C_7$-alkyl wherein phenyl or naphthyl is unsubstituted or substituted by one or more $C_1$-$C_7$-alkyl moieties; phenyl- or naphthyl-$C_1$-$C_7$-alkylsulfonylamino-$C_1$-$C_7$-alkyl; halo; hydroxy; $C_1$-$C_7$-alkoxy; $C_6$-$C_{18}$-aryl-$C_1$-$C_7$-alkoxy in which aryl is unsubstituted or substituted by $C_1$-$C_7$-alkyl, by $C_1$-$C_7$-alkoxy, by pyrrolidinyl, by pyrazolidinyl, by imidazolidinyl, by piperidinyl, by azepanyl, by piperazinyl, by amino, by N-mono- and/or N,N-di-$C_1$-$C_7$-alkylamino, by halo, by hydroxyl, by $C_1$-$C_7$-alkoxy, and/or by halo-$C_1$-$C_7$-alkyl; halo-$C_1$-$C_7$-alkoxy; hydroxy-$C_1$-$C_7$-alkoxy; $C_1$-$C_7$-alkoxy-$C_1$-$C_7$-alkoxy; ($C_1$-$C_7$-alkoxy-$C_1$-$C_7$-alkoxy)-$C_1$-$C_7$-alkoxy; [amino, mono- or di-($C_1$-$C_7$-alkyl)amino]-$C_1C_7$-alkoxy, N-$C_1$-$C_7$-alkanoylamino-$C_1$-$C_7$-alkoxy; N-unsubstituted-, N-mono- or N,N-di-($C_1$-$C_7$-alkyl)carbamoyl-$C_1$-$C_7$-alkoxy; phenyl- or naphthyloxy; phenyl- or naphthyl-$C_1$-$C_7$-alkyloxy; (pyrrolidinyl, pyrazolidinyl, imidazolidinyl, piperidinyl, azepanyl, piperazinyl, pyridinyl, pyrimidinyl, pyrazinyl, pyridazinyl, oxazolyl or thiazolyl)-$C_1$-$C_7$-alkoxy wherein pyrrolidinyl, pyrazolidinyl, imidazolidinyl, piperidinyl, azepanyl, piperazinyl, pyridinyl, pyrimidinyl, pyrazinyl, pyridazinyl, oxazolyl and thiazolyl are unsubstituted or substituted by $C_1$-$C_7$-alkyl, by pyrrolidinyl, by pyrazolidinyl, by imidazolidinyl, by piperidinyl, by azepanyl, by piperazinyl, by amino, by N-mono- and/or N,N-di-$C_1$-$C_7$-alkylamino, by halo, by $C_1$-$C_7$-alkoxy, and/or by halo-$C_1$-$C_7$-alkyl; (pyrrolidinyl, pyrazolidinyl, imidazolidinyl, piperidinyl, azepanyl, piperazinyl, pyridinyl, pyrimidinyl, pyrazinyl, pyridazinyl, oxazolyl or thiazolyl)-oxy-$C_1$-$C_7$-alkoxy wherein pyrrolidinyl, pyrazolidinyl, imidazolidinyl, piperidinyl, azepanyl, piperazinyl, pyridinyl, pyrimidinyl, pyrazinyl, pyridazinyl, oxazolyl and thiazolyl are unsubstituted or substituted by $C_1$-$C_7$-alkyl, by pyrrolidinyl, by pyrazolidinyl, by imidazolidinyl, by piperidinyl, by azepanyl, by piperazinyl, by amino, by N-mono- and/or N,N-di-$C_1$-$C_7$-alkylamino, by halo, by $C_1$-$C_7$-alkoxy, and/or by halo-$C_1$-$C_7$-alkyl; $C_1$-$C_7$-alkanoyloxy; benzoyl- or naphthoyloxy; $C_1$-$C_7$-alkylthio; halo-$C_1$-$C_7$-alkylthio; $C_1$-$C_7$-alkoxy-$C_1$-$C_7$-alkylthio; phenyl- or naphthylthio; phenyl- or naphthyl-$C_1$-$C_7$-alkylthio; $C_1$-$C_7$-alkanoylthio; benzoyl- or naphthaylthio; nitro; amino; mono- or di-[($C_1$-$C_7$-alkyl, $C_1$-$C_7$-alkanoyl, $C_1$-$C_7$-alkoxy-carbonyl, hydroxy-$C_1$-$C_7$-alkyl, $C_1$-$C_7$-alkoxy-$C_1$-$C_7$alkyl and/or (amino, mono- or di-($C_1$-$C_7$-alkyl)-amino)-$C_1$-$C_7$-alkyl]-amino; mono- or di-(naphthyl- or phenyl-$C_1$-$C_7$-alkyl)-amino; $C_1$-$C_7$-alkanoylamino; unsubstituted or amino-, N-mono- or N,N-di-($C_1$-$C_7$-alkyl and/or phenyl- or naphthyl-$C_1$-$C_7$alkyl)amino-substituted benzoyl- or naphthoylamino; $C_1$-$C_7$-alkoxycarbonylamino; (phenyl or naphthyl)-$C_1$-$C_7$-alkoxycarbonylamino; $C_1$-$C_7$-alkylsulfonylamino; phenyl- or naphthylsulfonylamino wherein phenyl or naphthyl is unsubstituted or substituted by one or more $C_1$-$C_7$-alkyl moieties; phenyl- or naphthyl-$C_1$-$C_7$-alkylsulfonylamino; $C_1$-$C_7$-alkanoyl; $C_1$-$C_7$-alkoxy-$C_1$-$C_7$-alkanoyl; carboxyl; $C_1$-$C_7$-alkoxy-carbonyl; phenoxy- or naphthoxycarbonyl; phenyl- or naphthyl-$C_1$-$C_7$-alkoxycarbonyl; $C_1$-$C_4$-alkylendioxy; carbamoyl; N-mono- or N,N-di-[$C_1$-$C_7$-alkyl, naphthyl-$C_1$-$C_7$-alkyl, phenyl-$C_1$-$C_7$-alkyl, N'-mono- or N',N'-di-($C_1$-$C_7$-alkyl)amino-$C_1$-$C_7$-alkyl, pyrrolidinyl-$C_1$-$C_7$-alkyl, pyrazolidinyl-$C_1$-$C_7$-alkyl, imidazolidinyl-$C_1$-$C_7$-alkyl, piperidinyl-$C_1$-$C_7$-alkyl, azepanyl-$C_1$-$C_7$-alkyl, piperazinyl- or N-($C_1$-$C_7$-alkyl)piperazinyl-$C_1$-$C_7$-alkyl, mono-$C_1$-$C_7$-alkoxy-$C_1$-$C_7$-alkyl, (N'-mono- or N',N'-di-($C_1$-$C_7$-alkyl)-amino); phenyl, pyridinyl, oxazolyl or thiazolyl each of which is unsubstituted or substituted by $C_1$-$C_7$-alkoxy, by halo, by pyrrolidino, by pyrazolidino, by imidazolidino, by piperidino, by azepan-1-yl, by piperazino, by hydroxyl-$C_1$-$C_7$-alkylamino, by hydroxyl-$C_1$-$C_7$-alkyl, by amino or by N-mono- or N,N-di-($C_1$-$C_7$-alkyl)amino; pyrrolidinyl, pyrazolidinyl, imidazolidinyl, piperidinyl, azepanyl, piperazinyl, pyrimidinyl, pyrazinyl and/or pyridazinyl]-amino-carbonyl, N- mono- or N,N-di-($C_1$-$C_7$-alkyl)-aminocarbonyl; N—$C_1$-$C_7$-alkoxy-$C_1$-$C_7$-alkylcarbamoyl; pyrrolidin-1-carbonyl; amino-N-pyrrolidin-1-carbonyl; N-mono- or N,N-di($C_1$-$C_7$-alkyl)amino-pyrrolidin-1-carbonyl; imidazolidin-1-carbonyl; piperidin-1-carbonylmorpholin-4-carbonyl; thiomorpholin-4-carbonyl; S-oxo-thiomorpholin-4-carbonyl; S,S-dioxothiomorpholin-4-carbonyl; piperazin-1-carbonyl; N—$C_1$-$C_7$-alkyl-piperazin-1-carbonyl; N—$C_1$-$C_7$-alkoxycarbonyl-piperazin-1-carbonyl; N-mono- or N,N-di-($C_1$-$C_7$-alkyl)-amino-substituted or unsubstituted pyrrolidinyl-$C_1$-$C_7$-alkyl; cyano; $C_1$-$C_7$-alkenylene or -alkinylene; $C_1$-$C_7$-alkylsulfonyl; phenyl- or naphthylsulfonyl wherein phenyl or naphthyl is unsubstituted or substituted by one to three, $C_1$-$C_7$-alkyl moieties; phenyl- or naphthyl-$C_1$-$C_7$-alkylsulfonyl; sulfamoyl; N-mono or N,N-di-($C_1$-$C_7$-alkyl, phenyl-, naphthyl-, phenyl-$C_1$-$C_7$-alkyl-, pyrrolidinyl-$C_1$-$C_7$-alkyl, pyrazolidinyl-$C_1$-$C_7$-alkyl, imidazolyl-$C_1$-$C_7$-alkyl, piperidinyl-$C_1$-$C_7$-alkyl, azepanyl-$C_1$-$C_7$-alkyl, piperazinyl-$C_1$-$C_7$-alkyl, N—$C_1$-$C_7$-alkylpiperazinyl-$C_1$-$C_7$-alkyl, naphthyl-$C_1$-$C_7$-alkyl, phenyl which is unsubstituted or substituted by $C_1$-$C_7$-alkoxy, by halo, by pyrrolidino, by pyrazolidino, by imidazolidino, by azepan-1-yl, by piperidino, by piperazino, by hydroxyl-$C_1$-$C_7$-alkyl or by N-mono- or N,N-di-($C_1$-$C_7$-alkyl)-$C_1$-$C_7$-alkyl; pyrrolidinyl, pyrazolidinyl, imidazolidinyl, piperidinyl, azepanyl, piperazinyl, pyridinyl, pyrimidinyl, pyrazinyl, pyridazinyl, oxazolyl and/or thiazolyl)-aminosulfonyl, pyrazolyl, pyrazolidinyl, pyrrolyl, pyrrolidinyl, pyridyl that is unsubstituted or substituted by $C_1$-$C_7$-alkoxy and/or by halo-$C_1$-$C_7$-alkyl, pyrrolidinyl, pyrazolidinyl, imidazolidinyl, piperidinyl, azepanyl, piperazinyl, mor-pholinyl, thiomorpholinyl, S-oxo-thiomorpholinyl, S,S-dioxothiomorpholinyl, piperazinyl, N—$C_1$-$C_7$-alkyl-piperazinyl, 4-(phenyl-$C_1$-$C_7$-alkyl)-piperazinyl, 4-(naphthyl-$C_1$-$C_7$-alkyl)-piperazinyl, 4-($C_1$-$C_7$-alkoxycarbonyl)-piperazinyl, 4-(phenyl-$C_1$-$C_7$-alkoxycarbonyl)-piperazinyl,
4-(naphthyl-$C_1$-$C_7$-alkoxycarbonyl)-piperazinyl, oxazolyl and thiazolyl;

unsubstituted or substituted heterocyclyl is a heterocyclic radical that is unsaturated, saturated or partially saturated and is a monocyclic or bicyclic or tricyclic ring; has 3 to 24 ring atoms; wherein one to four carbon ring atoms are replaced by a heteroatom selected from the group consisting of nitrogen, oxygen, sulfur S(=O) or S(=O)$_2$, the bonding ring having 4 to 12 ring atoms; which heterocyclyl is unsubstituted or substituted by one or more substituents independently selected from the group consisting of the substituents defined above for substituted alkyl or for substituted aryl;

unsubstituted or substituted cycloalkyl is $C_3$-$C_8$-cycloalkyl and is unsubstituted or substituted by one or more substituents independently selected from the substituents for substituted aryl above;

esterified carboxy is unsubstituted or substituted alkyloxy-carbonyl, unsubstituted or substituted aryloxy-carbonyl, unsubstituted or substituted cycloalkyloxy-carbonyl or unsubstituted or substituted heterocyclyloxy-carbonyl;

in unsubstituted or substituted heterocyclyl-carbonyl, heterocyclyl is unsubstituted or substituted by one or more substituents independently selected from those for substituted alkyl and substituted aryl and from oxo;

in unsubstituted or substituted carbamoyl, the N-substituents are selected from one or two substituents independently selected from unsubstituted or substituted $C_1$-$C_7$-alkyl, unsubstituted or substituted aryl, unsubstituted or substituted cycloalkyl and from unsubstituted or substituted heterocyclyl;

acyl is unsubstituted or substituted aryl-carbonyl or -sulfonyl, unsubstituted or substituted heterocyclylcarbonyl or -sulfonyl, unsubstituted or substituted cycloalkylcarbonyl or -sulfonyl, formyl or unsubstituted or substituted alkylcarbonyl or -sulfonyl, unsubstituted or substituted alkyloxycarbonyl or -oxysulfonyl, unsubstituted or substituted aryl-oxycarbonyl or -oxysulfonyl, unsubstituted or substituted heterocyclyloxy-carbonyl or -oxysulfonyl, unsubstituted or substituted cycloalkyloxycarbonyl or -oxysulfonyl or N-mono- or N,N-di-(unsubstituted or substituted aryl, unsubstituted or substituted heterocyclyl, unsubstituted or substituted cycloalkyl or unsubstituted or substituted alkyl)-aminocarbonyl; wherein unsubstituted or substituted aryl, unsubstituted or substituted heterocyclyl, unsubstituted or substituted cycloalkyl and unsubstituted or substituted alkyl are as described above;

and/or a tautomer, an N-oxide and/or a salt thereof.

4. A compound of the formula I according to claim 1, wherein $R^1$ is $C_1$-$C_7$-alkyl that is linear or branched and is unsubstituted or substituted by one to three, moieties independently selected from the group consisting of $C_1$-$C_7$-alkyl, of hydroxyl, of hydroxyl-$C_1$-$C_7$-alkyl, of $C_1$-$C_7$-alkoxy-$C_7$-$C_7$-alkyl, of $C_6$-$C_{14}$-aryl, wherein aryl is unsubstituted or substituted by one to three, moieties independently selected from the group consisting of $C_1$-$C_7$-alkyl, halo-$C_1$-$C_7$-alkyl, hydroxyl, $C_1$-$C_7$-alkoxy, $C_1$-$C_7$-alkoxy-$C_1$-$C_7$-alkoxy, [amino, mono- or di-($C_1$-$C_7$-alkyl)-amino]-$C_1$-$C_7$-alkoxy, amino, mono- or di-[$C_1$-$C_7$-alkyl, hydroxy-$C_1$-$C_7$-alkyl, $C_1$-$C_7$-alkoxy-$C_1$-$C_7$-alkyl, amino-$C_1$-$C_7$-alkyl, amino and/or mono- or di-($C_1$-$C_7$-alkyl)-amino-$C_1$-$C_7$-alkyl]-amino, halo, and saturated heterocyclyl-$C_1$-$C_7$-alkoxy wherein saturated heterocyclyl has 3 to 14 ring atoms of which 1 to 4 are a heteroatom independently selected from N, S, S(=O), S(=O)$_2$ and O and is unsubstituted or substituted with $C_1$-$C_7$-alkyl, pyrrolidinyl-, piperidinyl-, piperazinyl- or N—($C_1$-$C_7$-alkyl)-piperazinyl-$C_1$-$C_7$-alkoxy, and of mono- or bicyclic $C_3$-$C_{14}$-heterocyclyl with 3 to 14 ring atoms of which 1 to 4 are a heteroatom independently selected from N, S, S(=O), S(=O)$_2$ and O and is unsubstituted or substituted with $C_1$-$C_7$-alkyl, indolyl, isoindolyl, indazolyl, quinolinyl, isoquinolinyl, phthalazinyl, quinoxalinyl, quinazolinyl, cinnolinyl, benzofuranyl, isobenzofuranyl, chromenyl, isochromenyl, benzothiophenyl, thiochromenyl or isothiochromenyl, $R^2$ is $C_6$-$C_{14}$-aryl that is unsubstituted or substituted by one to three, moieties independently selected from the group consisting of $C_1$-$C_7$-alkyl-phenyl, methyl, hydroxyl, and halo, $R^3$ is hydrogen or $C_1$-$C_7$-alkyl that is unsubsituted by one to three, moieties independently selected from the group consisting of hydroxyl, amino and heterocyclyl-$C_1$-$C_7$-alkylamino wherein heterocyclyl has 3 to 14 ring atoms of which 1 to 4 are a heteroatom independently selected from N, S, S(=O), S(=O)$_2$ and O and is saturated, (morpholinyl, thiomorpholiny, S-oxothiomorpholinyl or S,S-dioxothiomorpholinyl)-$C_1$-$C_7$-alkylamino, cyano, carboxy, $C_1$-$C_7$-alkoxycarbonyl or $C_6$-$C_{14}$-aryl-$C_1$-$C_7$-alkoxycarbonyl;

heterocyclyl-carbonyl (heterocyclyl-C(=O)) wherein heterocyclyl is unsaturated or saturated, has 3 to 14 ring atoms of which 1 to 4 are a heteroatom independently selected from N, S, S(=O), S(=O)$_2$ and O, pyrrolidinyl, piperidinyl, piperazinyl, morpholinyl, thiomorpholinyl, S-oxothiomorpholinyl or S,S-dioxothiomorpholinyl, and is unsubstituted or substituted with one to three, moieties independently selected from the group consisting of $C_1$-$C_7$-alkyl, hydroxy-$C_1$-$C_7$-alkyl, hydroxy, oxo, amino or N-mono- or N,N-di-($C_1$-$C_7$-alkyl, {amino or mono- or di-$C_1$-$C_7$-alkylamino}-$C_1$-$C_7$-alkyl, $C_1$-$C_7$-alkanoyl and/or $C_1$-$C_7$-alkoxycarbonyl)-amino, $C_1$-$C_7$-alkanoyl, $C_1$-$C_7$-alkylsulfonyl and saturated heterocyclyl with 3 to 14 ring atoms and 1 to 4 heteroatoms independently selected from N, S, S(=O), S(=O)$_2$ and O, pyrrolidinyl, imidazolidinyl, piperidinyl, piperazinyl, morpholinyl, thiomorpholinyl, S-oxothiomorpholinyl or S,S-dioxothiomorpholinyl, wherein said saturated heterocyclyl is unsubstituted or substituted by one to three, moieties independently selected from $C_1$-$C_7$-alkyl, hydroxy-$C_1$-$C_7$-alkyl $C_1$-$C_7$-alkoxy-$C_1$-$C_7$-alkyl, oxo, amino and mono- or di-($C_1$-$C_7$-alkyl)-amino), carbamoyl, N-mono- or N,N-di-[$C_1$-$C_7$-alkyl, hydroxy-$C_1$-$C_7$-alkyl, $C_1$-$C_7$-alkoxy-$C_1$-$C_7$-alkyl, amino-$C_1$-$C_7$-alkyl, mono- or di-($C_1$-$C_7$-alkyl)-amino-$C_1$-$C_7$-alkyl, $C_6$-$C_{14}$-aryl wherein aryl is unsubstituted or substituted by one to three, moieties independently selected from the group consisting of $C_1$-$C_7$-alkyl, $C_1$-$C_7$-alkoxy, saturated heterocyclyl with 3 to 14 ring atoms and 1 to 4 heteroatoms independently selected from N, S, S(=O), S(=O)$_2$ and O, selected from pyrrolidinyl, imidazolidinyl, piperidinyl, piperazinyl, azepanyl, morpholinyl, thiomorpholinyl, S-oxo-thiomorpholinyl or S,S-dioxothiomorpholinyl, wherein said saturated heterocyclyl is unsubstituted or substituted with one to three, moieties independently selected from $C_1$-$C_7$-alkyl, hydroxy-$C_1$-$C_7$-alkyl, hydroxy, oxo and $C_1$-$C_7$-alkoxycarbonyl, $C_6$-$C_{14}$-aryl-$C_1$-$C_7$-alkyl, and saturated heterocyclyl or (saturated heterocyclyl)-$C_1$-

$C_1$-$C_7$-alkyl wherein saturated heterocyclyl in both cases has 3 to 14 ring atoms and 1 to 4 heteroatoms independently selected from N, S, S(=O), S(=O)$_2$ and O, selected from pyrrolidinyl, imidazolidinyl, piperidinyl, piperazinyl, azepanyl, morpholinyl, thiomorpholinyl, S-oxo-thiomorpholinyl, S,S-dioxothiomorpholinyl, indolyl or isoindolyl or (pyrrolidinyl, imidazolidinyl, piperidinyl, piperazinyl, azepanyl, morpholinyl, thiomorpholinyl, S-oxo-thiomorpholinyl, S,S-dioxothiomorpholinyl, indolyl or isoindolyl)-$C_1$-$C_7$-alkyl, wherein said saturated heterocyclyl is unsubstituted or substituted with one to three, moieties independently selected from $C_1$-$C_7$-alkyl, hydroxy-$C_1$-$C_7$-alkyl, $C_1$-$C_7$-alkoxy-$C_1$-$C_7$-alkyl, oxo, $C_1$-$C_7$-alkanoyl and $C_1$-$C_7$-alkoxycarbonyl]-carbamoyl, heteroaryl with 3 to 14 ring atoms and 1 to 5 ring heteroatoms independently selected from the group consisting of N, S, S(=O), S(=O)$_2$ and O, triazolyl or tetrazolyl, or cyano, $R^4$ is hydrogen, $C_1$-$C_7$-alkyl, halo or pyridyl, $R^4$ is hydrogen or $C_1$-$C_7$-alkyl;

X is hydrogen, $C_1$-$C_7$-alkyl, halo or cyano, and

Y is $C_1$-$C_7$-alkyl, halo or cyano, and/or a tautomer, an N-oxide and/or a pharmaceutically acceptable salt thereof.

5. A compound of the formula I according to claim 1, wherein $R^1$ is 3,3-dimethylbutyl, 4-methylbenzyl, 4-trifluoromethylbenzyl, 4-chloro-2-hydroxybenzyl, 4-bromobenzyl, 4-chlorobenzyl, 4-fluorobenzyl, 3,4- or 2,4-dichlorobenzyl, 4-chloro-3-fluorobenzyl, 3-chloro-4-fluorobenzyl or 4-chloro-2-fluorobenzyl, (R,S)- or (R)- or (S)-1-(halo-phenyl)-1-($C_1$-$C_7$-alkyl or hydroxy)-$C_1$-$C_7$-alkyl, (R,S)- or (R)- or (S)-1-(4-fluorophenyl, 4-chlorophenyl or 4-bromophenyl)-1-(methyl or hydroxy)-methyl, (R,S)- or (R)- or (S)-1-(halo-phenyl)-1-[(hydroxy or $C_1$-$C_7$-alkoxy)-$C_1$-$C_7$-alkyl]-$C_1$-$C_7$-alkyl, (R,S)- or (R)- or (S)-1-(4-chlorophenyl)-1-(hydroxymethyl or methoxymethyl)-methyl, $C_1$-$C_7$-alkyl-4-chloro-2-methyl-benzyl, 4-chloro-2-hydroxybenzyl, chloro-2-methoxybenzyl, 4-chloro-2-(2-hydroxyethoxy, 3-hydroxypropoxy or 2-methoxy-ethoxy)- benzyl, 2-[2-(N,N-dimethylamino)-ethoxy]-4-chloro-benzyl, 2-[(2-hydroxymethyl- or 3-hydroxypropyl)-amino]-4-chloro-benzyl, 2-[(2-methoxymethyl- or 3-methoxypropyl)-amino]-4-chloro-benzyl, 2-(2-dimethylaminoethyl-amino)-4-chloro-benzyl, 4-chloro-2-[2-(pyrrolidino-, piperidino-, piperazino- or 4-($C_1$-$C_7$-alkyl)-piperazin-1-yl)-ethoxy]-benzyl, indol-6-ylmethyl, benzofuran-6-ylmethyl, or benzothiophen-6-ylmethyl;

$R^2$ is phenyl, 2-methylphenyl, 2-fluoropheny, 3-fluorophenyl or 3-chloro-2-fluorophenyl, $R^3$ is hydrogen or hydroxymethyl, amino-$C_1$-$C_7$-alkyl, (morpholinyl, thiomorpholiny, S-oxothiomorpholinyl or S,S-dioxothiomorpholinyl)-$C_1$-$C_7$-alkylamino-$C_1$-$C_7$-alkyl, cyano, carboxy, methoxycarbonyl or ethoxycarbonyl, acetidin-1-ylcarbonyl, pyrrolidin-1-carbonyl, achiral or (R,S)- or preferably (R)- or (S)-[amino or N'-mono- or N',N'-di-($C_1$-$C_7$-alkyl and/or {amino or mono- or di-$C_1$-$C_7$-alkylamino}-$C_1$-$C_7$-alkyl)-amino]-pyrrolidin-carbonyl, (R,S)- or (R)- or (S)-3-(dimethylamino)-pyrrolidin-1-carbonyl, (R,S)- or (R)- or (S)-3-(diethylamino)-pyrrolidin-1-carbonyl, (R,S)- or (R)- or (S)-3-[N-2-(dimethylamino)-ethyl-amino]-pyrrolidin-1-carbonyl, (R,S)- or (R)- or (S)-3-[N-3-(dimethylamino)-propyl-amino]-pyrrolidin-1-carbonyl, (R,S)- or (R)- or (S)-3-[N-2-(dimethylamino)-ethyl-N-methyl-amino]-pyrrolidin-1-carbonyl, or (R,S)- or preferably (R)- or (S)-3-[N-3-(dimethylamino)-propyl-N-methyl-amino]-pyrrolidin-1-carbonyl or (R,S)-, (R,S)- or (R)- or (S)-pyrrolidinyl-pyrrolidin-carbonyl, (R,S)- or (R)- or (S)-3-(pyrrolidin-1-yl)-pyrrolidin-carbonyl, (R,S)- or (R)- or (S)-[(amino, mono- or di-($C_1$-$C_7$-alkyl)-amino)-piperidinyl]-pyrrolidincarbonyl, (R,S)- or (R)- or (S)-3-(4-dimethylamino-piperidin-1-yl)-pyrrolidin-1-carbonyl, (R,S)- or (R)- or (S)-[hydroxy-$C_1$-$C_7$-alkyl, hydroxy, amino or mono- or di-($C_1$-$C_7$-alkyl, $C_1$-$C_7$-alkanoyl, $C_1$-$C_7$-alkoxycarbonyl)-amino]-pyrrolidin-carbonyl, (R,S)- or (R)- or (S)-3-hydroxy-pyrrolidin-1-carbonyl, (R,S)- or (R)- or (S)-3-hydroxymethyl-pyrrolidin-1-carbonyl, (R,S)- or (R)- or (S)-3-amino-pyrrolidin-1-carbonyl, (R,S)- or y (R)- or (S)-3-ethylamino-pyrrolidin-1-carbonyl, (R,S)- or (R)-or (S)-3-tert-butoxycarbonylamino-pyrrolidin-1-carbonyl, (R,S)- or (R)- or (S)-3-(N-methyl-N-acetyl-amino)-pyrrolidin-1-carbonyl, (R,S)- or (R)- or (S)-(piperazinyl, $C_1$-$C_7$-alkylpiperazinyl, (hydroxy-$C_1$-$C_7$-alkyl)-piperazinyl morpholinyl, thiomorpholinyl, S-oxo-thiomorpholinyl or S,S-dioxo-thiomorpholinyl)-pyrrolidin-carbonyl, (R,S)- or (R)- or (S)-3-(4-methylpiperazino)-pyrrolidin-1-carbonyl, (R,S)- or (R)- or (S)-3-(4-(2-hydroxyethyl)-piperazino)-pyrrolidin-1-carbonyl, (R,S)- or (R)- or (S)-3-morpholino-pyrrolidin-1-carbonyl or (R,S)- or (R)- or (S)-3-dioxothiomorpholino-pyrrolidin-1-carbonyl, piperidinyl-carbonyl, piperidin-1-carbonyl (piperidin-1-yl-C(=O)—), (hydroxy, hydroxy-$C_1$-$C_7$-alkyl, amino or mono- or di-($C_1$-$C_7$-alkyl)amino)-piperidin-carbonyl, 4-hydroxymethyl-piperidin-1-carbonyl or 4-dimethylamino-piperidin-1-carbonyl, oxoimidazolidinyl-piperidincarbonyl, 4-(2-oxo-imidazolidin-1-yl)-piperidin-1 -carbonyl, (phenyl-oxoimidazolidinyl)-piperidincarbonyl, 4-(3-phenyl-2-oxo-imidazolidin-1-yl)-piperidin-1-carbonyl, pyrrolidinyl- or oxopyrrolidinyl-piperidincarbonyl, 4-(pyrrolidin-1-yl)-piperidin-1-carbonyl or 4-(2-oxo-pyrrolidin-1-yl-)-piperidin-1-carbonyl, piperazinyl- or N-($C_1$-$C_7$-alkyl)-piperazinyl-piperidin-carbonyl, 4-(4-methyl-piperazin-1-yl)-piperidin-1-carbonyl, (morpholinyl, thiomorpholinyl, S-oxo-thiomorpholinyl or S,S-dioxothiomorpholinyl)-piperidin-carbonyl, 4-morpholino-piperidin-1-carbonyl, (oxo-benzoimidazolidinyl)-piperidin-carbonyl, (2-oxo-1,3 -benzoimidazolidin-1-yl)-piperidin-carbonyl, piperazin-carbonyl, piperazin-1-carbonyl, ($C_1$-$C_7$-alkyl or hydroxyl-$C_1$-$C_7$-alkyl)-piperazin-carbonyl, 4methyl-, 4-(2-hydroxyethyl)- or 4-(3-hydroxypropyl)-piperazin-1-carbonyl, oxopiperazin-carbonyl, 2-oxo-piperazin-4-carbonyl, $C_1$-$C_7$-alkanoyl-piperazin-carbonyl, 1-acetyl-piperazin-4-carbonyl, $C_1$-$C_7$-alkylsulfonyl-piperazin-carbonyl, 4-methanesulfonyl-piperazin-1-carbonyl, morpholin-carbonyl (morpholinyl-C(=O)-), morpholin-1-carbonyl, (thiomorpholin, S-oxothiomorpholin or S,S-dioxothiomorpholin)-carbonyl, S,S-dioxothiomorpholin-1-carbonyl, carbamoyl (synonymous: amino-carbonyl, -C(=O)-NH$_2$), N-mono- or N,N-di-($C_1$-$C_7$-alkyl)-carbamoyl, N-methyl-, N,N-dimethyl-, N-ethyl- or N-tert-butyl-carbamoyl, N-[(hydroxy- or $C_1$-$C_7$-alkoxy)-$C_1$-$C_7$-alkyl]-carbamoyl, N-(2-hydroxyethyl)-carbamoyl, N-(3-hydroxypropyl)-carbamoyl, N-(2-methoxyethyl)-carbamoyl or N-(3-methoxypropyl)-carbamoyl, N-[(amino, mono- or di- ($C_1$-$C_7$-alkyl)-amino)-$C_1$-$C_7$-alkyl]-carbamoyl, N-(2-amino-ethyl)-carbamoyl, N-(2-(methylamino)-ethyl-carbamoyl, 2-(N,N-di-(methyl)-amino)-ethyl-carbamoyl, 3-(N,N-di-(methyl)-amino)-propyl-carbamoyl, N-[2-(N,N-di-(methyl)-amino)-ethyl]-N-methyl-carbamoyl, N-[3-(N,N-di-(methyl)-amino)-propyl]-N-methyl-carbamoyl, 2-(N,N-di-(ethyl)-amino)-ethyl-carbamoyl, 3-(N,N-di-(ethyl)-amino)-propyl-carbamoyl, N-[2-(N,N-di-(ethyl)-amino)-ethyl]-N-methyl-carbamoyl, N-[3-(N,N-di-(ethyl)-amino)-propyl]-N-methyl-carbamoyl, N-phenyl-carbamoyl, N-($C_1$-$C_7$-alkoxy-phenyl)-carbamoyl, N-(methoxyphenyl)-carbamoyl, [(pyrrolidinyl, piperidinyl, piperazinyl or 1-($C_1$-$C_7$-alkyl)-piperazinyl)-phenyl]-carbamoyl, N-[3-(piperazin-4-yl or 1-methyl-piperazin-4-yl)-phenyl]-carbamoyl, N-(phenyl-$C_1$-$C_7$-alkyl)-carbamoyl, N-benzyl-carbamoyl, N-(oxoimidazolidinyl-$C_1$-$C_7$-alkyl)-carbamoyl, N-[2-(2-oxoimidazol-1-yl)-ethyl]-carbamoyl, N-(pyrrolidinyl-$C_1$-$C_7$-alkyl)-carbamoyl, N-(pyrrolidinomethyl)-carbamoyl, N-(2-pyrrolidino-ethyl)-carbamoyl or N-(3-pyrrolidino-propyl)-carbamoyl, N-(oxopyrrolidinyl-$C_1$-$C_7$-alkyl)-carbamoyl, N-(2-oxo-pyrrolidinomethyl)-carbamoyl, N-[2-(2-oxopyrrolidino)-ethyl]-carbamoyl or N-[3-(2-oxopyrrolidino)-propyl]-carbamoyl, N-Piperidinyl-carbamoyl, N-piperidin-4-yl-carbamoyl, N-[($C_1$-$C_7$-alkyl)-piperidinyl]-carbamoyl, N-(1-methyl-piperidin-4-yl)-carbamoyl, N-[(hydroxyl-$C_1$-$C_7$-alkyl)-piperidinyl]-carbamoyl, N-[1-(2-hydroxyethyl)-piperidin-4-yl]-carbamoyl, N-[N-($C_1$-$C_7$-alkoxycarbonyl)-piperidinyl]-carbamoyl, N-[1-(tert-butoxycarbonyl)-piperidin-4-yl]-carbamoyl, N-(piperidinyl-$C_1$-$C_7$-alkyl)-carbamoyl, N-(piperidin-1-yl-methyl)-, N-[2-(piperidin-1-yl-)-ethyl]- or N-[3-(piperidin-1-yl)-propyl]-carbamoyl, N-(azepan-$C_1$-$C_7$-alkyl)-carbamoyl, N-(azepan-1-yl-methyl)-, N-[2-(piperidin-1-yl-)-ethyl]- or N-[3-(piperidin-1-yl)-propyl]-carbamoyl, N-(piperazinyl-$C_1$-$C_7$-alkyl)-carbamoyl, N-(piperazin-1-yl-methyl)-, N-[2-(piperazin-1-yl-)-ethyl]- or N-[3-(piperazin-1-yl)-propyl]-carbamoyl, N-(oxopiperazinyl-$C_1$-$C_7$-alkyl)-carbamoyl, N-[(2-oxo-piperazin-4-yl-)-methyl]-, N-[2-(2-oxo-piperazin-4-yl-)-ethyl]- or N-[3-(2-oxo-piperazin-4-yl)-propyl]-carbamoyl, N-(($C_1$-$C_7$-alkyl)-piperazinyl-$C_1$-$C_7$-alkyl)-carbamoyl, N-[(1-methyl-piperazin-4-yl-)-methyl]-, N-[2-(1-methyl-piperazin-4-yl-)-ethyl]- or N-[3-(1-methyl-piperazin-1-yl)-propyl]-carbamoyl, N-(1-(hydroxyl- $C_1$-$C_7$-alkyl)-piperazinyl-$C_1$-$C_7$-alkyl)-carbamoyl, N-[(1-(2-hydroxyethyl)-piperazin-4-yl-)-methyl]-, N-[2-(1-(2-hydroxyethyl)-piperazin-4-yl-)-ethyl]- or N-[3-(1-(2-hydroxyethyl)-piperazin-1-yl)-propyl]-carbamoyl, N-(1-($C_1$-$C_7$-alkanoyl)-piperazinyl-$C_1$-$C_7$-alkyl)-carba-moyl, N-[(1-acetyl-piperazin-4-yl-)-methyl]-, N-[2-(1-acetyl-piperazin-4-yl-)-ethyl]- or N-[3-(1-acetyl-piperazin-4-yl-)-propyl]-carbamoyl, N-(1-($C_1$-$C_7$-alkoxycarbonyl)-piperazinyl-$C_1$-$C_7$-alkyl)-carbamoyl, N-[(1-(tert-butoxycarbonyl)-piperazin-4-yl-)-methyl]-, N-[2-(1-(tert-butoxycarbonyl)-piperazin-4-y-)-ethyl]- or N-[3-(1-(tert-butoxycarbonyl)-piperazin-1-yl)-propyl]-carbamoyl, N-[(morpholinyl, thiomorpholinyl, S-oxo-thiomorpholinyl or S,S-dioxothiomorpholinyl)-$C_1$-$C_7$-alkyl]-carbamoyl, N-morpholinomethyl-, N-(2-morpholinoethyl)-, N-(3-morpholinopropyl)-carbamoyl, N-(S,S-dioxothiomorpholino)-methyl-, N[2-(S,S-dioxothiomorpholino)-ethyl]- or N-[3-(S,S-dioxothiomorpholino)-propyl]-carbamoyl, N-[dioxo-1H, 3H-isoindolyl)-$C_1$-$C_7$-alkyl)-carbamoyl, N-(1,7-dioxo-1H, 7H-isoindolin-2-yl-methyl)-, N-[2-(1,7-dioxo-1H, 7H-isoindolin-2-yl)-ethyl]- or N-[3-(1,7-dioxo-1H, 7H-isoindolin-2-yl)-propyl]-carbamoyl, triazolyl or tetrazolyl, tetrazol-5-yl, or cyano, $R^4$ is hydrogen, methyl, halo, or pyridin-3-, -4- or -2-yl, $R^A$ is hydrogen or $C_1$-$C_7$-alkyl;

X is hydrogen, $C_1$-$C_7$-alkyl, halo or cyano, and

Y is methyl, fluoro, chloro, bromo or cyano, and/or a tautomer, an N-oxide and/or a pharmaceutically acceptable salt thereof.

6. A compound of the formula I according to claim 1, wherein $R^1$ is 4-bromobenzyl, 4-chlorobenzyl, or 4-fluorobenzyl, $R^2$ is phenyl, $R^3$ is hydroxyl-$C_1$-$C_7$-alkyl, hydroxymethyl, carboxy, achiral or (R,S)- or (R)- or (S)-[amino or N'-mono- or N',N'-di-($C_1$-$C_7$-alkyl and/or {amino or mono- or di-$C_1$-$C_7$-alkylamino}-$C_1$-$C_7$-alkyl)-amino]-pyrrolidin-carbonyl, (R)- or (S)-3N-[2-(dimethylamino)-ethyl-N-methyl-amino]-pyrrolidin-1-carbonyl, amino or mono- or di-($C_1$-$C_7$-alkyl)amino-piperidin-carbonyl, 4-dimethylamino-piperidin-1-carbonyl, carbamoyl, N-$C_1$-$C_7$-alkylcarbamoyl, N-methyl- or N-ethylcarbamoyl, N-(($C_1$-$C_7$-alkyl)-piperazinyl-$C_1$-$C_7$-alkyl)-carbamoyl, N-[(1-methyl-piperazin-4-yl-)-methyl]-, N-[2-(1-methyl-piperazin-4-yl-)-ethyl]- or N-[3-(1-methyl-piperazin-1-yl)-propyl]-carbamoyl, or N-[(morpholinyl or thiomorpholinyl)-$C_1$-$C_7$-alkyl]-carbamoyl, N-morpholinomethyl-, N-(2-morpholinoethyl)-, N-(3 -morpholinopropyl)-carbamoyl, $R^4$ is hydrogen methyl, bromo or chloro, $R^A$ is hydrogen;

X is halo or fluoro, and

Y is halo or cyano;

and/or a tautomer, an N-oxide and/or a pharmaceutically acceptable salt thereof.

7. A compound of claim 1, selected from:
6-chloro-3-[3-(4-chloro-benzyl)-5-phenyl-3H-imidazol-4-yl]-1H-indole;
6-chloro-3-[3-(4-chloro-benzyl)-5-phenyl-3H-imidazol-4-yl]-1H-indole-2-carboxylic acid (2-morpholin-4-yl-ethyl)-amide;
6-chloro-3-[3-(4-chloro-benzyl)-5-phenyl-3H-imidazol-4-yl]-1H-indole-2-carboxylic acid;
6-chloro-3-[3-(4-chloro-benzyl)-5-phenyl-3H-imidazol-4-yl]-1H-indole-2-carboxylic acid ethyl ester;
6-chloro-3-[3-(4-chloro-benzyl)-5-phenyl-3H-imidazol-4-yl]-1H-indole-2-carboxylic acid [2-(1,3-dioxo-1,3-dihydro-isoindo2-yl)-ethyl]-amide;
4-[2-({6-chloro-3-[3-(4-chloro-benzyl)-5-phenyl-3H-imidazol-4-yl]-1H-indole-2-carbonyl}-amino)-ethyl]-piperazine-1-carboxylic acid tert-butyl ester;
4-[3-({6-chloro-3-[3-(4-chloro-benzyl)-5-phenyl-3H-imidazol-4-yl]-1H-indole-2-carbonyl}-amino)-propyl] piperazine-1-carboxylic acid tert-butyl ester;
4-({6-chloro-3-[3-(4-chloro-benzyl)-5-phenyl-3H-imidazol-4-yl]-1H-indole-2-carbonyl}-amino)-piperidine-1-carboxylic acid tert-butyl ester;
6-chloro-3-[3(4-chloro-benzyl)-5-phenyl-3H-imidazol-4-yl]-1H-indole-2-carboxylic acid [2-(tert-butyl-dimethyl-silanyloxy)-ethyl]-amide;
6-chloro-3-3-(4-chloro-benzyl)-5-phenyl-3H-imidazol-4-yl]-1H-indole-2-carboxylic acid [3-(tert-butyl-dimethyl-silanyloxy)-propyl]-amide;

((S)-1-{6-chloro-3-[3-(4-chloro-benzyl)-5-phenyl-3H-imidazol-4-yl]-1H-indole-2-carbonyl}-pyrrolidin-3-yl)-carbamic acid tert-butyl ester;
6-chloro-3-[3-(4-chloro-benzyl)-5-phenyl-3H-imidazol-4-yl]-5-fluoro-1H-indole-2-carboxylic acid;
6-chloro-3-[3-(4-chloro-benzyl)-5-phenyl-3H-imidazol-4-yl]-5-fluoro-1H-indole-2-carboxylic acid methyl ester;
((R)-1-{6-chloro-3-[3-(4-chloro-benzyl)-5-phenyl-3H-imidazol-4-yl]-1H-indole-2-carbonyl}-pyrrolidin-3-yl)-carbamic acid tert-butyl ester;
3-[3-(4-bromo-benzyl)-5-phenyl-3H-imidazol-4-yl]-6-chloro-1H-indole-2-carboxylic acid;
3-[3-(4-bromo-benzyl)-5-phenyl-3H-imidazol-4-yl]-6-chloro-1H-indole-2-carboxylic acid; ethyl ester
3-[3-(2-tert-butoxy-4-chloro-benzyl)-5-phenyl-3H-imidazol-4-yl]-6-chloro-5-fluoro-1H-indole;
3-[3-(4-chloro-benzyl)-5-phenyl-3H-imidazol-4-yl]-6-cyano-1H-indole-2-carboxylic acid;
3-[3-(4-chloro-benzyl)-5-phenyl-3H-imidazol-4-yl]-6-cyano-1H-indole-2-carboxylic acid methyl ester;
6-chloro-3-{3-[(S)-1-(4-chloro-phenyl)-ethyl]-5-phenyl-3H-imidazol-4-yl}-1H-indole-2-carboxylic acid;
6-chloro-3-{3-[(S)-1-(4-chloro-phenyl)-ethyl]-5-phenyl-3H-imidazol-4-yl}-1H-indole-2-carboxylic acid ethyl ester;
6-chloro-3-[3-(3,3-dimethyl-butyl)-5-phenyl-3H-imidazol-4-yl]-1H-indole-2-carboxylic acid amide;
6-chloro-3-[3-(3,3-dimethyl-butyl)-5-phenyl-3H-imidazol-4-yl]-1H-indole-2-carboxylic acid ethyl ester;
6-chloro-3-[3-(3,3-dimethyl-butyl)-5-phenyl-3H-imidazol-4-yl]-1H-indole-2-carboxylic acid amide;
6-chloro-3-[3-(4-chloro-benzyl)-5-phenyl-3H-imidazol-4-yl]-2-(1H-tetrazol-5-yl)-1H-indole;
6-chloro-3-[3-(4-chloro-benzyl)-5-phenyl-3H-imidazol-4-yl]-1H-indole-2-carbonitrile;
{6-chloro-3-[3-(4-chloro-benzyl)-5-phenyl-3H-imidazol-4-yl]-1H-indol-2-yl}-methanol;
{6-chloro-3-[3-(4-chloro-benzyl)-5-phenyl-3H-imidazol-4-yl]-1H-indol-2-ylmethyl}-(2-morpholin-4-yl-ethyl)-amine;
3-[1-(4-chloro-benzyl)-5-(6-chloro-5-fluoro-1H-indol-3-yl)-1H-imidazol-4-yl]-phenol;
6-chloro-3-[3-(4-chloro-benzyl)-5-(3-methoxy-phenyl)-3H-imidazol-4-yl]-5-fluoro-1H-indole;
{6-chloro-3-[3-(4-chloro-benzyl)-5-(3-hydroxy-phenyl)-3H-imidazol-4-yl]-1H-indol-2-yl}-((S)-3-dimethylamino-pyrrolidin-1-yl)-methanone;
{6-chloro-3-[3-(4-chloro-benzyl)-5-(3-methoxy-phenyl)-3H-imidazol-4-yl]-1H-indol-2-yl}-((S)-3-dimethylamino-pyrrolidin-1-yl)-methanone;
6-chloro-3-[3-(4-chloro-benzyl)-2-methyl-5-phenyl-3H-imidazol-4-yl]-1H-indole;
6-bromo-3-[2-chloro-3-(4-chloro-benzyl)-5-phenyl-3H-imidazol-4-yl]-1H-indole-2-carboxylic acid ethyl ester and
6-Chloro-3-[2-chloro-3-(4-chloro-benzyl)-5-phenyl-3H-imidazol-4-yl]-1H-indole-2-carboxylic acid ethyl ester,
and/or a tautomer, an N-oxide and/or a pharmaceutically acceptable salt thereof.

8. A compound of claim 1, selected from the group of compounds given in the following tables and by the following formula

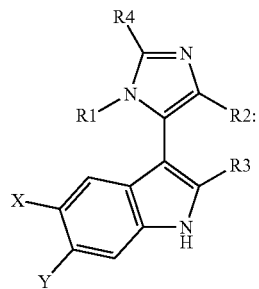

| Compound | X and Y | R$^1$ | R$^2$ | R$^3$ | R$^4$ |
|---|---|---|---|---|---|
| AA | X = H<br>Y = Cl | (neopentyl group) | (phenyl group) | H | H |
| AB | X = H<br>Y = Cl | (4-fluorobenzyl group) | (phenyl group) | H | H |
| AC | X = H<br>Y = Cl | (3-chloro-4-fluorobenzyl group) | (phenyl group) | H | H |

-continued
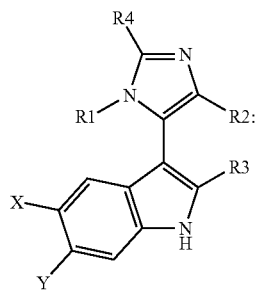
| Compound | X and Y | R¹ | R² | R³ | R⁴ |
|---|---|---|---|---|---|
| AD | X = H, Y = Cl | 2,4-dichlorobenzyl | phenyl | H | H |
| AE | X = H, Y = Cl | 3,4-dichlorobenzyl | phenyl | H | H |
| AF | X = H, Y = Cl | 4-chloro-2-fluorobenzyl | phenyl | H | H |
| AG | X = H, Y = Cl | 4-chloro-3-fluorobenzyl | phenyl | H | H |
| AH | X = F, Y = Cl | 4-chlorobenzyl | phenyl | H | H |
| AI | X = H, Y = Cl | 4-chloro-2-methylbenzyl | phenyl | H | H |
| AJ | X = H, Y = Br | 4-chlorobenzyl | phenyl | H | H |

-continued
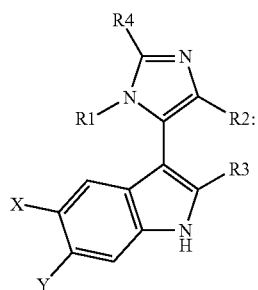
| Compound | X and Y | R¹ | R² | R³ | R⁴ |
|---|---|---|---|---|---|
| AK | X = H, Y = Me | 4-Cl-benzyl | phenyl | H | H |
| AL | X = H, Y = Cl | 4-Cl-benzyl | 2-F-phenyl | H | H |
| AM | X = H, Y = Cl | 4-Cl-benzyl | 3-F-phenyl | H | H |
| AO | X = H, Y = CN | 4-Cl-benzyl | phenyl | H | H |
| AP | X = F, Y = F | 4-Cl-benzyl | phenyl | H | H |
| AQ | X = H, Y = Cl | 4-CF₃-benzyl | phenyl | H | H |
| AR | X = H, Y = Cl | 1-(4-Cl-phenyl)ethyl | phenyl | H | H |

-continued
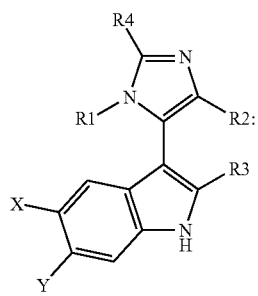
| Compound | X and Y | R¹ | R² | R³ | R⁴ |
|---|---|---|---|---|---|
| AS | X = H<br>Y = Cl | 4-Cl-C6H4-CH(CH3)- (wedge down) | phenyl | H | H |
| AT | X = H<br>Y = Cl | 4-Cl-C6H4-CH2- | phenyl | H | H |
| AU | X = F<br>Y = Cl | 4-Cl-C6H4-CH(CH3)- (wedge down) | phenyl | H | H |
| AV | X = F<br>Y = F | 4-Cl-C6H4-CH(CH3)- (wedge down) | phenyl | H | H |
| AX | X = H<br>Y = Cl | 4-Cl-C6H4-CH(CH2OH)- | phenyl | H | H |
| AY | X = H<br>Y = CN | 4-Cl-C6H4-CH(CH3)- (wedge down) | phenyl | H | H |

-continued
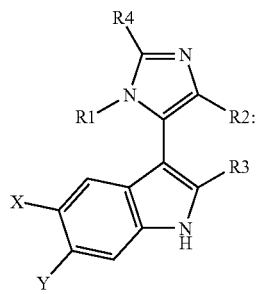
| Compound | X and Y | R¹ | R² | R³ | R⁴ |
|---|---|---|---|---|---|
| AZ | X = F<br>Y = Cl | 4-Cl-C₆H₄-CH(OH)-CH- (stereo) | phenyl | H | H |
| BA | X = H<br>Y = CN | 4-Cl-C₆H₄-CH(OH)-CH- (stereo) | phenyl | H | H |
| BB | X = G<br>Y = Cl | 4-Cl-C₆H₄-CH(CH₃)- (stereo) | phenyl | H | H |
| BC | X = H<br>Y = CN | 4-Cl-C₆H₄-CH(CH₃)- (stereo) | phenyl | H | H |
| BD | X = F<br>Y = F | 4-Cl-C₆H₄-CH(CH₃)- (stereo) | phenyl | H | H |
| BE | X = F<br>Y = Cl | 4-Cl-C₆H₄-CH(OH)-CH- (stereo) | phenyl | H | H |

-continued
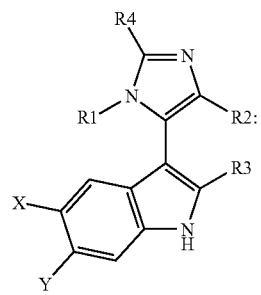
| Compound | X and Y | R¹ | R² | R³ | R⁴ |
|---|---|---|---|---|---|
| BF | X = H<br>Y = Cl | 4-Cl-C₆H₄-CH₂- | phenyl | -C(O)NH-CH₂CH₂CH₂-morpholine | H |
| BG | X = H<br>Y = Cl | 4-Cl-C₆H₄-CH₂- | phenyl | -C(O)NH-CH₂CH₂CH₂-(2-oxo-pyrrolidin-1-yl) | H |
| BH | X = H<br>Y = Cl | 4-Cl-C₆H₄-CH₂- | phenyl | -C(O)NH-CH₂CH₂-OCH₃ | H |
| BI | X = H<br>Y = Cl | 4-Cl-C₆H₄-CH₂- | phenyl | -C(O)NH-CH₂CH₂CH₂-OCH₃ | H |
| BJ | X = H<br>Y = Cl | 4-Cl-C₆H₄-CH₂- | phenyl | -C(O)NH-CH₂CH₂-pyrrolidin-1-yl | H |

-continued

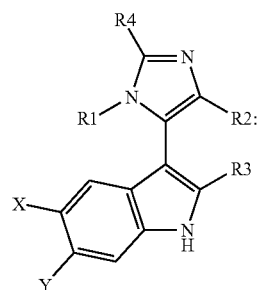

| Compound | X and Y | R¹ | R² | R³ | R⁴ |
|---|---|---|---|---|---|
| BK | X = H<br>Y = Cl | 4-chlorobenzyl | phenyl | -C(O)NH-CH₂CH₂CH₂-(pyrrolidin-1-yl) | H |
| BL | X = H<br>Y = Cl | 4-chlorobenzyl | phenyl | -C(O)NH-CH₂CH₂-NHCH₃ | H |
| BM | X = H<br>Y = Cl | 4-chlorobenzyl | phenyl | -C(O)NH-CH₂CH₂CH₂-(4-methylpiperazin-1-yl) | H |
| BN | X = H<br>Y = Cl | 4-chlorobenzyl | phenyl | -C(O)NH-CH₂CH₂-(2-oxopyrrolidin-1-yl) | H |
| BO | X = H<br>Y = Cl | 4-chlorobenzyl | phenyl | -C(O)NH-CH₂CH₂-(4-methylpiperazin-1-yl) | H |

-continued

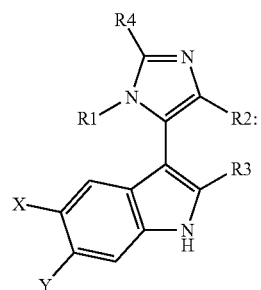

| Compound | X and Y | R¹ | R² | R³ | R⁴ |
|---|---|---|---|---|---|
| BP | X = H<br>Y = Cl | 4-Cl-benzyl | phenyl | -C(O)NH-CH₂CH₂-NH₂ | H |
| BQ | X = H<br>Y = Cl | 4-Cl-benzyl | phenyl | -C(O)NH-CH₂CH₂-(piperazin-1-yl) | H |
| BR | X = H<br>Y = Cl | 4-Cl-benzyl | phenyl | -C(O)NH-CH₂CH₂CH₂-(piperazin-1-yl) | H |
| BS | X = H<br>Y = Cl | 4-Cl-benzyl | phenyl | -C(O)NH-CH₂CH₂-(1,1-dioxo-thiomorpholin-4-yl) | H |
| BT | X = H<br>Y = Cl | 4-Cl-benzyl | phenyl | -C(O)NH-(1-methylpiperidin-4-yl) | H |
| BU | X = H<br>Y = Cl | 4-Cl-benzyl | phenyl | -C(O)-(3-dimethylaminopyrrolidin-1-yl) | H |

-continued

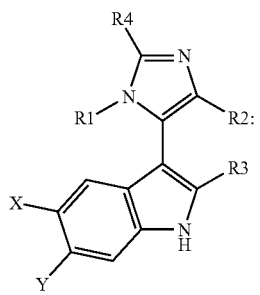

| Compound | X and Y | R¹ | R² | R³ | R⁴ |
|---|---|---|---|---|---|
| BV | X = H, Y = Cl | 4-chlorobenzyl | phenyl | -C(=O)NH-(piperidin-4-yl) | H |
| BX | X = H, Y = Cl | 4-chlorobenzyl | phenyl | -C(=O)NH-(1-(2-hydroxyethyl)piperidin-4-yl) | H |
| BY | X = H, Y = Cl | 4-chlorobenzyl | phenyl | -C(=O)-(4-(methylsulfonyl)piperazin-1-yl) | H |
| BZ | X = H, Y = Cl | 4-chlorobenzyl | phenyl | -C(=O)-(4-(dimethylamino)piperidin-1-yl) | H |
| CA | X = H, Y = Cl | 4-chlorobenzyl | phenyl | -C(=O)NH-CH₂-(1-methylpiperidin-4-yl) | H |
| CB | X = H, Y = Cl | 4-chlorobenzyl | phenyl | -C(=O)NH-CH₃ | H |

-continued
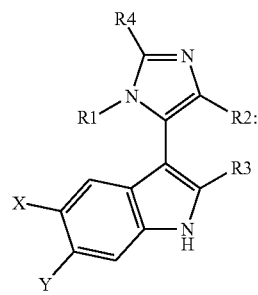
| Compound | X and Y | R¹ | R² | R³ | R⁴ |
|---|---|---|---|---|---|
| CC | X = H, Y = Cl | 4-chlorobenzyl | phenyl | -C(O)NH-ethyl | H |
| CD | X = H, Y = Cl | 4-chlorobenzyl | phenyl | -C(O)NH-CH₂CH₂OH | H |
| CE | X = H, Y = Cl | 4-chlorobenzyl | phenyl | -C(O)NH-CH₂CH₂CH₂OH | H |
| CF | X = H, Y = Cl | 4-chlorobenzyl | phenyl | -C(O)-(1-piperidinyl-4-yl)-3-phenylimidazolidin-2-one | H |
| CG | X = H, Y = Cl | 4-chlorobenzyl | phenyl | -C(O)-(1-piperidinyl-4-yl)-2-oxopyrrolidine | H |

-continued

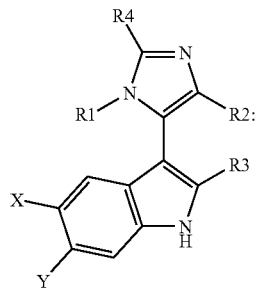

| Compound | X and Y | R¹ | R² | R³ | R⁴ |
|---|---|---|---|---|---|
| CH | X = H<br>Y = Cl | 4-chlorobenzyl | phenyl | 1-acyl-4-(2-oxoimidazolidin-1-yl)piperidine | H |
| CI | X = H<br>Y = Cl | 4-chlorobenzyl | phenyl | 1-acyl-4-(2-oxo-2,3-dihydrobenzimidazol-1-yl)piperidine | H |
| CJ | X = H<br>Y = Cl | 4-chlorobenzyl | phenyl | (3R)-1-acyl-3-(dimethylamino)pyrrolidine | H |
| CK | X = H<br>Y = Cl | 4-chlorobenzyl | phenyl | N-[2-(2-oxoimidazolidin-1-yl)ethyl]acetamide | H |
| CL | X = H<br>Y = Cl | 4-chlorobenzyl | phenyl | 1-acyl-4-(4-methylpiperazin-1-yl)piperidine | H |

-continued

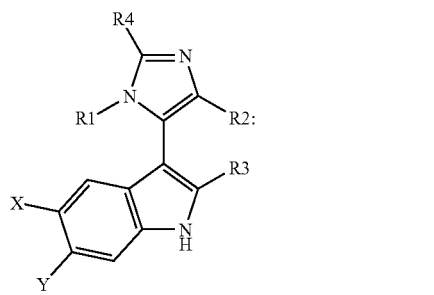

| Compound | X and Y | R¹ | R² | R³ | R⁴ |
|---|---|---|---|---|---|
| CM | X = H<br>Y = Cl | 4-Cl-phenylmethyl | phenyl | C(=O)NH-CH₂CH₂-piperidinyl | H |
| CN | X = H<br>Y = Cl | 4-Cl-phenylmethyl | phenyl | C(=O)-morpholinyl | H |
| CO | X = H<br>Y = Cl | 4-Cl-phenylmethyl | 4-Cl-phenylmethyl | C(=O)-(4-methylpiperazinyl) | H |
| CP | X = H<br>Y = Cl | 4-Cl-phenylmethyl | phenyl | C(=O)-(4-morpholinylpiperidinyl) | H |
| CQ | X = H<br>Y = Cl | 4-Cl-phenylmethyl | phenyl | C(=O)NH-CH₂CH₂-N(Et)₂ | H |
| CR | X = H<br>Y = Cl | 4-Cl-phenylmethyl | phenyl | C(=O)NH-CH₂CH₂-azepanyl | H |

-continued

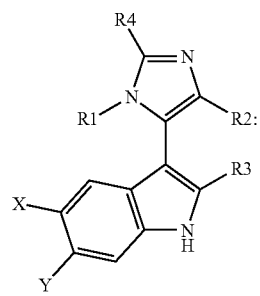

| Compound | X and Y | R¹ | R² | R³ | R⁴ |
|---|---|---|---|---|---|
| CS | X = H, Y = Cl | 4-Cl-phenyl-CH₂- | phenyl | 4-(pyrrolidin-1-yl)piperidine-1-carbonyl | H |
| CT | X = H, Y = Cl | 4-Cl-phenyl-CH₂- | phenyl | 4-acetylpiperazine-1-carbonyl | H |
| CU | X = H, Y = Cl | 4-Cl-phenyl-CH₂- | phenyl | 3-oxopiperazine-1-carbonyl | H |
| CV | X = H, Y = Cl | 4-Cl-phenyl-CH₂- | phenyl | 4-(2-hydroxyethyl)piperazine-1-carbonyl | H |
| CW | X = H, Y = Cl | 4-Cl-phenyl-CH₂- | phenyl | 3-(hydroxymethyl)pyrrolidine-1-carbonyl | H |
| CX | X = H, Y = Cl | 4-Cl-phenyl-CH₂- | phenyl | (3R)-3-(dimethylamino)pyrrolidine-1-carbonyl | H |

-continued

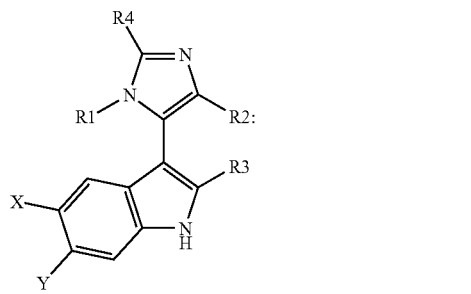

| Compound | X and Y | R¹ | R² | R³ | R⁴ |
|---|---|---|---|---|---|
| CY | X = H, Y = Cl | 4-Cl-benzyl | phenyl | -C(O)NH-CH₂CH₂-(3-oxopiperazin-1-yl) | H |
| CZ | X = H, Y = Cl | 4-Cl-benzyl | phenyl | -C(O)-(3S)-3-hydroxypyrrolidin-1-yl | H |
| DA | X = H, Y = Cl | 4-Cl-benzyl | phenyl | -C(O)-(3R)-3-hydroxypyrrolidin-1-yl | H |
| DB | X = H, Y = Cl | 4-Cl-benzyl | phenyl | -C(O)-3-aminopyrrolidin-1-yl | H |
| DC | X = H, Y = Cl | 4-Cl-benzyl | phenyl | -C(O)-3-(ethylamino)pyrrolidin-1-yl | H |
| DD | X = H, Y = Cl | 4-Cl-benzyl | phenyl | -C(O)-3-(N-methylacetamido)pyrrolidin-1-yl | H |
| DE | X = H, Y = Cl | 4-Cl-benzyl | phenyl | -C(O)NH-CH₂CH₂-(4-acetylpiperazin-1-yl) | H |

-continued

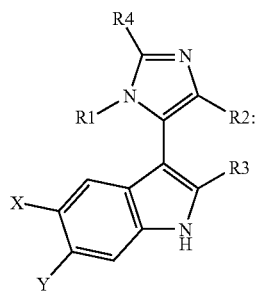

| Compound | X and Y | R¹ | R² | R³ | R⁴ |
|---|---|---|---|---|---|
| DF | X = F<br>Y = Cl | 4-Cl-benzyl | phenyl | -C(O)NH-CH₂CH₂-(4-methylpiperazin-1-yl) | H |
| DG | X = F<br>Y = Cl | 4-Cl-benzyl | phenyl | -C(O)-(3R)-(dimethylamino)pyrrolidin-1-yl | H |
| DH | X = F<br>Y = Cl | 4-Cl-benzyl | phenyl | -C(O)-4-(pyrrolidin-1-yl)piperidin-1-yl | H |
| DI | X = F<br>Y = Cl | 4-Cl-benzyl | phenyl | -C(O)NH-CH₂CH₂-(1,1-dioxo-thiomorpholin-4-yl) | H |
| DJ | X = H<br>Y = Cl | 4-Cl-benzyl | phenyl | -C(O)-(3)-aminopyrrolidin-1-yl | H |
| DK | X = H<br>Y = Cl | 4-Cl-benzyl | phenyl | -C(O)-(3R)-morpholin-4-yl-pyrrolidin-1-yl | H |

-continued

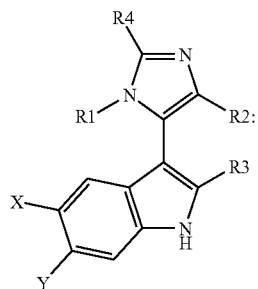

| Compound | X and Y | R¹ | R² | R³ | R⁴ |
|---|---|---|---|---|---|
| DL | X = H, Y = Cl | 4-bromobenzyl | phenyl | -C(=O)NH-CH₂CH₂-N(4-methylpiperazin-1-yl) | H |
| DM | X = H, Y = Cl | 4-chlorobenzyl | phenyl | -C(=O)-(3R)-3-(pyrrolidin-1-yl)pyrrolidin-1-yl | H |
| DN | X = F, Y = Cl | 4-chlorobenzyl | phenyl | -C(=O)-4-(2-oxoimidazolidin-1-yl)piperidin-1-yl | H |
| DO | X = F, Y = Cl | 4-chlorobenzyl | phenyl | -C(=O)-4-(4-methylpiperazin-1-yl)piperidin-1-yl | H |
| DP | X = H, Y = Cl | 4-chlorobenzyl | phenyl | -C(=O)NH-CH₂CH₂-N[4-(2-hydroxyethyl)piperazin-1-yl] | H |
| DQ | X = H, Y = Cl | 4-chlorobenzyl | phenyl | -C(=O)-(3R)-3-[4-(dimethylamino)piperidin-1-yl]pyrrolidin-1-yl | H |

-continued
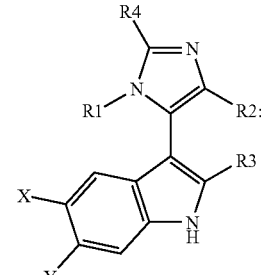
| Compound | X and Y | R¹ | R² | R³ | R⁴ |
|---|---|---|---|---|---|
| DR | X = H<br>Y = Cl | 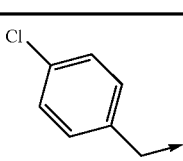 | 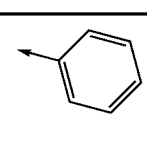 | 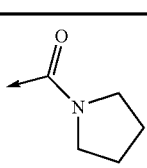 | H |
| DS | X = H<br>Y = Cl | 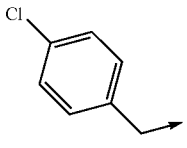 | 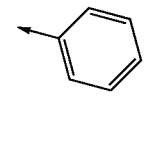 | 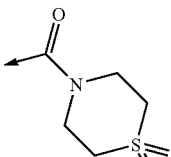 | H |
| DT | X = F<br>Y = Cl | 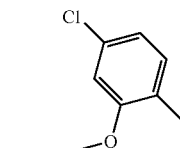 | 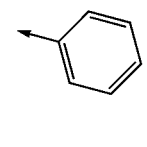 | H | H |
| DU | X = F<br>Y = Cl | 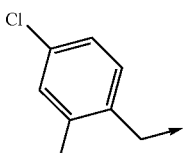 | 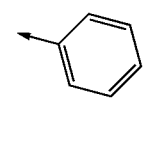 | H | H |
| DV | X = H<br>Y = Cl | 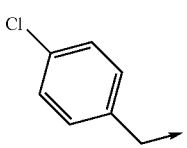 | 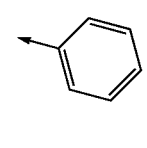 | 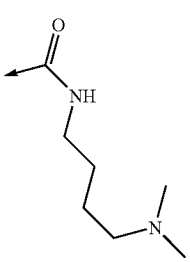 | H |
| DW | X = H<br>Y = Cl | 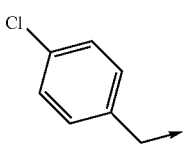 | 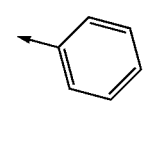 | 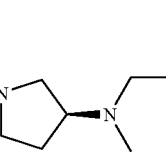 | H |

-continued
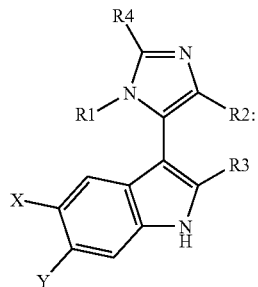
| Compound | X and Y | R¹ | R² | R³ | R⁴ |
|---|---|---|---|---|---|
| DX | X = F<br>Y = Cl | 4-chlorobenzyl | phenyl | -C(O)NH-(CH₂)₃-pyrrolidin-1-yl | H |
| DY | X = G<br>Y = Cl | 4-chlorobenzyl | phenyl | -C(O)NH-(CH₂)₃-morpholin-4-yl | H |
| DZ | X = F<br>Y = Cl | 4-chloro-2-(2-methoxyethoxy)benzyl | phenyl | H | H |
| EA | X = F<br>Y = Cl | 4-chloro-2-(3-methoxypropoxy)benzyl | phenyl | H | H |
| EB | X = F<br>Y = Cl | 1-(4-fluorophenyl)ethyl | phenyl | H | H |

-continued
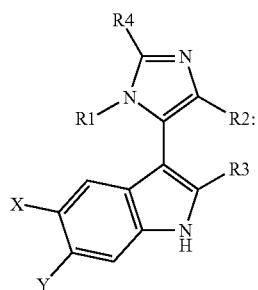
| Compound | X and Y | R¹ | R² | R³ | R⁴ |
|---|---|---|---|---|---|
| EC | X = F<br>Y = Cl | 5-chloro-2-hydroxybenzyl | phenyl | H | H |
| ED | X = F<br>Y = Cl | 1-(4-bromophenyl)ethyl | phenyl | H | H |
| EF | X = H<br>Y = Cl | 4-chlorobenzyl | phenyl | -C(O)N(CH₃)CH₂CH₂CH₂N(CH₃)₂ | H |
| EG | X = H<br>Y = Cl | 4-chlorobenzyl | phenyl | -C(O)NHCH₂CH₂N(CH₃)₂ | H |
| EH | X = H<br>Y = Cl | 4-chlorobenzyl | phenyl | -C(O)NHCH₂CH₂CH₂N(CH₃)₂ | H |

-continued
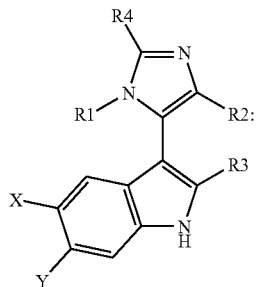
| Compound | X and Y | R¹ | R² | R³ | R⁴ |
|---|---|---|---|---|---|
| EI | X = H<br>Y = Cl | 4-Cl-benzyl | phenyl | C(O)NH-tBu | H |
| EJ | X = F<br>Y = Cl | 5-Cl-2-(2-hydroxyethoxy)benzyl | phenyl | H | H |
| EK | X = F<br>Y = Cl | 5-Cl-2-(3-hydroxypropoxy)benzyl | phenyl | H | H |
| EL | X = F<br>Y = Cl | 5-Cl-2-(2-dimethylaminoethoxy)benzyl | phenyl | H | H |
| EM | X = F<br>Y = Cl | 5-Cl-2-((3-methoxypropyl)amino)benzyl | phenyl | H | H |

-continued
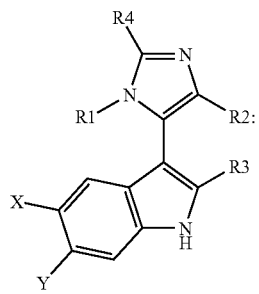
| Compound | X and Y | R¹ | R² | R³ | R⁴ |
|---|---|---|---|---|---|
| EN | X = F, Y = Cl | 5-Cl-2-(NHCH₂CH₂OCH₃)phenylmethyl | phenyl | H | H |
| EO | X = F, Y = Cl | 5-Cl-2-(NHCH₂CH₂OH)phenylmethyl | phenyl | H | H |
| EP | X = F, Y = Cl | 5-Cl-2-(NHCH₂CH₂CH₂OH)phenylmethyl | phenyl | H | H |
| EQ | X = F, Y = Cl | 5-Cl-2-(NHCH₂CH₂N(CH₃)₂)phenylmethyl | phenyl | H | H |
| ER | X = H, Y = Cl | 4-Cl-phenylmethyl | phenyl | C(O)N(CH₃)₂ | H |

-continued

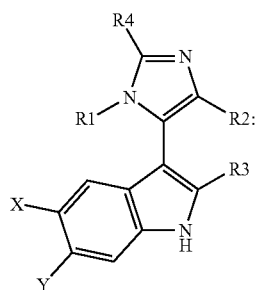

| Compound | X and Y | R¹ | R² | R³ | R⁴ |
|---|---|---|---|---|---|
| ES | X = H<br>Y = Cl | 4-Cl-benzyl | phenyl | -C(O)-N(CH₃)-CH₂CH₂-N(CH₃)₂ | H |
| ET | X = H<br>Y = Cl | 4-Cl-benzyl | phenyl | -C(O)-azetidinyl | H |
| EU | X = H<br>Y = Cl | 4-Cl-benzyl | phenyl | -C(O)-pyrrolidinyl-(4-methylpiperazinyl) | H |
| EV | X = H<br>Y = Cl | 4-Cl-benzyl | phenyl | -C(O)-pyrrolidinyl-(4-(2-hydroxyethyl)piperazinyl) | H |
| EW | X = H<br>Y = Cl | 4-Cl-benzyl | phenyl | -C(O)-pyrrolidinyl-(CH₂)₃-N(CH₃)₂ | H |
| EX | X = H<br>Y = Cl | 4-Cl-benzyl | phenyl | -C(O)-pyrrolidinyl-N(CH₃)-CH₂CH₂-N(CH₃)₂ | H |
| EY | X = H<br>Y = Cl | 4-Cl-benzyl | phenyl | -C(O)-pyrrolidinyl-(thiomorpholine-1,1-dioxide) | H |

-continued

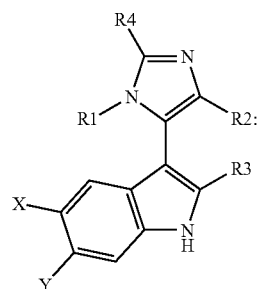

| Compound | X and Y | R¹ | R² | R³ | R⁴ |
|---|---|---|---|---|---|
| EZ | X = H<br>Y = Cl | 4-Cl-benzyl | phenyl | 1-acyl-3-(diethylamino)pyrrolidine | H |
| FA | X = H<br>Y = CN | 4-Cl-benzyl | phenyl | C(O)NH-CH₂CH₂-(4-methylpiperazin-1-yl) | H |
| FB | X = H<br>Y = CN | 4-Cl-benzyl | phenyl | 1-acyl-3-(dimethylamino)pyrrolidine | H |
| FC | X = F<br>Y = Cl | 4-Cl-benzyl | o-tolyl | H | H |
| FD | X = F<br>Y = Cl | 1-(4-methylphenyl)ethyl | phenyl | H | H |
| FE | X = H<br>Y = Cl | 1-(4-chlorophenyl)ethyl | phenyl | C(O)NH-CH₂CH₂-(4-methylpiperazin-1-yl) | H |
| FF | X = F<br>Y = Cl | (1H-indol-6-yl)methyl | phenyl | H | H |

-continued

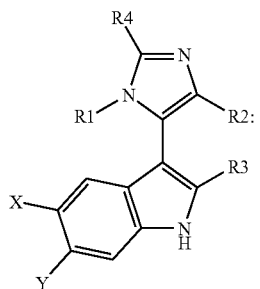

| Compound | X and Y | R¹ | R² | R³ | R⁴ |
|---|---|---|---|---|---|
| FG | X = F<br>Y = Cl | benzothiophen-5-ylmethyl | phenyl | H | H |
| FH | X = H<br>Y = Cl | 4-chlorobenzyl | phenyl | N,N-dimethylsulfamoyl | H |
| FI | X = F<br>Y = Cl | 5-chloro-2-(hydroxymethyl)benzyl | phenyl | H | H |
| FJ | X = H<br>Y = Cl | 1-(4-chlorophenyl)ethyl | phenyl | C(O)NH-CH₂CH₂-piperazinyl-CH₂CH₂-imidazol-1-yl | H |
| FK | X = H<br>Y = Cl | 4-chlorobenzyl | phenyl | C(O)NH-CH₂CH₂-(4-ethylpiperazin-1-yl) | H |
| FL | X = H<br>Y = Cl | 4-chlorobenzyl | phenyl | C(O)NH-CH₂CH₂-(4-isopropylpiperazin-1-yl) | H |
| FM | X = H<br>Y = Cl | 5-chloro-2-(hydroxymethyl)benzyl | phenyl | C(O)NH-CH₂CH₂-(4-methylpiperazin-1-yl) | H |

-continued

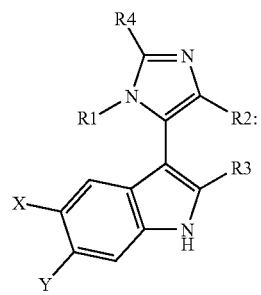

| Compound | X and Y | R¹ | R² | R³ | R⁴ |
|---|---|---|---|---|---|
| FN | X = H, Y = Cl | 5-chloro-2-(hydroxymethyl)benzyl | phenyl | 1-acyl-3-(3-(dimethylamino)propylamino)pyrrolidine | H |
| FO | X = F, Y = Cl | 4-methoxybenzyl | phenyl | H | H |
| FP | X = H, Y = Cl | 4-chlorobenzyl | phenyl | -C(O)NH-CH₂CH₂-N(piperazine)-CH₂-(3-pyridyl) | H |
| FQ | X = H, Y = Cl | 4-chlorobenzyl | phenyl | -C(O)NH-CH₂CH₂-N(piperazine)-CH₂CH₂-N(CH₃)₂ | H |
| FR | X = H, Y = Cl | 4-chlorobenzyl | phenyl | -C(O)NH-CH₂CH₂-N(piperazine)-CH₂CH₂-(1-pyrrolidinyl) | H |
| FS | X = H, Y = Cl | 4-chlorobenzyl | phenyl | -C(O)NH-CH₂CH₂-N(piperazine)-CH₂CH₂CH₂-OCH₃ | H |

-continued

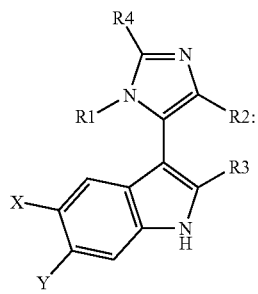

| Compound | X and Y | R¹ | R² | R³ | R⁴ |
|---|---|---|---|---|---|
| FT | X = H, Y = Cl | 4-chlorobenzyl | phenyl | -C(O)NH-CH₂CH₂-N(piperazine)-(4-fluorophenyl) | H |
| FU | X = H, Y = Cl | 5-chloro-2-(hydroxymethyl)benzyl | phenyl | -C(O)-N(pyrrolidine)-N(CH₃)₂ | H |
| FV | X = H, Y = Cl | 4-chlorobenzyl | phenyl | -C(O)NH-CH₂CH₂-N(piperazine)-(pyridin-4-yl) | H |
| FW | X = H, Y = Cl | 4-chlorobenzyl | phenyl | -C(O)NH-CH₂CH₂-N(piperazine)-CH₂CH₂-OCH₃ | H |
| FX | X = H, Y = Cl | 4-chlorobenzyl | phenyl | -C(O)NH-CH₂CH₂-N(piperazine)-(pyridin-4-yl) | H |
| FY | X = H, Y = Cl | 4-chlorobenzyl | phenyl | -C(O)NH-CH₂CH₂-N(piperazine)-(pyridin-2-yl) | H |

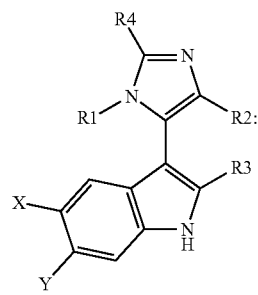

| Compound | X and Y | R¹ | R² | R³ | R⁴ |
|---|---|---|---|---|---|
| FZ | X = H, Y = Cl | 4-chlorobenzyl | phenyl | -C(O)NH-CH₂CH₂-N(piperazine)-CH₂-phenyl (4-benzylpiperazinyl ethyl amide) | H |
| GA | X = H, Y = Cl | 5-chloro-2-(hydroxymethyl)benzyl | phenyl | -C(O)NH-CH₂CH₂-N(thiomorpholine 1,1-dioxide) | H |
| GB | X = H, Y = Cl | 4-chlorobenzyl | phenyl | -C(O)NH-CH₂CH₂-N(piperazine)-(3-pyridyl) | H |
| GC | X = H, Y = Cl | 4-chlorobenzyl | phenyl | -C(O)NH-CH₂CH₂-N(piperazine)-(3-methoxyphenyl) | H |
| GD | X = H, Y = Cl | 4-chlorobenzyl | phenyl | -C(O)NH-CH₂-(4-pyridyl) | H |

-continued
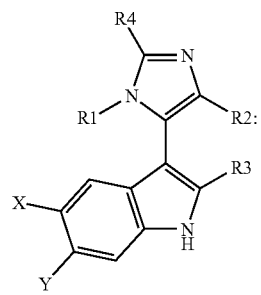
| Compound | X and Y | R¹ | R² | R³ | R⁴ |
|---|---|---|---|---|---|
| GE | X = H<br>Y = Cl | 4-Cl-benzyl | phenyl | -C(O)-NH-CH₂-(pyridin-3-yl) | H |
| GF | X = H<br>Y = Cl | 4-Cl-benzyl | phenyl | -C(O)-NH-CH₂-(pyridin-2-yl) | H |
| GC | X = H<br>Y = Cl | 4-Cl-benzyl | phenyl | -C(O)-NH-CH₂CH₂-(pyridin-4-yl) | H |
| GH | X = H<br>Y = Cl | 4-Cl-benzyl | phenyl | -C(O)-NH-CH₂CH₂-N(piperazinyl)-CH₂-(pyridin-2-yl) | H |
| GI | X = H<br>Y = Cl | 4-Cl-benzyl | phenyl | -C(O)-NH-CH₂CH₂-N(piperazinyl)-cyclopentyl | H |

-continued

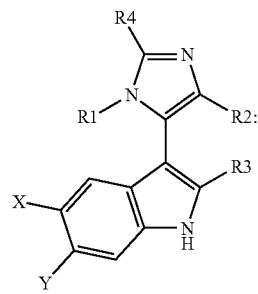

| Compound | X and Y | R¹ | R² | R³ | R⁴ |
|---|---|---|---|---|---|
| GJ | X = H, Y = Cl | 4-chlorobenzyl | phenyl | -C(O)NH-CH₂CH₂-(2-pyridyl) | H |
| GK | X = H, Y = Cl | 4-chlorobenzyl | phenyl | -C(O)NH-CH₂CH₂-N(piperazine)-CH₂-cyclohexyl | H |
| GL | X = H, Y = Cl | 4-chlorobenzyl | phenyl | -C(O)NH-CH₂CH₂-N(piperidine)-4-morpholinyl | H |
| GM | X = H, Y = Cl | 4-chlorobenzyl | phenyl | -C(O)NH-CH₂CH₂-(3-pyridyl) | H |
| GN | X = H, Y = Cl | 4-chlorobenzyl | phenyl | -C(O)NH-CH₂CH₂-N(piperidine)-4-piperidinyl | H |
| GO | X = H, Y = Cl | 4-chlorobenzyl | phenyl | -C(O)NH-CH₂CH₂-N(piperidine)-4-pyrrolidinyl | H |

-continued

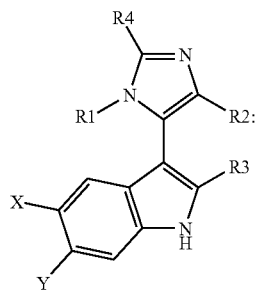

| Compound | X and Y | R¹ | R² | R³ | R⁴ |
|---|---|---|---|---|---|
| GP | X = H, Y = Cl | 5-chloro-2-(hydroxymethyl)phenyl | phenyl | -C(O)NH-CH₂CH₂-N(piperazine)-isopropyl | H |
| GQ | X = H, Y = Cl | 4-chlorophenyl (α-methyl) | phenyl | -C(O)NH-CH₂CH₂-N(piperazine)-isopropyl | H |
| GR | X = H, Y = Cl | 4-chlorobenzyl | phenyl | -C(O)NH-CH₂CH₂-N(piperazine)-CH₂-(tetrahydrofuran-2-yl) | H |
| GS | X = H, Y = Cl | 4-chlorobenzyl | phenyl | -C(O)NH-CH₂CH₂-N(piperazine)-CH₂-(pyridin-4-yl) | H |
| GT | X = H, Y = Cl | 4-chlorophenyl (α-methyl) | phenyl | -C(O)NH-CH₂CH₂-N(piperazine)-ethyl | H |
| GU | X = H, Y = Cl | 4-chlorophenyl (α-methyl) | phenyl | -C(O)NH-CH₂CH₂-N(piperazine)-CH₂-(pyridin-3-yl) | H |

-continued

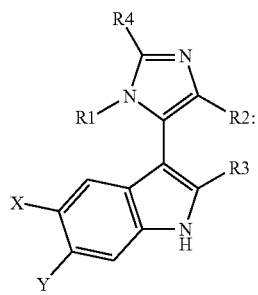

| Compound | X and Y | R¹ | R² | R³ | R⁴ |
|---|---|---|---|---|---|
| GV | X = H, Y = Cl | 5-Cl-2-(hydroxymethyl)benzyl | phenyl | -C(=O)NH-CH₂CH₂-N(piperazine)-CH₂-(4-pyridyl) | H |
| GW | X = H, Y = Cl | 5-Cl-2-(hydroxymethyl)benzyl | phenyl | -C(=O)NH-CH₂CH₂-N(piperazine)-CH₂-(2-pyridyl) | H |
| GX | X = H, Y = Cl | 5-Cl-2-(hydroxymethyl)benzyl | phenyl | -C(=O)NH-CH₂CH₂-N(piperazine)-(4-pyridyl) | H |
| GY | X = H, Y = Cl | 5-Cl-2-(hydroxymethyl)benzyl | phenyl | -C(=O)NH-CH₂CH₂-N(piperazine)-(3-pyridyl) | H |
| GZ | X = H, Y = Cl | 5-Cl-2-(hydroxymethyl)benzyl | phenyl | -C(=O)NH-CH₂CH₂-N(piperazine)-CH₂-phenyl | H |

-continued

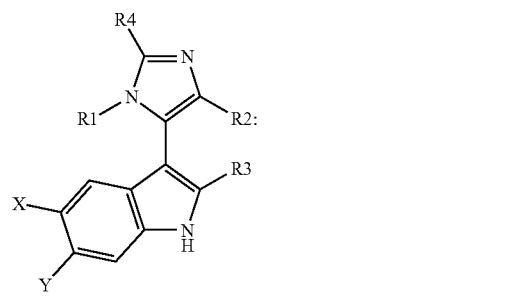

| Compound | X and Y | R¹ | R² | R³ | R⁴ |
|---|---|---|---|---|---|
| HA | X = H, Y = Cl | 5-chloro-2-(hydroxymethyl)benzyl | phenyl | -C(O)NH-CH₂CH₂-N(piperazine)-CH₂-(3-pyridyl) | H |
| HB | X = H, Y = Cl | 4-chlorobenzyl | phenyl | -C(O)-N(pyrrolidine, 3-O-CH₂-(3-pyridyl)) | H |
| HC | X = H, Y = Cl | 1-(4-chlorophenyl)ethyl | phenyl | -C(O)NH-CH₂CH₂-N(piperazine)-CH₂-(4-pyridyl) | H |
| HD | X = H, Y = Cl | 1-(4-chlorophenyl)ethyl | phenyl | -C(O)NH-CH₂CH₂-N(piperazine)-(3-pyridyl) | H |
| HE | X = H, Y = Cl | 4-chlorobenzyl | phenyl | -C(O)-N(pyrrolidine, 3-NH-CH₂CH₂CH₂-OH) | H |
| HF | X = H, Y = Cl | 1-(4-chlorophenyl)ethyl | phenyl | -C(O)NH-CH₂CH₂-N(piperazine)-CH₂-(2-pyridyl) | H |

-continued

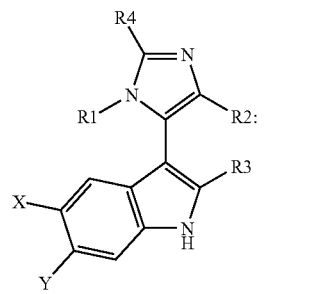

| Compound | X and Y | R¹ | R² | R³ | R⁴ |
|---|---|---|---|---|---|
| HG | X = H<br>Y = Cl | 4-Cl-C₆H₄-CH₂- | C₆H₅- | (3R)-1-acyl-3-[N-methyl-N-(2-acetoxyethyl)amino]pyrrolidine | H |
| HH | X = H<br>Y = Cl | 4-Cl-C₆H₄-CH₂- | C₆H₅- | (3R)-1-acyl-3-[N-methyl-N-(2-hydroxyethyl)amino]pyrrolidine | H |
| HI | X = H<br>Y = Cl | 4-Cl-C₆H₄-CH₂- | C₆H₅- | (3R)-1-acyl-3-(2-pyridylmethoxy)pyrrolidine | H |
| HJ | X = H<br>Y = Cl | 4-Cl-C₆H₄-CH₂- | C₆H₅- | (3R)-1-acyl-3-(4-pyridylmethoxy)pyrrolidine | H |
| HK | X = H<br>Y = Cl | 4-Cl-C₆H₄-CH₂- | C₆H₅- | -C(O)NH-CH₂CH₂-[4-(dimethylamino)piperidin-1-yl] | H |
| HL | X = H<br>Y = Cl | 4-Cl-C₆H₄-CH₂- | C₆H₅- | -C(O)NH-CH₂CH₂-[4-(pentan-3-yl)piperazin-1-yl] | H |
| HM | X = H<br>Y = Cl | (S)-1-(4-Cl-C₆H₄)ethyl- | C₆H₅- | -C(O)NH-CH₂CH₂-(4-isopropylpiperazin-1-yl) | H |

-continued

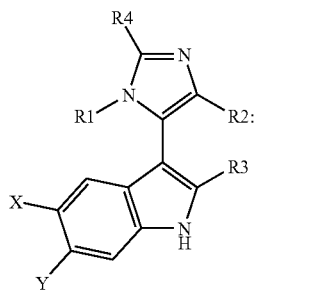

| Compound | X and Y | R¹ | R² | R³ | R⁴ |
|---|---|---|---|---|---|
| HN | X = H, Y = Cl | 4-Cl-benzyl | phenyl | acetyl-pyrrolidin-3-yl-amino-ethyl acetate | H |
| HO | X = H, Y = Cl | 4-Cl-benzyl | phenyl | acetamido-ethyl-(4-diethylamino)piperidine | H |
| HP | X = H, Y = Cl | 4-Cl-benzyl | phenyl | acetamido-ethyl-(4-isobutyl)piperazine | H |
| HQ | X = H, Y = Cl | 4-Cl-benzyl | phenyl | acetamido-ethyl-(4-adamantyl)piperazine | H |
| HR | X = H, Y = Cl | 4-Cl-benzyl | phenyl | acetyl-pyrrolidin-3-yl-amino-ethyl-pyrrolidine | H |
| HS | X = H, Y = Cl | 4-Cl-benzyl | phenyl | acetyl-pyrrolidin-3-yl-amino-propyl-pyrrolidine | H |
| HT | X = H, Y = Cl | 4-Cl-benzyl | phenyl | acetyl-pyrrolidin-3-yl-amino-ethanol | H |

-continued

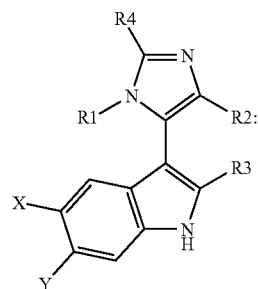

| Compound | X and Y | R¹ | R² | R³ | R⁴ |
|---|---|---|---|---|---|
| HU | X = H, Y = Cl | 4-chlorobenzyl | phenyl | 1-acyl-3-(N-methyl-N-(2-methoxyethyl)amino)pyrrolidine | H |
| HV | X = H, Y = Cl | 4-chlorobenzyl | phenyl | -C(O)NH-CH₂CH₂-(4-dipropylaminopiperidin-1-yl) | H |
| HW | X = H, Y = Cl | 1-(4-chlorophenyl)ethyl | phenyl | -C(O)NH-CH₂CH₂-(4-(pyridin-4-yl)piperazin-1-yl) | H |
| HX | X = H, Y = Cl | 4-chlorobenzyl | phenyl | -C(O)NH-CH₂CH₂-(4-tert-butylpiperazin-1-yl) | H |
| HY | X = H, Y = Cl | 4-chlorobenzyl | phenyl | -C(O)NH-CH₂CH₂-(4-(pyrimidin-2-yl)piperazin-1-yl) | H |
| HZ | X = H, Y = Cl | 4-chloro-2-fluorobenzyl | phenyl | -C(O)NH-CH₂CH₂-(4-methylpiperazin-1-yl) | H |

-continued

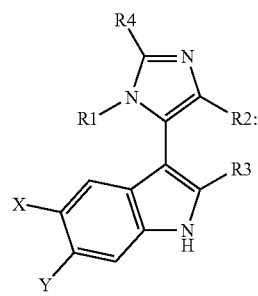

| Compound | X and Y | R¹ | R² | R³ | R⁴ |
|---|---|---|---|---|---|
| IA | X = H, Y = Cl | 4-chlorobenzyl | phenyl | 4-(pyridin-2-yl)piperazine-1-carbonyl | H |
| IB | X = H, Y = Cl | 4-chlorobenzyl | phenyl | 4-(pyridin-3-yl)piperazine-1-carbonyl | H |
| IC | X = H, Y = Cl | 4-chlorobenzyl | phenyl | 4-(pyridin-4-yl)piperazine-1-carbonyl | H |
| ID | X = H, Y = Cl | 4-chlorobenzyl | phenyl | 4-(pyridin-2-ylmethyl)piperazine-1-carbonyl | H |
| IE | X = H, Y = Cl | 4-chlorobenzyl | phenyl | N-methyl-N-(2-(4-methylpiperazin-1-yl)ethyl)carbamoyl | H |

-continued

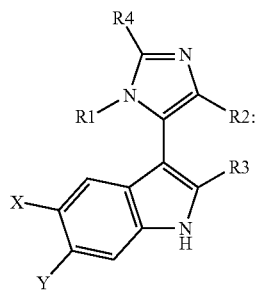

| Compound | X and Y | R¹ | R² | R³ | R⁴ |
|---|---|---|---|---|---|
| IF | X = H<br>Y = Cl | 4-chlorobenzyl | phenyl | C(O)-piperazine-N-CH₂-(3-pyridyl) | H |
| IG | X = H<br>Y = Cl | 4-chlorobenzyl | phenyl | C(O)-piperazine-N-CH₂CH₂-(4-pyridyl) | H |
| IH | X = H<br>Y = Cl | 4-chlorobenzyl | phenyl | C(O)-piperazine-N-CH₂CH₂-(2-pyridyl) | H |
| II | X = H<br>Y = Cl | 4-chlorobenzyl | phenyl | C(O)NH-CH₂CH₂-piperazine (NH) | H |
| IJ | X = H<br>Y = Cl | 4-chlorobenzyl | 4-methylphenyl | C(O)NH-CH₂CH₂-(4-methylpiperazine) | H |
| IK | X = H<br>Y = Cl | 1-(4-chlorophenyl)ethyl | phenyl | C(O)NH-CH₂CH₂-piperazine (NH) | H |

-continued

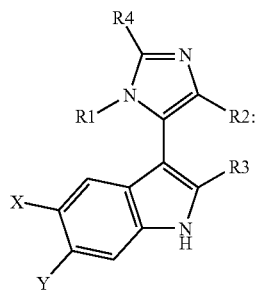

| Compound | X and Y | R¹ | R² | R³ | R⁴ |
|---|---|---|---|---|---|
| IL | X = H<br>Y = Cl | 4-chlorobenzyl | 2-fluorophenyl | -C(O)NH-CH₂CH₂-(4-methylpiperazin-1-yl) | H |
| IM | X = H<br>Y = Cl | 1-(4-chlorophenyl)ethyl (S) | phenyl | -C(O)-(4-dimethylaminopiperidin-1-yl) | H |
| IN | X = H<br>Y = Cl | 5-chloro-2-(hydroxymethyl)benzyl | phenyl | -C(O)-(4-dimethylaminopiperidin-1-yl) | H |
| IO | X = H<br>Y = Cl | 4-chlorobenzyl | phenyl | -C(O)NH-CH₂CH₂-(4-benzylpiperidin-1-yl) | H |
| IP | X = H<br>Y = Cl | 4-chlorobenzyl | phenyl | -C(O)NH-CH₂CH₂-(4-(pyridin-2-ylmethyl)piperidin-1-yl) | H |
| IQ | X = H<br>Y = Cl | 3,3-dimethylbutyl | phenyl | -C(O)-(3-(N-methyl-N-(3-dimethylaminopropyl)amino)pyrrolidin-1-yl) | H |

-continued

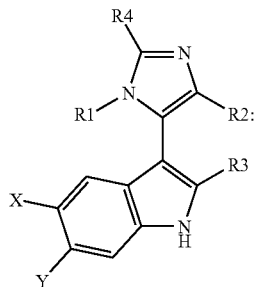

| Compound | X and Y | R¹ | R² | R³ | R⁴ |
|---|---|---|---|---|---|
| IR | X = H, Y = Cl | 4-Cl-benzyl | phenyl | -C(O)NH-CH2CH2-(4-tert-butylpiperidin-1-yl) | H |
| IS | X = H, Y = Cl | 4-Cl-benzyl | phenyl | -C(O)NH-CH2CH2-[4-(3-methoxypropyl)piperidin-1-yl] | H |
| IT | X = H, Y = Cl | 4-Cl-benzyl | phenyl | -C(O)NH-CH2CH2-[4-(2-pyrrolidin-1-yl-ethyl)piperidin-1-yl] | H |
| IU | X = H, Y = Cl | 4-Cl-benzyl | phenyl | -C(O)NH-CH2CH2-NH-(pyridin-2-yl) | H |
| IV | X = H, Y = Cl | 4-Cl-benzyl | phenyl | -C(O)NH-CH2CH2-NH-(pyridin-4-yl) | H |
| IW | X = H, Y = Cl | 4-Cl-benzyl | phenyl | -C(O)NH-CH2CH2-(4-hydroxypiperidin-1-yl) | H |

-continued

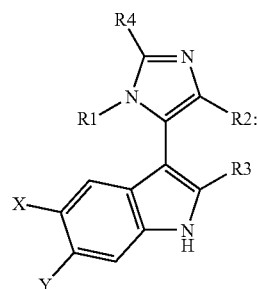

| Compound | X and Y | R¹ | R² | R³ | R⁴ |
|---|---|---|---|---|---|
| IX | X = F<br>Y = Cl | 4-Cl, 2-Br-benzyl | phenyl | H | H |
| IY | X = H<br>Y = Cl | 4-Cl-benzyl | phenyl | -C(O)NH-CH₂CH₂-N(piperidine-4-yl-O-phenyl) | H |
| IZ | X = H<br>Y = Cl | 4-Cl-benzyl | phenyl | -C(O)NH-CH₂CH₂-N(piperidine-4-yl-pyridin-4-yl) | H |
| JA | X = H<br>Y = Cl | 4-Cl-benzyl | phenyl | -C(O)NH-CH₂CH₂-(piperidine-4-yl)-NH | H |
| JB | X = H<br>Y = Cl | 4-Cl-benzyl | phenyl | -C(O)NH-CH₂CH₂-N(piperidine-4-yl-O-CH₂CH₂OCH₃) | H |
| JC | X = H<br>Y = Cl | 4-Cl-benzyl | phenyl | -C(O)NH-CH₂CH₂-N(piperazine-N'-CH₂CH₂-pyridin-2-yl) | H |

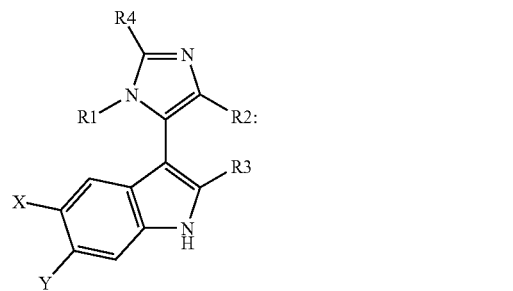

| Compound | X and Y | R¹ | R² | R³ | R⁴ |
|---|---|---|---|---|---|
| JD | X = H, Y = Cl | 4-Cl-phenyl-CH₂ | phenyl | -C(O)-NH-CH₂CH₂-N(2-methylpiperazine)-4-benzyl | H |
| JE | X = H, Y = Cl | 4-Cl-phenyl-CH₂ | phenyl | -C(O)-N(piperidine)-3-N(CH₃)₂ | H |
| JF | X = H, Y = Cl | 4-Cl-phenyl-CH₂ | phenyl | -C(O)-N(piperidine)-3-OH | H |
| JG | X = H, Y = Cl | 4-Cl-phenyl-CH₂ | phenyl | -C(O)-NH-CH₂CH₂-N(piperidine-spiro-indane) | H |
| JH | X = H, Y = Cl | 4-Cl-phenyl-CH₂ | phenyl | -C(O)-NH-CH₂CH₂-N(piperidine)-4-OH-4-benzyl | H |
| JI | X = H, Y = Cl | 4-Cl-phenyl-CH₂ | phenyl | -C(O)-NH-CH₂CH₂-N(piperidine)-4-OH-4-phenyl | H |

-continued

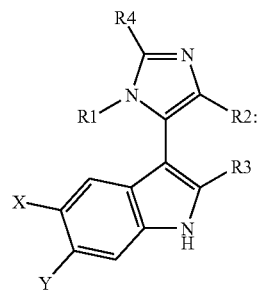

| Compound | X and Y | R¹ | R² | R³ | R⁴ |
|---|---|---|---|---|---|
| JJ | X = H<br>Y = Cl | 4-Cl-phenyl-CH₂ | phenyl | -C(O)NH-CH₂CH₂-(4-benzyl-4,7-diazaspiro[2.5]octan-7-yl) | H |
| JK | X = F<br>Y = Cl | 4-Cl-phenyl-CH₂ | 4-Cl-phenyl-CH₂ | H | H |
| JL | X = H<br>Y = Cl | 4-Cl-phenyl-CH₂ | phenyl | -C(O)NH-CH₂CH₂-((2S,5R)-2,5-dimethyl-4-(pyridin-3-ylmethyl)piperazin-1-yl) | H |
| JM | X = H<br>Y = Cl | 4-Cl-phenyl-CH₂ | phenyl | -C(O)NH-CH₂CH₂-(4-(2,3-dihydro-1H-inden-1-yl)piperazin-1-yl) | H |
| JN | X = H<br>Y = Cl | 4-Cl-phenyl-CH₂ | phenyl | -C(O)NH-CH₂CH₂-(4-(2-(1H-imidazol-1-yl)ethyl)piperazin-1-yl) | H |
| JO | X = H<br>Y = Cl | 4-Cl-phenyl-CH₂ | phenyl | -C(O)NH-CH₂CH₂-(4-(2-phenoxyethyl)piperazin-1-yl) | H |

-continued

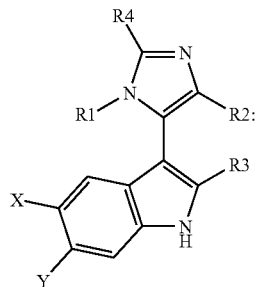

| Compound | X and Y | R¹ | R² | R³ | R⁴ |
|---|---|---|---|---|---|
| JP | X = H, Y = Cl | 4-Cl-benzyl | phenyl | -C(O)NH-CH₂CH₂-(benzimidazol-1-yl) | H |
| JQ | X = H, Y = Cl | 4-Cl-benzyl | phenyl | -C(O)NH-CH₂CH₂-N(piperazine)-CH₂CH₂-morpholine | H |
| JR | X = H, Y = Cl | 4-Cl-benzyl | phenyl | -C(O)NH-CH₂CH₂-N(piperazine)-CH₂-(1-methylpiperidin-4-yl) | H |
| JS | X = H, Y = Cl | 4-Cl-benzyl | phenyl | -C(O)NH-CH₂CH₂-N(piperazine)-CH₂CH₂-OEt | H |
| JT | X = H, Y = Cl | 4-Cl-benzyl | phenyl | -C(O)NH-CH₂CH₂-N(piperazine)-CH₂CH₂-phenyl | H |
| JU | X = H, Y = Cl | 1-(4-Cl-phenyl)ethyl | phenyl | -C(O)NH-CH₂CH₂-N(piperazine)-CH₂CH₂CH₂-OMe | H |

-continued

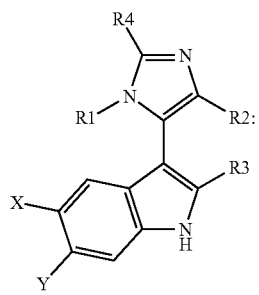

| Compound | X and Y | R¹ | R² | R³ | R⁴ |
|---|---|---|---|---|---|
| JV | X = H<br>Y = Cl | 4-chlorophenyl (CH, methyl stereo) | phenyl | -C(O)NH-CH₂CH₂-piperazinyl-CH₂-(1-methylpiperidin-4-yl) | H |
| JW | X = H<br>Y = Cl | 4-chlorophenyl (CH, methyl stereo) | phenyl | -C(O)NH-CH₂CH₂-piperazinyl-CH₂CH₂-morpholinyl | H |
| JX | X = H<br>Y = Cl | 4-chlorophenyl (CH, methyl stereo) | phenyl | -C(O)NH-CH₂CH₂-piperidinyl-CH₂CH₂-pyrrolidinyl | H |
| JY | X = H<br>Y = Cl | 4-chlorophenyl (CH, methyl stereo) | phenyl | -C(O)NH-CH₂CH₂-(3-oxopiperazinyl)-CH₂-(pyridin-3-yl) | H |
| JZ | X = H<br>Y = Cl | 4-chlorobenzyl | phenyl | -C(O)NH-CH₂CH₂-piperazinyl-CH₂-C(O)NH-(pyridin-2-yl) | H |

-continued

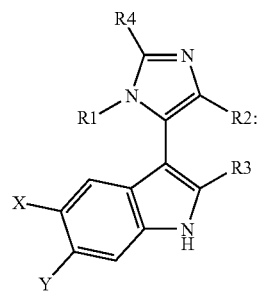

| Compound | X and Y | R¹ | R² | R³ | R⁴ |
|---|---|---|---|---|---|
| KA | X = H<br>Y = Cl | 4-Cl-phenyl-CH₂- | phenyl- | -C(=O)NH-CH₂CH₂-piperazine-CH₂-C(=O)NH-(3-pyridyl) | H |
| KB | X = H<br>Y = Cl | 4-Cl-phenyl-CH₂- | phenyl- | -C(=O)NH-CH₂CH₂-piperazine-CH₂-C(=O)-pyrrolidinyl | H |
| KC | X = H<br>Y = Cl | 4-Cl-phenyl-CH₂- | phenyl- | -C(=O)NH-CH₂CH₂-(2-phenylimidazol-1-yl) | H |
| KD | X = H<br>Y = Cl | 4-Cl-phenyl-CH(Me)- | phenyl- | -C(=O)NH-CH₂CH₂-piperazine-CH₂CH₂-(2-pyridyl) | H |
| KE | X = H<br>Y = Cl | 4-Cl-phenyl-CH(Me)- | phenyl- | -C(=O)NH-CH₂CH₂-piperazine-CH(Et)(Et) | H |

-continued

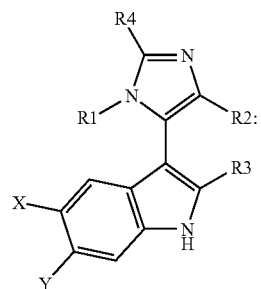

| Compound | X and Y | R¹ | R² | R³ | R⁴ |
|---|---|---|---|---|---|
| KF | X = H<br>Y = Cl | 4-Cl-C6H4-CH(CH3)- | phenyl | -C(O)-NH-CH2CH2-N(piperidin-1-yl)piperidine | H |
| KG | X = H<br>Y = Cl | 4-Cl-C6H4-CH(CH3)- | phenyl | -C(O)-NH-CH2CH2-piperazine-CH2-cyclohexyl | H |
| KH | X = H<br>Y = Cl | 4-Cl-C6H4-CH(CH3)- | phenyl | -C(O)-azetidine-piperazine | H |
| KI | X = H<br>Y = Cl | 4-Cl-C6H4-CH(CH3)- | phenyl | -C(O)-NH-CH2CH2-piperazine-CH2-C(O)-pyrrolidine | H |
| KJ | X = H<br>Y = Cl | 4-Cl-C6H4-CH(CH3)- | phenyl | -C(O)-NH-CH2CH2-N(piperazin-2-one)-CH2-pyridin-3-yl | H |

-continued

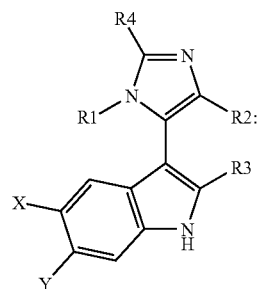

| Compound | X and Y | R¹ | R² | R³ | R⁴ |
|---|---|---|---|---|---|
| KK | X = H, Y = Cl | 5-chloropyridin-2-ylmethyl | phenyl | -C(O)NH-CH₂CH₂-piperazine-N-CH₂-(pyridin-3-yl) | H |
| KL | X = H, Y = Cl | (R)-1-(4-chlorophenyl)ethyl | phenyl | -C(O)NH-CH₂-C(O)-piperazine-N-CH₂-(pyridin-3-yl) | H |
| KM | X = H, Y = Cl | (R)-1-(4-chlorophenyl)ethyl | phenyl | -C(O)NH-CH₂CH₂-piperazine-N-NH-(pyridin-2-yl) | H |
| KN | X = H, Y = Cl | (R)-1-(4-chlorophenyl)ethyl | phenyl | -C(O)NH-CH₂CH₂-piperazine-N-N(CH₃)-(pyridin-2-yl) | H |
| KO | X = H, Y = Cl | (R)-1-(4-chlorophenyl)ethyl | phenyl | -C(O)NH-CH₂CH₂-piperazine-N-O-(pyridin-2-yl) | H |

-continued
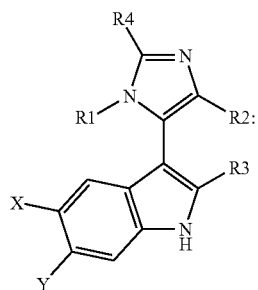
| Compound | X and Y | R¹ | R² | R³ | R⁴ |
|---|---|---|---|---|---|
| KP | X = F<br>Y = Cl | 4-chlorophenyl-CH(CH₂COOH)- | phenyl | H | H |
| KQ | X = F<br>Y = Cl | 4-chlorophenyl-CH(CH₂C(O)NHCH₃)- | phenyl | H | H |
| KR | X = F<br>Y = Cl | 4-chlorophenyl-CH(CH₂C(O)NH-CH₂CH₂OCH₃)- | phenyl | H | H |
| KS | X = F<br>Y = Cl | 4-chlorophenyl-CH(CH₂C(O)NH-CH₂CH₂N(CH₃)₂)- | phenyl | H | H |

-continued
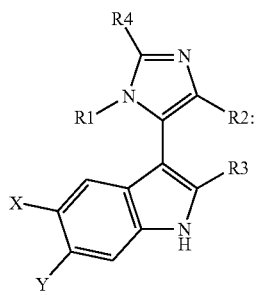
| Compound | X and Y | R¹ | R² | R³ | R⁴ |
|---|---|---|---|---|---|
| KT | X = F<br>Y = Cl | 4-chlorophenyl attached to CH(CH₃)–C(O)–N(4-methylpiperazin-1-yl) | phenyl | H | H |
| KU | X = H<br>Y = Cl | 4-chlorobenzyl | phenyl | –C(O)NH–CH₂CH₂–N(piperazinyl)–C(O)-(pyridin-3-yl) | H |
| KV | X = H<br>Y = Cl | 4-chlorobenzyl | phenyl | –C(O)NH–CH₂CH₂–N(piperazinyl)–CH(CH₃)-(pyridin-2-yl) | H |
| KW | X = H<br>Y = Cl | 4-chlorobenzyl | phenyl | –C(O)NH–CH₂CH₂–N(piperazinyl)–C(O)-(6-fluoropyridin-3-yl) | H |

-continued

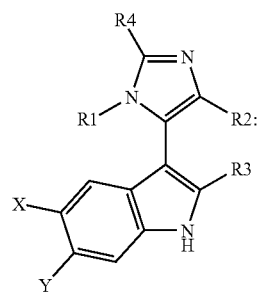

| Compound | X and Y | R¹ | R² | R³ | R⁴ |
|---|---|---|---|---|---|
| KX | X = H<br>Y = Cl | 4-Cl-benzyl | phenyl | -C(O)NH-CH₂CH₂-piperazine-C(O)-(2-pyridyl) | H |
| KY | X = H<br>Y = Cl | 4-Cl-benzyl | phenyl | -C(O)NH-CH₂CH₂-piperazine-C(O)-(4-pyridyl) | H |
| KZ | X = H<br>Y = Cl | 4-Cl-benzyl | phenyl | -C(O)NH-CH₂CH₂-piperazine-C(O)-cyclohexyl | H |
| LA | X = H<br>Y = Cl | 4-Cl-benzyl | phenyl | -C(O)NH-CH₂CH₂-piperazine-CH(CH₃)-(pyrazinyl) | H |
| LB | X = H<br>Y = Cl | 4-Cl-benzyl | phenyl | -C(O)NH-CH₂CH₂-piperazine-C(O)-C(CH₃)₃ | H |

-continued

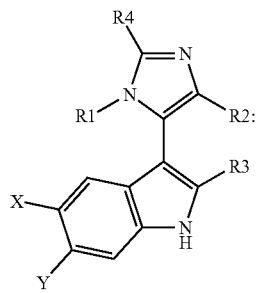

| Compound | X and Y | R¹ | R² | R³ | R⁴ |
|---|---|---|---|---|---|
| LC | X = H<br>Y = Cl | 4-Cl-phenyl-CH₂- | phenyl | -C(O)-NH-CH₂CH₂-(piperazine)-C(O)-CH(Et)₂ | H |
| LD | X = H<br>Y = Cl | 4-Cl-phenyl-CH₂- | phenyl | -C(O)-NH-CH₂CH₂-(piperazine)-C(O)-(6-methylpyridin-3-yl) | H |
| LE | X = H<br>Y = Cl | 4-Cl-phenyl-CH₂- | phenyl | -C(O)-NH-CH₂CH₂-(piperazine)-C(O)-(pyrazin-2-yl) | H |
| LF | X = H<br>Y = Cl | 4-Cl-phenyl-CH₂- | phenyl | -C(O)-NH-CH₂CH₂-(piperazine)-C(O)-(6-methylpyridin-2-yl) | H |
| LG | X = H<br>Y = Cl | 4-Cl-phenyl-CH₂- | phenyl | -C(O)-NH-CH₂CH₂-(piperazine)-C(O)-(6-fluoropyridin-2-yl) | H |

-continued

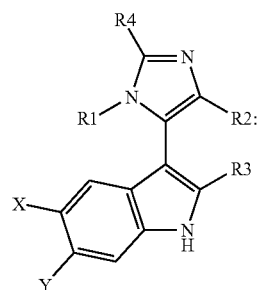

| Compound | X and Y | R¹ | R² | R³ | R⁴ |
|---|---|---|---|---|---|
| LH | X = H, Y = Cl | 4-Cl-benzyl | phenyl | -C(O)NH-CH2CH2-piperazine-N-CH(CH3)-(3-pyridyl) | H |
| LI | X = H, Y = Cl | 1-(4-Cl-phenyl)ethyl | phenyl | -C(O)NH-CH2CH2-piperazine-N-C(O)-(3-pyridyl) | H |
| LJ | X = H, Y = Cl | 1-(4-Cl-phenyl)ethyl | phenyl | -C(O)NH-CH2CH2-piperazine-N-C(O)-(2-pyrazinyl) | H |
| LK | X = H, Y = Cl | 4-Cl-benzyl | phenyl | -C(O)NH-CH2CH2-piperazine-N-C(O)-(tetrahydropyran-4-yl) | H |
| LL | X = H, Y = Cl | 1-(4-Cl-phenyl)ethyl | phenyl | -C(O)NH-CH2CH2-piperazine-N-C(O)-(6-methyl-2-pyridyl) | H |

-continued

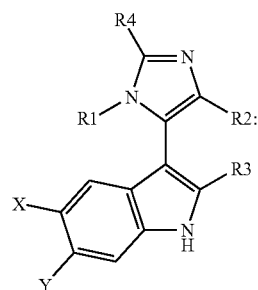

| Compound | X and Y | R¹ | R² | R³ | R⁴ |
|---|---|---|---|---|---|
| LM | X = H, Y = Cl | 4-chlorobenzyl | phenyl | -C(O)NH-CH₂CH₂-N(piperazine)-C(O)NH-(3-pyridyl) | H |
| LN | X = H, Y = Cl | 4-chlorobenzyl | phenyl | -C(O)NH-CH₂CH₂-N(piperazine)-SO₂-(3-pyridyl) | H |
| LO | X = H, Y = Cl | 4-chlorobenzyl | phenyl | -C(O)NH-CH₂CH₂-(piperidine-4-yl)-N-CH₂-(3-pyridyl) | H |
| LP | X = H, Y = Cl | 4-chlorobenzyl | phenyl | -C(O)NH-CH₂CH₂-(piperidine-4-yl)-N-C(O)-(2-pyridyl) | H |
| LQ | X = H, Y = Cl | (S)-1-(4-chlorophenyl)ethyl | phenyl | -C(O)NH-CH₂CH₂-N(piperazine)-C(O)CH₂-(3-pyridyl) | H |

-continued

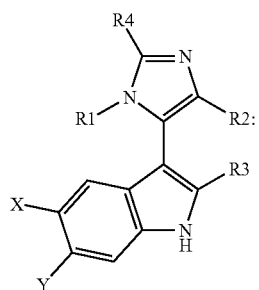

| Compound | X and Y | R¹ | R² | R³ | R⁴ |
|---|---|---|---|---|---|
| LR | X = H, Y = Cl | 4-Cl-C₆H₄-CH(CH₃)- | phenyl | -C(O)NH-CH₂CH₂-N(piperazine)-C(O)-(1-methylpiperidin-4-yl) | H |
| LS | X = H, Y = Cl | 4-Cl-C₆H₄-CH(CH₃)- | phenyl | -C(O)NH-CH₂CH₂-N(piperazine)-C(O)-(1-methylpiperidin-3-yl) | H |
| LT | X = H, Y = Cl | 4-Cl-C₆H₄-CH(CH₃)- | phenyl | -C(O)NH-CH₂CH₂-N(piperazine)-C(O)-CH₂-OCH₃ | H |
| LU | X = H, Y = Cl | 4-Cl-C₆H₄-CH(CH₃)- | phenyl | -C(O)NH-CH₂CH₂-N(piperazine)-C(O)-CH₂-(pyridin-2-yl) | H |
| LV | X = H, Y = Cl | 4-Cl-C₆H₄-CH₂- | phenyl | 4,5-dihydrooxazol-2-yl | H |
| LW | X = H, Y = Cl | 4-Cl-C₆H₄-CH₂- | phenyl | 2-oxo-1,3,4-oxadiazol-5-yl | H |

-continued

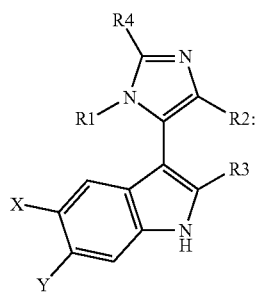

| Compound | X and Y | R¹ | R² | R³ | R⁴ |
|---|---|---|---|---|---|
| LX | X = H, Y = Cl | 4-chlorobenzyl | phenyl | 5-(pyridin-3-ylamino)-1,3,4-oxadiazol-2-yl | H |
| LY | X = H, Y = Cl | 4-chlorobenzyl | phenyl | 5-((pyridin-3-ylmethyl)amino)-1,3,4-oxadiazol-2-yl | H |
| LZ | X = H, Y = Cl | 4-chlorobenzyl | phenyl | 5-(pentan-3-ylamino)-1,3,4-oxadiazol-2-yl | H |
| MA | X = H, Y = Cl | 4-chlorobenzyl | phenyl | 3-(pyridin-3-ylmethyl)-2-oxo-2,3-dihydro-1,3,4-oxadiazol-5-yl | H |
| MB | X = H, Y = Cl | 5-chloro-2-((4-methylpiperazin-1-yl)methyl)benzyl | phenyl | H | H |
| MC | X = F, Y = Cl | 5-chloro-2-(((2-methoxyethyl)amino)methyl)benzyl | phenyl | H | H |

-continued

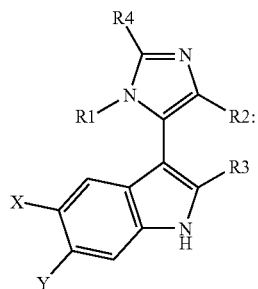

| Compound | X and Y | R¹ | R² | R³ | R⁴ |
|---|---|---|---|---|---|
| MD | X = F<br>Y = Cl | 5-Cl, 2-(morpholinomethyl)benzyl | phenyl | H | H |
| ME | X = F<br>Y = Cl | 5-Cl, 2-((methylamino)methyl)benzyl | phenyl | H | H |
| MF | X = H<br>Y = Cl | 4-chlorobenzyl | phenyl | -C(O)NH-CH₂CH₂-[1-(pyridin-2-ylmethyl)imidazolidin-2-one-3-yl] | H |
| MG | X = H<br>Y = Cl | 1-(4-chlorophenyl)ethyl | phenyl | -C(O)NH-CH₂CH₂-[4-(tetrahydro-2H-pyran-4-carbonyl)piperazin-1-yl] | H |
| MH | X = H<br>Y = Cl | 1-(4-chlorophenyl)ethyl | phenyl | -C(O)NH-CH₂CH₂-[4-(2-(pyrrolidin-1-yl)acetyl)piperazin-1-yl] | H |
| MI | X = H<br>Y = Cl | 4-chlorobenzyl | phenyl | -C(O)-[3-((2-acetoxyethyl)amino)pyrrolidin-1-yl] | H |

-continued
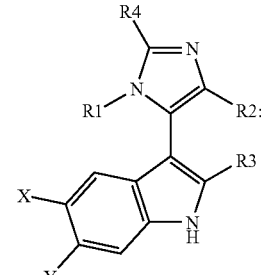
| Compound | X and Y | R¹ | R² | R³ | R⁴ |
|---|---|---|---|---|---|
| MJ | X = H<br>Y = Cl | 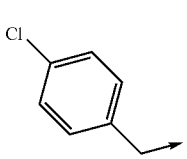 | 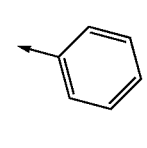 | 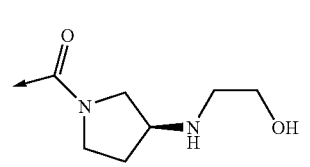 | H |
| MK | X = H<br>Y = Cl | 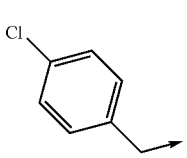 | 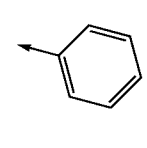 | 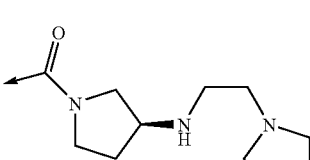 | H |
| ML | X = H<br>Y = Cl | 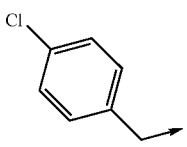 | 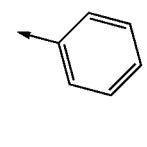 | 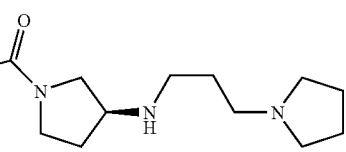 | H |
| MM | X = H<br>Y = Cl | 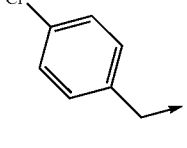 | 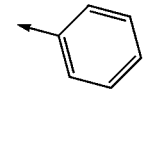 | 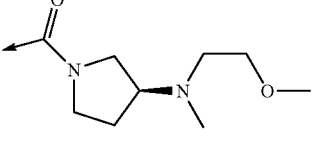 | H |
| MN | X = H<br>Y = Cl | 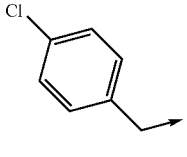 | 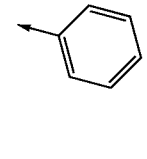 | H | H |
| MO | X = H<br>Y = Cl | 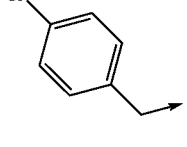 | 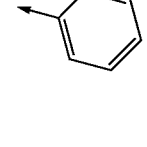 | 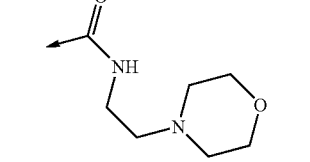 | H |
| MP | X = H<br>Y = Cl | 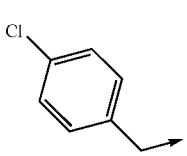 | 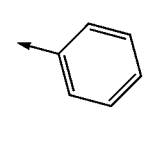 | 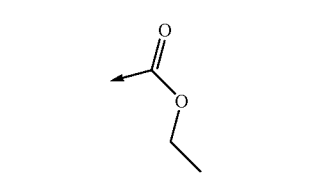 | H |

-continued

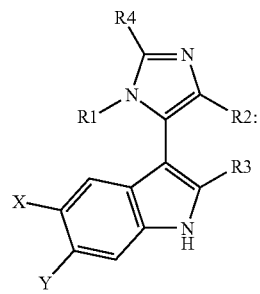

| Compound | X and Y | R¹ | R² | R³ | R⁴ |
|---|---|---|---|---|---|
| MQ | X = H, Y = Cl | neopentyl (CH₂CH₂C(CH₃)₃) | phenyl | -C(O)NH₂ | H |
| MR | X = H, Y = Cl | 4-chlorobenzyl | phenyl | -C(O)NH₂ | H |
| MS | X = H, Y = Cl | 4-chlorobenzyl | phenyl | 1H-tetrazol-5-yl | H |
| MT | X = H, Y = Cl | 4-chlorobenzyl | phenyl | -CN | H |
| MU | X = H, Y = Cl | 4-chlorobenzyl | phenyl | -CH₂OH | H |
| MV | X = H, Y = Cl | 4-chlorobenzyl | phenyl | -CH₂NH-CH₂CH₂-morpholino | H |
| MW | X = F, Y = Cl | 4-chlorobenzyl | 3-hydroxyphenyl | H | H |
| MX | X = F, Y = Cl | 4-chlorobenzyl | 3-methoxyphenyl | H | H |

-continued

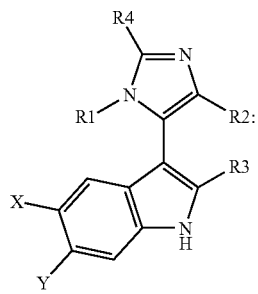

| Compound | X and Y | R¹ | R² | R³ | R⁴ |
|---|---|---|---|---|---|
| MY | X = H, Y = Cl | 4-Cl-benzyl | 3-hydroxyphenyl | (3R)-dimethylamino-pyrrolidine-1-carbonyl | H |
| MZ | X = H, Y = Cl | 4-Cl-benzyl | 3-methoxyphenyl | (3R)-dimethylamino-pyrrolidine-1-carbonyl | H |
| NA | X = H, Y = Cl | 4-Cl-benzyl | phenyl | H | Me |
| NB | X = H, Y = Cl | 4-Cl-benzyl | phenyl | ethoxycarbonyl | Br |
| NC | X = H, Y = Cl | 4-Cl-benzyl | phenyl | ethoxycarbonyl | Cl |
| ND | X = H, Y = Cl | 4-Cl-benzyl | phenyl | (3R)-dimethylamino-pyrrolidine-1-carbonyl | 3-pyridyl |
| NE | X = H, Y = Cl | 4-Cl-benzyl | phenyl | (3R)-dimethylamino-pyrrolidine-1-carbonyl | 6-methoxy-3-pyridyl |

-continued

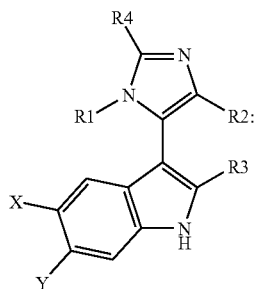

| Compound | X and Y | R¹ | R² | R³ | R⁴ |
|---|---|---|---|---|---|
| NF | X = H, Y = Cl | 4-chlorobenzyl | phenyl | 1-acetyl-3-(dimethylamino)pyrrolidinyl | pyrimidin-5-yl |
| NG | X = H, Y = Cl | 4-chlorobenzyl | phenyl | H | diethoxymethyl |
| NH | X = H, Y = Cl | 4-chlorobenzyl | phenyl | H | hydroxymethyl |
| NI | X = H, Y = Cl | 4-chlorobenzyl | phenyl | H | pyridin-4-yl |
| NJ | X = H, Y = Cl | 4-chlorobenzyl | phenyl | H | 1-hydroxyethyl |
| NK | X = H, Y = Cl | 4-chlorobenzyl | phenyl | H | 3-(dimethylamino)propyl(methyl)aminomethyl |
| NL | X = H, Y = Cl | 4-chlorobenzyl | phenyl | H | (4-ethylpiperazin-1-yl)methyl |

-continued

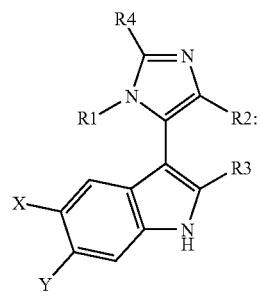

| Compound | X and Y | R¹ | R² | R³ | R⁴ |
|---|---|---|---|---|---|
| NM | X = H<br>Y = Cl | 4-Cl-benzyl | phenyl | H | morpholinomethyl (N-CH₂- morpholine) |
| NN | X = H<br>Y = Cl | 4-Cl-benzyl | phenyl | H | -CH₂N(CH₃)₂ |
| NO | X = H<br>Y = Cl | 4-Cl-benzyl | phenyl | H | piperazinyl-CH₂CH₂-OC(O)CH₃ |
| NP | X = H<br>Y = Cl | 4-Cl-benzyl | phenyl | H | -CH₂CH₂C(O)OCH₂CH₃ |
| NQ | X = H<br>Y = Cl | 4-Cl-benzyl | phenyl | H | -CH₂CH₂C(O)OH |
| NR | X = H<br>Y = Cl | 4-Cl-benzyl | phenyl | H | -CH₂CH₂CH₂OH |
| NS | X = H<br>Y = Cl | 4-Cl-benzyl | phenyl | H | -CH₂CH₂C(O)N(CH₃)₂ |

-continued

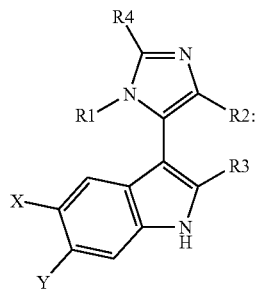

| Compound | X and Y | R¹ | R² | R³ | R⁴ |
|---|---|---|---|---|---|
| NT | X = X<br>Y = Cl | 4-Cl-benzyl | phenyl | H | -CH₂CH₂C(O)N(Me)(CH₂CH₂OMe) |
| NU | X = H<br>Y = Cl | 4-Cl-benzyl | phenyl | H | -CH₂CH₂C(O)NH(CH₂CH₂OMe) |
| NV | X = H<br>Y = Cl | 4-Cl-benzyl | phenyl | H | -CH₂CH₂C(O)N(Me)(CH₂CH₂CH₂NMe₂) |
| NW | X = H<br>Y = Cl | 4-Cl-benzyl | phenyl | H | -CH₂CH₂CH₂N(Me)(CH₂CH₂OMe) |
| NX | X = H<br>Y = Cl | 4-Cl-benzyl | phenyl | H | -CH₂CH₂CH₂N(Me)(CH₂CH₂CH₂NMe₂) |
| NY | X = H<br>Y = Cl | 4-Cl-benzyl | phenyl | H | 1H-pyrrol-3-yl |
| NZ | X = H<br>Y = Cl | 4-Cl-benzyl | phenyl | -C(O)NH-CH₂CH₂-(4-methylpiperazin-1-yl) | Me |

-continued

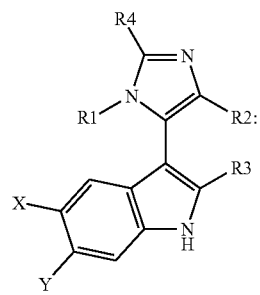

| Compound | X and Y | R¹ | R² | R³ | R⁴ |
|---|---|---|---|---|---|
| OA | X = H<br>Y = Cl | 4-chlorophenyl-CH₂ | phenyl | -C(O)-piperidin-4-yl-N(CH₃)-CH₂CH₂CH₂-N(CH₃)₂ | H |
| OB | X = H<br>Y = Cl | 4-chlorophenyl-CH₂ | phenyl | -C(O)-piperidin-4-yl-N(CH₃)-CH₂CH₂CH₂CH₂-N(CH₃)₂ | H |
| OC | X = H<br>Y = Cl | 4-chlorophenyl-CH₂ | phenyl | -C(O)-NH-CH₂-C(O)-piperazinyl-CH₂-(1-methylpiperidin-4-yl) | H |
| OD | X = H<br>Y = Cl | 4-chlorophenyl-CH₂ | phenyl | -C(O)-NH-CH₂CH₂-piperazinyl-C(O)-piperidin-4-yl(NH) | H |

-continued
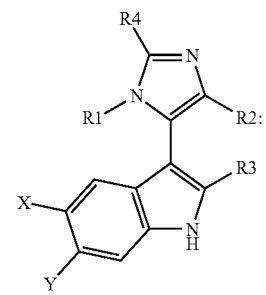
| Compound | X and Y | R¹ | R² | R³ | R⁴ |
|---|---|---|---|---|---|
| OE | X = H, Y = Cl | 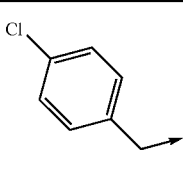 | 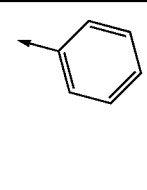 | 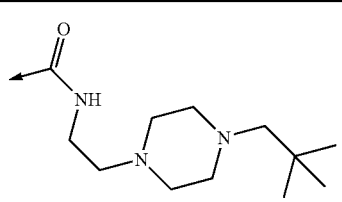 | H |
| OF | X = H, Y = Cl | 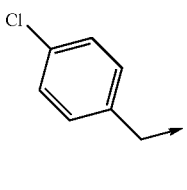 | 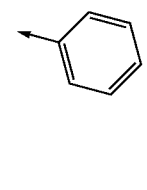 | 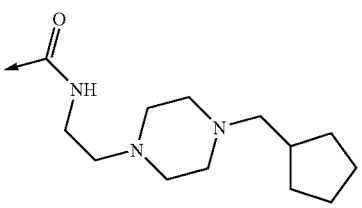 | H |
| OG | X = H, Y = Cl | 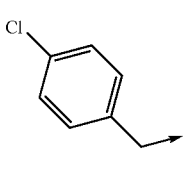 | 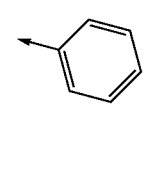 | 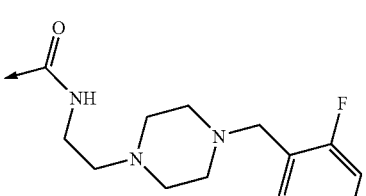 | H |
| OH | X = H, Y = Cl | 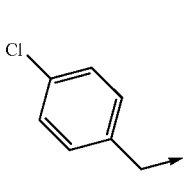 | 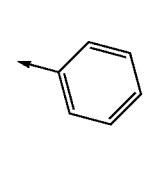 | 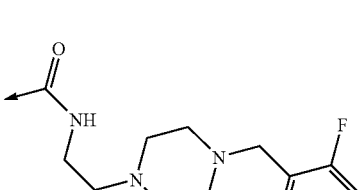 | H |
| OI | X = H, Y = Cl | 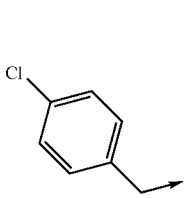 | 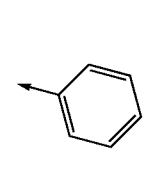 | 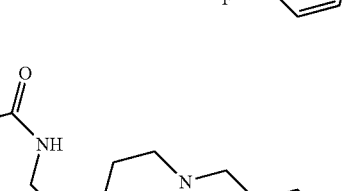 | H |

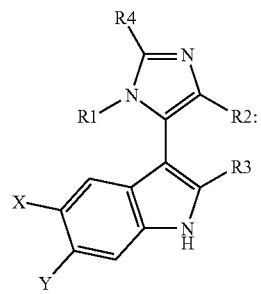

| Com-pound | X and Y | $R^1$ | $R^2$ | $R^3$ | $R^4$ |
|---|---|---|---|---|---|
| OJ | X = H<br>Y = Cl | | | | H |
| OK | X = H<br>Y = Cl | | | | H | and/or a tautomer, an N-oxide and/or a pharmaceutically acceptable salt thereof.

9. A pharmaceutical composition comprising a compound of the formula I, and/or a tautomer, an N-oxide and/or a pharmaceutically acceptable salt thereof, according to claim 1 and at least one pharmaceutically acceptable carrier material.

10. A method of treatment comprising administering a compound of the formula I, and/or a tautomer, an N-oxide and/or a pharmaceutically acceptable salt thereof, according to claim 1 to a person in need of such treatment in an effective amount for the therapeutic treatment of cancer selected from leukemia, rhabdomyosarcoma, osteosarcomas, carcinoma of the brain, in a patient having cancer.

11. A method for the manufacture of a compound of the formula I, comprising

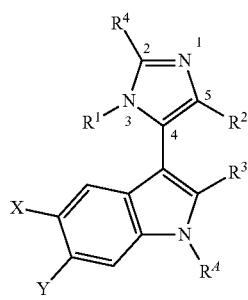

(I)

a) for the manufacture of a compound of the formula I wherein $R^4$ is hydrogen and $R^1$ is unsubstituted or substituted alkyl, unsubstituted or substituted alkenyl or unsubstituted or substituted alkinyl, unsubstituted or substituted aryl or unsubstituted or substituted heterocyclyl;

$R^2$ is unsubstituted or substituted alkyl, unsubstituted or substituted alkenyl, unsubstituted or substituted alkinyl, unsubstituted or substituted aryl or unsubstituted or substituted heterocyclyl;

$R^3$ is hydrogen, halogen, unsubstituted or substituted alkyl, unsubstituted or substituted alkenyl, unsubstituted or substituted alkinyl, unsubstituted or substituted aryl, carboxy, cyano, esterified carboxy, unsubstituted or substituted heterocyclyl-carbonyl (heterocyclyl-C)(=O)—), unsubstituted or substituted carbamoyl or unsubstituted or substituted heterocyclyl;

$R^4$ is hydrogen or unsubstituted or substituted alkyl or acyl;

X is hydrogen, $C_1$-$C_7$-alkyl, halo-$C_1$-$C_7$-alkyl, $C_1$-$C_7$-alkoxy, halo or cyano; and Y is $C_1$-$C_7$-alkyl, halo-$C_1$-$C_7$-alkyl, $C_1$-$C_7$-alkoxy, halo or cyano;

reacting a formylindole derivative of the formula II

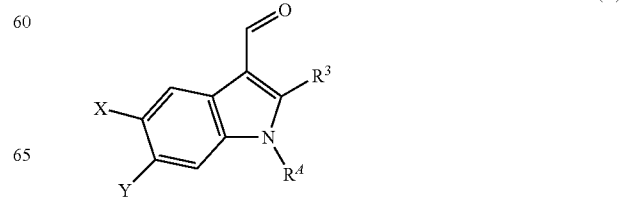

(II)

with an amino compound of the formula III,

R¹—NH₂  (III)

in the presence of a tosyl-methyl isocyanide of the formula IV,

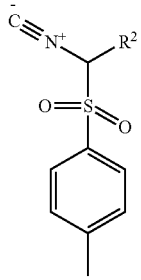

(IV)

or
b) coupling an indole-boronic acid of the formula V,

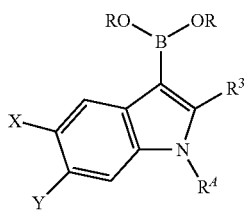

(V)

wherein each R is hydrogen, aryl, alkenyl or alkyl, or wherein the two R form a bridge, lower alkyl or R and R together form 1,1,2,2-tetramethyl-1,2-ethylene, with a halo-imidazole of the formula VI,

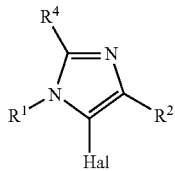

(VI)

wherein $R^1$, $R^2$ and $R^4$ are as defined for a compound of the formula I in claim 1 and Hal is bromo or iodo, where in the reaction functional groups in the starting materials can be present in protected form and in the obtainable compounds of the formula I carrying one or more protecting groups such protecting groups are removed;

and, if desired, a compound of the formula I obtainable according to the reaction given above is converted into a different compound of the formula I, an obtainable salt of a compound of the formula I is converted into a different salt thereof, an obtainable free compound of the formula I is converted into a salt thereof, and/or an obtainable isomer of a compound of the formula I is separated from one or more different obtainable isomers of the formula.

\* \* \* \* \*

UNITED STATES PATENT AND TRADEMARK OFFICE
CERTIFICATE OF CORRECTION

Page 1 of 1

PATENT NO. : 8,053,457 B2
APPLICATION NO. : 12/593721
DATED : November 8, 2011
INVENTOR(S) : Boettcher et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 136 days.

Signed and Sealed this
Sixth Day of March, 2012

David J. Kappos
*Director of the United States Patent and Trademark Office*